US009284335B2

(12) United States Patent
Allan et al.

(10) Patent No.: US 9,284,335 B2
(45) Date of Patent: *Mar. 15, 2016

(54) SUBSTITUTED PYRIDO[3,2-E][1,2,4]TRIAZOLO[1,5-C]PYRIMIDINES, PYRIDO[2,3-E][1,2,4]TRIAZOLO[1,5-C]PYRIMIDINES AND/OR [1,2,4]TRIAZOLO[1,5-C]PTERIDINES FOR TREATMENT OF CENTRAL NERVOUS SYSTEM DISEASES AND DISORDERS

(71) Applicant: DART NEUROSCIENCE (CAYMAN) LTD., Grand Cayman (KY)

(72) Inventors: Amy Allan, Encinitas, CA (US); Bryan Branstetter, Carlsbad, CA (US); Brian Dyck, San Diego, CA (US); Laurent Gomez, San Diego, CA (US); Tami Jo Marrone, Carlsbad, CA (US); Marco Peters, San Diego, CA (US); Michael I. Weinhouse, San Diego, CA (US)

(73) Assignee: Dart NeuroScience (Cayman) Ltd., Grand Cayman (KY)

( * ) Notice: Subject to any disclaimer, the term of this patent is extended or adjusted under 35 U.S.C. 154(b) by 0 days.

This patent is subject to a terminal disclaimer.

(21) Appl. No.: 14/408,942

(22) PCT Filed: Jun. 18, 2013

(86) PCT No.: PCT/US2013/046415
§ 371 (c)(1),
(2) Date: Dec. 17, 2014

(87) PCT Pub. No.: WO2013/192229
PCT Pub. Date: Dec. 27, 2013

(65) Prior Publication Data
US 2015/0158885 A1 Jun. 11, 2015

Related U.S. Application Data

(60) Provisional application No. 61/661,091, filed on Jun. 18, 2012.

(51) Int. Cl.
*A61K 31/519* (2006.01)
*C07D 239/70* (2006.01)
*C07D 519/00* (2006.01)
*C07D 495/14* (2006.01)
*C07D 498/08* (2006.01)
*C07D 491/147* (2006.01)
*C07D 491/22* (2006.01)
*C07D 495/22* (2006.01)
*C07D 471/14* (2006.01)
*C07D 487/14* (2006.01)
*C07D 491/107* (2006.01)

(52) U.S. Cl.
CPC ............ *C07D 519/00* (2013.01); *C07D 471/14* (2013.01); *C07D 487/14* (2013.01); *C07D 491/107* (2013.01); *C07D 491/147* (2013.01); *C07D 491/22* (2013.01); *C07D 495/14* (2013.01); *C07D 495/22* (2013.01); *C07D 498/08* (2013.01)

(58) Field of Classification Search
CPC ............................ A61K 31/519; C07D 239/70
USPC ............................................ 514/267; 544/252
See application file for complete search history.

(56) References Cited

U.S. PATENT DOCUMENTS

| 4,585,772 | A | 4/1986 | Junge et al. |
| 4,938,949 | A | 7/1990 | Borch et al. |
| 5,128,338 | A | 7/1992 | Bourguignon et al. |
| 7,868,015 | B2 | 1/2011 | Tully et al. |
| 7,947,731 | B2 | 5/2011 | Tully et al. |
| 2008/0051437 | A1 | 2/2008 | Hallam et al. |
| 2009/0053140 | A1 | 2/2009 | Scott et al. |

(Continued)

FOREIGN PATENT DOCUMENTS

| EP | 217 748 A2 | 4/1987 |
| WO | WO 2007/143705 A2 | 12/2007 |
| WO | WO 2009/075784 A1 | 6/2009 |

(Continued)

OTHER PUBLICATIONS

Jordan, V. C. Nature Reviews: Drug Discovery, 2, 2003, 205.*

(Continued)

*Primary Examiner* — Douglas M Willis
(74) *Attorney, Agent, or Firm* — Knobbe Martens Olson & Bear LLP

(57) ABSTRACT

Described herein are compounds and chemical entities of Formula (I), methods of their synthesis, compositions comprising them, and their use in treating numerous diseases and disorders, including cognitive deficits associated with CNS diseases and disorders.

26 Claims, 3 Drawing Sheets

(56) References Cited

U.S. PATENT DOCUMENTS

2009/0163545 A1 6/2009 Goldfarb
2010/0029697 A1 2/2010 Debenham et al.

FOREIGN PATENT DOCUMENTS

| WO | WO 2010/065149 A1 | 6/2010 |
| WO | WO 2010/065153 A1 | 6/2010 |
| WO | WO 2010/098839 A1 | 9/2010 |
| WO | WO 2010/132127 A1 | 11/2010 |
| WO | WO 2011/153129 A1 | 12/2011 |
| WO | WO 2011/153135 A1 | 12/2011 |
| WO | WO 2011/153136 A1 | 12/2011 |
| WO | WO 2011/153138 A1 | 12/2011 |
| WO | WO 2012/171016 A1 | 12/2012 |
| WO | WO 2013/192229 * | 12/2013 |

OTHER PUBLICATIONS

Hackam, et al. JAMA, 296(14), 2006, 1731-1732.*
Database Registry Chemical Abstracts Service, Columbus Ohio, Accession No. RN 838843-34-8, Entered STN: Feb. 28, 2005.
International Search Report and Written Opinion mailed on Oct. 30, 2013 in International Application No. PCT/US2013/046403, filed Jun. 18, 2013.
International Search Report and Written Opinion mailed on Oct. 23, 2013 in International Application No. PCT/US2013/046415, filed Jun. 18, 2013.

* cited by examiner

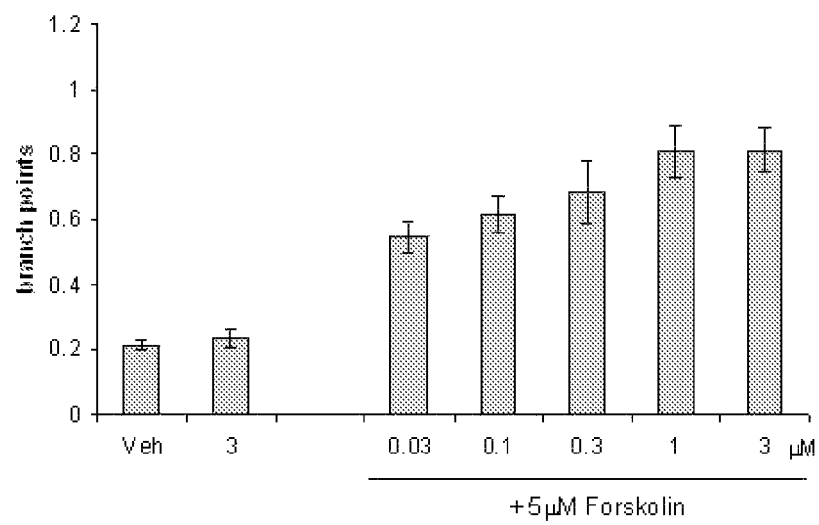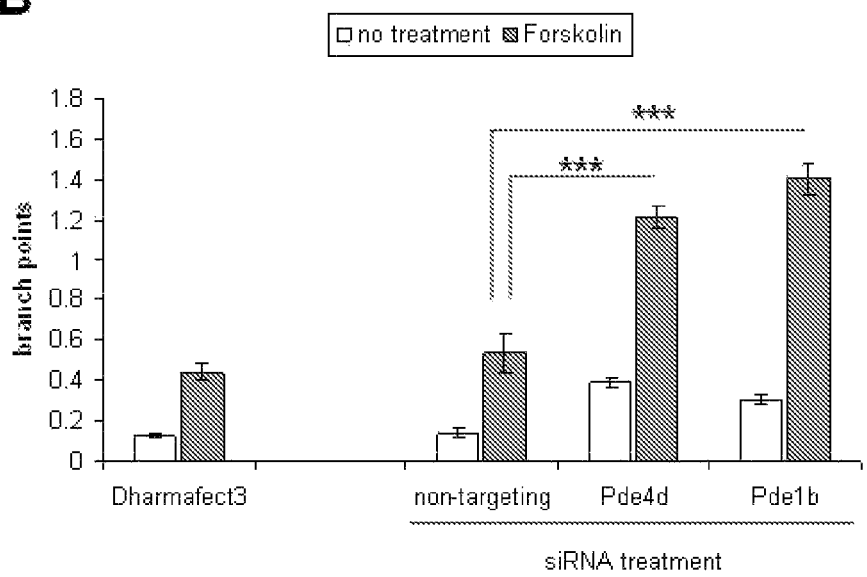
FIG. 3A-B

SUBSTITUTED PYRIDO[3,2-E][1,2,4]TRIAZOLO[1,5-C]PYRIMIDINES, PYRIDO[2,3-E][1,2,4]TRIAZOLO[1,5-C]PYRIMIDINES AND/OR [1,2,4]TRIAZOLO[1,5-C]PTERIDINES FOR TREATMENT OF CENTRAL NERVOUS SYSTEM DISEASES AND DISORDERS

CROSS REFERENCE TO RELATED APPLICATIONS

Any and all priority claims identified in the Application Data Sheet, or any correction thereto, are hereby incorporated by reference under 37 CFR 1.57. For example, this application is a U.S. National Phase of International Application No. PCT/US2013/046415, filed on Jun. 18, 2013 designating the U.S. and published on Dec. 27, 2013 as WO 2013/192229, which claims the benefit of U.S. Provisional Application 61/661,091, filed on Jun. 18, 2012, which is incorporated herein by reference in its entirety.

FIELD OF THE INVENTION

The present invention relates to certain substituted pyridine-fused azolopyrimidin-5-(6h)-one compounds and derivatives of such compounds; pharmaceutical compositions containing them, methods of making them, and their use in various methods, including the inhibition of PDE1 enzymes; and the treatment of one or more disorders, including neurological disorders, cardiovascular disorders, renal disorders, and other conditions and diseases involving PDE1 or cyclic nucleotide signaling.

BACKGROUND OF THE INVENTION

The cyclic nucleotides 5'-3' cyclic adenosine monophosphate (cAMP) and 5'-3' cyclic guanosine monophosphate (cGMP) are second messenger molecules, relaying signals from receptors on the cell surface to target molecules inside the cell. The cyclic nucleotide phosphodiesterases (PDEs) are a group of enzymes (which can be localized to different cellular compartments) that hydrolyze the phosphodiester bond of cyclic nucleotides and thereby inactivate their function. PDEs can therefore play important roles in signal transduction by modulating the localization, amplitude, and duration of cyclic nucleotide signaling within the cell.

PDEs comprise at least eleven families: PDE1-PDE11, each categorized by distinct molecular, kinetic, regulatory, and inhibitory properties. PDE family members are differentially expressed in various tissues and can localize to distinct sub-cellular domains. This diversity enables PDEs to modulate local intracellular cAMP and cGMP gradients in response to discrete external stimuli (Conti and Beavo, *Annu. Rev. Biochem.* 2007, 76, 481-511).

Among the PDE families, PDE1 is unique in its requirement for full activation by calcium ($Ca^{2+}$) and calmodulin (CaM). Calcium enters the cell and forms a complex with CaM. Binding of the $Ca^{2+}$/CaM complexes to multiple domains near the N-terminus of PDE1 can result in full phosphodiesterase activity. PDE1 is therefore a point of convergence and integration for multiple signaling pathways that regulate numerous downstream targets and cellular events (Sharma et al., *Int. J. Mol. Med.* 2006, 18, 95-105).

The PDE1 family comprises three genes (pde1a, pde1b, and pde1c), and each encodes multiple isoforms via alternative splicing and differential transcription. All PDE1 enzymes appear to hydrolyze both cAMP and cGMP, although they can differ in their relative affinities for each (Bender and Beavo, *Pharmacol. Rev.* 2006, 58, 488-520).

PDE1 is expressed in many tissues, underscoring a role in many physiological processes. Regions of PDE expression include, but are not limited to, the heart, lungs, veins and arteries, smooth muscle, skeletal muscle, skin, adrenal gland, thyroid, pancreas, esophagus, stomach, small intestine, colon, liver, leukocytes, testis, ovary, bladder, kidney, and the nervous system. In the brain, PDE1 isoforms are expressed in the cerebral cortex, frontal lobe, hippocampus, cerebellum, and amygdala, regions involved in memory formation and other cognitive processes. PDE1b expression, in particular, correlates closely with brain regions showing high levels of dopaminergic innervation. In the cardiovascular system, PDE1 appears to play a central role in organizing cAMP microdomains and mediating hormonal specificity in cardiac cells (Maurice et al., *Mol. Pharm.* 2003, 64, 533-546). Indeed, human PDE1b is highly expressed in numerous cardiovascular regions, including the pericardium, heart atrium (left), heart apex, Purkinje fibers, and pulmonic valve.

More generally, cyclic nucleotide signaling pathways, including those involving PDE1, are implicated in numerous pathological processes (Keravis and Lugnier, *Br. J. Pharmacol.* 2012, 165, 1288-1305). For example, alterations in these pathways have been implicated in various disorders of the brain, including depression, schizophrenia and cognitive disorders. Inhibiting PDE1 activity in the nervous system, for example, can increase cAMP or cGMP levels and consequently induce expression of neuronal plasticity-related genes, neurotrophic factors, and neuroprotective molecules. Based on such properties, PDE1 inhibitors are promising therapeutic candidates in treating many CNS disorders and associated cognitive impairments. Similarly, PDE1 enzymes and cyclic nucleotides are emerging as key mediators of pathological processes that underlie many vascular disorders, including hypertension, myocardial infarction, and heart failure (Miller et al., *Basic Res. Cardiol.* 2011, 106, 1023-1039 and Miller et al, *Circ. Res.* 2009, 105, 956-964). In addition, PDE1 is implicated in the development and progression of renal disease, where cAMP and cGMP regulate a variety of signaling pathways, including those that modulate mitogenesis, inflammation, and extracellular matrix synthesis (Wang et al., *Kidney Int.* 2010, 77. 129-140; Cheng et al., *Soc. Exp. Biol. Med.* 2007, 232, 38-51 and Dousa, *Kidney Int.* 1999, 55, 29-62).

Accordingly, there is a need to develop treatments for CNS and other disorders, as well as disorders that are due, at least in part, to an aberration or dysregulation of an intracellular signaling pathway regulated by PDE1.

Various small-molecule PDE1 enzyme inhibitors have been reported e.g., imidazopyrazolopyrimidinones (Intra-Cellular Therapeutics Intl. Pat. Appl. Publ. WO 2012171016, Dec. 13, 2012), pyrrolopyrimidinones (Intra-Cellular Therapeutics Intl. Pat. Appl. Publ. WO 2011153138, Dec. 8, 2011; Intl. Pat. Appl. Publ. WO 2011153136, Dec. 8, 2011; Intl. Pat. Appl. Publ. WO 2011153135, Dec. 8, 2011; Intl. Pat. Appl. Publ. WO 2011153129, Dec. 8, 2011), imidazopurinone (Intra-Cellular Therapeutics Intl. Pat. Appl. Publ. WO 2010132127, Nov. 18, 2010), pyrazolopyrimidinedione (Intra-Cellular Therapeutics Intl. Pat. Appl. Publ. WO 2010098839, Sep. 2, 2010), pyrazolopyrimidinone (Intra-Cellular Therapeutics Intl. Pat. Appl. Publ. WO 2010065153, Jun. 10, 2010; WO 2010065149, Jun. 10, 2010; Intl. Pat. Appl. Publ. WO 2009075784, Jun. 18, 2009).

However, there remains a need for potent PDE1 inhibitors with desirable pharmaceutical properties. It is therefore desirable to develop improved PDE1 inhibitors showing higher potency, greater specificity, and better side effect profiles. The present invention meets these and other needs in the art by disclosing substituted pyridine-fused and azolopyrimidin-5-(6h)-one compounds as potent and well-tolerated PDE1 inhibitors.

SUMMARY OF THE INVENTION

The invention provides a chemical entity of Formula (I):

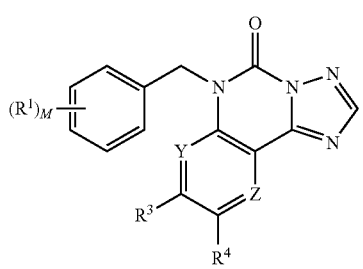

(I)

wherein
$R^1$, $R^3$, $R^4$, Y, Z and M have any of the values described herein.

In one aspect the chemical entity is selected from the group consisting of compounds of Formula (I), pharmaceutically acceptable salts of compounds of Formula (I), pharmaceutically acceptable prodrugs of compounds of Formula (I), and pharmaceutically acceptable metabolites of compounds of Formula (I). In a specific aspect, the chemical entity is a compound of Formula (I), or a pharmaceutically acceptable salt thereof.

Chemical entities and compounds of Formula (I) are useful in wide range of methods. Isotopically-labeled compounds and prodrugs can be used in metabolic and reaction kinetic studies, detection and imaging techniques, and radioactive treatments. The chemical embodiments of the present invention can be used to inhibit PDE1, and PDE1b, in particular; to treat a disorder mediated by PDE1, and PDE1b, in particular; to enhance neuronal plasticity; to treat neurological disorders, including neurodegenerative disorders, cognitive disorders, and cognitive deficits associated with CNS disorders; to confer neuroprotection; and to treat peripheral disorders, including obesity, diabetes, cardiometabolic disorders, and their associated co-morbidities. The chemical embodiments of the present invention are also useful as augmenting agents to enhance the efficiency of cognitive and motor training, to facilitate neurorecovery and neurorehabilitation, and to increase the efficiency of non-human animal training protocols. The invention is further directed to the general and specific embodiments defined, respectively, by the independent and dependent claims appended hereto, which are incorporated by reference herein.

The invention further relates to the use of a compound, chemical entity, or composition of the instant invention in a method of treating disorders that include an aberrant or dysregulated signaling pathway mediated by PDE1, and more specifically, PDE1b. Such PDE1-related signaling pathways, preferably in the nervous system, include, but are not limited to, those involving nitric oxide, natriuretic peptides, dopamine, noradrenalin, neurotensin, cholecystokinin, vasoactive intestinal peptide, serotonin, glutamate, GABA, acetylcholine, adenosine, cannabinoids, natriuretic peptides, and endorphins. In a specific aspect, the compounds and compositions are useful in treating disorders characterized by alterations in dopamine signaling.

BRIEF DESCRIPTION OF THE DRAWINGS

FIG. 3 is a bar graph showing the effect on neurite outgrowth of (A) rolipram-mediated inhibition of PDE4, and (B) siRNA-mediated inhibition of Pde4d or Pde1b. Bars represent the mean±SEM of neurite length and branching of at least 100 NS1 cells; n=8 wells/bar.

DETAILED DESCRIPTION OF THE INVENTION

Figure 1:
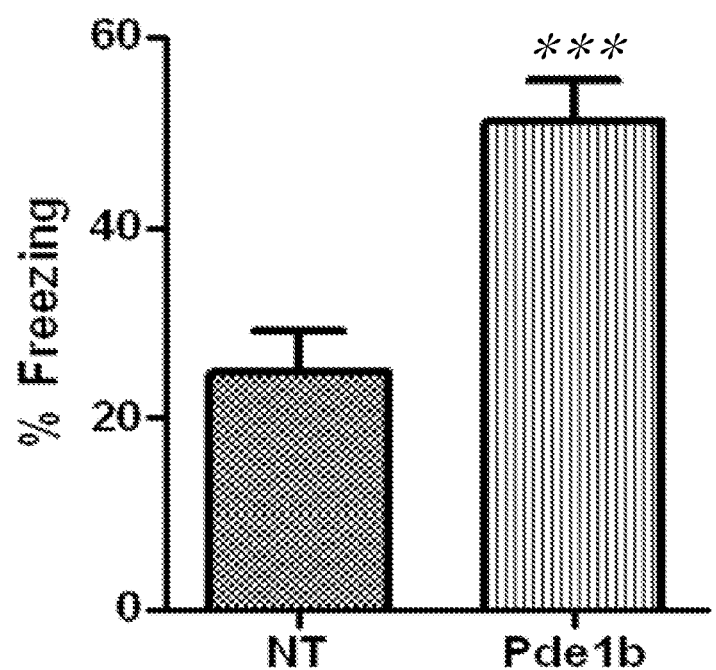
FIG. 1 is bar graph showing the effect of siRNA-mediated knockdown of PDE1b in mouse hippocampal tissue on one-day memory in a contextual fear-conditioning assay.

The invention may be more fully appreciated by reference to the following description, including the examples. Unless otherwise defined, all technical and scientific terms used herein have the same meaning as commonly understood by one of ordinary skill in the art. Although methods and materials similar or equivalent to those described herein can be used in the practice or testing of the present invention, suitable methods and materials are described herein. In addition, the materials, methods, and examples are illustrative only and not intended to be limiting.

For the sake of brevity, all publications, including patent applications, patents, and other citations mentioned herein, are incorporated by reference in their entirety. Citation of any such publication, however, shall not be construed as an admission that it is prior art to the present invention.

ABBREVIATIONS

The specification includes numerous abbreviations, whose meanings are listed in the following Table:

| Abbreviation | Definition |
|---|---|
| ACN | Acetonitrile |
| BINAP | 2,2'-Bis(diphenylphosphino)-1,1'-binaphthyl |
| BOC | tert-butoxycarbonyl |
| BOC anhydride | Di-tert-butyl dicarbonate |
| CELITE ® | Diatomaceous earth |
| m-CPBA | meta-Chloroperoxybenzoic acid |
| DAST | Diethylaminosulfur trifluoride |
| DBU | 1,8-Diazabicyclo[5.4.0]undec-7-ene |
| DCE | Dichloroethane |
| DCM | Dichloromethane |
| Diglyme | (2-Methoxyethyl) ether |
| DIPEA | N,N-ethyl-diisopropylamine or N,N-Diisopropyl-ethyl amine |
| DMA | N,N-Dimethylacetamide |
| DMAP | 4-Dimethylamino pyridine |
| DME | Dimethoxyethane |
| DMF | N,N-Dimethylformamide |
| DMSO | Dimethylsulfoxide |
| dppf | 1,1'-Bis(diphenylphosphino)ferrocene |
| EDCI | N-(3-Dimethylaminopropyl)-N'-ethylcarbodiimide hydrochloride |
| EtOAc, or EA | Ethyl Acetate |
| EtOH | Ethanol |
| IPA | Isopropyl alcohol |
| HOAc or AcOH | Acetic Acid |
| HOAT | 1-Hydroxy-7-azabenzotriazole |
| HPLC | High-performance liquid chromatography |
| KHMDS | Potassium bis(trimethylsilyl)amide |

-continued

| Abbreviation | Definition |
|---|---|
| LAH | Lithium aluminum hydride |
| LiHMDS, | Lithium bis(trimethylsilyl)amide |
| LCMS, LC/MS | Liquid chromatography-mass spectrometry |
| MeOH | Methanol |
| MsCI | Methanesulfonyl chloride |
| MTBE | Methyl tert-butyl ether |
| NMP | 1-Methyl-2-pyrrolidinone |
| Pd/C | Palladium on activated carbon |
| $Pd_2(dba)_3$ | Tris(dibenzylideneacetone)dipalladium (0) |
| $PdCl_2$(dppf)-dcm | [1'1'-Bis(diphenylphosphino)ferrocene]palladium(ll) dichloride |
| $Pd(OAc)_2$ | Palladium(II)acetate |
| $Pd(PPh_3)_4$ | Palladium-tetrakis(triphenylphosphine) |
| TEA, $Et_3N$ | Triethylamine |
| TFA | Trifluoroacetic acid |
| THF | Tetrahydrofuran |

TERMS AND DEFINITIONS

The use of subheadings such as "General," "Chemistry," "Compositions," Formulations," etc., in this section, as well as in other sections of this application, are solely for convenience of reference and not intended to be limiting.

General

As used herein, the term "about" or "approximately" means within an acceptable range for a particular value as determined by one skilled in the art, and may depend in part on how the value is measured or determined, e.g., the limitations of the measurement system or technique. For example, "about" can mean a range of up to 20%, up to 10%, up to 5%, or up to 1% or less on either side of a given value. Alternatively, with respect to biological systems or processes, the term "about" can mean within an order of magnitude, within 5-fold, or within 2-fold on either side of a value. Numerical quantities given herein are approximate unless stated otherwise, meaning that the term "about" or "approximately" can be inferred when not expressly stated.

To provide a more concise description, some of the quantitative expressions given herein are not qualified with the term "about". It is understood that, whether the term "about" is used explicitly or not, every quantity given herein is meant to refer to the actual given value, and it is also meant to refer to the approximation of such given value that would reasonably be inferred based on the ordinary skill in the art, including equivalents and approximations due to the experimental and/or measurement conditions for such given value. Whenever a yield is given as a percentage, such yield refers to a mass of the entity for which the yield is given with respect to the maximum amount of the same entity for which that could be obtained under the particular stoichiometric conditions. Concentrations that are given as percentages refer to mass ratios, unless indicated differently.

As used herein, the terms "a," "an," and "the" are to be understood as meaning both singular and plural, unless explicitly stated otherwise. Thus, "a," "an," and "the" (and grammatical variations thereof where appropriate) refer to one or more.

A group of items linked with the conjunction "and" should not be read as requiring that each and every one of those items be present in the grouping, but rather should be read as "and/or" unless expressly stated otherwise. Similarly, a group of items linked with the conjunction "or" should not be read as requiring mutual exclusivity among that group, but rather should also be read as "and/or" unless expressly stated otherwise. Furthermore, although items, elements or components of the invention may be described or claimed in the singular, the plural is contemplated to be within the scope thereof, unless limitation to the singular is explicitly stated.

The terms "comprising" and "including" are used herein in their open, non-limiting sense. Other terms and phrases used in this document, and variations thereof, unless otherwise expressly stated, should be construed as open ended, as opposed to limiting. As examples of the foregoing: the term "example" is used to provide exemplary instances of the item in discussion, not an exhaustive or limiting list thereof; adjectives such as "conventional," "traditional," "normal," "criterion," "known" and terms of similar meaning should not be construed as limiting the item described to a given time period or to an item available as of a given time, but instead should be read to encompass conventional, traditional, normal, or criterion technologies that may be available or known now or at any time in the future. Likewise, where this document refers to technologies that would be apparent or known to one of ordinary skill in the art, such technologies encompass those apparent or known to the skilled artisan now or at any time in the future.

The presence of broadening words and phrases such as "one or more," "at least," "but not limited to" or other like phrases in some instances shall not be read to mean that the narrower case is intended or required in instances where such broadening phrases may be absent. As will become apparent to one of ordinary skill in the art after reading this document, the illustrated embodiments and their various alternatives may be implemented without confinement to the illustrated examples.

Chemistry

The term "alkyl" refers to a fully saturated aliphatic hydrocarbon group. The alkyl moiety may be a straight- or branched-chain alkyl group having from 1 to 12 carbon atoms in the chain. Examples of alkyl groups include, but are not limited to, methyl (Me, which also may be structurally depicted by the symbol, "—"), ethyl (Et), n-propyl, isopropyl, butyl, isobutyl, sec-butyl, ten-butyl (tBu), pentyl, isopentyl, tert-pentyl, hexyl, isohexyl, and groups that in light of the ordinary skill in the art and the teachings provided herein would be considered equivalent to any one of the foregoing examples. Alkyl groups may be optionally substituted with one or more substituents including, but not limited to, hydroxyl, alkoxy, thioalkoxy, amino, and aminoalkyl.

The term "alkenyl" refers to optionally substituted unsaturated aliphatic moieties having at least one carbon-carbon double bond and including E and Z isomers of said alkenyl moiety. Examples of alkenyl radicals include ethenyl, propenyl, butenyl, 1,4-butadienyl, cyclopentenyl, cyclohexenyl and the like.

The term "alkynyl" refers to an optionally substituted unsaturated aliphatic moieties having at least one carbon-carbon triple bond and includes straight and branched chain alkynyl groups. Examples of alkynyl radicals include ethynyl, propynyl, butynyl and the like.

The term "haloalkyl" refers to a straight- or branched-chain alkyl group having from 1 to 12 carbon atoms in the chain optionally substituting hydrogens with halogens. Examples of haloalkyl groups include, but are not limited to, $-CF_3$, $-CHF_2$, $-CH_2F$, $-CH_2CF_3$, $-CH_2CHF_2$, $-CH_2CH_2F$, $-CH_2CH_2Cl$, $-CH_2CF_2CF_3$ and other groups that in light of the ordinary skill in the art and the teachings provided herein, would be considered equivalent to any one of the foregoing examples.

The term "alkoxy" includes a straight chain or branched alkyl group with an oxygen atom linking the alkyl group to the rest of the molecule. Alkoxy includes methoxy, ethoxy, propoxy, isopropoxy, butoxy, t-butoxy, pentoxy and so on. "Aminoalkyl", "thioalkyl", and "sulfonylalkyl" are analogous to alkoxy, replacing the terminal oxygen atom of alkoxy with, respectively, NH (or NR), S, and $SO_2$.

The term "haloalkoxy" refer to alkoxy groups optionally substituting hydrogens with halogens. Examples of haloalkoxy groups include, but are not limited to, —$OCF_3$, —$OCH_2CF_3$, —$OCH_2CHF_2$, —$OCH_2CH_2Cl$, —$OCH_2CF_2CF_3$ and other groups that in light of the ordinary skill in the art and the teachings provided herein, would be considered equivalent to any one of the foregoing examples.

The term "amino" refers to the —$NH_2$ group.

The term "alkylamino" refers to the —NRR' group, where R and R' are independently selected from hydrogen (however, R and R' cannot both be hydrogen), alkyl, and aryl groups; or R and R', taken together, can form a cyclic ring system. Examples of amino groups include, but are not limited to, —$NH(CH_3)$, —$N(CH_3)_2$, —$NPhenyl(CH_3)$, —NHPhenyl, —$N(CH_2CH_3)(CH_3)$, and the like.

The term "cyano" refers to the group —CN.

The term "aryl" refers to a monocyclic, or fused or spiro polycyclic, aromatic carbocycle (ring structure having ring atoms that are all carbon), having from 3 to 12 ring atoms per ring. (Carbon atoms in aryl groups are sp2 hybridized.) Illustrative examples of aryl groups include the following moieties:

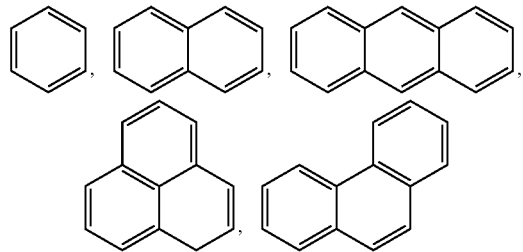

and the like.

The term "aryloxy" refers to a group having the formula, —O—R, wherein R is an aryl group.

The term "cycloalkyl" refers to a saturated or partially saturated carbocycle, such as monocyclic, fused polycyclic, bridged monocyclic, bridged polycyclic, spirocyclic, or spiro polycyclic carbocycle having from 3 to 12 ring atoms per carbocycle. Where the term cycloalkyl is qualified by a specific characterization, such as monocyclic, fused polycyclic, bridged polycyclic, spirocyclic, and spiro polycyclic, then such term cycloalkyl refers only to the carbocycle so characterized. Illustrative examples of cycloalkyl groups include the following entities, in the form of properly bonded moieties:

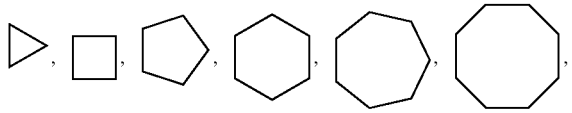

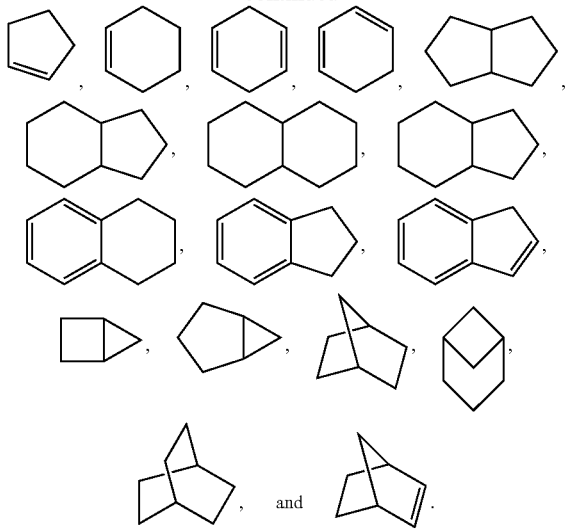

A "heterocycloalkyl" refers to a monocyclic, or fused, bridged, or spiro polycyclic ring structure that is saturated or partially saturated and has from 3 to 12 ring atoms per ring structure selected from carbon atoms and up to three heteroatoms selected from nitrogen, oxygen, and sulfur. The ring structure may optionally contain up to two oxo groups on carbon or sulfur ring members. Illustrative entities, in the form of properly bonded moieties, include:

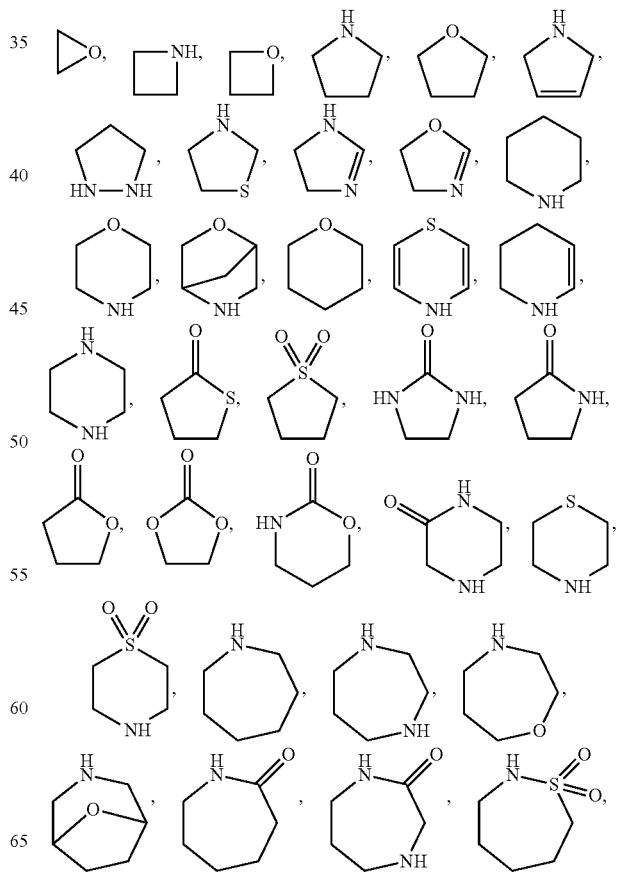

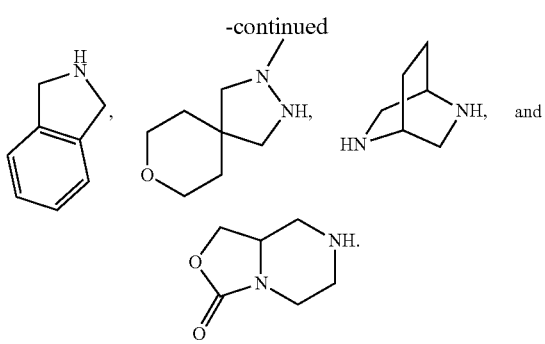

The term "heteroaryl" refers to a monocyclic, fused bicyclic, or fused polycyclic aromatic heterocycle (ring structure having ring atoms selected from carbon atoms and up to four heteroatoms selected from nitrogen, oxygen, and sulfur) having from 3 to 12 ring atoms per heterocycle. Illustrative examples of heteroaryl groups include the following entities, in the form of properly bonded moieties:

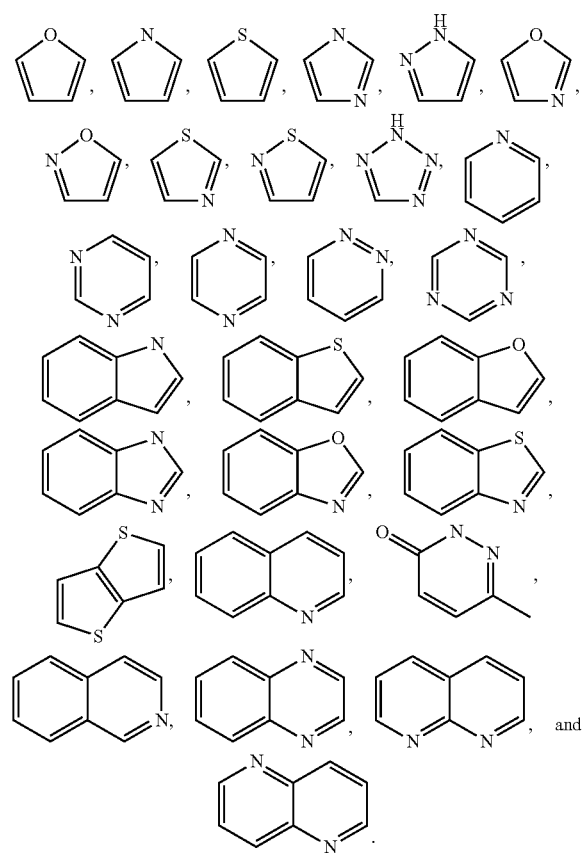

Those skilled in the art will recognize that the species of cycloalkyl, heterocycloalkyl, and heteroaryl groups listed or illustrated above are not exhaustive, and that additional species within the scope of these defined terms may also be selected.

The term "halogen" represents chlorine, fluorine, bromine or iodine. The term "halo" represents chloro, fluoro, bromo or iodo.

The term "heteroatom" used herein refers to, for example, O (oxygen), S (sulfur), or N (nitrogen).

The term "substituted" means that the specified group or moiety bears one or more substituents. Where the term "substituted" is used to describe a structural system, unless specified otherwise, the substitution is meant to occur at any valency-allowed position on the system. The term "unsubstituted" means that the specified group bears no substituents. The term "optionally substituted" means that the specified group is unsubstituted or substituted with one or more additional substitutents individually and independently selected from the group comprising: cycloalkyl, aryl, heteroaryl, heterocycloalkyl, —CN, —OH, —NO$_2$, —SO$_2$NH$_2$, —CONH$_2$, —CO$_2$H, —COH, amino, —(C$_{1-6}$ alkyl)amino, di(C$_{1-6}$alkyl)amino, —N3, cyanate, isocyanate, thiocyanate, isothiocyanate, aryloxy, and arylthio. In cases where a specified moiety or group is not expressly noted as being optionally substituted or substituted with any specified substituent, it is understood that such a moiety or group is intended to be unsubstituted.

Formulas

Any formula given herein is intended to represent compounds having structures depicted by the structural formula as well as certain variations or forms. In particular, compounds of any formula given herein may have asymmetric centers and therefore exist in different enantiomeric forms. All optical isomers and stereoisomers of the compounds of the general formula, and mixtures thereof, are considered within the scope of the formula. Thus, any formula given herein is intended to represent a racemate, one or more enantiomeric forms, one or more diastereomeric forms, one or more atropisomeric forms, and mixtures thereof. Furthermore, certain structures may exist as geometric isomers (i.e., cis and trans isomers), as tautomers, or as atropisomers.

The symbols — and ▬ are used as meaning the same spacial arrangement in chemical structures shown herein. Analogously, the symbols ııııı and ·····ı are used as meaning the same spatial arrangement in chemical structures shown herein.

Compounds

As used herein, a "compound" refers to any one of: (a) the actually recited form of such compound; and (b) any of the forms of such compound in the medium in which the compound is being considered when named. For example, reference herein to a compound such as R—COOH, encompasses reference to any one of, for example, R—COOH(s), R—COOH(sol), and R—COO-(sol). In this example, R—COOH(s) refers to the solid compound, as it could be for example in a tablet or some other solid pharmaceutical composition or preparation; R—COOH(sol) refers to the undissociated form of the compound in a solvent; and R—COO-(sol) refers to the dissociated form of the compound in a solvent, such as the dissociated form of the compound in an aqueous environment, whether such dissociated form derives from R—COOH, from a salt thereof, or from any other entity that yields R—COO— upon dissociation in the medium being considered.

As used herein, the term "chemical entity" collectively refers to a compound, along with the derivatives of the compound, including salts, chelates, solvates, conformers, noncovalent complexes, metabolites, and prodrugs.

In one aspect the chemical entity is selected from the group consisting of compounds of Formula (I), pharmaceutically acceptable salts of compounds of Formula (I), pharmaceutically acceptable prodrugs of compounds of Formula (I), and pharmaceutically acceptable metabolites of compounds of Formula (I). In a specific aspect, the chemical entity is a compound of Formula (I), or a pharmaceutically acceptable salt.

In another example, an expression such as "exposing an entity to a compound of formula R—COOH" refers to the exposure of such entity to the form, or forms, of the compound R—COOH that exists, or exist, in the medium in which such exposure takes place. In still another example, an expression such as "reacting an entity with a compound of formula R—COOH" refers to the reacting of (a) such entity in the chemically relevant form, or forms, of such entity that exists, or exist, in the medium in which such reacting takes place, with (b) the chemically relevant form, or forms, of the compound R—COOH that exists, or exist, in the medium in which such reacting takes place. In this regard, if such entity is for example in an aqueous environment, it is understood that the compound R—COOH is in such same medium, and therefore the entity is being exposed to species such as R—COOH(aq) and/or R—COO-(aq), where the subscript "(aq)" stands for "aqueous" according to its conventional meaning in chemistry and biochemistry. A carboxylic acid functional group has been chosen in these nomenclature examples; this choice is not intended, however, as a limitation but it is merely an illustration. It is understood that analogous examples can be provided in terms of other functional groups, including but not limited to hydroxyl, basic nitrogen members, such as those in amines, and any other group that interacts or transforms according to known manners in the medium that contains the compound. Such interactions and transformations include, but are not limited to, dissociation, association, tautomerism, solvolysis, including hydrolysis, solvation, including hydration, protonation and deprotonation. No further examples in this regard are provided herein because these interactions and transformations in a given medium are known by any one of ordinary skill in the art.

In another example, a "zwitterionic" compound is encompassed herein by referring to a compound that is known to form a zwitterion, even if it is not explicitly named in its zwitterionic form. Terms such as zwitterion, zwitterions, and their synonyms zwitterionic compound(s) are standard IUPAC-endorsed names that are well known and part of standard sets of defined scientific names. In this regard, the name zwitterion is assigned the name identification CHEBI:27369 by the Chemical Entities of Biological Interest (ChEBI) dictionary of molecular entities. As is generally well known, a zwitterion or zwitterionic compound is a neutral compound that has formal unit charges of opposite sign. Sometimes these compounds are referred to by the term "inner salts". Other sources refer to these compounds as "dipolar ions", although the latter term is regarded by still other sources as a misnomer. As a specific example, aminoethanoic acid (the amino acid glycine) has the formula $H_2NCH_2COOH$, and it exists in some media (in this case in neutral media) in the form of the zwitterion $+H_3NCH_2COO-$. Zwitterions, zwitterionic compounds, inner salts, and dipolar ions in the known and well established meanings of these terms are within the scope of this invention, as would in any case be so appreciated by those of ordinary skill in the art. Because there is no need to name each and every embodiment that would be recognized by those of ordinary skill in the art, no structures of the zwitterionic compounds that are associated with the compounds of this invention are given explicitly herein. They are, however, part of the embodiments of this invention. No further examples in this regard are provided herein because the interactions and transformations in a given medium that lead to the various forms of a given compound are known by any one of ordinary skill in the art.

Isotopes may be present in the compounds described. Each chemical element present in a compound either specifically or generically described herein may include any isotope of said element. Any formula given herein is also intended to represent isotopically labeled forms of the compounds. Isotopically labeled compounds have structures depicted by the formulas given herein except that one or more atoms are replaced by an atom having a selected atomic mass or mass number. Examples of isotopes that can be incorporated into compounds of the invention include isotopes of hydrogen, carbon, nitrogen, oxygen, phosphorus, sulfur, fluorine, chlorine, and iodine, such as $^2H$, $^3H$, $^{11}C$, $^{13}C$, $^{14}C$, $^{15}N$, $^{18}O$, $^{17}O$, $^{31}P$, $^{32}P$, $^{35}S$, $^{18}F$, $^{36}Cl$, and $^{125}I$.

When referring to any formula given herein, the selection of a particular moiety from a list of possible species for a specified variable is not intended to define the same choice of the species for the variable appearing elsewhere. In other words, where a variable appears more than once, the choice of the species from a specified list is independent of the choice of species for the same variable elsewhere in the formula, unless otherwise stated.

By way of a first example on substituent terminology, if substituent $S^1_{example}$ is one of $S_1$ and $S_2$, and substituent $S^2_{example}$ is one of $S_3$ and $S_4$, then these assignments refer to embodiments of this invention given according to the choices $S^1_{example}$ is $S_1$ and $S^2_{example}$ is $S_3$; $S^1_{example}$ is $S_1$ and $S^2_{example}$ is $S_4$; $S^1_{example}$ is $S_2$ and $S^2_{example}$ is $S_3$; $S^1_{example}$ is $S_2$ and $S^2_{example}$ is $S_4$; and equivalents of each one of such choices. The shorter terminology "$S^1_{example}$ is one of $S_1$ and $S_2$ and "$S^2_{example}$ is one of $S_3$ and $S_4$ is accordingly used herein for the sake of brevity but not by way of limitation. The foregoing first example on substituent terminology, which is stated in generic terms, is meant to illustrate the various substituent assignments described herein. The foregoing convention given herein for substituents extends, when applicable, to members such as $R^1$, $R^3$, $R^4$, $R^{10}$, $R^{11}$, $R^{12}$, $R^{13}$, M, Y and Z and any other generic substituent symbol used herein.

Furthermore, when more than one assignment is given for any member or substituent, embodiments of this invention comprise the various groupings that can be made from the listed assignments, taken independently, and equivalents thereof. By way of a second example on substituent terminology, if it is herein described that substituent $S_{example}$ is one of $S_1$, $S_2$ and $S_3$, the listing refers to embodiments of this invention for which $S_{example}$ is $S_1$; $S_{example}$ is $S_2$; $S_{example}$ is $S_3$; $S_{example}$ is one of $S_1$ and $S_2$; $S_{example}$ is one of $S_1$ and $S_3$; $S_{example}$ is one of $S_2$ and $S_3$; $S_{example}$ is one of $S_1$, $S_2$ and $S_3$; and $S_{example}$ is any equivalent of each one of these choices. The shorter terminology "$S_{example}$ is one of $S_1$, $S_2$ and $S_3$" is accordingly used herein for the sake of brevity, but not by way of limitation. The foregoing second example on substituent terminology, which is stated in generic terms, is meant to illustrate the various substituent assignments described herein. The foregoing convention given herein for substituents extends, when applicable, to members such as $R^1$, $R^3$, $R^4$, $R^{10}$, $R^{11}$, $R^{12}$, $R^{13}$, M, Y and Z and any other generic substituent symbol used herein.

The nomenclature "$C_{i-j}$" with j>i, when applied herein to a class of substituents, is meant to refer to embodiments of this invention for which each and every one of the number of carbon members, from i to j including i and j, is independently realized. By way of example, the term $C_{1-3}$ refers independently to embodiments that have one carbon member ($C_1$), embodiments that have two carbon members ($C_2$), and embodiments that have three carbon members ($C_3$).

The term $C_{n-m}$alkyl refers to an aliphatic chain, whether straight or branched, with the total number N of carbon members in the chain that satisfies $n \leq N \leq m$, with $m > n$.

Any disubstituent referred to herein is meant to encompass the various attachment possibilities when more than one of such possibilities are allowed. For example, reference to disubstituent -A-B—, where $A \neq B$, refers herein to such disubstituent with A attached to a first substituted member and B attached to a second substituted member, and it also refers to such disubstituent with A attached to the second member and B attached to the first substituted member.

According to the foregoing interpretive considerations on assignments and nomenclature, it is understood that explicit reference herein to a set implies, where chemically meaningful and unless indicated otherwise, independent reference to embodiments of such set, and reference to each and every one of the possible embodiments of subsets of the set referred to explicitly.

The term "prodrug" means a precursor of a designated compound that, following administration to a subject, yields the compound in vivo via a chemical or physiological process such as solvolysis or enzymatic cleavage, or under physiological conditions (e.g., a prodrug on being brought to physiological pH is converted to the compound of Formula (I)).

A "pharmaceutically acceptable prodrug" is a prodrug that is preferably non-toxic, biologically tolerable, and otherwise biologically suitable for administration to the subject. Illustrative procedures for the selection and preparation of suitable prodrug derivatives are described, for example, in "Design of Prodrugs", ed. H. Bundgaard, Elsevier, 1985.

A "metabolite" means a pharmacologically active product of metabolism in the body of a compound of Formula (I) or salt thereof. Preferably, the metabolite is in an isolated form outside the body.

Compositions

The term "composition," as in pharmaceutical composition, is intended to encompass a product comprising the active ingredient(s), and the inert ingredient(s) (pharmaceutically acceptable excipients) that make up the carrier, as well as any product which results, directly or indirectly, from combination, complexation, or aggregation of any two or more of the ingredients, or from dissociation of one or more of the ingredients, or from other types of reactions or interactions of one or more of the ingredients. Accordingly, the pharmaceutical compositions of the present invention encompass any composition made by admixing a compound of Formula (I) and a pharmaceutically acceptable excipient.

The term "pharmaceutically acceptable," as used in connection with compositions of the invention, refers to molecular entities and other ingredients of such compositions that are physiologically tolerable and do not typically produce untoward reactions when administered to an animal (e.g., human). The term "pharmaceutically acceptable" may also mean approved by a regulatory agency of the Federal or a state government or listed in the U.S. Pharmacopeia or other generally recognized pharmacopeia for use in animals (e.g. mammals), and more particularly in humans.

A "pharmaceutically acceptable excipient" refers to a substance that is non-toxic, biologically tolerable, and otherwise biologically suitable for administration to a subject, such as an inert substance, added to a pharmacological composition or otherwise used as a vehicle, carrier, or diluents to facilitate administration of an agent and that is compatible therewith. Examples of excipients include calcium carbonate, calcium phosphate, various sugars and types of starch, cellulose derivatives, gelatin, vegetable oils, and polyethylene glycols. Suitable pharmaceutical carriers include those described in Remington: The Science and Practice of Pharmacy, 21$^{st}$ Ed., Lippincott Williams & Wilkins (2005).

A "pharmaceutically acceptable salt" is intended to mean a salt of a free acid or base of a compound represented by Formula (I) that is non-toxic, biologically tolerable, or otherwise biologically suitable for administration to the subject. See, generally, G. S. Paulekuhn et al., Trends in Active Pharmaceutical Ingredient Salt Selection based on Analysis of the Orange Book Database, *J. Med. Chem.* 2007, 50, 6665-6672; Berge et al., Pharmaceutical Salts, *J. Pharm. Sci.* 1977, 66, 1-19; Stahl and Wermuth (eds), Pharmaceutical Salts; Properties, Selection, and Use: 2nd Revised Edition, Wiley-VCS, Zurich, Switzerland (2011). Examples of pharmaceutically acceptable salts are those that are pharmacologically effective and suitable for contact with the tissues of patients without undue toxicity, irritation, or allergic response. A compound of Formula (I) may possess a sufficiently acidic group, a sufficiently basic group, or both types of functional groups, and accordingly react with a number of inorganic or organic bases, and inorganic and organic acids, to form a pharmaceutically acceptable salt bases, and inorganic and organic acids, to form a pharmaceutically acceptable salt.

The term "carrier" refers to an adjuvant, vehicle, or excipients, with which the compound is administered. In preferred embodiments of this invention, the carrier is a solid carrier. Suitable pharmaceutical carriers include those described in Remington: The Science and Practice of Pharmacy, 21$^{st}$ Ed., Lippincott Williams & Wilkins (2005).

The term "dosage form," as used herein, is the form in which the dose is to be administered to the subject or patient. The drug is generally administered as part of a formulation that includes nonmedical agents. The dosage form has unique physical and pharmaceutical characteristics. Dosage forms, for example, may be solid, liquid or gaseous. "Dosage forms" may include for example, a capsule, tablet, caplet, gel caplet (gelcap), syrup, a liquid composition, a powder, a concentrated powder, a concentrated powder admixed with a liquid, a chewable form, a swallowable form, a dissolvable form, an effervescent, a granulated form, and an oral liquid solution. In a specific embodiment, the dosage form is a solid dosage form, and more specifically, comprises a tablet or capsule.

As used herein, the term "inert" refer to any inactive ingredient of a described composition. The definition of "inactive ingredient" as used herein follows that of the U.S. Food and Drug Administration, as defined in 21 C.F.R. 201.3(b)(8), which is any component of a drug product other than the active ingredient.

Methods and Uses

As used herein, the term "disorder" is used interchangeably with "disease" or "condition". For example, a CNS disorder also means a CNS disease or a CNS condition.

As used herein, the term "cognitive impairment" is used interchangeably with "cognitive dysfunction" or "cognitive deficit," all of which are deemed to cover the same therapeutic indications.

The term "treat," as used herein, is interchangeable with "treatment" and "treating" and includes:
  (i) prevention of the disease, disorder, or condition, i.e., reducing the incidence of and/or ameliorating the effect and/or duration of a disease, disorder, or condition from occurring in subjects that may get, be exposed to and/or be predisposed to the disease, disorder or condition, but may not yet have been diagnosed as having it; or are diagnosed as having the disease, disease, or condition; or are at risk of developing such disease, disorder, or condition;
(ii) inhibition of the disease, disorder, or condition, i.e., preventing or delaying the onset of a disease, disorder, or condition; arresting further development or progression of a disease, disorder, or condition in a subject already suffering from or having one or more symptoms of the disease, disorder, or condition; or reducing the risk of a disease, disorder, or condition worsening;
(iii) amelioration of the disease, disorder, or condition, i.e., attenuating, relieving, reversing or eliminating the disease, disorder, or condition, or one or more of symptoms thereof.

As used in the present disclosure, the term "effective amount" is interchangeable with "therapeutically effective amount" and means an amount or dose of a compound or composition effective in treating the particular disease, condition, or disorder disclosed herein, and thus "treating" includes producing a desired preventative, inhibitory, relieving, or ameliorative effect. In methods of treatment according to the invention, "an effective amount" of at least one compound according to the invention is administered to a subject (e.g., a mammal).

The term "animal" is interchangeable with "subject" and may be a vertebrate, in particular, a mammal, and more particularly, a human, and includes a laboratory animal in the context of a clinical trial or screening or activity experiment. Thus, as can be readily understood by one of ordinary skill in the art, the compositions and methods of the present invention are particularly suited to administration to any vertebrate, particularly a mammal, and more particularly, a human.

As used herein, a "control animal" or a "normal animal" is an animal that is of the same species as, and otherwise comparable to (e.g., similar age, sex), the animal that is trained under conditions sufficient to induce transcription-dependent memory formation in that animal.

By "enhance," "enhancing," or "enhancement" is meant the ability to potentiate, increase, improve or make greater or better, relative to normal, a biochemical or physiological action or effect. For example, enhancing long term memory formation refers to the ability to potentiate or increase long term memory formation in an animal relative to the normal long term memory formation of the animal. As a result, long term memory acquisition is faster or better retained. Enhancing performance of a cognitive task refers to the ability to potentiate or improve performance of a specified cognitive task by an animal relative to the normal performance of the cognitive task by the animal.

As used herein, the term "training protocol," or "training," refers to either "cognitive training" or "motor training." The phrase "in conjunction" means that a compound or composition of the present invention enhances CREB pathway function during cognitive or motor training.

Reference will now be made to the embodiments of the present invention, examples of which are illustrated by and described in conjunction with the accompanying drawings and examples. While certain embodiments are described herein, it is understood that the described embodiments are not intended to limit the scope of the invention. On the contrary, the present disclosure is intended to cover alternatives, modifications, and equivalents that can be included within the invention as defined by the appended claims.

Compounds

In its many embodiments, the invention is directed to a chemical entity of Formula (I):

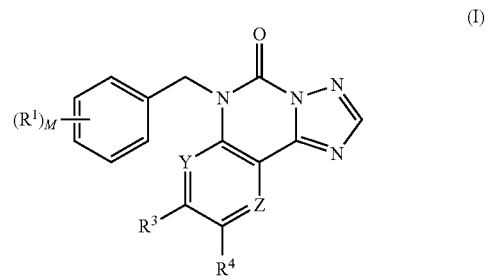

wherein:
Y and Z are each independently —CH— or —N—, with the proviso that at least one Y or Z member is —N—;
M is 0-5;
$R^1$ is each independently selected from H, halo, —CN, —$C_{1-6}$alkyl, —$C_{1-6}$alkynyl —$C_{1-6}$haloalkyl, —$C_{1-6}$thioalkyl, —$C_{1-6}$thiohaloalkyl, —$C_{1-6}$alkoxy, —$C_{1-6}$haloalkoxy, —$SO_2C_{1-6}$alkyl, aryl, heteroaryl and heterocycloalkyl; or
two $R^1$ members are on adjacent carbons and taken together with the carbons to which they are attached form a 5-6 member saturated or unsaturated monocylic ring system comprising one or more oxygen or nitrogen atoms, wherein the ring system is optionally substituted with one or more groups selected from halo, —$C_{1-6}$alkyl, —$C_{1-6}$alkoxy, and —$C_1$-$C_6$haloalkoxy;
$R^3$ and $R^4$ are each independently selected from the group consisting of H, halo, —CN, —OH, —$C_{1-6}$alkyl, —$C_{1-6}$haloalkyl, —$C_{1-6}$alkenyl, —$CH_2$O-aryl, —$C_{1-6}$alkoxy, —$C_{1-6}$haloalkoxy, —$C(O)CH_3$, —$CH(OH)(CF_3)$, —$(CR^{10}R^{11})_{0-3}NR^{12}R^{13}$, aryl, heteroaryl, heterocycloalkyl, wherein each aryl, heteroaryl and heterocycloalkyl is optionally unsubstituted or substituted with a member each independently selected from the group consisting of —$CH_3$ and —$OCH_3$;
$R^{10}$ and $R^{11}$ are each independently selected from the group consisting of: —H, halo, —$C_{1-6}$alkyl, —$C_{1-6}$haloalkyl, and —OH;
$R^{12}$ and $R^{13}$ are each independently selected from the group consisting of —H, —$C_{1-6}$alkyl, —$CO_2$-benzyl, —$C_{1-6}$alkyl(aryl), —$C_{1-6}$alkyl(heterocycloalkyl), optionally unsubstituted or substituted aryl, —$C_{3-6}$cycloalkyl, heteroaryl, and heterocycloalkyl;
or $R^{12}$ and $R^{13}$ are taken together with the nitrogen to which they are attached form an optionally substituted heterocycloalkyl.

In some embodiments, the chemical entity is selected from the group consisting of compounds of Formula (I), pharmaceutically acceptable salts of compounds of Formula (I), pharmaceutically acceptable prodrugs of compounds of Formula (I); and pharmaceutically active metabolites of compounds of Formula (I). In a particular aspect, the chemical entity is a compound, or pharmaceutically acceptable salt thereof, of Formula (I).

In certain embodiments, of Formula (I), Y is —N—.
In certain embodiments, of Formula (I), Z is —N—.
In certain embodiments, of Formula (I), Y and Z are —N—.
Some embodiments are given by compounds of Formula (I) where M is 1, 2, 3, 4, or 5.
Some embodiments are given by compounds of Formula (I) where M is 1, 2, 3 or 4.
Some embodiments are given by compounds of Formula (I) where M is 1, 2, or 3.

In certain embodiments, of Formula (I), M is 1, 2, 3, 4, or 5 and $R^1$ is each independently H, —Br, —Cl, —F, —I, —CN, —$C_{1-6}$alkyl, —$C_{1-6}$alkynyl, —$SCH_3$, —$OCF_3$, —$OCF_2H$, —$C_{1-6}$alkoxy, —$SCF_3$, —$SO_2CH_3$ or 2-oxopyrrolidine or pyrazole.

In certain embodiments of Formula (I), two $R^1$ members are on adjacent carbons and taken together with the carbons to which they are attached form a fused 5-member ring selected from 1-methyl-1H-pyrazole or dioxolane.

In some of these embodiments, M is 1, 2, 3, 4 and $R^1$ is each independently H, —Cl, —F or —$C_{1-6}$alkoxy.

Some embodiments are given by compounds of Formula (I) where Y is —N—, $R^3$ is selected from —H, —CH(OCH$_3$)$_2$, —CH$_2$O-phenyl, or —(CR$^{10}$R$^{11}$)$_{1-3}$NR$^{12}$R$^{13}$, where $R^{10}$ and $R^{11}$ are each H, $R^{12}$ is H or —$C_{1-6}$alkyl, $R^{13}$ is selected from phenyl, benzyl, (3-methyloxetan-3-yl)methyl, (tetrahydrofuran-3-yl)methyl or cyclopropyl (methyl).

In some of these embodiments, $R^4$ is H or —$CH_3$ and $R^3$ is —(CR$^{10}$R$^{11}$)$_{1-3}$NR$^{12}$R$^{13}$.

Some embodiments are given by compounds of Formula (I) where $R^3$ is —(CR$^{10}$R$^{11}$)NR$^{12}$R$^{13}$, $R^{10}$ and $R^{11}$ are each independently H, —OH, or —$CH_3$, and $R^{12}$ and $R^{13}$ are taken together with the nitrogen to which they are attached to form a heterocycloalkyl ring selected from morpholine, (2S,6R)-2,6-dimethylmorpholine, 4-(methylsulfonyl)piperazin-1-yl or isoindolin-2-yl.

In some of these embodiments, $R^3$ is —(CR$^{10}$R$^{11}$)$_{1-2}$NR$^{12}$R$^{13}$, $R^{10}$ and $R^{11}$ are each independently H, —OH, or —$CH_3$, and $R^{12}$ and $R^{13}$ are taken together with the nitrogen to which they are attached to form a heterocycloalkyl ring selected from morpholine, (2S,6R)-2,6-dimethylmorpholine or 4-(methylsulfonyl)piperazin-1-yl.

In certain embodiments, of Formula (I), $R^3$ is H or —$CH_3$ and $R^4$ is —(CR$^{10}$R$^{11}$)$_{1-3}$NR$^{12}$R$^{13}$.

In certain embodiments, of Formula (I), $R^3$ is —H, —$CH_3$, $R^4$ is H, —Br, —$C_{1-6}$alkyl, —$C_{1-6}$alkenyl, —C(O)CH$_3$, —CH(OH)CF$_3$, —CH$_2$OCH$_2$OCH$_3$, optionally substituted phenyl, optionally substituted pyridyl, and —(CR$^{10}$R$^{11}$)$_{1-3}$NR$^{12}$R$^{13}$, $R^{10}$ and $R^{11}$ are each independently H, —$CH_3$, or —OH, and $R^{12}$ and $R^{13}$ are each independently —H, —$C_{1-6}$alkyl, —CO$_2$-benzyl, —CH(CH$_3$)phenyl, optionally substituted cycloalkyl, and optionally substituted heterocycloalkyl.

In some of these embodiments, $R^3$ is —H, —$CH_3$, $R^4$ is —(CR$^{10}$R$^{11}$)$_{1-3}$NR$^{12}$R$^{13}$, $R^{10}$ and $R^{11}$ are each independently —H, —F, —$CH_3$, —$CF_3$, or —OH, and $R^{12}$ and $R^{13}$ are taken together with the nitrogen to which they are attached to form a heterocycloalkyl ring selected from (2R,5R)-2,5-dimethylmorpholine, (2R,6S)-2,6-dimethylmorpholine, (2S,5S)-2,5-dimethylmorpholine, (2S,6R)-2,6-dimethylmorpholine, (3S,5R)-2-methoxyethyl)piperazine, (4-((tetrahydrofuran-3-yl)methyl)piperazine), 1,4-oxazepane, 1-methyl-8-oxa-1,2-diazaspiro[4.5]decane, 2,2-dimethylmorpholine, 2,5-dimethylmorpholine, 2-ethylmorpholine, 2-methylmorpholine, 2-oxa-5-azabicyclo[2.2.1]heptane, 3-(dimethylamino)pyrrolidine, 3,3-dimethylmorpholine, 3,5-dimethylpiperazine, 3-hydroxyazetidine, 3-methyl-6-oxopyridazin-1(6H)-yl, 3-methylmorpholine, 4-(2,2,2-trifluoroacetyl)piperazine, 4-(methylsulfonyl)piperazine, 4-(propan-2-yl)piperazine, 4-(tetrahydrofuran-3-carbonyl)piperazine, 4-acetyl-1,4-diazepane, 4-cyclopropylpiperazine, 4-methoxypiperidine, 4-methyl-1,4-diazepane, 4-methyl-piperazine, 8-oxa-3-azabicyclo[3.2.1]octane, isoindoline, morpholine, N,N-dimethylpiperazine-1-sulfonamide, piperazine, piperidine, tetrahydro-1H-oxazolo[3,4-a]pyrazin-3(5H)-one, and thiomorpholine.

In some of these embodiments, $R^4$ is morpholinomethyl, (3-methylmorpholino)methyl, (2,6-dimethylmorpholino)methyl, ((2S,6R)-2,6-dimethylmorpholino)methyl, ((2R,6S)-2,6-dimethylmorpholin-4-yl)methyl, (4-(methylsulfonyl)piperazin-1-yl)methyl, 1-hydroxy-2-morpholinoethyl, 2-((2S,6R)-2,6-dimethylmorpholino)-1-hydroxyethyl, and $R^3$ is H or —$CH_3$.

Further embodiments are provided by pharmaceutically acceptable salts of compounds of Formula (I), pharmaceutically acceptable prodrugs of compounds of Formula (I), and pharmaceutically active metabolites of compounds of Formula (I).

In certain embodiments, a compound, or a pharmaceutically acceptable salt thereof, of Formula (I), is selected from the group consisting of:

| Example # | Compound Name |
|---|---|
| 1 | 9-Bromo-6-(4-methoxybenzyl)pyrido[3,2-e][1,2,4]triazolo[1,5-c]pyrimidin-5(6H)-one; |
| 2 | 8-Bromo-6-(4-methoxybenzyl)pyrido[2,3-e][1,2,4]triazolo[1,5-c]pyrimidin-5(6H)-one; |
| 3 | 8-(Dimethoxymethyl)-6-(4-methoxybenzyl)pyrido[3,2-e][1,2,4]triazolo[1,5-c]pyrimidin-5(6H)-one; |
| 4 | 9-Bromo-6-(4-methoxybenzyl)-[1,2,4]triazolo[1,5-c]pteridin-5(6H)-one; |
| 5 | 9-(3,4-Dimethoxyphenyl)-6-(4-methoxybenzyl)pyrido[3,2-e][1,2,4]triazolo[1,5-c]pyrimidin-5(6H)-one; |
| 6 | 6-(4-Methoxybenzyl)-9-(6-methoxypyridin-3-yl)pyrido[3,2-e][1,2,4]triazolo[1,5-c]pyrimidin-5(6H)-one; |
| 7 | 6-(4-Methoxybenzyl)-9-(2-methoxypyridin-3-yl)pyrido[3,2-e][1,2,4]triazolo[1,5-c]pyrimidin-5(6H)-one; |
| 8 | 6-(4-Methoxybenzyl)-9-(3-methyl-6-oxopyridazin-1(6H)-yl)pyrido[3,2-e][1,2,4]triazolo[1,5-c]pyrimidin-5(6H)-one; |
| 9 | 9-(4-Cyclopropylpiperazin-1-yl)-6-(4-methoxybenzyl)pyrido[3,2-e][1,2,4]triazolo[1,5-c]pyrimidin-5(6H)-one; |
| 10 | 9-(((1S,2S)-2-Aminocyclohexyl)amino)-6-(4-methoxybenzyl)pyrido[3,2-e][1,2,4]triazolo[1,5-c]pyrimidin-5(6H)-one; |
| 11 | 6-(4-Methoxybenzyl)-9-(methyl(1-methylpiperidin-4-yl)amino)-[1,2,4]triazolo[1,5-c]pteridin-5(6H)-one; |
| 12 | 9-((2-(Dimethylamino)ethyl)(methyl)amino)-6-(4-methoxybenzyl)-[1,2,4]triazolo[1,5-c]pteridin-5(6H)-one; |

-continued

| Example # | Compound Name |
|---|---|
| 13 | 6-(4-Methoxybenzyl)-9-(4-(2-methoxyethyl)piperazin-1-yl)pyrido[3,2-e][1,2,4]triazolo[1,5-c]pyrimidin-5(6H)-one; |
| 14 | 9-(3-(Dimethylamino)pyrrolidin-1-yl)-6-(4-methoxybenzyl)pyrido[3,2-e][1,2,4]triazolo[1,5-c]pyrimidin-5(6H)-one; |
| 15 | 9-(4-(Dimethylamino)piperidin-1-yl)-6-(4-methoxybenzyl)pyrido[3,2-e][1,2,4]triazolo[1,5-c]pyrimidin-5(6H)-one; |
| 16 | 6-(4-Methoxybenzyl)-9-(methyl(tetrahydro-2H-pyran-4-yl)amino)pyrido[3,2-e][1,2,4]triazolo[1,5-c]pyrimidin-5(6H)-one; |
| 17 | 9-((2S,6R)-2,6-Dimethylmorpholino)-6-(4-methoxybenzyl)pyrido[3,2-e][1,2,4]triazolo[1,5-c]pyrimidin-5(6H)-one; |
| 18 | 9-((3-(Dimethylamino)propyl)(methyl)amino)-6-(4-methoxybenzyl)pyrido[3,2-e][1,2,4]triazolo[1,5-c]pyrimidin-5(6H)-one; |
| 19 | 6-(4-Methoxybenzyl)-9-(4-(methylsulfonyl)piperazin-1-yl)pyrido[3,2-e][1,2,4]triazolo[1,5-c]pyrimidin-5(6H)-one; |
| 20 | Benzyl (2-(6-(4-methoxybenzyl)-5-oxo-5,6-dihydropyrido[3,2-e][1,2,4]triazolo[1,5-c]pyrimidin-9-yl)ethyl)carbamate; |
| 21 | 6-(4-Methoxybenzyl)-8-(morpholinomethyl)pyrido[3,2-e][1,2,4]triazolo[1,5-c]pyrimidin-5(6H)-one; |
| 22 | 6-(4-Methoxybenzyl)-9-(piperidin-1-ylmethyl)pyrido[3,2-e][1,2,4]triazolo[1,5-c]pyrimidin-5(6H)-one; |
| 23 | 6-(4-Methoxybenzyl)-9-(thiomorpholinomethyl)pyrido[3,2-e][1,2,4]triazolo[1,5-c]pyrimidin-5(6H)-one; |
| 24 | 6-(4-Chlorobenzyl)-9-(morpholinomethyl)pyrido[3,2-e][1,2,4]triazolo[1,5-c]pyrimidin-5(6H)-one; |
| 25 | 6-(4-Chlorobenzyl)-9-(piperidin-1-ylmethyl)pyrido[3,2-e][1,2,4]triazolo[1,5-c]pyrimidin-5(6H)-one; |
| 26 | 6-(4-Chlorobenzyl)-9-(((2S,6R)-2,6-dimethylmorpholino)methyl)pyrido[3,2-e][1,2,4]triazolo[1,5-c]pyrimidin-5(6H)-one; |
| 27 | 9-(2-Aminoethyl)-6-(4-methoxybenzyl)pyrido[3,2-e][1,2,4]triazolo[1,5-c]pyrimidin-5(6H)-one; |
| 28 | 6-(4-Methoxybenzyl)-9-(2-((tetrahydro-2H-pyran-4-yl)amino)ethyl)pyrido[3,2-e][1,2,4]triazolo[1,5-c]pyrimidin-5(6H)-one; |
| 29 | 6-(4-Methoxybenzyl)-9-(2-((1-phenylethyl)amino)ethyl)pyrido[3,2-e][1,2,4]triazolo[1,5-c]pyrimidin-5(6H)-one; |
| 30 | 6-(4-Methoxybenzyl)-9-vinylpyrido[3,2-e][1,2,4]triazolo[1,5-c]pyrimidin-5(6H)-one; |
| 31 | 6-(4-Methoxybenzyl)-9-((methoxymethoxy)methyl)pyrido[3,2-e][1,2,4]triazolo[1,5-c]pyrimidin-5(6H)-one; |
| 32 | 9-(1-Ethoxyvinyl)-6-(4-methoxybenzyl)pyrido[3,2-e][1,2,4]triazolo[1,5-c]pyrimidin-5(6H)-one; |
| 33 | 9-(Hydroxymethyl)-6-(4-methoxybenzyl)pyrido[3,2-e][1,2,4]triazolo[1,5-c]pyrimidin-5(6H)-one; |
| 34 | 9-(2-Oxa-5-azabicyclo[2.2.1]heptan-5-ylmethyl)-6-(4-methoxybenzyl)pyrido[3,2-e][1,2,4]triazolo[1,5-c]pyrimidin-5(6H)-one; |
| 35 | 9-((Dimethylamino)methyl)-6-(4-methoxybenzyl)pyrido[3,2-e][1,2,4]triazolo[1,5-c]pyrimidin-5(6H)-one; |
| 36 | 9-(((2S,6R)-2,6-Dimethylmorpholino)methyl)-6-(4-methoxybenzyl)pyrido[3,2-e][1,2,4]triazolo[1,5-c]pyrimidin-5(6H)-one; |
| 37 | 6-(4-Methoxybenzyl)-9-((4-methylpiperazin-1-yl)methyl)pyrido[3,2-e][1,2,4]triazolo[1,5-c]pyrimidin-5(6H)-one; |
| 38 | 9-((3,3-Dimethylmorpholino)methyl)-6-(4-methoxybenzyl)pyrido[3,2-e][1,2,4]triazolo[1,5-c]pyrimidin-5(6H)-one; |
| 39 | 9-((2,2-Dimethylmorpholino)methyl)-6-(4-methoxybenzyl)pyrido[3,2-e][1,2,4]triazolo[1,5-c]pyrimidin-5(6H)-one; |
| 40 | 9-((2-Ethylmorpholino)methyl)-6-(4-methoxybenzyl)pyrido[3,2-e][1,2,4]triazolo[1,5-c]pyrimidin-5(6H)-one; |
| 41 | 9-((2,5-Dimethylmorpholino)methyl)-6-(4-methoxybenzyl)pyrido[3,2-e][1,2,4]triazolo[1,5-c]pyrimidin-5(6H)-one; |
| 42 | 6-(4-Methoxybenzyl)-9-((2,2,6,6-tetrafluoromorpholino)methyl)pyrido[3,2-e][1,2,4]triazolo[1,5-c]pyrimidin-5(6H)-one; |
| 43 | 9-(8-Oxa-3-azabicyclo[3.2.1]octan-3-ylmethyl)-6-(4-methoxybenzyl)pyrido[3,2-e][1,2,4]triazolo[1,5-c]pyrimidin-5(6H)-one; |
| 44 | 6-(4-Methoxybenzyl)-9-((1-methyl-8-oxa-1,2-diazaspiro[4.5]decan-2-yl)methyl)pyrido[3,2-e][1,2,4]triazolo[1,5-c]pyrimidin-5(6H)-one; |
| 45 | 6-(4-Methoxybenzyl)-9-((2-methylmorpholino)methyl)pyrido[3,2-e][1,2,4]triazolo[1,5-c]pyrimidin-5(6H)-one; |
| 46 | 6-(4-Methoxybenzyl)-9-((3-methylmorpholino)methyl)pyrido[3,2-e][1,2,4]triazolo[1,5-c]pyrimidin-5(6H)-one; |
| 47 | 9-(((2S,6R)-2,6-Dimethylmorpholino)methyl)-6-(4-methoxybenzyl)-[1,2,4]triazolo[1,5-c]pteridin-5(6H)-one; |
| 48 | 6-(4-Methoxybenzyl)-9-((4-methyl-1,4-diazepan-1-yl)methyl)pyrido[3,2-e][1,2,4]triazolo[1,5-c]pyrimidin-5(6H)-one; |
| 49 | 9-((1,4-Oxazepan-4-yl)methyl)-6-(4-methoxybenzyl)pyrido[3,2-e][1,2,4]triazolo[1,5-c]pyrimidin-5(6H)-one; |
| 50 | 9-((4-Acetyl-1,4-diazepan-1-yl)methyl)-6-(4-methoxybenzyl)pyrido[3,2-e][1,2,4]triazolo[1,5-c]pyrimidin-5(6H)-one; |

| Example # | Compound Name |
|---|---|
| 51 | 9-((Cyclohexyl(methyl)amino)methyl)-6-(4-methoxybenzyl)pyrido[3,2-e][1,2,4]triazolo[1,5-c]pyrimidin-5(6H)-one; |
| 52 | 6-(4-Methoxybenzyl)-9-((4-methoxypiperidin-1-yl)methyl)pyrido[3,2-e][1,2,4]triazolo[1,5-c]pyrimidin-5(6H)-one; |
| 53 | 6-(4-Methoxybenzyl)-9-((methyl(tetrahydro-2H-pyran-4-yl)amino)methyl)pyrido[3,2-e][1,2,4]triazolo[1,5-c]pyrimidin-5(6H)-one; |
| 54 | 6-(4-Methoxybenzyl)-9-((4-(2-methoxyethyl)piperazin-1-yl)methyl)pyrido[3,2-e][1,2,4]triazolo[1,5-c]pyrimidin-5(6H)-one; |
| 55 | 9-((Isopropyl(2-methoxyethyl)amino)methyl)-6-(4-methoxybenzyl)pyrido[3,2-e][1,2,4]triazolo[1,5-c]pyrimidin-5(6H)-one; |
| 56 | 6-(4-Methoxybenzyl)-8-((4-methylpiperazin-1-yl)methyl)pyrido[2,3-e][1,2,4]triazolo[1,5-c]pyrimidin-5(6H)-one; |
| 57 | 6-(4-Methoxybenzyl)-8-(morpholinomethyl)pyrido[2,3-e][1,2,4]triazolo[1,5-c]pyrimidin-5(6H)-one; |
| 58 | 6-(4-Methoxybenzyl)-8-(piperidin-1-ylmethyl)pyrido[2,3-e][1,2,4]triazolo[1,5-c]pyrimidin-5(6H)-one; |
| 59 | 6-(4-Methoxybenzyl)-8-(thiomorpholinomethyl)pyrido[2,3-e][1,2,4]triazolo[1,5-c]pyrimidin-5(6H)-one; |
| 60 | 8-(((2S,6R)-2,6-Dimethylmorpholino)methyl)-6-(4-methoxybenzyl)pyrido[2,3-e][1,2,4]triazolo[1,5-c]pyrimidin-5(6H)-one; |
| 61 | 6-(4-Methoxybenzyl)-9-(((2-methoxyethyl)(methyl)amino)methyl)pyrido[3,2-e][1,2,4]triazolo[1,5-c]pyrimidin-5(6H)-one; |
| 62 | 7-((6-(4-Methoxybenzyl)-5-oxo-5,6-dihydropyrido[3,2-e][1,2,4]triazolo[1,5-c]pyrimidin-9-yl)methyl)tetrahydro-1H-oxazolo[3,4-a]pyrazin-3(5H)-one; |
| 63 | 9-(((2S,5S)-2,5-Dimethylmorpholino)methyl)-6-(4-methoxybenzyl)pyrido[3,2-e][1,2,4]triazolo[1,5-c]pyrimidin-5(6H)-one; |
| 64 | 9-(((2R,5R)-2,5-Dimethylmorpholino)methyl)-6-(4-methoxybenzyl)pyrido[3,2-e][1,2,4]triazolo[1,5-c]pyrimidin-5(6H)-one; |
| 65 | 6-(4-Methoxybenzyl)-9-(piperazin-1-ylmethyl)pyrido[3,2-e][1,2,4]triazolo[1,5-c]pyrimidin-5(6H)-one; |
| 66 | 9-(((3S,5R)-3,5-Dimethylpiperazin-1-yl)methyl)-6-(4-methoxybenzyl)pyrido[3,2-e][1,2,4]triazolo[1,5-c]pyrimidin-5(6H)-one; |
| 67 | 6-(4-Methoxybenzyl)-9-((4-((tetrahydrofuran-3-yl)methyl)piperazin-1-yl)methyl)pyrido[3,2-e][1,2,4]triazolo[1,5-c]pyrimidin-5(6H)-one; |
| 68 | 6-(4-Methoxybenzyl)-9-((4-(methylsulfonyl)piperazin-1-yl)methyl)pyrido[3,2-e][1,2,4]triazolo[1,5-c]pyrimidin-5(6H)-one; |
| 69 | 4-((6-(4-Methoxybenzyl)-5-oxo-5,6-dihydropyrido[3,2-e][1,2,4]triazolo[1,5-c]pyrimidin-9-yl)methyl)-N,N-dimethylpiperazine-1-sulfonamide; |
| 70 | 6-(4-Methoxybenzyl)-9-((4-(2,2,2-trifluoroacetyl)piperazin-1-yl)methyl)pyrido[3,2-e][1,2,4]triazolo[1,5-c]pyrimidin-5(6H)-one; |
| 71 | 6-(4-Methoxybenzyl)-9-((4-(tetrahydrofuran-3-carbonyl)piperazin-1-yl)methyl)pyrido[3,2-e][1,2,4]triazolo[1,5-c]pyrimidin-5(6H)-one; |
| 72 | 6-(4-Methoxybenzyl)-9-(morpholinomethyl)pyrido[3,2-e][1,2,4]triazolo[1,5-c]pyrimidin-5(6H)-one; |
| 73 | 8-(((2S,6R)-2,6-Dimethylmorpholino)methyl)-6-(4-methoxybenzyl)pyrido[3,2-e][1,2,4]triazolo[1,5-c]pyrimidin-5(6H)-one; |
| 74 | 6-(4-Methoxybenzyl)-8-((((3-methyloxetan-3-yl)methyl)amino)methyl)pyrido[3,2-e][1,2,4]triazolo[1,5-c]pyrimidin-5(6H)-one; |
| 75 | 6-(4-Methoxybenzyl)-8-((methyl((tetrahydrofuran-3-yl)methyl)amino)methyl)pyrido[3,2-e][1,2,4]triazolo[1,5-c]pyrimidin-5(6H)-one; |
| 76 | 8-((Cyclopropyl(methyl)amino)methyl)-6-(4-methoxybenzyl)pyrido[3,2-e][1,2,4]triazolo[1,5-c]pyrimidin-5(6H)-one; |
| 77 | 6-(4-Methoxybenzyl)-8-((4-(methylsulfonyl)piperazin-1-yl)methyl)pyrido[3,2-e][1,2,4]triazolo[1,5-c]pyrimidin-5(6H)-one; |
| 78 | 8-((Benzylamino)methyl)-6-(4-methoxybenzyl)pyrido[3,2-e][1,2,4]triazolo[1,5-c]pyrimidin-5(6H)-one; |
| 79 | 6-(4-Methoxybenzyl)-8-((phenylamino)methyl)pyrido[3,2-e][1,2,4]triazolo[1,5-c]pyrimidin-5(6H)-one; |
| 80 | 8-(Isoindolin-2-ylmethyl)-6-(4-methoxybenzyl)pyrido[3,2-e][1,2,4]triazolo[1,5-c]pyrimidin-5(6H)-one; |
| 81 | 9-Acetyl-6-(4-methoxybenzyl)pyrido[3,2-e][1,2,4]triazolo[1,5-c]pyrimidin-5(6H)-one; |
| 82 | 9-(1-((2S,6R)-2,6-Dimethylmorpholino)ethyl)-6-(4-methoxybenzyl)pyrido[3,2-e][1,2,4]triazolo[1,5-c]pyrimidin-5(6H)-one; |
| 83 | 9-(1-Hydroxy-2-morpholinoethyl)-6-(4-methoxybenzyl)pyrido[3,2-e][1,2,4]triazolo[1,5-c]pyrimidin-5(6H)-one; |
| 84 | 9-(2-((2S,6R)-2,6-Dimethylmorpholino)-1-hydroxyethyl)-6-(4-methoxybenzyl)pyrido[3,2-e][1,2,4]triazolo[1,5-c]pyrimidin-5(6H)-one; |
| 85 | 9-(1-Fluoro-2-morpholinoethyl)-6-(4-methoxybenzyl)pyrido[3,2-e][1,2,4]triazolo[1,5-c]pyrimidin-5(6H)-one; |
| 86 | 9-(2-((2S,6R)-2,6-Dimethylmorpholino)-1-fluoroethyl)-6-(4-methoxybenzyl)pyrido[3,2-e][1,2,4]triazolo[1,5-c]pyrimidin-5(6H)-one; |
| 87 | 6-(4-Methoxybenzyl)-9-(2,2,2-trifluoro-1-hydroxyethyl)pyrido[3,2-e][1,2,4]triazolo[1,5-c]pyrimidin-5(6H)-one; |

-continued

| Example # | Compound Name |
|---|---|
| 88 | 6-(4-Methoxybenzyl)-9-(2,2,2-trifluoro-1-morpholinoethyl)pyrido[3,2-e][1,2,4]triazolo[1,5-c]pyrimidin-5(6H)-one; |
| 89 | 9-(((2S,6R)-2,6-Dimethylmorpholino)methyl)-6-(4-(trifluoromethoxy)benzyl)pyrido[3,2-e][1,2,4]triazolo[1,5-c]pyrimidin-5(6H)-one; |
| 90 | 9-(((2S,6R)-2,6-Dimethylmorpholino)methyl)-6-(4-fluoro-3-methylbenzyl)pyrido[3,2-e][1,2,4]triazolo[1,5-c]pyrimidin-5(6H)-one; |
| 91 | 9-(((2S,6R)-2,6-Dimethylmorpholino)methyl)-6-(4-fluorobenzyl)pyrido[3,2-e][1,2,4]triazolo[1,5-c]pyrimidin-5(6H)-one; |
| 92 | 9-(((2S,6R)-2,6-Dimethylmorpholino)methyl)-6-(3-fluoro-4-methoxybenzyl)pyrido[3,2-e][1,2,4]triazolo[1,5-c]pyrimidin-5(6H)-one; |
| 93 | 9-(((2S,6R)-2,6-Dimethylmorpholino)methyl)-6-(2-fluoro-4-methoxybenzyl)pyrido[3,2-e][1,2,4]triazolo[1,5-c]pyrimidin-5(6H)-one; |
| 94 | 6-(3-bromo-4-Fluorobenzyl)-9-(((2S,6R)-2,6-dimethylmorpholino)methyl)pyrido[3,2-e][1,2,4]triazolo[1,5-c]pyrimidin-5(6H)-one; |
| 95 | 4-((9-(((2S,6R)-2,6-Dimethylmorpholino)methyl)-5-oxopyrido[3,2-e][1,2,4]triazolo[1,5-c]pyrimidin-6(5H)-yl)methyl)benzonitrile; |
| 96 | 6-(4-(tert-Butyl)benzyl)-9-(((2S,6R)-2,6-dimethylmorpholino)methyl)pyrido[3,2-e][1,2,4]triazolo[1,5-c]pyrimidin-5(6H)-one; |
| 97 | 3-((9-(((2S,6R)-2,6-Dimethylmorpholino)methyl)-5-oxopyrido[3,2-e][1,2,4]triazolo[1,5-c]pyrimidin-6(5H)-yl)methyl)benzonitrile; |
| 98 | 9-(((2S,6R)-2,6-Dimethylmorpholino)methyl)-6-(4-(methylsulfonyl)benzyl)pyrido[3,2-e][1,2,4]triazolo[1,5-c]pyrimidin-5(6H)-one; |
| 99 | 9-(((2S,6R)-2,6-Dimethylmorpholino)methyl)-6-(2-methylbenzyl)pyrido[3,2-e][1,2,4]triazolo[1,5-c]pyrimidin-5(6H)-one; |
| 100 | 9-(((2S,6R)-2,6-Dimethylmorpholino)methyl)-6-(3-iodobenzyl)pyrido[3,2-e][1,2,4]triazolo[1,5-c]pyrimidin-5(6H)-one; |
| 101 | 6-(3,5-Difluorobenzyl)-9-(((2S,6R)-2,6-dimethylmorpholino)methyl)pyrido[3,2-e][1,2,4]triazolo[1,5-c]pyrimidin-5(6H)-one; |
| 102 | 6-(2-Bromo-4-methoxybenzyl)-9-(((2S,6R)-2,6-dimethylmorpholino)methyl)pyrido[3,2-e][1,2,4]triazolo[1,5-c]pyrimidin-5(6H)-one; |
| 103 | 6-(2,6-Difluoro-4-methoxybenzyl)-9-(((2S,6R)-2,6-dimethylmorpholino)methyl)pyrido[3,2-e][1,2,4]triazolo[1,5-c]pyrimidin-5(6H)-one; |
| 104 | 9-(((2S,6R)-2,6-Dimethylmorpholino)methyl)-6-((1-methyl-1H-indazol-6-yl)methyl)pyrido[3,2-e][1,2,4]triazolo[1,5-c]pyrimidin-5(6H)-one; |
| 105 | 6-(4-(1H-Pyrazol-1-yl)benzyl)-9-(((2S,6R)-2,6-dimethylmorpholino)methyl)pyrido[3,2-e][1,2,4]triazolo[1,5-c]pyrimidin-5(6H)-one; |
| 106 | 6-(4-(Difluoromethoxy)-2-fluorobenzyl)-9-(((2S,6R)-2,6-dimethylmorpholino)methyl)pyrido[3,2-e][1,2,4]triazolo[1,5-c]pyrimidin-5(6H)-one; |
| 107 | 6-(3,5-Difluoro-4-methoxybenzyl)-9-(((2S,6R)-2,6-dimethylmorpholino)methyl)pyrido[3,2-e][1,2,4]triazolo[1,5-c]pyrimidin-5(6H)-one; |
| 108 | 6-(2,3-Difluoro-4-methoxybenzyl)-9-(((2S,6R)-2,6-dimethylmorpholino)methyl)pyrido[3,2-e][1,2,4]triazolo[1,5-c]pyrimidin-5(6H)-one; |
| 109 | 9-(((2S,6R)-2,6-Dimethylmorpholino)methyl)-6-(2-((trifluoromethyl)thio)benzyl)pyrido[3,2-e][1,2,4]triazolo[1,5-c]pyrimidin-5(6H)-one; |
| 110 | 6-(3-Chloro-4-fluorobenzyl)-9-(((2S,6R)-2,6-dimethylmorpholino)methyl)pyrido[3,2-e][1,2,4]triazolo[1,5-c]pyrimidin-5(6H)-one; |
| 111 | 6-(3,4-Dichlorobenzyl)-9-(((2S,6R)-2,6-dimethylmorpholino)methyl)pyrido[3,2-e][1,2,4]triazolo[1,5-c]pyrimidin-5(6H)-one; |
| 112 | 6-(2-Chloro-4-methoxybenzyl)-9-(((2S,6R)-2,6-dimethylmorpholino)methyl)pyrido[3,2-e][1,2,4]triazolo[1,5-c]pyrimidin-5(6H)-one; |
| 113 | 6-(2-(Difluoromethoxy)benzyl)-9-(((2S,6R)-2,6-dimethylmorpholino)methyl)pyrido[3,2-e][1,2,4]triazolo[1,5-c]pyrimidin-5(6H)-one; |
| 114 | 6-(4-Chloro-3-fluorobenzyl)-9-(((2S,6R)-2,6-dimethylmorpholino)methyl)pyrido[3,2-e][1,2,4]triazolo[1,5-c]pyrimidin-5(6H)-one; |
| 115 | 6-(3-Chloro-5-fluorobenzyl)-9-(((2S,6R)-2,6-dimethylmorpholino)methyl)pyrido[3,2-e][1,2,4]triazolo[1,5-c]pyrimidin-5(6H)-one; |
| 116 | 9-(((2S,6R)-2,6-Dimethylmorpholino)methyl)-6-(4-(2-oxopyrrolidin-1-yl)benzyl)pyrido[3,2-e][1,2,4]triazolo[1,5-c]pyrimidin-5(6H)-one; |

| Example # | Compound Name |
|---|---|
| 117 | 9-(((2S,6R)-2,6-Dimethylmorpholino)methyl)-6-(4-ethoxybenzyl)pyrido[3,2-e][1,2,4]triazolo[1,5-c]pyrimidin-5(6H)-one; |
| 118 | 6-(3,4-Difluorobenzyl)-9-(((2S,6R)-2,6-dimethylmorpholino)methyl)pyrido[3,2-e][1,2,4]triazolo[1,5-c]pyrimidin-5(6H)-one; |
| 119 | 9-(((2S,6R)-2,6-Dimethylmorpholino)methyl)-6-(4-(methylthio)benzyl)pyrido[3,2-e][1,2,4]triazolo[1,5-c]pyrimidin-5(6H)-one; |
| 120 | 6-(2-Chloro-4-(methylsulfonyl)benzyl)-9-(((2S,6R)-2,6-dimethylmorpholino)methyl)pyrido[3,2-e][1,2,4]triazolo[1,5-c]pyrimidin-5(6H)-one; |
| 121 | 6-(4-Methoxybenzyl)-8-(phenoxymethyl)pyrido[3,2-e][1,2,4]triazolo[1,5-c]pyrimidin-5(6H)-one; |
| 122 | 6-(2,3-Difluoro-4-methoxybenzyl)-9-((4-isopropylpiperazin-1-yl)methyl)pyrido[3,2-e][1,2,4]triazolo[1,5-c]pyrimidin-5(6H)-one; |
| 123 | 6-(2,3-Difluoro-4-methoxybenzyl)-9-(piperidin-1-ylmethyl)pyrido[3,2-e][1,2,4]triazolo[1,5-c]pyrimidin-5(6H)-one; |
| 124 | 9-(((2S,6R)-2,6-Dimethylmorpholino)methyl)-6-(2,4,5-trifluorobenzyl)pyrido[3,2-e][1,2,4]triazolo[1,5-c]pyrimidin-5(6H)-one; |
| 125 | 9-(((2S,6R)-2,6-Dimethylmorpholino)methyl)-6-(4-isopropylbenzyl)pyrido[3,2-e][1,2,4]triazolo[1,5-c]pyrimidin-5(6H)-one; |
| 126 | 6-(4-(Difluoromethoxy)benzyl)-9-(((2S,6R)-2,6-dimethylmorpholino)methyl)pyrido[3,2-e][1,2,4]triazolo[1,5-c]pyrimidin-5(6H)-one; |
| 127 | 9-(((2S,6R)-2,6-Dimethylmorpholino)methyl)-6-(4-ethoxy-3,5-difluorobenzyl)pyrido[3,2-e][1,2,4]triazolo[1,5-c]pyrimidin-5(6H)-one; |
| 128 | 9-(((2S,6R)-2,6-Dimethylmorpholino)methyl)-6-(4-ethynylbenzyl)pyrido[3,2-e][1,2,4]triazolo[1,5-c]pyrimidin-5(6H)-one; |
| 129 | 9-(((2S,6R)-2,6-Dimethylmorpholino)methyl)-6-(4-iodobenzyl)pyrido[3,2-e][1,2,4]triazolo[1,5-c]pyrimidin-5(6H)-one; |
| 130 | 6-(3,4-Dimethoxybenzyl)-9-(((2S,6R)-2,6-dimethylmorpholino)methyl)pyrido[3,2-e][1,2,4]triazolo[1,5-c]pyrimidin-5(6H)-one; |
| 131 | 6-(3-Chloro-5-fluoro-4-methoxybenzyl)-9-(((2S,6R)-2,6-dimethylmorpholino)methyl)pyrido[3,2-e][1,2,4]triazolo[1,5-c]pyrimidin-5(6H)-one; |
| 132 | 9-(((2S,6R)-2,6-Dimethylmorpholino)methyl)-6-(4-methoxy-3-methylbenzyl)pyrido[3,2-e][1,2,4]triazolo[1,5-c]pyrimidin-5(6H)-one; |
| 133 | 9-(((2S,6R)-2,6-Dimethylmorpholino)methyl)-6-(3-methoxybenzyl)pyrido[3,2-e][1,2,4]triazolo[1,5-c]pyrimidin-5(6H)-one; |
| 134 | 6-(2,5-Difluorobenzyl)-9-(((2S,6R)-2,6-dimethylmorpholino)methyl)pyrido[3,2-e][1,2,4]triazolo[1,5-c]pyrimidin-5(6H)-one; |
| 135 | 6-(2,4-Difluorobenzyl)-9-(((2R,6S)-2,6-dimethylmorpholino)methyl)pyrido[3,2-e][1,2,4]triazolo[1,5-c]pyrimidin-5(6H)-one; |
| 136 | 9-(((2R,6S)-2,6-Dimethylmorpholino)methyl)-6-(4-(trifluoromethyl)benzyl)pyrido[3,2-e][1,2,4]triazolo[1,5-c]pyrimidin-5(6H)-one; |
| 137 | 9-(((2R,6S)-2,6-Dimethylmorpholino)methyl)-6-(4-fluoro-3-methoxybenzyl)pyrido[3,2-e][1,2,4]triazolo[1,5-c]pyrimidin-5(6H)-one; |
| 138 | 9-(((2R,6S)-2,6-Dimethylmorpholino)methyl)-6-(2-fluoro-4-methylbenzyl)pyrido[3,2-e][1,2,4]triazolo[1,5-c]pyrimidin-5(6H)-one; |
| 139 | 6-(2-Chloro-4,5-difluorobenzyl)-9-(((2R,6S)-2,6-dimethylmorpholino)methyl)pyrido[3,2-e][1,2,4]triazolo[1,5-c]pyrimidin-5(6H)-one; |
| 140 | 6-(3-Chloro-2,4-difluorobenzyl)-9-(((2R,6S)-2,6-dimethylmorpholino)methyl)pyrido[3,2-e][1,2,4]triazolo[1,5-c]pyrimidin-5(6H)-one; |
| 141 | 9-(((2R,6S)-2,6-Dimethylmorpholino)methyl)-6-(3,4,5-trimethoxybenzyl)pyrido[3,2-e][1,2,4]triazolo[1,5-c]pyrimidin-5(6H)-one; |
| 142 | 6-(2,4-dichlorobenzyl)-9-(((2R,6S)-2,6-Dimethylmorpholino)methyl)pyrido[3,2-e][1,2,4]triazolo[1,5-c]pyrimidin-5(6H)-one; |
| 143 | 6-(2,4-Dichloro-5-fluorobenzyl)-9-(((2R,6S)-2,6-dimethylmorpholino)methyl)pyrido[3,2-e][1,2,4]triazolo[1,5-c]pyrimidin-5(6H)-one; |
| 144 | 6-(2-Chloro-4-fluorobenzyl)-9-(((2R,6S)-2,6-dimethylmorpholino)methyl)pyrido[3,2-e][1,2,4]triazolo[1,5-c]pyrimidin-5(6H)-one; |
| 145 | 6-(4-Chloro-2-fluorobenzyl)-9-(((2R,6S)-2,6-dimethylmorpholino)methyl)pyrido[3,2-e][1,2,4]triazolo[1,5-c]pyrimidin-5(6H)-one; |
| 146 | 9-(((2S,6R)-2,6-Dimethylmorpholino)methyl)-6-(2,3,5,6-tetrafluoro-4-methoxybenzyl)pyrido[3,2-e][1,2,4]triazolo[1,5-c]pyrimidin-5(6H)-one; |
| 147 | 6-(4-Chloro-2,6-difluorobenzyl)-9-(((2S,6R)-2,6-dimethylmorpholino)methyl)pyrido[3,2-e][1,2,4]triazolo[1,5-c]pyrimidin-5(6H)-one; |

| Example # | Compound Name |
|---|---|
| 148 | 9-(((2R,6S)-2,6-Dimethylmorpholino)methyl)-6-(4-fluoro-3,5-dimethylbenzyl)pyrido[3,2-e][1,2,4]triazolo[1,5-c]pyrimidin-5(6H)-one; |
| 149 | 9-(((2R,6S)-2,6-Dimethylmorpholino)methyl)-6-(2,3,4-trifluorobenzyl)pyrido[3,2-e][1,2,4]triazolo[1,5-c]pyrimidin-5(6H)-one; |
| 150 | 6-(2,3-dichlorobenzyl)-9-(((2R,6S)-2,6-Dimethylmorpholino)methyl)pyrido[3,2-e][1,2,4]triazolo[1,5-c]pyrimidin-5(6H)-one; |
| 151 | 6-(2,3-Difluoro-4-methylbenzyl)-9-(((2R,6S)-2,6-dimethylmorpholino)methyl)pyrido[3,2-e][1,2,4]triazolo[1,5-c]pyrimidin-5(6H)-one; |
| 152 | 6-(4-Chloro-3-(trifluoromethoxy)benzyl)-9-(((2R,6S)-2,6-dimethylmorpholino)methyl)pyrido[3,2-e][1,2,4]triazolo[1,5-c]pyrimidin-5(6H)-one; |
| 153 | 6-(3,5-Dimethoxybenzyl)-9-(((2R,6S)-2,6-dimethylmorpholino)methyl)pyrido[3,2-e][1,2,4]triazolo[1,5-c]pyrimidin-5(6H)-one; |
| 154 | 6-(3-Chloro-4-ethoxy-5-fluorobenzyl)-9-(((2R,6S)-2,6-dimethylmorpholino)methyl)pyrido[3,2-e][1,2,4]triazolo[1,5-c]pyrimidin-5(6H)-one; |
| 155 | 9-(((2R,6S)-2,6-Dimethylmorpholino)methyl)-6-(4-ethoxy-2,3-difluorobenzyl)pyrido[3,2-e][1,2,4]triazolo[1,5-c]pyrimidin-5(6H)-one; |
| 156 | 9-(((2R,6S)-2,6-Dimethylmorpholino)methyl)-6-(3,4,5-trifluorobenzyl)pyrido[3,2-e][1,2,4]triazolo[1,5-c]pyrimidin-5(6H)-one; |
| 157 | 6-Benzyl-9-(((2R,6S)-2,6-dimethylmorpholino)methyl)pyrido[3,2-e][1,2,4]triazolo[1,5-c]pyrimidin-5(6H)-one; |
| 158 | 6-(3,4-Dimethylbenzyl)-9-(((2R,6S)-2,6-dimethylmorpholino)methyl)pyrido[3,2-e][1,2,4]triazolo[1,5-c]pyrimidin-5(6H)-one; |
| 159 | 6-(2,4-Dimethylbenzyl)-9-(((2R,6S)-2,6-dimethylmorpholino)methyl)pyrido[3,2-e][1,2,4]triazolo[1,5-c]pyrimidin-5(6H)-one; |
| 160 | 9-(((2S,6R)-2,6-Dimethylmorpholino)methyl)-6-(2,3,5,6-tetrafluoro-4-methylbenzyl)pyrido[3,2-e][1,2,4]triazolo[1,5-c]pyrimidin-5(6H)-one; |
| 161 | 6-(Benzo[d][1,3]dioxol-5-ylmethyl)-9-(((2R,6S)-2,6-dimethylmorpholino)methyl)pyrido[3,2-e][1,2,4]triazolo[1,5-c]pyrimidin-5(6H)-one; |
| 162 | 6-(4-Methoxybenzyl)-9-(morpholinomethyl)-[1,2,4]triazolo[1,5-c]pteridin-5(6H)-one; |
| 163 | 6-(4-Methoxybenzyl)-9-((2-methylmorpholino)methyl)-[1,2,4]triazolo[1,5-c]pteridin-5(6H)-one; |
| 164 | 6-(4-Methoxybenzyl)-9-(piperidin-1-ylmethyl)-[1,2,4]triazolo[1,5-c]pteridin-5(6H)-one; |
| 165 | 6-(4-Methoxybenzyl)-9-((4-methoxypiperidin-1-yl)methyl)-[1,2,4]triazolo[1,5-c]pteridin-5(6H)-one; |
| 166 | 9-((4-Acetylpiperazin-1-yl)methyl)-6-(4-methoxybenzyl)-[1,2,4]triazolo[1,5-c]pteridin-5(6H)-one; |
| 167 | 9-((1,4-Oxazepan-4-yl)methyl)-6-(2,3-difluoro-4-methoxybenzyl)pyrido[3,2-e][1,2,4]triazolo[1,5-c]pyrimidin-5(6H)-one; |
| 168 | 6-(2,3-Difluoro-4-methoxybenzyl)-9-((3-methylmorpholino)methyl)pyrido[3,2-e][1,2,4]triazolo[1,5-c]pyrimidin-5(6H)-one; and |
| 169 | 6-(2,3-Difluoro-4-methoxybenzyl)-9-((3-hydroxyazetidin-1-yl)methyl)pyrido[3,2-e][1,2,4]triazolo[1,5-c]pyrimidin-5(6H)-one. |

Isotopically-Labeled Compounds

The invention also includes isotopically-labeled compounds, which are identical to those recited in Formula I, but for the fact that one or more atoms are replaced by an atom having an atomic mass or mass number different from the atomic mass or mass number usually found in nature. Examples of isotopes that can be incorporated into compounds of the invention include isotopes of carbon, chlorine, fluorine, hydrogen, iodine, nitrogen, oxygen, phosphorous, sulfur, and technetium, including $^{11}C$, $^{13}C$, $^{14}C$, $^{36}Cl$, $^{18}F$, $^{2}H$, $^{3}H$, $^{123}I$, $^{125}I$, $^{13}N$, $^{15}N$, $^{15}O$, $^{17}O$, $^{18}O$, $^{31}P$, $^{32}P$, $^{35}S$, and $^{99m}Tc$. Compounds of the present invention (and derivatives of such compounds, such as pharmaceutically acceptable salts and prodrugs) that contain the aforementioned isotopes or other isotopes of other atoms are within the scope of the invention. Isotopically-labeled compounds of the present invention are useful in drug and substrate tissue distribution and target occupancy assays. For example, isotopically labeled compounds are particularly useful in SPECT (single photon emission computed tomography) and in PET (positron emission tomography), as discussed further herein.

Derivatives

The present invention also provides derivatives of a chemical entity of Formula (I), which include, but are not limited to, a salt, solvate, conformer or crystalline form/polymorph. In a specific aspect, the derivative of a chemical entity is a pharmaceutically acceptable salt of a compound of Formula (I).

Salts

Accordingly, in one embodiment the invention includes pharmaceutically acceptable salts of the compounds represented by Formula (I), and methods using such salts.

Examples of pharmaceutically acceptable salts include sulfates, pyrosulfates, bisulfates, sulfites, bisulfites, phosphates, monohydrogen-phosphates, dihydrogenphosphates, metaphosphates, pyrophosphates, chlorides, bromides, iodides, acetates, borate, nitrate, propionates, decanoates, caprylates, acrylates, formates, isobutyrates, caproates, heptanoates, propiolates, oxalates, malonates, succinates, suberates, sebacates, fumarates, maleates, butyne-1,4-dioates, hexyne-1,6-dioates, benzoates, chlorobenzoates, methylbenzoates, dinitrobenzoates, hydroxybenzoates, methoxybenzoates, phthalates, sulfonates, xylenesulfonates, phenylacetates, phenylpropionates, phenylbutyrates, citrates, lactates, y-hydroxybutyrates, glycolates, tartrates, methane-sulfonates, propanesulfonates, naphthalene-1-sulfonates, naphthalene-2-sulfonates, besylate, mesylate and mandelates.

When the compound of Formula (I) contains a basic nitrogen, the desired pharmaceutically acceptable salt may be prepared by any suitable method available in the art, for example, treatment of the free base with an inorganic acid, such as hydrochloric acid, hydrobromic acid, sulfuric acid, sulfamic acid, nitric acid, boric acid, phosphoric acid, and the like, or with an organic acid, such as acetic acid, phenylacetic acid, propionic acid, stearic acid, lactic acid, ascorbic acid, maleic acid, hydroxymaleic acid, isethionic acid, succinic acid, valeric acid, fumaric acid, malonic acid, pyruvic acid, oxalic acid, glycolic acid, salicylic acid, oleic acid, palmitic acid, lauric acid, a pyranosidyl acid, such as glucuronic acid or galacturonic acid, an alpha-hydroxy acid, such as mandelic acid, citric acid, or tartaric acid, an amino acid, such as aspartic acid, glutaric acid or glutamic acid, an aromatic acid, such as benzoic acid, 2-acetoxybenzoic acid, naphthoic acid, or cinnamic acid, a sulfonic acid, such as laurylsulfonic acid, p-toluenesulfonic acid, methanesulfonic acid, ethanesulfonic acid, any compatible mixture of acids such as those given as examples herein, and any other acid and mixture thereof that are regarded as equivalents or acceptable substitutes in light of the ordinary level of skill in this technology.

When the compound of Formula (I) is an acid, such as a carboxylic acid or sulfonic acid, the desired pharmaceutically acceptable salt may be prepared by any suitable method, for example, treatment of the free acid with an inorganic or organic base, such as an amine (primary, secondary or tertiary), an alkali metal hydroxide, alkaline earth metal hydroxide, any compatible mixture of bases such as those given as examples herein, and any other base and mixture thereof that are regarded as equivalents or acceptable substitutes in light of the ordinary level of skill in this technology. Illustrative examples of suitable salts include organic salts derived from amino acids, such as N-methyl-O-glucamine, lysine, choline, glycine and arginine, ammonia, carbonates, bicarbonates, primary, secondary, and tertiary amines, and cyclic amines, such as tromethamine, benzylamines, pyrrolidines, piperidine, morpholine, and piperazine, and inorganic salts derived from sodium, calcium, potassium, magnesium, manganese, iron, copper, zinc, aluminum, and lithium.

Solvates

In other embodiments, the invention provides a solvate of a compound of Formula (I), and the use of such solvates in methods of present invention. Certain compounds of Formula (I) or pharmaceutically acceptable salts of compounds of Formula (I) may be obtained as solvates. In some embodiments, the solvent is water and the solvates are hydrates.

More particularly, solvates include those formed from the interaction or complexes of compounds of the invention with one or more solvents, either in solution or as a solid or crystalline form. Such solvent molecules are those commonly used in the pharmaceutical art, which are known to be innocuous to the recipient, e.g., water, ethanol, ethylene glycol, and the like. Other solvents may be used as intermediate solvates in the preparation of more desirable solvates, such as MeOH, methyl t-butyl ether, EtOAc, (S)-propylene glycol, (R)-propylene glycol, 1,4-butyne-diol, and the like. Hydrates include compounds formed by an incorporation of one or more water molecules.

Conformers and Crystalline Forms/Polymorphs

In other embodiments, the invention provides conformer and crystalline forms of a compound of Formula (I), and the use of these derivatives in methods of present invention. A conformer is a structure that is a conformational isomer. Conformational isomerism is the phenomenon of molecules with the same structural formula but different conformations (conformers) of atoms about a rotating bond.

A polymorph is a composition having the same chemical formula, but a different solid state or crystal structure. In certain embodiments of the invention, compounds of Formula (I) were obtained in crystalline form. In addition, certain crystalline forms of compounds of Formula (I) or pharmaceutically acceptable salts of compounds of Formula (I) may be obtained as co-crystals. In still other embodiments, compounds of Formula (I) may be obtained in one of several polymorphic forms, as a mixture of crystalline forms, as a polymorphic form, or as an amorphous form.

Prodrugs

The invention also relates to prodrugs of the compounds of Formula (I), and the use of such pharmaceutically acceptable prodrugs in methods of the present invention, particularly therapeutic methods. Exemplary prodrugs include compounds having an amino acid residue, or a polypeptide chain of two or more (e.g., two, three or four) amino acid residues, covalently joined through an amide or ester bond to a free amino, hydroxy, or carboxylic acid group of a compound of Formula (I). Examples of amino acid residues include the twenty naturally occurring amino acids, commonly designated by three letter symbols, as well as 4-hydroxyproline, hydroxylysine, demosine, isodemosine, 3-methylhistidine, norvalin, beta-alanine, gamma-aminobutyric acid, citrulline homocysteine, homoserine, ornithine and methionine sulfone.

Additional types of prodrugs may be produced, for instance, by derivatizing free carboxyl groups of structures of Formula (I) as amides or alkyl esters. Examples of amides include those derived from ammonia, primary $C_{1-6}$alkyl amines and secondary di($C_{1-6}$alkyl) amines. Secondary amines include 5- or 6-membered heterocycloalkyl or heteroaryl ring moieties. Examples of amides include those that are derived from ammonia, $C_{1-3}$alkyl primary amines, and di($C_{1-2}$alkyl)amines Examples of esters of the invention include $C_{1-6}$alkyl, $C_{1-6}$cycloalkyl, phenyl, and phenyl($C_{1-6}$ alkyl) esters. Preferred esters include methyl esters. Prodrugs may also be prepared by derivatizing free hydroxy groups using groups including hemisuccinates, phosphate esters, dimethylaminoacetates, and phosphoryloxymethyloxycarbonyls, following procedures such as those outlined in Fleisher et al., *Adv. Drug Delivery Rev.* 1996, 19, 115-130.

Carbamate derivatives of hydroxy and amino groups may also yield prodrugs. Carbonate derivatives, sulfonate esters, and sulfate esters of hydroxy groups may also provide prodrugs. Derivatization of hydroxy groups as (acyloxy)methyl and (acyloxy)ethyl ethers, wherein the acyl group may be an alkyl ester, optionally substituted with one or more ether, amine, or carboxylic acid functionalities, or where the acyl group is an amino acid ester as described above, is also useful to yield prodrugs. Prodrugs of this type may be prepared as described in Robinson et al., *J. Med. Chem.* 1996, 39, 10-18. Free amines can also be derivatized as amides, sulfonamides or phosphonamides. All of these prodrug moieties may incorporate groups including ether, amine, and carboxylic acid functionalities.

Prodrugs may be determined using routine techniques known or available in the art (e.g., Bundgard (ed.), 1985, Design of prodrugs, Elsevier; Krogsgaard-Larsen et al., (eds.), 1991, Design and Application of Prodrugs, Harwood Academic Publishers).

Metabolites

The present invention also relates to a metabolite of a compound of Formula (I), as defined herein, and salts thereof. The present invention further relates to the use of such metabolites, and salts thereof, in methods of present invention, including therapeutic methods.

Metabolites of a compound may be determined using routine techniques known or available in the art. For example, isolated metabolites can be enzymatically and synthetically produced (e.g., Bertolini et al., *J. Med. Chem.* 1997, 40, 2011-2016; Shan et al., *J. Pharm. Sci.* 1997, 86, 765-767; Bagshawe, *Drug Dev. Res.* 1995, 34, 220-230; and Bodor, *Adv Drug Res.* 1984, 13, 224-231).

Compositions

In some embodiments compounds of Formula (I) and pharmaceutically acceptable salts thereof are used, alone or in combination with one or more additional active ingredients, to formulate pharmaceutical compositions. A pharmaceutical composition of the invention comprises: (a) an effective amount of at least one active agent in accordance with the invention; and (b) a pharmaceutically acceptable excipient.

Formulations and Administration

Numerous standard references are available that describe procedures for preparing various formulations suitable for administering the compounds according to the invention. Examples of potential formulations and preparations are contained, for example, in the Handbook of Pharmaceutical Excipients, American Pharmaceutical Association (current edition); Pharmaceutical Dosage Forms: Tablets (Lieberman, Lachman and Schwartz, editors) current edition, published by Marcel Dekker, Inc., as well as Remington's Pharmaceutical Sciences (Osol, ed.), 1980, 1553-1593.

Any suitable route of administration may be employed for providing an animal, especially a human, with an effective dosage of a compound of the present invention. For example, oral, rectal, topical, parenteral, ocular, pulmonary, nasal, and the like may be employed. Dosage forms include tablets, troches, dispersions, suspensions, solutions, capsules, creams, ointments, aerosols, and the like.

Suitable carriers, diluents and excipients are well known to those skilled in the art and include materials such as carbohydrates, waxes, water soluble and/or swellable polymers, hydrophilic or hydrophobic materials, gelatin, oils, solvents, water, and the like. The particular carrier, diluent, or excipient used will depend upon the means and purpose for which the compound of the present invention is being applied. Solvents are generally selected based on solvents recognized by persons skilled in the art as safe (GRAS) to be administered to an animal. In general, safe solvents are non-toxic aqueous solvents such as water and other non-toxic solvents that are soluble or miscible in water. Suitable aqueous solvents include water, ethanol, propylene glycol, polyethylene glycols (e.g., PEG400, PEG300), etc. and mixtures thereof. The formulations may also include one or more buffers, stabilizing agents, surfactants, wetting agents, lubricating agents, emulsifiers, suspending agents, preservatives, antioxidants, opaquing agents, glidants, processing aids, colorants, sweeteners, perfuming agents, flavoring agents and other known additives to provide an elegant presentation of the drug (i.e., a compound of the present invention or pharmaceutical composition thereof) or aid in the manufacturing of the pharmaceutical product (i.e., medicament).

The formulations may be prepared using conventional dissolution and mixing procedures. For example, the bulk drug substance (i.e., a compound of the present invention or stabilized form of the compound (e.g., complex with a cyclodextrin derivative or other known complexation agent)) is dissolved in a suitable solvent in the presence of one or more of the excipients described above. The compound of the present invention is typically formulated into pharmaceutical dosage forms to provide an easily controllable and appropriate dosage of the drug.

The pharmaceutical composition (or formulation) for application may be packaged in a variety of ways, depending upon the method used to administer the drug. Generally, an article for distribution includes a container having deposited therein the pharmaceutical formulation in an appropriate form. Suitable containers are well-known to those skilled in the art and include materials such as bottles (plastic and glass), sachets, ampoules, plastic bags, metal cylinders, and the like. The container may also include a tamper-proof assemblage to prevent indiscreet access to the contents of the package. In addition, the container has deposited thereon a label that describes the contents of the container. The label may also include appropriate warnings.

The present compounds may be systemically administered, e.g., orally, in combination with a pharmaceutically acceptable vehicle such as an inert diluent or an assimilable edible carrier. They may be enclosed in hard or soft shell gelatin capsules, may be compressed into tablets, or may be incorporated directly with the food of the patient's diet. For oral therapeutic administration, the active compound may be combined with one or more excipients and used in the form of ingestible tablets, buccal tablets, troches, capsules, elixirs, suspensions, syrups, wafers, and the like. Such compositions and preparations should contain at least 0.1% of active compound. The percentage of the compositions and preparations may, of course, be varied and may conveniently be between about 2 to about 60% of the weight of a given unit dosage form. The amount of active compound in such therapeutically useful compositions is such that an effective dosage level will be obtained.

The tablets, troches, pills, capsules, and the like may also contain the following: binders such as gum tragacanth, acacia, corn starch or gelatin; excipients such as dicalcium phosphate; a disintegrating agent such as corn starch, potato starch, alginic acid and the like; a lubricant such as magnesium stearate; and a sweetening agent such as sucrose, fructose, lactose or aspartame or a flavoring agent such as peppermint, oil of wintergreen, or cherry flavoring may be added. When the unit dosage form is a capsule, it may contain, in addition to materials of the above type, a liquid carrier, such as a vegetable oil or a polyethylene glycol. Various other materials may be present as coatings or to otherwise modify the physical form of the solid unit dosage form. For instance, tablets, pills, or capsules may be coated with gelatin, wax, shellac or sugar and the like. A syrup or elixir may contain the active compound, sucrose or fructose as a sweetening agent, methyl and propylparabens as preservatives, a dye and flavoring such as cherry or orange flavor. Of course, any material used in preparing any unit dosage form should be pharmaceutically acceptable and substantially non-toxic in the amounts employed. In addition, the active compound may be incorporated into sustained-release preparations and devices.

The active compound may also be administered intravenously or intraperitoneally by infusion or injection. Solutions of the active compound or its salts can be prepared in water, optionally mixed with a nontoxic surfactant. Dispersions can also be prepared in glycerol, liquid polyethylene glycols, triacetin, and mixtures thereof and in oils. Under ordinary conditions of storage and use, these preparations contain a preservative to prevent the growth of microorganisms.

The pharmaceutical dosage forms suitable for injection or infusion can include sterile aqueous solutions or dispersions or sterile powders comprising the active ingredient which are adapted for the extemporaneous preparation of sterile injectable or infusible solutions or dispersions, optionally encapsulated in liposomes. In all cases, the ultimate dosage form should be sterile, fluid, and stable under the conditions of manufacture and storage. The liquid carrier or vehicle can be a solvent or liquid dispersion medium comprising, for example, water, ethanol, a polyol (for example, glycerol, propylene glycol, liquid polyethylene glycols, and the like), vegetable oils, nontoxic glyceryl esters, and suitable mixtures thereof. The proper fluidity can be maintained, for example, by the formation of liposomes, by the maintenance of the required particle size in the case of dispersions or by the use of surfactants. The prevention of the action of microorganisms can be brought about by various antibacterial and antifungal agents, for example, parabens, chlorobutanol, phenol, sorbic acid, thimerosal, and the like. In many cases, it will be preferable to include isotonic agents, for example, sugars, buffers or sodium chloride. Prolonged absorption of the injectable compositions can be brought about by the use in the compositions of agents delaying absorption, for example, aluminum monostearate and gelatin.

Sterile injectable solutions are typically prepared by incorporating the active compound in the required amount in the appropriate solvent with a variety of the other ingredients enumerated above, as required, followed by filter sterilization. In the case of sterile powders for the preparation of sterile injectable solutions, common methods of preparation are vacuum drying and the freeze drying techniques, which yield a powder of the active ingredient plus any additional desired ingredient present in the previously sterile-filtered solutions.

For topical administration, the present compounds may be applied in pure form, i.e., when they are liquids. However, it will generally be desirable to administer them to the skin as compositions or formulations, in combination with a dermatologically acceptable carrier, which may be a solid or a liquid.

Useful solid carriers include finely divided solids such as talc, clay, microcrystalline cellulose, silica, alumina, and the like. Useful liquid carriers include water, alcohols or glycols or water-alcohol/glycol blends, in which the present compounds can be dissolved or dispersed at effective levels, optionally with the aid of non-toxic surfactants. Adjuvants such as fragrances and additional antimicrobial agents can be added to optimize the properties for a given use. The resultant liquid compositions can be applied from absorbent pads, used to impregnate bandages and other dressings, or sprayed onto the affected area using pump-type or aerosol sprayers.

Thickeners such as synthetic polymers, fatty acids, fatty acid salts and esters, fatty alcohols, modified celluloses or modified mineral materials can also be employed with liquid carriers to form spreadable pastes, gels, ointments, soaps, and the like, for application directly to the skin of the user.

Dosages

Useful dosages of the compounds of Formula (I) can be determined by comparing their in vitro activity and in vivo activity in animal models. Methods for the extrapolation of effective dosages in mice, and other animals, to humans are known to the art. Useful dosages of the compounds of formula I can be determined by comparing their in vitro activity, and in vivo activity in animal models. Methods for the extrapolation of effective dosages in mice, and other animals, to humans are known to the art (e.g., U.S. Pat. No. 4,938,949).

Optimal dosages to be administered in the therapeutic methods of the present invention may be determined by those skilled in the art and will depend on multiple factors, including the particular composition in use, the strength of the preparation, the mode and time of administration, and the advancement of the disease or condition. Additional factors may include characteristics on the subject being treated, such as age, weight, gender, and diet.

In general, however, a suitable dose will be in the range of from about 0.01 to about 100 mg/kg, more specifically from about 0.1 to about 100 mg/kg, such as 10 to about 75 mg/kg of body weight per day, 3 to about 50 mg per kilogram body weight of the recipient per day, 0.5 to 90 mg/kg/day, or 1 to 60 mg/kg/day (or any other value or range of values therein). The compound is conveniently administered in a unit dosage form; for example, containing about 1 to 1000 mg, particularly about 10 to 750 mg, and more particularly, about 50 to 500 mg of active ingredient per unit dosage form.

Preferably, the active ingredient should be administered to achieve peak plasma concentrations of the active compound of from about 0.5 to about 75 µM, preferably, about 1 to 50 µM, and more preferably, about 2 to about 30 µM. This may be achieved, for example, by the intravenous injection of a 0.05 to 5% solution of the active ingredient, optionally in saline, or orally administered as a bolus containing about 1 to 100 mg of the active ingredient. Desirable blood levels may be maintained by continuous infusion to provide about 0.01 to 5.0 mg/kg/hr or by intermittent infusions containing about 0.4 to 15 mg/kg of the active ingredient(s).

The desired dose may conveniently be presented in a single dose or as divided doses administered at appropriate intervals, for example, as two, three, four or more sub-doses per day. The sub-dose itself may be further divided, e.g., into a number of temporally-distinct administrations used according to the compositions and methods of the present invention.

Effective amounts or doses of the active agents of the present invention may be ascertained by routine methods such as modeling, dose escalation studies or clinical trials, and by taking into consideration routine factors, e.g., the mode or route of administration or drug delivery, the pharmacokinetics of the agent, the severity and course of the disease, disorder, or condition, the subject's previous or ongoing therapy, the subject's health status and response to drugs, and the judgment of the treating physician. Such compositions and preparations should contain at least 0.1% of active compound. The percentage of the compositions and preparations may, of course, be varied and may conveniently be between 2 to about 60% of the weight of a given unit dosage form. The amount of active compound in such therapeutically useful composition is such that an effective dosage level will be obtained. An exemplary dose is in the range of from about 0.001 to about 200 mg of active agent per kg of subject's body weight per day, preferably about 0.05 to 100 mg/kg/day, or about 1 to 35 mg/kg/day, or about 0.1 to 10 mg/kg/daily in single or divided dosage units (e.g., BID, TID, QID). For a 70-kg human, an illustrative range for a suitable dosage amount is from 1 to 200 mg/day, or about 5 to 50 mg/day.

Methods and Uses

Uses of Isotopically-Labeled Compounds

In one aspect, the present invention provides a method of using isotopically labeled compounds and prodrugs of the present invention in: (i) metabolic studies (preferably with $^{14}C$), reaction kinetic studies (with, for example $^{2}H$ or $^{3}H$); (ii) detection or imaging techniques [such as positron emission tomography (PET) or single-photon emission computed tomography (SPECT)] including drug or substrate tissue distribution assays; or (iii) in radioactive treatment of patients.

Isotopically labeled compounds and prodrugs of the invention thereof can generally be prepared by carrying out the procedures disclosed in the schemes or in the examples and preparations described below by substituting a readily available isotopically labeled reagent for a non-isotopically labeled reagent. An $^{18}F$ or $^{11}C$ labeled compound may be particularly preferred for PET, and an $I^{123}$ labeled compound may be particularly preferred for SPECT studies. Further substitution with heavier isotopes such as deuterium (i.e., $^{2}H$) may afford certain therapeutic advantages resulting from greater metabolic stability, for example increased in vivo half-life or reduced dosage requirements.

Therapeutic Methods

Generally

The present invention provides methods of treating a disease, condition, or disorder in an animal by inhibiting PDE1, and more specifically, PDE1B. The methods generally comprise the step of administering a therapeutically effective amount of a compound of the present invention, or a pharmaceutically salt thereof, to a patient in need thereof to treat the disorder or disease. In certain embodiments, the present invention provides a use of a compound as described herein in the manufacture of a medicament for treating a disease, condition, or disorder by inhibiting PDE1, and PDE1B specifically.

PDE1-related indications that can be treated by compounds and compositions of the present invention include, but are not limited to, nervous system disorders, cardiovascular disorders, metabolic diseases, gastrointestinal and liver diseases, cancer disorders, hematological disorders, pulmonary and vascular diseases, neurological disorders and urological disorders.

PDE1-related indications also encompass diseases (e.g., Parkinson's disease or cocaine addiction) that include aberrant or dysregulated signaling pathways mediated by PDE1 (e.g., Parkinson's disease or cocaine addiction), and more specifically, PDE1B. Such PDE1-related signaling pathways, preferably in the nervous system, include, but are not limited to, those involving nitric oxide, natriuretic peptides (e.g., ANP, BNP, CNP), dopamine, noradrenalin, neurotensin, cholecystokinin (CCK), vasoactive intestinal peptide (VIP), serotonin, glutamate (e.g., NMDA receptor, AMPA receptor), GABA, acetylcholine, adenosine (e.g., A2A receptor), cannabinoids, natriuretic peptides (e.g., ANP, BNP, CNP), and endorphins. Accordingly, compounds of the present invention are useful in treating disorders that include an aberrant or dysregulated signaling pathway mediated by PDE1, and specifically, PDE1B. In a specific aspect, they are useful in treating disorders characterized by alterations in dopamine signaling. See, e.g., Nishi and Snyder, 2010, J Pharmacol. Sci. 114, 6-16.

CNS Disorders

The present invention includes the use of a compound or composition herein in a method of treating a CNS disorder, comprising administration of an effective amount of the compound or composition to a patient in need thereof. More specifically, a compound or composition of the present invention can be used in a method to treat a cognitive impairment associated with a CNS disorder.

CNS disorders within the scope of the present invention include, but are not limited to, Alzheimer's disease, Parkinson's disease, Huntington's disease, attention deficit disorder (ADD), attention deficit hyperactivity disorder (ADHD), neurodegenerative disorders, Tourette's syndrome, tic disorders, Lesch-Nyan disease, pain, dystonias, substance or drug abuse, fetal alcohol syndrome, schizophrenia, schizoaffective disorder, depression, affective disorder, manic-depressive disorder, obsessive-compulsive disorder, eating disorder, panic-disorder, anxiety disorder, migraine, myoclonus, premenstrual syndrome, post-traumatic stress syndrome, carcinoid syndrome, stroke, epilepsy, sleep or circadian rhythm disorder, sexual disorder, stress disorder, hypertension, and nervous system cancers.

In specific embodiments, the CNS disorder is Huntington's disease, schizophrenia, Parkinson's disease, Alzheimer's disease, schizophrenia, mild-cognitive impairment, and ADHD.

In other embodiments, the CNS disorder is substance or drug abuse, or fetal alcohol syndrome.

In one aspect, the compounds of the present invention are useful in improving neuronal plasticity—an essential property of the brain that is impaired in numerous CNS disorders. By inhibiting PDE1 activity, compounds of the present invention can enhance levels of $Ca^{2+}$ and cAMP/cGMP, triggering a signaling cascade that ultimately activates transcription factors, including the cAMP responsive element binding protein (CREB). CREB activation can then increase expression of neuronal plasticity-related genes, neurotrophic factors, and neuroprotective molecules—which in turn can promote the functional and morphological changes necessary for neuronal plasticity to occur. (See e.g., Tully et al., 2003, Nat. Rev. Drug. Discov. 2, 267-277; Alberini, 2009, Physiol. Rev. 89, 121-145.

More generally, cyclic nucleotide signaling pathways, including those involving PDE1, are critical regulators of neural function and plasticity, and alterations in these pathways have been implicated in various disorders of the brain. For example, In Alzheimer's disease, there is evidence that accumulation of amyloid-β protein decreases CREB phosphorylation, resulting in cognitive deficits. Vitolo et al., 2002, Proc. Natl. Acad. Sci. USA. 99, 13217-13221. Indeed, pharmacological methods to increase cAMP levels can restore neuronal plasticity and LTP in Alzheimer's models. Vitolo et al., 2002, Proc. Natl. Acad. Sci. USA. 99, 13217-13221. Similarly, intra-cellular signaling of dopamine D1 and various serotonin receptors, which signal through cyclic nucleotides, is known to be defective in various disorders, including depression, schizophrenia and cognitive disorders. In addition, altered cAMP/cGMP levels are associated with Parkinson's disease, and PDE1B activity is increased in a Parkinson's model. Sancesario et al., 2004, Eur. J. Neurosci. 20, 989-1000). Moreover, chronic elevation in calcium levels (which has been linked to cell death) is implicated in Alzheimer's disease, as well as other neurodegenerative diseases, such as Parkinson's and Huntington's. Because calcium signaling can regulate PDE1 function, inhibitors of the present invention are useful in treating such disorders.

Cognitive Impairments

In certain embodiments, compounds and compositions of the present invention are used in methods for treating a cognitive impairment associated with a neurological disorder. For the purposes of the present invention, the term "cognitive impairment" is used interchangeably with "cognitive disorder," "cognitive dysfunction," "cognitive deficit," and "cognitive disability" throughout this application, and all are deemed to cover similar therapeutic indications.

In specific embodiments, the invention provides various methods relying on the use of compounds and compositions of the present invention to treat a cognitive deficit associated with a CNS disorder, such as a cognitive impairment affecting memory formation. In another aspect, a compound or composition of the present invention is administered with a cognitive training protocol to treat a cognitive disorder. In a specific aspect, the cognitive deficit is associated with a CNS disorder selected from one or more of the group comprising dementias and neurodegenerative disorders, progressive CNS diseases, psychiatric disorders, developmental and genetic conditions, age-associated memory impairments, and learning disabilities.

Cognitive disorders can significantly impair social and occupational functioning, adversely impacting the autonomy and quality of life of the affected individual. An estimated four to five million Americans (about 2% of all ages and 15% of those older than 65) have some form and degree of cognitive impairment. Abrams et al., Merck Manual of Geriatrics, Whitehouse Station (NJ), Medical Services (1995).

Cognitive disorders reflect problems in cognition, i.e., the general processes by which knowledge is acquired, retained and used. Accordingly, cognitive disorders can encompass impairments in cognitive functions such as concentration, perception, attention, information processing, learning, memory, and/or language. Cognitive disorders can also encompass impairments in psychomotor learning, which include physical skills, such as movement and coordination; disruptions in fine motor skills, such as the ability to use precision instruments or tools; and deficits in gross motor skills, such as those elicited in dance, musical, or athletic performance.

Cognitive disorders can also encompass impairments in executive functions, which include abilities underlying the planning and execution of goal-oriented behaviors. Such abilities include flexibility, i.e., the capacity for quickly switching to the appropriate mental mode; anticipation and prediction based on pattern recognition; reasoning and problem-solving; decision making; working memory, i.e., the capacity to hold and manipulate internally (or externally) derived information in real time; emotional self-regulation, including the ability to recognize and manage one's emotions for good performance; sequencing, such as the ability to dissect complex actions into manageable units and prioritize them in the right order; and self-inhibition, i.e., the ability to withstand distraction and internal urges.

Cognitive disorders commonly occur in association with CNS disorders (also referred to as CNS conditions or CNS diseases). Such CNS disorders include, but are not limited to, the following categories (which are not mutually exclusive):

(1) dementias, such as those associated with Alzheimer's disease, Parkinson's disease; Huntington's disease, Pick's disease, Creutzfeldt-Jakob, ALS, AIDS Dementia, and other neurodegenerative disorders; as well as cognitive disabilities associated with progressive diseases involving the nervous system, such as multiple sclerosis.

(2) psychiatric disorders, which include affective disorders (mood disorders), such as depression and bipolar disorder; psychotic disorders, such as schizophrenia and delusional disorder; and neurotic and anxiety disorders, such as phobias, panic disorders, obsessive-compulsive disorder, generalized anxiety disorder, eating disorders, and posttraumatic stress disorder;

(3) developmental and genetic conditions affecting cognitive function, such as autism spectrum disorders; fetal alcohol spectrum disorders (FASD); Rubinstein-Taybi syndrome, down syndrome, and other forms of mental retardation; and progressive disorders involving the nervous system, such as multiple sclerosis;

(4) trauma-dependent losses of cognitive functions, such as impairments in memory, language, or motor skills resulting from brain trauma; head injury; cerebrovascular disorders, such as stroke, ischemia, hypoxia, and viral infection (e.g., encephalitis); excitotoxicity; seizures; and alcohol abuse;

(5) age-associated memory impairments, including those affecting patients in early stages of cognitive decline, as in Mild Cognitive Impairment (MCI); and (6) learning disabilities, such as perceptual handicaps, dyslexia, and attention deficit disorders.

In some cases, cognitive impairments can be a direct result of a CNS disorder. For example, impairments in speech and language may be a direct result of a stroke or head-injury that damages the brain regions controlling speech and language, as in aphasia.

In other cases, cognitive impairments may be associated with a complex developmental syndrome, CNS disorder, or genetic syndrome. For example, such impairments include cognitive deficits associated with schizophrenia or Parkinson's disease, or deficits in executive control that accompany autism or mental retardation.

In still other cases, such impairments can result from progressive diseases that impact CNS function, such as multiple sclerosis (MS). About one-half of MS patients will experience problems with cognitive function, such as slowed thinking, decreased concentration, and impaired memory. Such problems typically occur later in the course of MS, although in some cases they occur much earlier—if not at the onset of disease.

Augmented Cognitive Training

In some embodiments, the compounds and compositions of the instant invention are administered in conjunction with cognitive training to improve the efficiency of such training.

The phrase "in conjunction" means that a compound or composition of the present invention enhances CREB pathway function during cognitive training. As used herein, the term "cognitive training" is interchangeable with "training protocol," "training," and "cognitive training protocol."

Training Protocols

Cognitive training protocols and the underlying principles are well known in the art. See, e.g., U.S. Pat. No. 7,868,015 (and references cited therein); Klingberg et al., 2005, J. Am. Acad. Child. Adolesc. Psychiatry 44, 177-186; Belleville et al., 2006, Dement. Geriatr. Cogn. Disord. 22, 486-499; Jaeggi et al., 2008, Proc. Natl. Acad. Sci. USA 105, 6829-6833; Lustig et al., 2009, Neuropsychol. Rev. 19, 504-522; Park and Reuter-Lorenz, 2009, Ann. Rev. Psych. 60, 173-196; Chein et al., 2010, Psychon. Bull. Rev. 17, 193-199; Klingberg, 2010, Trends Cogn. Sci. 14, 317-324; Owen et al., 2010, Nature 465, 775-778; Jaeggi et al., 2011, Proc. Natl. Acad. Sci. USA 108, 10081-10086.

Cognitive training protocols are directed to numerous cognitive dimensions, including memory, concentration and attention, perception, learning, planning, sequencing, and judgment. One or more protocols (or modules) underling a cognitive training program can be provided to a subject.

In some embodiments, the protocols can be used to treat, or rehabilitate, cognitive impairments in afflicted subjects. Such protocols may be restorative or remedial, intended to reestablish prior skills and cognitive functions, or they may be focused on delaying or slowing cognitive decline due to neurological disease. Other protocols may be compensatory, providing a means to adapt to a cognitive deficit by enhancing function of related and uninvolved cognitive domains. In other embodiments, the protocols can be used to improve particular skills or cognitive functions in otherwise healthy individuals. For example, a cognitive training program might include modules focused on delaying or preventing cognitive decline that normally accompanies aging; here the program is designed to maintain or improve cognitive health.

In general, a cognitive training protocol (or module) comprises a set of distinct exercises that can be process-specific or skill-based:

Process-specific training focuses on improving a particular cognitive domain such as attention, memory, language, or executive functions. Here the goal of cognitive training is to obtain a general improvement that transfers from the trained activities to untrained activities associated with the same cognitive function or domain. For example, an auditory cognitive training protocol can be used to treat a student with impaired auditory attention. At the end of training, the student should show a generalized improvement in auditory attention, manifested by an increased ability to attend to and concentrate on verbal information presented in class—and therefore to remember to write down and complete homework assignments. Similarly, a cognitive training protocol may be directed to impaired executive function in an autistic subject, preventing the subject from carrying out instructions to complete an activity, such as making a meal, cleaning one's room, or preparing for school in the morning. Cognitive training allows the subject to focus his attention and concentration and as a result, complete the sequence of tasks required for such activities.

Skill-based cognitive training is aimed at improving performance of a particular activity or ability. Here the goal of cognitive training is to obtain a general improvement in the skill or ability. For example, a training protocol may focus on learning a new language, performing a musical instrument, or improving memory. The different exercises within such a protocol will focus on core components underlying skill. Modules for increasing memory, for example, may include tasks directed to the recognition and use of fact, and the acquisition and comprehension of explicit knowledge rules.

Some cognitive rehabilitation programs may rely on a single strategy (such as computer-assisted cognitive training) targeting either an isolated cognitive function or multiple functions concurrently. For example, the CogState testing method comprises a customizable range of computerized cognitive tasks able to measure baseline and change in cognitive domains underlying attention, memory, executive function, as well as language and social-emotional cognition. See, e.g., Yoshida et al., 2011, PloS ONE 6, e20469; Frederickson et al., 2010, Neuroepidemiology 34, 65-75. Other cognitive rehabilitation programs may use an integrated or interdisciplinary approach. Cognitive training programs may involve computer games, handheld game devices, interactive exercises, and may employ feedback and adaptive models.

Augmenting Agents

Cognitive training generally requires multiple training sessions to attain the desired benefits. This can be costly and time-consuming, deterring subject compliance and the realization of real world benefits that endure over time.

The efficiency of cognitive training can be improved by administering certain agents (known as augmenting agents) in conjunction with cognitive training. Such augmenting agents have the ability to enhance CREB pathway function. More particularly, this method (known as augmented cognitive training or ACT) can decrease the number of training sessions required to improve performance of a cognitive function, relative to the improvement observed by cognitive training alone. See, e.g., U.S. Pat. No. 7,868,015; U.S. Pat. No. 7,947,731; U.S. 2008/0051437.

In a particular embodiment, the method comprises the steps of: (a) providing cognitive training to a subject in need of treatment of a cognitive deficit under conditions sufficient to produce an improvement in performance by said animal of a cognitive function whose impairment is associated with said cognitive deficit; (b) administering a compound or composition of the present invention to the animal in conjunction with said cognitive training; repeating steps (a) and (b) one or more times; and (d) reducing the number of training sessions sufficient to produce the improvement in performance, relative to the improvement in performance produced by cognitive training alone.

More generally, compounds and compositions of the present invention can be used in conjunction with any psychotherapeutic approach that is intended to modulate cognitive function in the brain, thereby enhancing the efficacy of the such therapy by reducing the number of sessions—and hence time—necessary to attain benefits.

In a specific aspect, the cognitive deficit treated by these methods is or includes memory impairment, and more particularly, a defect in long-term memory. Long-term memory (LTM) generally comprises two main biological properties. First, formation of long-term memory requires synthesis of new proteins. Second, it involves cAMP-responsive transcription and is mediated through the cAMP-response element binding protein (CREB) family transcription factors. Accordingly, in some embodiments, compounds of the present invention are useful in enhancing memory formation in an animal, and more particularly, transcription-dependent memory.

Behavioral Assays

Numerous behavioral assays are available to assess the ability of a candidate compound to enhance memory formation, including the contextual conditioning, temporal conditioning, and object recognition assays. (See Biological Examples) Other, non-limiting examples of appropriate training protocols to assess memory include those that incorporate or relate to multiple training sessions, spaced training sessions, contextual fear training with single or multiple trials, trace fear conditioning with single or multiple trials, contextual memory generally, temporal memory, spatial memory, episodic memory, passive avoidance memory, active avoidance memory, food preference memory, conditioned taste avoidance, and social recognition memory.

The training protocols can also be used in accordance with the present invention as will be understood by those of ordinary skill in the art. These training protocols can be directed towards the evaluation of, without limitation, hippocampus-, cortex, and/or amygdale-dependent memory formation or cognitive performance.

Cardiovascular Disorders

PDE1 enzymes and cyclic nucleotides are emerging as key mediators of pathological processes that underlie many vascular disorders, including hypertension and myocardial infarction. For example, PDE1 appears to play a role in regulating cardiomyocyte hypertrophy via a mechanism involving cross-talk between Ca2+ and cyclic nucleotide signaling. See, e.g., Miller et al., 2011, Basic Res. Cardiol. 106, 1023-1039; Miller et al, 2009, Circ. Res. 105, 956-964. Moreover, PDE1 enzymes constitute the majority of cAMP- and cGMP-hydrolytic activity in human myocardium, implicating them in regulating signaling pathways involved in heart failure Accordingly, the present invention includes the use of a compound or composition herein in a method of treating a cardiovascular disorder, comprising administration of an effective amount of the compound or composition to a patient in need thereof.

Cardiovascular diseases within the scope of the present invention encompass, but are not limited to, angina pectoris, coronary artery disease, hypertension, congestive heart failure, myocardial infarction, ischemic diseases of the heart, atrial and ventricular arrhythmias, hypertensive vascular diseases, peripheral vascular diseases, and atherosclerosis.

In some embodiments, methods of treating a cardiovascular disorder in accord with the present invention comprise increasing cGMP concentration, cAMP concentration, or both, in any part of the heart muscle of a subject, the method comprising administering to the subject a compound or composition described herein.

In other embodiments, compounds of the present invention may be useful in lowering the heart rate or blood pressure in an animal.

Renal Disorders

PDE1 inhibitors are emerging therapeutic agents for progressive renal disease. See, e.g., Cheng et al., 2007, Soc. Exp. Biol. Med. 232, 38-51. Consistent with these findings, recent studies indicate that cAMP and cGMP regulate a variety of signaling pathways involved in the development and progression of renal disease, including pathways that modulate mitogenesis, inflammation, and extracellular matrix synthesis. See e.g., Wang et al., 2010, Kidney Int. 77. 129-140.

Accordingly, the present invention provides compound or compositions in methods for treating a renal disorder, comprising administering an effective amount of the compound or composition to a patient in need thereof. In a particular aspect, the renal disorder is selected from one or more of the group comprising renal artery stenosis, pyelonephritis, glomerulonephritis, kidney tumors, polycystic kidney disease, injury to the kidney, and damage resulting from radiation of the kidney.

Hematological Disorders

PDE1B is highly expressed in the hematological system, including leukocytes (peripheral blood), bone marrow stromal cells, bone marrow CD33+ cells, cord blood CD34+ cells, neutrophils cord blood, neutrophils peripheral blood, spleen, spleen liver cirrhosis. Accordingly, the present invention includes methods to treat a hematological disorder, comprising administering a compound or composition herein to a patient in need thereof. Hematological diseases within the scope of the present invention comprises disorders of the blood and all its constituents, including, but not limited to anemias, myeloproliferative disorders, hemorrhagic disorders, leukopenia, eosinophilic disorders, leukemias, lymphomas, plasma cell dyscrasias, and disorders of the spleen.

Gastrointestinal and Liver Diseases

PDE1B shows differential expression between diseased (e.g., cancerous) and healthy stomach tissue, diseased (e.g., cancerous) versus healthy ileum tissue, diseased (cirrhotic) versus and healthy liver. Accordingly, the present invention includes methods to treat a gastrointestinal disorder, comprising administering a compound or composition herein to a patient in need thereof. Gastrointestinal diseases within the scope of the present invention comprise, but are not limited to, disorders of the esophagus, stomach, duodenum, pancreas, bowel, and liver.

Cancer Disorders

PDE1B shows high expression in numerous cancer tissues, including tumors of the stomach, ileum, ovary, breast, and kidney, as well as differential expression between cancerous and healthy stomach, ileum, lung, ovary, breast, and kidney. Accordingly, the present invention includes methods to treat a cancer disorder, comprising administering a compound or composition herein to a patient in need thereof. Cancer disorders within the scope of the present invention comprise, but are not limited to, neoplasms, dysplasias, hyperplasias, and neoplasms, including cancers of the stomach, ileum, ovary, breast, and kidney.

Neurodegenerative Disorders

The present invention provides a method for treating the effects of injuries or diseases that result in neuronal degeneration or a method for promoting neurogenesis or neurite outgrowth These methods involve administering to a patient in need thereof an effective amount of a compound or composition of the present invention. It has been found that the PDE1 inhibitors of the present invention promote neurite outgrowth and neurogenesis.

Alternatively, at least one compound of the present invention is used to treat stem cells or neuronal progenitor cells prior to the cells being administered to the patient by implantation at the site of neuronal degeneration. In some embodiments, methods described herein involve modulating neurogenesis or neurite outgrowth ex vivo with a compound such that a composition containing neural stem cells, neural progenitor cells and/or differentiated neural cells can be subsequently administered to an individual to treat a disease or condition. In some embodiments, the method of treatment comprises the steps of contacting a neural stem cell or neural progenitor cell with one or more compounds of the invention to modulate neurite outgrowth and transplanting the cells into a patient in need or treatment. Methods of transplanting stem and progenitor cells are known in the art. In some embodiments, methods described herein allow treatment of diseases or conditions by directly replacing or replenishing damaged or dysfunctional neurons.

The method of the present invention which promotes neurogenesis is involved in cell renewal in the central nervous system (CNS) and includes all types of CNS cells.

In one embodiment, methods of the present invention are used to treat primary nervous system injury, e.g. closed head injuries and blunt trauma, such as those caused by participation in dangerous sports, penetrating trauma, such as gunshot wounds, hemorrhagic stroke, ischemic stroke, glaucoma, cerebral ischemia, or damages caused by surgery such as tumor excision or may even promote nerve regeneration in order to enhance or accelerate the healing of such injuries or of neurodegenerative diseases such as those discussed below. In addition, the method may be used to treat a disease or disorder resulting in a degenerative process.

In another embodiment, methods of the present invention are used to inhibit secondary degeneration which may otherwise follow primary nervous system injury.

The compounds of the invention may be used to treat various diseases or disorders of the central or peripheral nervous system, including diabetic neuropathy, amyotrophic lateral sclerosis (ALS). Peripheral nerve injuries and peripheral or localized neuropathies including, but not limited to, porphyria, acute sensory neuropathy, chronic ataxic neuropathy, complications of various drugs and toxins, amyloid polyneuropathies, adrenomyeloneuropathy, giant axonal neuropathy may be treated by this method.

In addition the compounds can be used for post-operative treatments such as for tumor removal from CNS and other forms of surgery on the CNS. The compounds can also be used for treatment of spinal cord trauma.

EXAMPLES

The present disclosure will be further illustrated by the following non-limiting Examples. These Examples are understood to be exemplary only, and they are not to be construed as limiting the scope of the invention herein, and as defined by the appended claims.

PREPARATIVE EXAMPLES

Exemplary compounds useful in methods of the invention will now be described by reference to the illustrative synthetic schemes for their general preparation below and the specific examples to follow.

Synthetic Schemes

One skilled in the art will recognize that, to obtain the various compounds herein, starting materials may be suitably selected so that the ultimately desired substituents will be carried through the reaction scheme with or without protection as appropriate to yield the desired product. Alternatively, it may be necessary or desirable to employ, in the place of the ultimately desired substituent, a suitable group that may be carried through the reaction scheme and replaced as appropriate with the desired substituent. Unless otherwise specified, the variables are as defined above in reference to Formula (I). Reactions may be performed between −78° C. and the reflux temperature of the solvent. Reactions may be heated employing conventional heating or microwave heating. Reactions may also be conducted in sealed pressure vessels above the normal reflux temperature of the solvent.

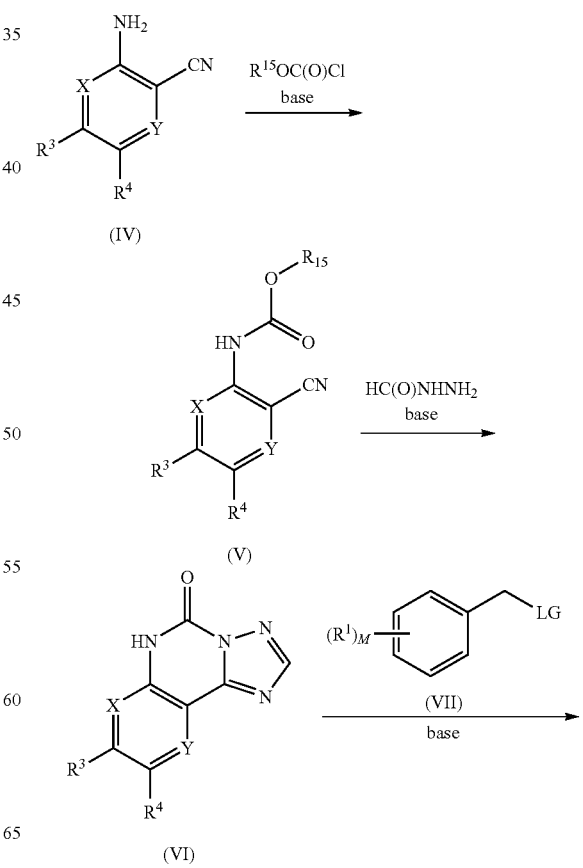

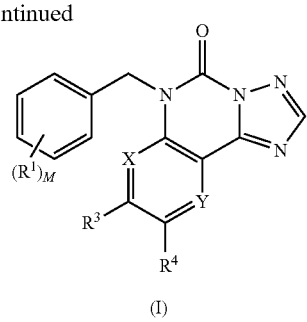

According to Scheme 1, commercially available or synthetically accessible compounds of formula (IV) are alkoxyformylated with a reagent such as chloroformates of formula $R^{15}OC(O)Cl$, where $R^{15}$ is —$CH_3$ or —$CH_2CH_3$, and the like, a base such as pyridine, disodium carbonate, lithium bis(trimethylsilyl)amide, and the like, in a solvent such as THF, DCM, DCE, or a mixture thereof, a temperatures ranging from −78° C. to room temperature, for a period of 12 to 24 h, provides carbamates of formula (V). Carbamates of formula (V), when heated with formylhydrazine, a base such as tri-n-propylamine, in a solvent such as 2-methoxyethanol, 1-methylpyrrolidinone, and the like, at temperatures ranging from room temperature to 130° C., for a period of 12 to 30 h, afford the triazolopyrimidinone compounds of formula (VI). Compounds of Formula (I) are prepared from triazolopyrimidinone compounds of formula (VI), by reaction with a suitable electrophile of formula (VII), where LG is a leaving group such as —Cl, —Br, —O—$SO_2CH_3$, and the like, a base such as $K_2CO_3$, NaH, and the like, in a suitable solvent such as DMF, 1-methylpyrrolidinone, and the like, at temperatures ranging from room temperature to 60° C., for a period of 12 to 30 h.

Compounds of formula (IV), where $R^4$ is —$(CR^{10}R^{11})_{1-3}NR^{12}R^{13}$, are prepared by the reaction of commercially available 2-amino-5-bromonicotinonitrile with synthetically accessible aminomethyl(trifluoroborates).

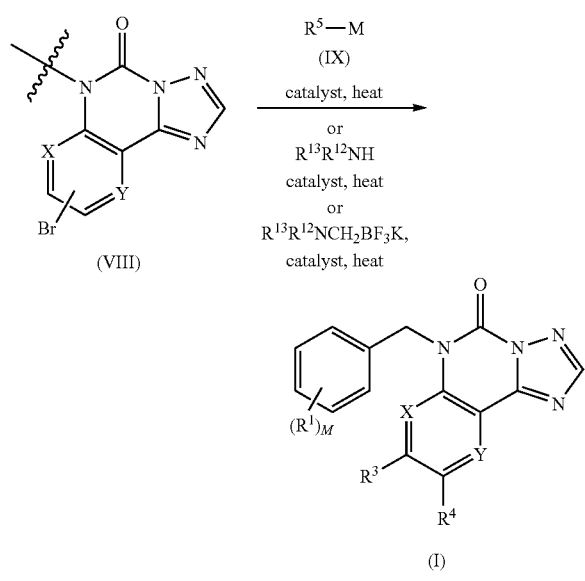

According to Scheme 2, bromo compounds of formula (VIII), are reacted under palladium or copper catalyzed coupling conditions, for example, under Suzuki reaction conditions, by the reaction of bromo compounds of formula (VIII), with commercially available or synthetically accessible boronic acids or esters of formula (IX), where $R^5$ is aryl or heteroaryl, and M is boron, in a solvent such as DME, ACN, toluene, EtOH, $H_2O$, or a mixture thereof, in the presence of a base such as, $NaHCO_3$, $Na_2CO_3$, $K_2CO_3$, $K_3PO_4$, $Cs_2CO_3$, and the like, and on organotransition metal catalyst such as $Pd_2(dba)_3$, $Pd(dppf)_2$, $Pd(PPh_3)_4$, and the like, using conventional or microwave heating, at temperatures ranging from 80 to 120° C. provides compounds of Formula (I), where $R^3$ or $R^4$ is aryl or heteroaryl.

Bromo compounds of formula (VIII), are reacted under Stille conditions, by reaction with an alkyl, or alkynyl organometallic reagents such as tributyl(vinyl)stannane, and the like, a palladium catalyst such as $Pd(PPh_3)_4$, in a solvent such as toluene, dioxane and the like, at temperatures ranging from 80 to 120° C. for a period of 16 h provides vinyl compounds of Formula (I), where $R^3$ or $R^4$ is —CH=$CH_2$, —$CH_2OCH_2OCH_3$, and —$C(CH_2)(OCH_2CH_3)$. Other examples of vinylorganometallic reagents that may be employed are potassium trifluoro(vinyl)borates, organozinc and organomagnesium reagents.

In addition to Suzuki and Stille conditions, other coupling reactions known in the art may be employed, for example, reaction with organozinc, organomagnesium, reagents and the like.

Bromo compounds of formula (VIII), are reacted under copper coupling conditions, for example, by reaction a heteroaryl such as but not limited to 6-methylpyridazin-3(2H)-one, CuI, an additive such as trans-1,2-diaminocyclohexane, a base such as $Cs_2CO_3$, and the like, in a solvent such as dioxane, employing conventional or microwave heating, at temperatures ranging from 80 to 120° C., for a period of 10-16 h, to provide compounds of Formula (I), where $R^3$ or $R^4$ is heteroaryl.

Alternately, bromo compounds of formula (VIII), are reacted under palladium coupling conditions, for example, by reaction with a amine of formula —$NHR^{12}R^{13}$, $Pd(OAc)_2$, a ligand such as BINAP, a base such as $Cs_2CO_3$, and the like, in a solvent such as toluene, employing conventional or microwave heating, at temperatures ranging from 80 to 120° C., for a period of 10 to 18 h, to provide compounds of Formula (I).

Additional cross-coupling reactions of bromo compounds of formula (VIII), with aminomethyl(trifluoroborates) of formula $R^{12}R^{13}NCH_2BF_3K$, a catalyst such as $PdCl_2$(dppf)-DCM, $Pd(PPh_3)_4$, 2-dicyclohexylphosphino-2,4,6-triisopropylbiphenyl, Pd(OAc)2, and the like, a base such as $Cs_2CO_3$, $K_2CO_3$, t-BuOK, $K_3PO_4$, in a solvent such as toluene, 1,4-dioxane, DMF, DMA, at temperatures ranging from 80 to 120° C., for a period of 10-16 h, provide compounds of Formula (I).

Similarly, the transformations depicted in Scheme 2 can be performed on intermediates (IV), (V) or (VI) of Scheme 1, when they are substituted with bromine, and the resulting products carried through the sequence as described.

Scheme 3

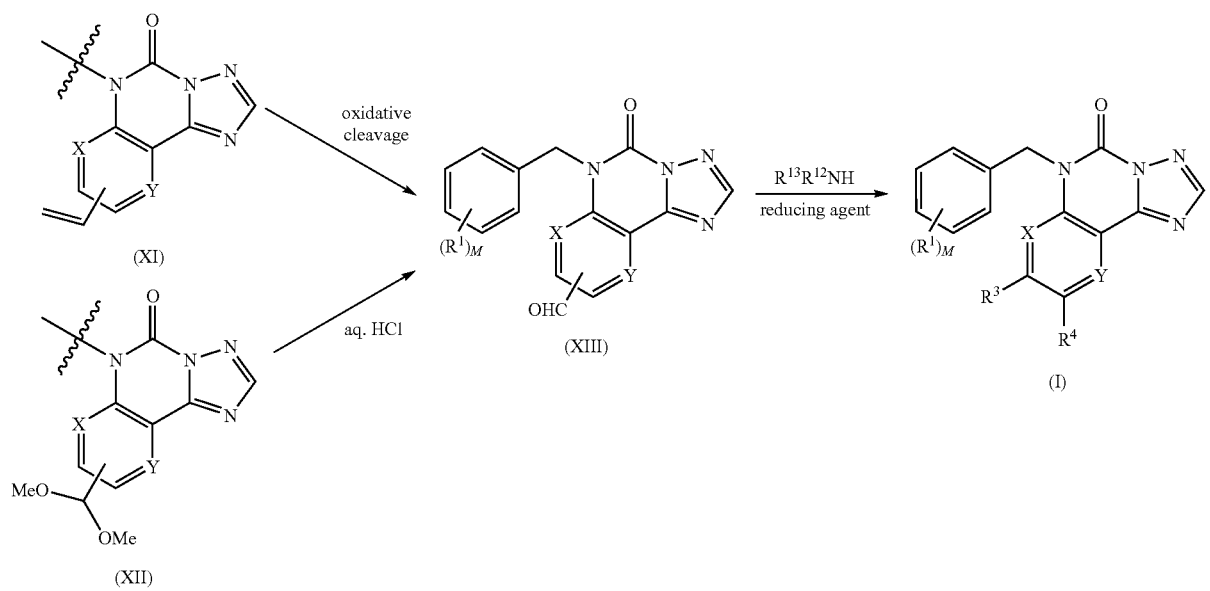

According to Scheme 3, vinyl compounds of formula (XI) are oxidized to aldehydes of formula (XIII) using a suitable oxidative cleavage method, for example, osmium(VIII) oxide, sodium periodate in water-THF, at temperatures ranging from 40 to 60° C., for a period of 2 to 4 h. Aldehydes of formula (XIII) are also prepared from acetals of formula (XII), by heating with an appropriate acid such as, aq. HCl, at temperatures ranging from room temperature to 100° C., for a period of 4 to 24 h. Direct heating of bromo compounds of formula (VIII), with carbon monoxide, a palladium catalyst, heating under pressure may provide aldehyde compounds of formula (XIII). Reductive amination of aldehyde compounds of formula (XIII), employing methods known to one skilled in the art, for example, reacting compounds of formula (XIII) with a suitable amine of formula $HNR^{12}R^{13}$, in the presence of a reducing agent such as $NaBH(OAc)_3$, $NaBH_4$, or NaCNBH$_3$, in a solvent such as DCE, DCM, methanol, or a mixture thereof, with optional additives such as acetic acid of an appropriate Lewis acid, provide compounds of Formula (I), where $R^3$ or $R^4$ is —$CH_2NR^{12}R^{13}$.

Scheme 4

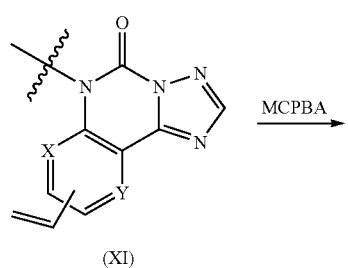

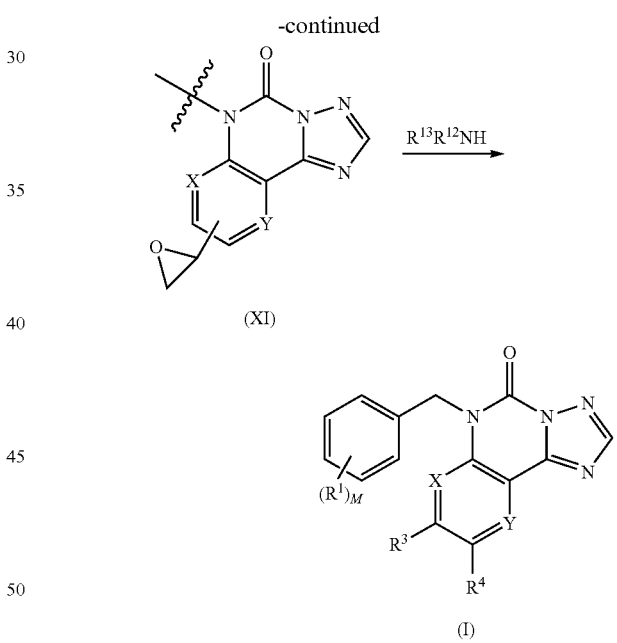

Vinyl compounds of formula (XI) are reacted under epoxide forming conditions, known to one skilled in the art, for example, reaction with m-CPBA, in a solvent such as DCM, at temperatures ranging from 10 to 30° C., for a period of 12 to 18 h. Ring opening with nitrogen nucleophiles of formula $R^{13}R^{12}NH$ in a solvent such as MeOH, provides β-amino-alcohols of compounds of Formula (I) where $R^3$ or $R^4$ is —$(CR^{10}R^{11})_2NR^{12}R^{13}$ where either $R^{10}$ or $R^{11}$ is —OH or H. Treatment of alcohols of Formula (I) where $R^3$ or $R^4$ is —$(CR^{10}R^{11})_2NR^{12}R^{13}$, where either $R^{10}$ or $R^{11}$ is —OH or H, with a fluorinating agent such as DAST gives rise to compounds of Formula (I) where $R^3$ or $R^4$ is —$(CR^{10}R^{11})_2NR^{12}R^{13}$, where either $R^{10}$ or $R^{11}$ is —F or H.

Scheme 5

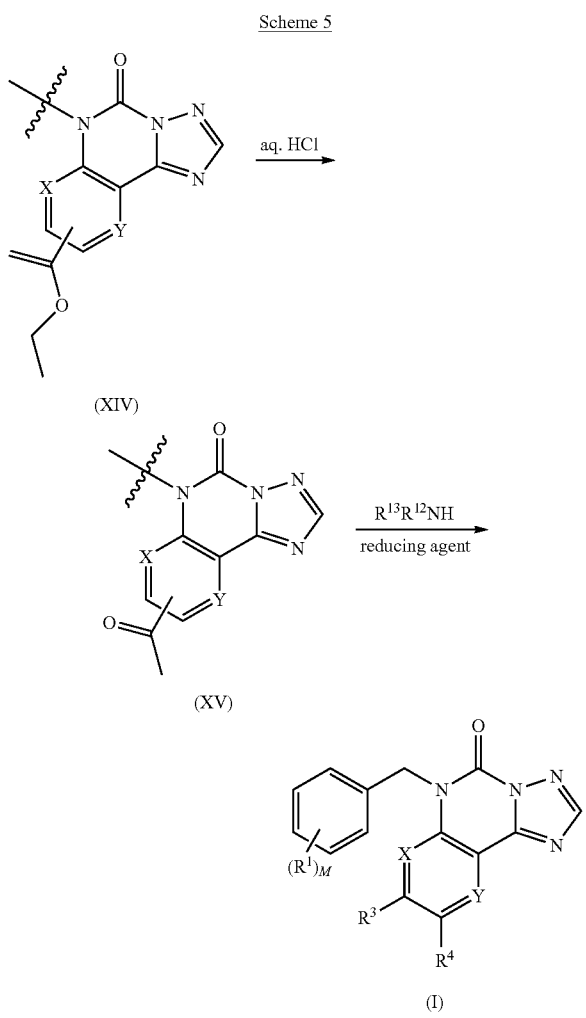

According to Scheme 5, vinyl ether compounds of formula (XIV) are hydrolyzed, with an acid such as aq. HCl, in a solvent such as dioxane, for a period of 2 to 8 h, to provide acetyl compounds of formula (XV). Reductive amination of acetyl compounds of formula (XV), employing methods known to one skilled in the art, as previously described, provides compounds of Formula (I), where $R^3$ or $R^4$ is —$CR^{10}R^{11}NR^{12}R^{13}$, where either $R^{10}$ or $R^{11}$ is —$CH_3$.

In the above Schemes, where the compounds of Formula (I) contain a protecting group, such as a tert-butoxycarbonyl (BOC), methoxymethyl (MOM) ethers, or benzyl group. The protecting group is removed by deprotection conditions known to one skilled in the art. For example, a tert-butoxycarbonyl group is removed using an organic acid such as TFA (neat or in a solvent such as $CH_2Cl_2$) or an inorganic acid such as HCl (in a solvent such as 1,4-dioxane, ether, methanol, isopropanol, or formic acid, or a mixture thereof) at temperatures ranging from room temperature to 60° C.

Compounds of Formula (I) may be converted to their corresponding salts using methods known to those skilled in the art. For example, compounds of Formula (I) may be treated with TFA, HCl, maleic acid, or citric acid in a solvent such as $Et_2O$, DCM, THF, or MeOH to provide the corresponding salt forms.

Compounds prepared according to the schemes described above may be obtained as single enantiomers, diastereomers, or regioisomers, by enantio-, diastereo-, or regiospecific synthesis, or by resolution. Where compounds according to this invention have at least one chiral center, they may accordingly exist as enantiomers. Where compounds possess two or more chiral centers, they may additionally exist as diastereomers. It is to be understood that all such isomers and mixtures thereof are encompassed within the scope of the present invention. Compounds prepared according to the schemes above may alternately be obtained as racemic (1:1) or non-racemic (not 1:1) mixtures of mixtures as diastereomers or regioisomers. Where racemic and non-racemic mixtures of enantiomers are obtained, single enantiomers may be isolated using conventional separation methods known to one skilled in the art, such as chiral chromatography, recrystallization, diastereomeric salt formation, derivatization into diastereomeric adducts, biotransformation, or enzymatic transformation. Where regioisomeric or diastereomeric mixtures are obtained, single isomers may be separated using conventional methods such as chromatography or crystallization.

The following examples are provided to further illustrate the invention and various preferred embodiments.

EXAMPLES

Chemistry

In obtaining the compounds described in the examples below, and the corresponding analytical data, the following experimental and analytical protocols were followed unless otherwise indicated.

Unless otherwise stated, reaction mixtures were magnetically stirred at room temperature (rt) under nitrogen atmosphere. Where solutions were "dried", they were generally dried over a drying agent such as $Na_2SO_4$ or $MgSO_4$. Where mixtures, solutions, and extracts were "concentrated", they were typically concentrated on a rotary evaporator under reduced pressure.

Reactions under microwave irradiation conditions were carried out in a CEM Discover-SP with Activent microwave reaction apparatus, model number 909150, or Biotage Initiator, model number 355302.

Normal-phase flash column chromatography (FCC) was performed on silica gel ($SiO_2$) using packed or prepackaged cartridges, eluting with the indicated solvents.

LC/MS were obtained on a Waters 2695 Separations Unit, 2487 Dual Absorbance Detector, Micromass ZQ fitted with ESI Probe, or a Waters Acquity™ Ultra performance LC (UPLC) with PDA e and SQ detectors.

Preparative HPLC was performed on a Shimadzu SIL-10AP system using a Waters SunFire OBD 30 mm×100 mm×2.5 μm (particle size) $C^{18}$ column with a 15 minute gradient of 10-100% acetonitrile in water and 0.05% trifluoroacetic acid added as a modifier to both phases. Elution profiles were monitored by UV at 254 and 220 nm.

Nuclear magnetic resonance (NMR) spectra were obtained in a Varian 400 MHz or Bruker 400 MHz NMR. Samples were analyzed in either deuterated acetone (($CD_3)_2CO$)), chloroform ($CDCl_3$), methanol-$d_4$ ($CD_3OD$), or dimethyl sulfoxide-$d_6$ (DMSO-$d_6$). For $CDCl_3$ samples, the residual central resonance peak at 7.26 for $^1H$ was used for chemical shift assignment for $^1H$ NMR spectra. For $CD_3OD$ the residual central resonance peak at 3.31 for $^1H$ was used for chemical shift assignment and for DMSO-$d_6$ the residual central resonance peak at 2.50 ppm for $^1H$ was used for chemical shift assignment. The format of the $^1H$ NMR data below is: chemical shift in ppm downfield the tetramethylsilane reference (multiplicity, coupling constant J in Hz, integration).

Chemical names were generated using ChemDraw Ultra 12.0 (CambridgeSoft Corp., Cambridge, Mass.) or ChemAxon.

Example 1

9-Bromo-6-(4-methoxybenzyl)pyrido[3,2-e][1,2,4]triazolo[1,5-c]pyrimidin-5(6H)-one

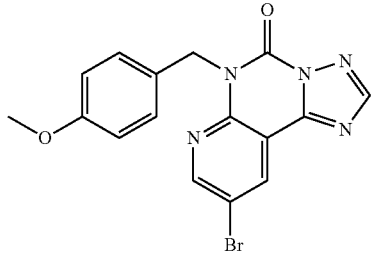 [SMILES: COc1ccc(Cn2c(=O)n3ncnc3c3cc(Br)cnc32)cc1]

Step A. Methyl 5-bromo-3-cyanopyridin-2-ylcarbamate. Lithium bis(trimethylsilyl)amide in THF (1.0 N, 22 mL, 22 mmol) was added to a stirred solution of 2-amino-5-bromopyridine-3-carbonitrile (2.0 g, 10 mmol) in THF (30 mL) at −78° C. The mixture was stirred at −78° C. for 30 minutes. Methyl chloroformate (1.06 g, 11.1 mmol) was added and the mixture was warmed to room temperature and stirred for 2 h. The reaction mixture was cooled in ice bath and quenched with saturated aqueous ammonium chloride (50 mL). The aqueous layer was extracted with EtOAc (3×50 mL) and the combined organic layers were washed with brine (2×50 mL), dried ($Na_2SO_4$) and concentrated under reduced pressure. Purification (LC, 10% EtOAc in petroleum ether) afforded the title compound (1.43 g, 63%). $^1$H NMR (400 MHz, $CDCl_3$) δ 3.85 (s, 3H), 7.45 (br s, 1H), 8.05 (s, 1H), 8.65 (s, 1H). [M−H]=254.0.

Step B: 9-Bromopyrido[3,2-e][1,2,4]triazolo[1,5-c]pyrimidin-5(6H)-one. Formyl hydrazine (60 mg, 1.0 mmol) was added to a solution of methyl 5-bromo-3-cyanopyridin-2-ylcarbamate (255 mg, 1.0 mmol) in 1-methylpyrrolidinone (5 mL). The resulting mixture was stirred at 120° C. for 3 h. The mixture was cooled to room temperature and poured into ice-water (20 mL). The resulting solid was separated by filtration, washed with water and hexanes and dried under vacuum to afford the title compound (160 mg, 60%). $^1$H NMR (400 MHz, DMSO-$d_6$) δ 8.60 (s, 1H), 8.70 (s, 1H), 8.80 (s, 1H), 13.00 (br s, 1H). [M+H]=266.3.

Step C. 9-Bromo-6-(4-methoxybenzyl)pyrido[3,2-e][1,2,4]triazolo[1,5-c]pyrimidin-5(6H)-one. 1-(Chloromethyl)-4-methoxybenzene (3.10 mL, 22.9 mmol) was added to a stirred solution of 9-bromopyrido[3,2-e][1,2,4]triazolo[1,5-c]pyrimidin-5(6H)-one (3.02 g, 11.35 mmol) and potassium carbonate (4.71 g, 34.1 mmol) in 1-methylpyrrolidinone (60 mL). The mixture was heated at 40° C. for 14 h. The mixture was filtered, and the resulting solid was washed liberally with DCM. The combined organic layers were concentrated under vacuum and the residue was triturated with EtOAc (40 mL) to afford the title compound (3.07 g, 70%) as a brown powder. $^1$H NMR (400 MHz, $CDCl_3$) δ 3.77 (s, 3H), 5.72 (s, 2H), 6.83 (d, J=8.66 Hz, 2H), 7.58 (d, J=8.66 Hz, 2H), 8.37 (s, 1H), 8.76 (d, J=2.38 Hz, 1H), 8.82 (d, J=2.38 Hz, 1H). [M+H]=386.1.

Example 2

8-Bromo-6-(4-methoxybenzyl)pyrido[2,3-e][1,2,4]triazolo[1,5-c]pyrimidin-5(6H)-one

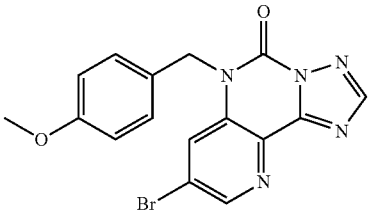 [SMILES: COc1ccc(Cn2c(=O)n3ncnc3c3ncc(Br)cc32)cc1]

$^1$H NMR (400 MHz, $CDCl_3$) δ 3.80 (br s, 3H), 5.52 (br s, 2H), 6.91 (d, J=8.16 Hz, 2H), 7.27-7.30 (m, 2H), 7.95 (br s, 1H), 8.50 (br s, 1H), 8.77 (br s, 1H). [M+H]=386.

Example 3

8-(Dimethoxymethyl)-6-(4-methoxybenzyl)pyrido[3,2-e][1,2,4]triazolo[1,5-c]pyrimidin-5(6H)-one

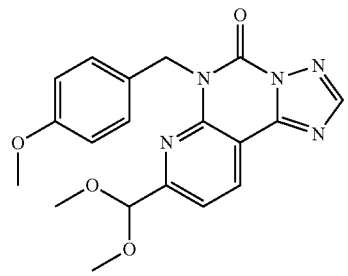 [SMILES: COc1ccc(Cn2c(=O)n3ncnc3c3ccc(C(OC)OC)nc32)cc1]

$^1$H NMR (400 MHz, $CDCl_3$) δ 3.46 (s, 6H), 3.76 (s, 3H), 5.50 (s, 1H), 5.76 (s, 2H), 6.78-6.88 (m, 2H), 7.68 (d, J=2.01 Hz, 3H), 8.35 (s, 1H), 8.66 (d, J=8.03 Hz, 1H). [M+H]=382.2.

Example 4

9-Bromo-6-(4-methoxybenzyl)-[1,2,4]triazolo[1,5-c]pteridin-5(6H)-one

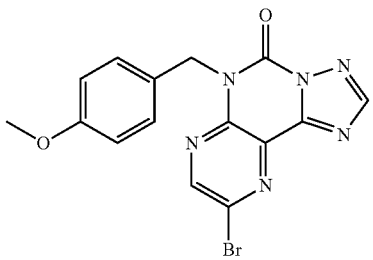 [SMILES: COc1ccc(Cn2c(=O)n3ncnc3c3nc(Br)cnc32)cc1]

$^1$H NMR (400 MHz, $CDCl_3$) δ 3.77 (s, 3H), 5.68 (s, 2H), 6.83 (d, J=8.53 Hz, 2H), 7.54 (d, J=8.66 Hz, 2H), 8.50 (s, 1H), 8.81 (s, 1H). [M+H]=387.

Example 5

9-(3,4-Dimethoxyphenyl)-6-(4-methoxybenzyl)pyrido[3,2-e][1,2,4]triazolo[1,5-c]pyrimidin-5(6H)-one

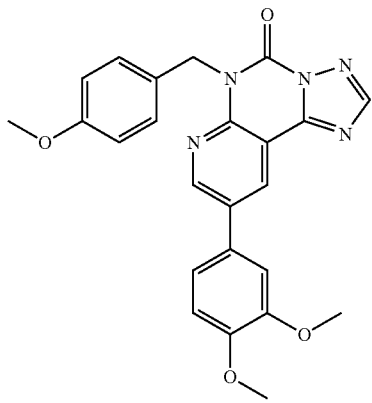 [SMILES: COc1ccc(Cn2c(=O)n3ncnc3c3cc(-c4ccc(OC)c(OC)c4)cnc32)cc1]

9-(3,4-Dimethoxyphenyl)-6-(4-methoxybenzyl)pyrido[3,2-e][1,2,4]triazolo[1,5-c]pyrimidin-5(6H)-one. 9-Bromo-6-(4-methoxybenzyl)pyrido[3,2-e][1,2,4]triazolo[1,5-c]pyrimidin-5(6H)-one (Example 1, 75 mg, 0.19 mmol), 3,4-dimethoxyphenylboronic acid (75 mg, 0.41 mmol), potassium phosphate (104 mg, 0.49 mmol) and DME (3 mL) were combined and nitrogen was bubbled through for 10 minutes. Pd$_2$(dba)$_3$ (13 mg, 0.01 mmol) was added and the mixture was heated for 2 h at 120° C. in the microwave. Purification (HPLC, 10-80% ACN-water) afforded the title compound (6 mg, 7%) as a white solid. $^1$H NMR (400 MHz, CDCl$_3$) δ 3.76 (s, 3H), 3.96 (s, 3H), 3.99 (s, 3H), 5.78 (s, 2H), 6.83-6.84 (m, 2H), 7.02 (d, J=6.7 Hz, 1H), 7.15 (d, J=1.6 Hz, 1H), 7.24 (dd, J=6.7, 1.5 Hz, 1H), 7.62-7.64 (m, 2H), 8.37 (s, 1H), 8.76 (d, J=1.9 Hz, 1H), 8.99 (d, J=1.9 Hz, 1H). [M+H]=444.2.

Examples 6 and 7 were made in a manner analogous to Example 5, with the appropriate starting material and reagent substitutions.

Example 6

6-(4-Methoxybenzyl)-9-(6-methoxypyridin-3-yl)pyrido[3,2-e][1,2,4]triazolo[1,5-c]pyrimidin-5(6H)-one

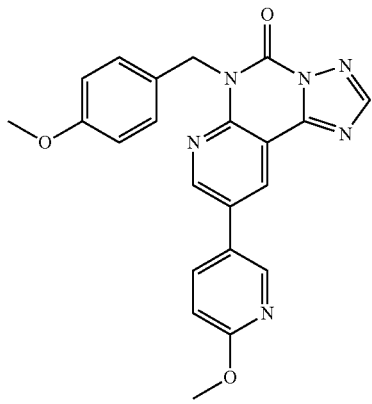 [SMILES: COc1ccc(Cn2c(=O)n3ncnc3c3cc(-c4ccc(OC)nc4)cnc32)cc1]

$^1$H NMR (400 MHz, DMSO-d$_6$) δ 3.70 (s, 3H), 3.92 (s, 3H), 5.63 (s, 2H), 6.86 (d, J=7.0 Hz, 2H), 6.98 (d, J=7.0 Hz, 1H), 7.38 (d, J=7.0 Hz, 2H), 8.26 (dd, J=7.0, 2.1 Hz, 1H), 8.65 (s, 1H), 8.70 (d, J=1.9 Hz, 1H), 8.87 (d, J=1.9 Hz, 1H), 9.14 (d, J=1.9 Hz, 1H). [M+H]=415.1.

Example 7

6-(4-Methoxybenzyl)-9-(2-methoxypyridin-3-yl)pyrido[3,2-e][1,2,4]triazolo[1,5-c]pyrimidin-5(6H)-one

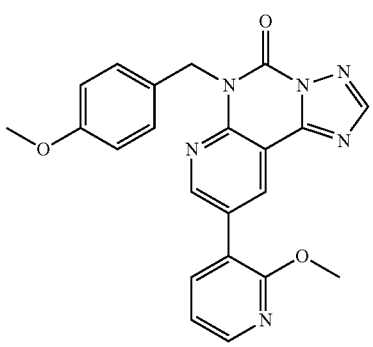 [SMILES: COc1ccc(Cn2c(=O)n3ncnc3c3cc(-c4cccnc4OC)cnc32)cc1]

$^1$H NMR (400 MHz, DMSO-d$_6$) δ 3.71 (s, 3H), 3.94 (s, 3H), 5.62 (s, 2H), 6.86 (d, J=7.0 Hz, 2H), 7.18 (dd, J=5.9, 4.0 Hz, 1H), 7.39 (d, J=7.0 Hz, 2H), 8.02 (dd, J=5.9, 1.5 Hz, 1H), 8.28 (dd, J=4.0, 1.5 Hz, 1H), 8.62 (s, 1H), 8.82 (d, J=1.8 Hz, 1H), 8.99 (d, J=1.9 Hz, 1H). [M+H]=415.1.

Example 8

6-(4-Methoxybenzyl)-9-(3-methyl-6-oxopyridazin-1(6H)-yl)pyrido[3,2-e][1,2,4]triazolo[1,5-c]pyrimidin-5(6H)-one

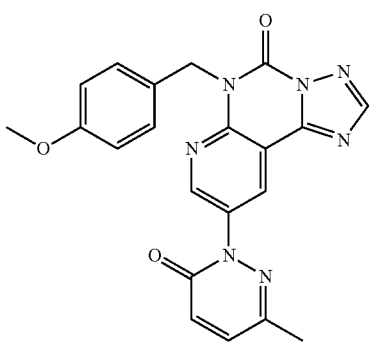 [SMILES: COc1ccc(Cn2c(=O)n3ncnc3c3cc(-n4nc(C)ccc4=O)cnc32)cc1]

6-(4-Methoxybenzyl)-9-(3-methyl-6-oxopyridazin-1(6H)-yl)pyrido[3,2-e][1,2,4]triazolo[1,5-c]pyrimidin-5(6H)-one. 9-Bromo-6-(4-methoxybenzyl)pyrido[3,2-e][1,2,4]triazolo[1,5-c]pyrimidin-5(6H)-one (Example 1, 75 mg, 0.19 mmol), 6-methylpyridazin-3(2H)-one (43 mg, 0.39 mmol), copper(I) iodide (44 mg, 0.23 mmol), dioxane (3 mL), trans-1,2-diaminocyclohexane (0.030 mL, 0.25 mmol) and Cs$_2$CO$_3$ (152 mg, 0.47 mmol) were combined and heated at 120° C. for 12 h in the microwave. The mixture was filtered, and purified (HPLC, 10-80% ACN-water) to afford the title compound (9 mg, 11%) as a white solid. $^1$H NMR (400 MHz, CDCl$_3$) δ 2.44 (s, 3H), 3.76 (s, 3H), 5.77 (s, 2H), 6.81-6.83 (m, 2H), 7.03 (d, J=7.7 Hz, 1H), 7.60-7.61 (m, 2H), 8.36 (s, 1H), 8.99 (d, J=2.1 Hz, 1H), 9.25 (d, J=2.1 Hz, 1H). [M+H]=416.1.

Example 9

9-(4-cyclopropylpiperazin-1-yl)-6-(4-methoxybenzyl)pyrido[3,2-e][1,2,4]triazolo[1,5-c]pyrimidin-5(6H)-one

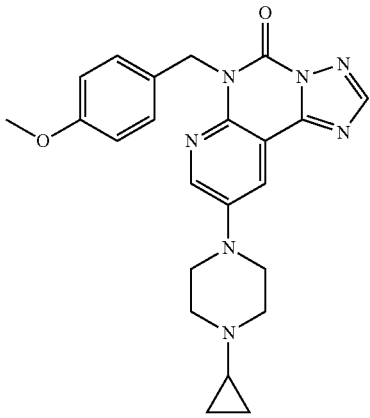 [SMILES: COc1ccc(Cn2c(=O)n3ncnc3c3cc(N4CCN(C5CC5)CC4)cnc32)cc1]

9-(4-Cyclopropylpiperazin-1-yl)-6-(4-methoxybenzyl)pyrido[3,2-e][1,2,4]triazolo[1,5-c]pyrimidin-5(6H)-one. 9-Bromo-6-(4-methoxybenzyl)pyrido[3,2-e][1,2,4]triazolo[1,5-c]pyrimidin-5(6H)-one (Example 1, 63 mg, 0.16 mmol) and 1-cyclopropylpiperazine (103 mg, 0.82 mmol) were dissolved in toluene (2 mL) and nitrogen was bubbled through the mixture while BINAP (41 mg, 0.07 mmol), $Cs_2CO_3$ (159 mg, 0.49 mmol) and $Pd(OAc)_2$ (7 mg, 0.03 mmol) were added. The mixture was heated at 100° C. for 16 h. The reaction mixture was concentrated under a stream of nitrogen and the residue was taken up in DMF and filtered. Purification (preparative HPLC, 10-70% ACN in water) afforded the title compound (25 mg, 27%) as a yellow solid. $^1$H NMR (400 MHz, CDCl$_3$) δ 0.84-1.00 (m, 2H), 1.38 (d, J=3.01 Hz, 2H), 2.01 (s, 2H), 2.35-2.51 (m, 1H), 3.50 (s, 4H), 3.61 (br s, 4H), 3.76 (s, 3H), 5.70 (s, 2H), 6.82 (d, J=8.53 Hz, 2H), 7.57 (d, J=8.41 Hz, 2H), 8.07 (d, J=2.89 Hz, 1H), 8.33 (s, 1H), 8.47 (d, J=2.89 Hz, 1H). [M+H]=432.2.

Examples 10 thru 19 were made in a manner analogous to Example 9, with the appropriate starting material and reagent substitutions.

Example 10

9-(((1S,2S)-2-Aminocyclohexyl)amino)-6-(4-methoxybenzyl)pyrido[3,2-e][1,2,4]triazolo[1,5-c]pyrimidin-5(6H)-one

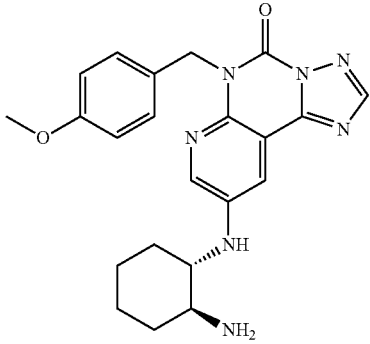 [SMILES: COc1ccc(Cn2c(=O)n3ncnc3c3cc(N[C@H]4CCCC[C@@H]4N)cnc32)cc1]

$^1$H NMR (400 MHz, CDCl$_3$) δ 1.20-1.45 (m, 4H), 1.68-1.77 (m, 2H), 1.98-2.06 (m, 2H), 2.93-2.97 (m, 2H), 3.70 (s, 3H), 5.53 (s, 2H), 6.15 (d, J=8.1 Hz, 1H), 6.83-6.86 (m, 2H), 7.31-7.34 (m, 2H), 7.82 (d, J=2.3 Hz, 1H), 7.88 (br s, 3H), 8.29 (d, J=2.3 Hz, 1H), 8.57 (s, 1H). [M+H]=420.2.

Example 11

6-(4-Methoxybenzyl)-9-(methyl(1-methylpiperidin-4-yl)amino)-[1,2,4]triazolo[1,5-c]pteridin-5(6H)-one

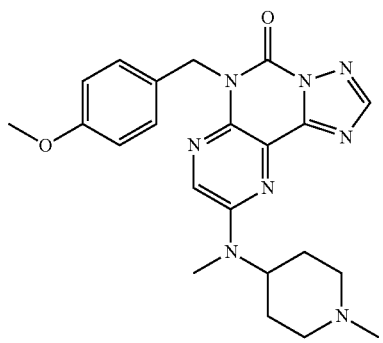

$^1$H NMR (400 MHz, CDCl$_3$) δ 1.92 (d, J=13.30 Hz, 2H), 2.40-2.58 (m, 2H), 2.84 (s, 3H), 3.03 (br s, 2H), 3.11 (s, 3H), 3.67 (d, J=11.80 Hz, 2H), 3.77 (s, 3H), 5.18 (tt, J=12.25, 3.75 Hz, 1H), 5.66 (s, 2H), 6.83 (d, J=8.78 Hz, 2H), 7.56 (d, J=8.66 Hz, 2H), 8.27 (s, 1H), 8.43 (s, 1H). [M+H]=435.3.

Example 12

9-((2-(Dimethylamino)ethyl)(methyl)amino)-6-(4-methoxybenzyl)-[1,2,4]triazolo[1,5-c]pteridin-5(6H)-one

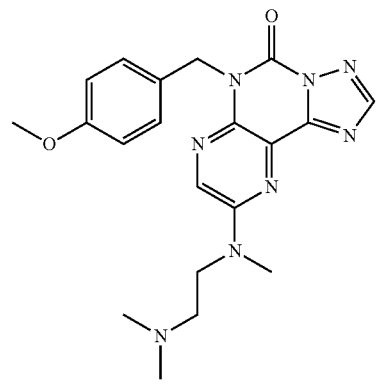 [SMILES: COc1ccc(Cn2c(=O)n3ncnc3c3nc(N(C)CCN(C)C)cnc32)cc1]

$^1$H NMR (400 MHz, CDCl$_3$) δ 3.02 (s, 6H), 3.29 (s, 3H), 3.40 (t, J=6.15 Hz, 2H), 3.76 (s, 3H), 4.18 (t, J=6.15 Hz, 2H), 5.65 (s, 2H), 6.83 (d, J=8.66 Hz, 2H), 7.56 (d, J=8.66 Hz, 2H), 8.27 (s, 1H), 8.37 (s, 1H), 12.76 (br s, 1H). [M+H]=409.2.

Example 13

6-(4-Methoxybenzyl)-9-(4-(2-methoxyethyl)piperazin-1-yl)pyrido[3,2-e][1,2,4]triazolo[1,5-c]pyrimidin-5(6H)-one

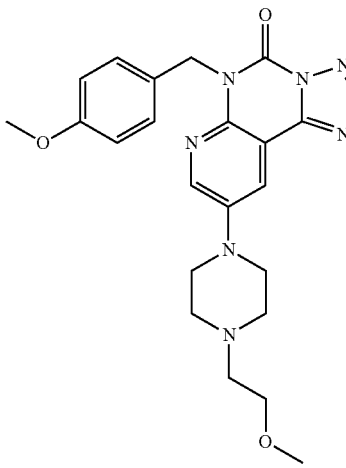

$^1$H NMR (400 MHz, CDCl$_3$-d) δ 3.29-3.35 (m, 2H), 3.40 (s, 3H), 3.64 (br s, 8H), 3.77 (s, 3H), 3.81-3.87 (m, 2H), 5.71 (s, 2H), 6.83 (d, J=8.53 Hz, 2H), 7.57 (d, J=8.41 Hz, 2H), 8.08 (d, J=2.89 Hz, 1H), 8.34 (s, 1H), 8.49 (d, J=2.76 Hz, 1H). [M+H]=450.3.

Example 14

9-(3-(Dimethylamino)pyrrolidin-1-yl)-6-(4-methoxybenzyl)pyrido[3,2-e][1,2,4]triazolo[1,5-c]pyrimidin-5(6H)-one

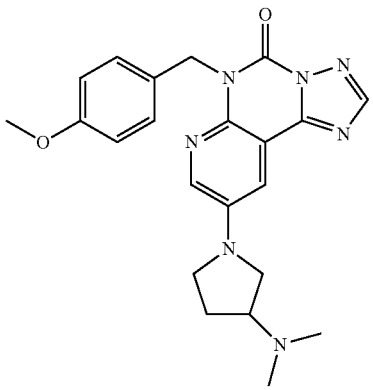 [SMILES: COc1ccc(Cn2c(=O)n3ncnc3c3cc(N4CCC(N(C)C)C4)cnc32)cc1]

$^1$H NMR (400 MHz, CDCl$_3$-d) δ 2.58 (d, J=8.03 Hz, 2H), 2.91 (s, 6H), 3.45-3.59 (m, 3H), 3.76 (s, 3H), 3.78-3.95 (m, 3H), 5.71 (s, 2H), 6.82 (d, J=8.41 Hz, 2H), 7.58 (d, J=8.78 Hz, 2H), 7.70 (d, J=3.01 Hz, 1H), 8.22 (d, J=2.63 Hz, 1H), 8.33 (s, 1H). [M+H]=420.2.

Example 15

9-(4-(Dimethylamino)piperidin-1-yl)-6-(4-methoxybenzyl)pyrido[3,2-e][1,2,4]triazolo[1,5-c]pyrimidin-5(6H)-one

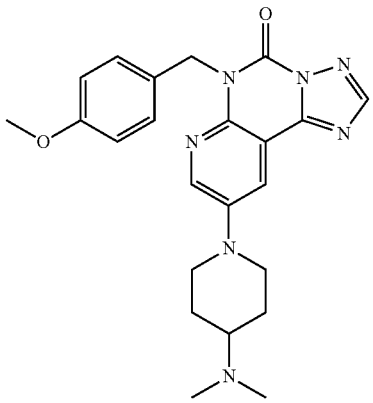 [SMILES: COc1ccc(Cn2c(=O)n3ncnc3c3cc(N4CCC(N(C)C)CC4)cnc32)cc1]

$^1$H NMR (400 MHz, CDCl$_3$) δ 1.90-2.08 (m, 2H), 2.27 (d, J=9.91 Hz, 2H), 2.85 (s, 6H), 2.96 (t, J=12.11 Hz, 2H), 3.25-3.38 (m, 1H), 3.77 (s, 3H), 3.94 (d, J=11.92 Hz, 2H), 5.71 (s, 2H), 6.83 (d, J=8.53 Hz, 2H), 7.58 (d, J=8.53 Hz, 2H), 8.05 (d, J=2.89 Hz, 1H), 8.34 (s, 1H), 8.51 (d, J=2.89 Hz, 1H). [M+H]=434.3.

Example 16

6-(4-Methoxybenzyl)-9-(methyl(tetrahydro-2H-pyran-4-yl)amino)pyrido[3,2-e][1,2,4]triazolo[1,5-c]pyrimidin-5(6H)-one

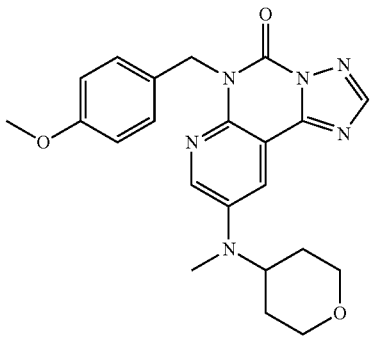 [SMILES: COc1ccc(Cn2c(=O)n3ncnc3c3cc(N(C)C4CCOCC4)cnc32)cc1]

$^1$H NMR (400 MHz, DMSO-d$_6$) δ 1.54 (d, J=11.67 Hz, 2H), 1.64-1.81 (m, 2H), 2.80 (s, 3H), 3.40-3.48 (m, 2H), 3.63 (s, 3H), 3.86 (dd, J=11.04, 4.02 Hz, 2H), 4.03 (t, J=11.42 Hz, 1H), 5.47 (s, 2H), 6.78 (d, J=8.66 Hz, 2H), 7.27 (d, J=8.53 Hz, 2H), 7.78 (d, J=3.01 Hz, 1H), 8.47 (d, J=3.14 Hz, 1H), 8.50 (s, 1H). [M+H]=421.1.

Example 17

9-((2S,6R)-2,6-Dimethylmorpholino)-6-(4-methoxybenzyl)pyrido[3,2-e][1,2,4]triazolo[1,5-c]pyrimidin-5(6H)-one

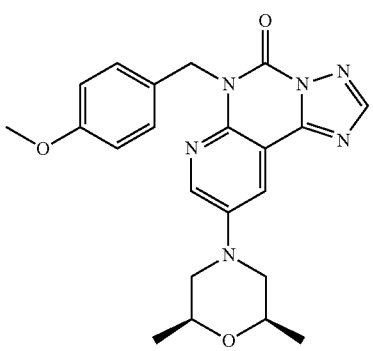 [SMILES: COc1ccc(Cn2c(=O)n3ncnc3c3cc(N4C[C@@H](C)O[C@@H](C)C4)cnc32)cc1]

$^1$H NMR (400 MHz, DMSO-d$_6$) δ 1.11 (d, J=6.15 Hz, 6H), 2.33 (t, J=10.98 Hz, 2H), 3.63 (s, 3H), 3.64-3.69 (m, 2H), 3.73 (d, J=11.80 Hz, 2H), 5.48 (s, 2H), 6.77 (d, J=8.53 Hz, 2H), 7.27 (d, J=8.41 Hz, 2H), 7.93 (d, J=2.76 Hz, 1H), 8.51 (s, 1H), 8.54 (d, J=2.76 Hz, 1H). [M+H]=421.1.

Example 18

9-((3-(Dimethylamino)propyl)(methyl)amino)-6-(4-methoxybenzyl)pyrido[3,2-e][1,2,4]triazolo[1,5-c]pyrimidin-5(6H)-one

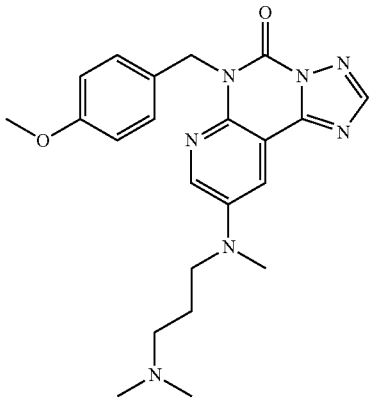 [SMILES: COc1ccc(Cn2c(=O)n3ncnc3c3cc(N(C)CCCN(C)C)cnc32)cc1]

$^1$H NMR (400 MHz, DMSO-d$_6$) δ 1.93 (dt, J=15.12, 7.37 Hz, 2H), 2.79 (d, J=4.14 Hz, 6H), 3.05 (s, 3H), 3.10-3.19 (m, 2H), 3.51-3.56 (m, 2H), 3.71 (s, 3H), 5.56 (s, 2H), 6.86 (d, J=8.53 Hz, 2H), 7.34 (d, J=8.41 Hz, 2H), 7.78 (d, J=2.89 Hz, 1H), 8.44 (d, J=2.89 Hz, 1H), 8.59 (s, 1H), 9.43 (br s, 1H). [M+H]=422.2.

Example 19

6-(4-Methoxybenzyl)-9-(4-(methylsulfonyl)piperazin-1-yl)pyrido[3,2-e][1,2,4]triazolo[1,5-c]pyrimidin-5(6H)-one

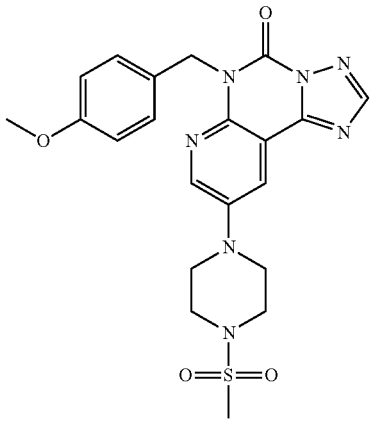 [SMILES: COc1ccc(Cn2c(=O)n3ncnc3c3cc(N4CCN(S(C)(=O)=O)CC4)cnc32)cc1]

$^1$H NMR (400 MHz, DMSO-d$_6$) δ 2.88 (s, 3H), 3.23 (d, J=5.27 Hz, 4H), 3.34-3.43 (m, 4H), 3.63 (s, 3H), 5.48 (s, 2H), 6.78 (d, J=8.53 Hz, 2H), 7.27 (d, J=8.41 Hz, 2H), 8.00 (d, J=2.89 Hz, 1H), 8.52 (s, 1H), 8.57 (d, J=2.89 Hz, 1H). [M+H]=470.1.

Example 20

Benzyl (2-(6-(4-methoxybenzyl)-5-oxo-5,6-dihydropyrido[3,2-e][1,2,4]triazolo[1,5-c]pyrimidin-9-yl)ethyl)carbamate

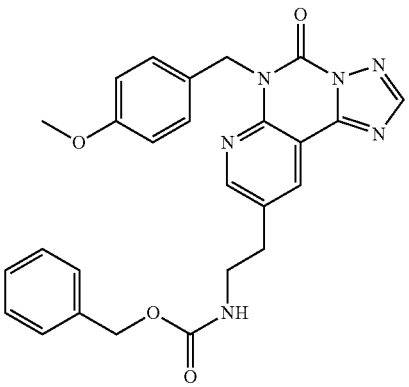 [SMILES: COc1ccc(Cn2c(=O)n3ncnc3c3cc(CCNC(=O)OCc4ccccc4)cnc32)cc1]

Benzyl 2-(6-(4-methoxybenzyl)-5-oxo-5,6-dihydropyrido[3,2-e][1,2,4]triazolo[1,5-c]pyrimidin-9-yl)ethylcarbamate.
9-Bromo-6-(4-methoxybenzyl)pyrido[3,2-e][1,2,4]triazolo[1,5-c]pyrimidin-5(6H)-one (Example 1, 30 mg, 0.078 mol), potassium (2-(benzyloxycarbonylamino)ethyl)trifluoroborate (30 mg, 0.11 mol), Cs$_2$CO$_3$ (122 mg, 0.38 mmol), PdCl$_2$(dppf)-DCM (5 mg, 0.01 mol), toluene (0.75 mL) and degassed water (0.25 mL) were added in order. The mixture was heated at 80° C. for 16 h, concentrated under a stream of nitrogen. The crude residue was taken up in DMF (1.5 mL), filtered and purified (HPLC, 0-85% ACN in water) to afford the title compound (6 mg, 12%) as a white solid. $^1$H NMR (400 MHz, DMSO-d$_6$) δ 2.92 (t, J=5.4 Hz, 2H), 3.35-3.36 (m, 2H), 3.69 (s, 3H), 4.94 (s, 2H), 5.58 (s, 2H), 6.83-6.85 (m, 2H), 7.24-7.26 (m, 2H), 7.35-7.37 (m, 2H), 7.40 (dd, J=4.4, 4.4 Hz, 1H), 8.51 (d, J=1.5 Hz, 1H), 8.61 (s, 1H), 8.65 (d, J=1.6 Hz, 1H). [M+H]=485.2.

Examples 21 thru 26 were made in a manner analogous to Example 9, with the appropriate starting material and reagent substitutions.

Example 21

6-(4-Methoxybenzyl)-8-(morpholinomethyl)pyrido[3,2-e][1,2,4]triazolo[1,5-c]pyrimidin-5(6H)-one

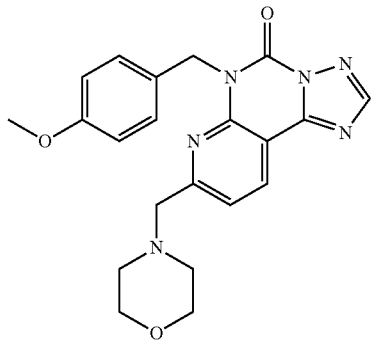 [SMILES: COc1ccc(Cn2c(=O)n3ncnc3c3ccc(CN4CCOCC4)nc32)cc1]

1H NMR (DMSO-d$_6$) δ 3.62-3.20 (m, 6H), 3.71 (s, 3H), 4.05-3.90 (m, 2H), 4.56 (s, 2H), 5.60 (s, 2H), 6.87-6.84 (m, 2H), 7.38 (d, J=7.0 Hz, 2H), 8.67 (s, 1H), 8.86-8.40 (m, 2H), 10.15 (br s, 1H). [M+H]=407.2.

Example 22

6-(4-Methoxybenzyl)-9-(piperidin-1-ylmethyl)pyrido[3,2-e][1,2,4]triazolo[1,5-c]pyrimidin-5(6H)-one

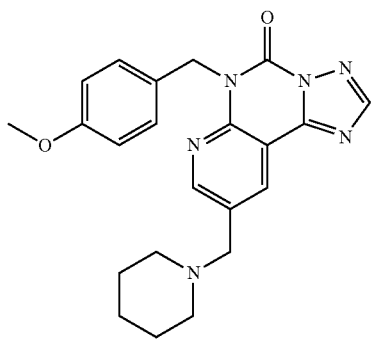 [SMILES: COc1ccc(Cn2c(=O)n3ncnc3c3cc(CN4CCCCC4)cnc32)cc1]

$^1$H NMR (400 MHz, CDCl$_3$) δ 1.98 (br s, 6H), 2.57-2.93 (m, 2H), 3.56-3.72 (m, 2H), 3.78 (s, 3H), 4.38 (s, 2H), 5.76 (s, 2H), 6.85 (d, J=8.66 Hz, 2H), 7.60 (d, J=8.66 Hz, 2H), 8.37 (s, 1H), 8.73 (s, 1H), 8.97 (s, 1H). [M+H]=405.3.

Example 23

6-(4-Methoxybenzyl)-9-(thiomorpholinomethyl)pyrido[3,2-e][1,2,4]triazolo[1,5-c]pyrimidin-5(6H)-one

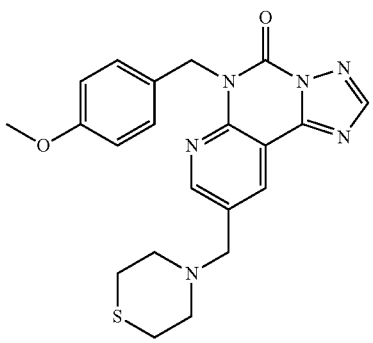 [SMILES: COc1ccc(Cn2c(=O)n3ncnc3c3cc(CN4CCSCC4)cnc32)cc1]

$^1$H NMR (400 MHz, CDCl$_3$) δ 3.03 (br s, 4H), 3.47 (br s, 4H), 3.78 (s, 3H), 4.38 (s, 2H), 5.75 (s, 2H), 6.84 (d, J=8.66 Hz, 2H), 7.59 (d, J=8.66 Hz, 2H), 8.37 (s, 1H), 8.74 (d, J=2.01 Hz, 1H), 8.93 (d, J=2.13 Hz, 1H). [M+H]=423.2.

Example 24

6-(4-Chlorobenzyl)-9-(morpholinomethyl)pyrido[3,2-e][1,2,4]triazolo[1,5-c]pyrimidin-5(6H)-one

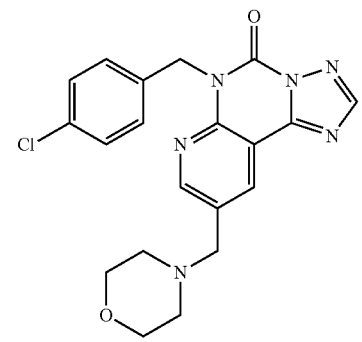 [SMILES: O=c1n(Cc2ccc(Cl)cc2)c2ncc(CN3CCOCC3)cc2c2ncnn12]

$^1$H NMR (400 MHz, CDCl$_3$) δ 3.54 (br s, 3H), 4.04 (t, J=4.45 Hz, 4H), 4.41 (s, 2H), 5.78 (s, 2H), 7.30 (d, J=8.78 Hz, 5H), 7.54-7.68 (m, 2H), 8.43 (s, 1H), 8.82 (s, 1H), 8.97 (s, 1H). [M+H]=411.1.

Example 25

6-(4-Chlorobenzyl)-9-(piperidin-1-ylmethyl)pyrido[3,2-e][1,2,4]triazolo[1,5-c]pyrimidin-5(6H)-one

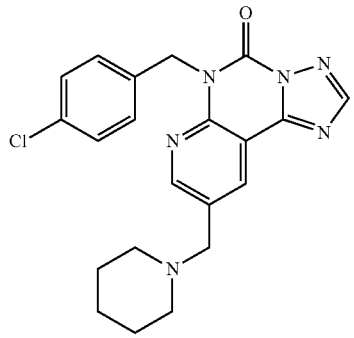

$^1$H NMR (400 MHz, CDCl$_3$) δ 1.96 (br s, 3H), 2.01-2.24 (m, 2H), 2.75 (t, J=11.73 Hz, 2H), 3.55 (br s, 3H), 3.68 (d, J=11.04 Hz, 3H), 4.38 (s, 2H), 5.78 (s, 2H), 7.31 (d, J=8.41 Hz, 2H), 7.60 (d, J=8.41 Hz, 2H), 8.42 (s, 1H), 8.82 (d, J=1.88 Hz, 1H), 9.04 (d, J=1.76 Hz, 1H). [M+H]=409.1.

Example 26

6-(4-Chlorobenzyl)-9-(((2S,6R)-2,6-dimethylmorpholino)methyl)pyrido[3,2-e][1,2,4]triazolo[1,5-c]pyrimidin-5(6H)-one

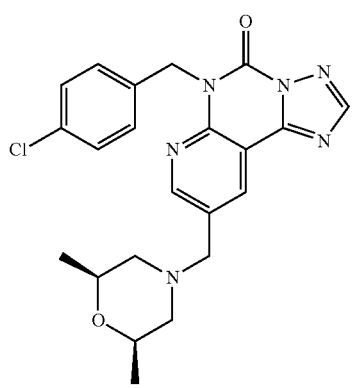 [SMILES: C[C@@H]1CN(Cc2cnc3c(c2)c2ncnn2c(=O)n3Cc2ccc(Cl)cc2)C[C@H](C)O1]

$^1$H NMR (400 MHz, CDCl$_3$) δ 1.26 (d, J=6.27 Hz, 6H), 2.50 (t, J=11.11 Hz, 2H), 3.48 (d, J=11.29 Hz, 2H), 4.14 (dd, J=10.16, 5.90 Hz, 2H), 4.36 (s, 2H), 5.78 (s, 2H), 7.31 (d, J=8.53 Hz, 2H), 7.60 (d, J=8.53 Hz, 2H), 8.44 (s, 1H), 8.83 (d, J=1.63 Hz, 1H), 9.04 (s, 1H). [M+H]=439.2.

Example 27

9-(2-Aminoethyl)-6-(4-methoxybenzyl)pyrido[3,2-e][1,2,4]triazolo[1,5-c]pyrimidin-5(6H)-one

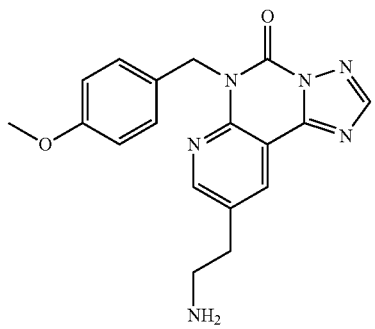 [SMILES: COc1ccc(Cn2c(=O)n3ncnc3c3cc(CCN)cnc32)cc1]

Step A. tert-Butyl 2-(6-(4-methoxybenzyl)-5-oxo-5,6-dihydropyrido[3,2-e][1,2,4]triazolo[1,5-c]pyrimidin-9-yl)ethylcarbamate. The title compound was made in a manner analogous to Example 20, with the appropriate starting material and reagent substitutions.

Step B. 9-(2-Aminoethyl)-6-(4-methoxybenzyl)pyrido[3,2-e][1,2,4]triazolo[1,5-c]pyrimidin-5(6H)-one. tert-Butyl 2-(6-(4-methoxybenzyl)-5-oxo-5,6-dihydropyrido[3,2-e][1,2,4]triazolo[1,5-c]pyrimidin-9-yl)ethylcarbamate (6 mg, 0.011 mmol) was treated with DCM (2 mL) and 2,2,2-trifluoroacetic acid (2 mL), stirred for 1 h and concentrated under vacuum. The residue was suspended in chloroform (3 mL) and concentrated and dissolved in methanol (3 mL) and concentrated again to afford 4 mg (12%) of the TFA salt of the title compound as a white solid. $^1$H NMR (400 MHz, DMSO-d$_6$) δ 3.05 (t, J=6.0 Hz, 2H), 3.21 (t, J=5.9 Hz, 2H), 3.70 (s, 3H), 5.59 (s, 2H), 6.84-6.87 (m, 2H), 7.35-7.37 (m, 2H), 7.83-7.86 (m, 3H), 8.62 (d, J=1.8 Hz, 1H), 8.63 (s, 1H), 8.71 (d, J=1.9 Hz, 1H). [M+H]=351.2.

Example 28

6-(4-Methoxybenzyl)-9-(2-((tetrahydro-2H-pyran-4-yl)amino)ethyl)pyrido[3,2-e][1,2,4]triazolo[1,5-c]pyrimidin-5(6H)-one

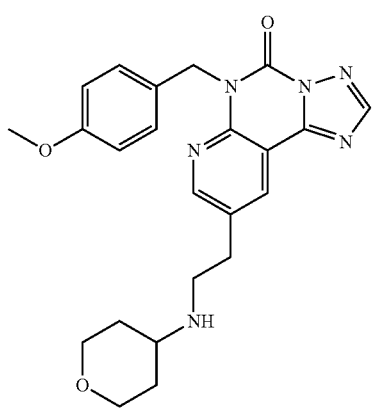 [SMILES: COc1ccc(Cn2c(=O)n3ncnc3c3cc(CCNC4CCOCC4)cnc32)cc1]

6-(4-Methoxybenzyl)-9-(2-(tetrahydro-2H-pyran-4-ylamino)ethyl)pyrido[3,2-e][1,2,4]triazolo[1,5-c]pyrimidin- 5(6H)-one. 9-(2-Aminoethyl)-6-(4-methoxybenzyl)pyrido[3,2-e][1,2,4]triazolo[1,5-c]pyrimidin-5(6H)-one (Example 27, 38 mg, 0.11 mmol), DCM (1 mL), methanol (0.5 mL), tetrahydro-4H-pyran-4-one (65 mg, 0.65 mmol), and TEA (18 µL, 0.13 mmol) were combined and stirred for 20 minutes. Sodium cyanoborohydride (24 mg, 0.38 mmol) was added and the mixture was stirred for 18 h. Water (0.1 mL) was added, the mixture was stirred for 1 h, and then concentrated under a stream of nitrogen. The residue was taken up in DMF, filtered and purified by HPLC to afford the trifluoroacetic acid salt of the title compound (24 mg, 40%) as a white solid. $^1$H NMR (400 MHz, DMSO-$d_6$) δ 1.54 (qd, J=9.8, 6.1 Hz, 2H), 1.97 (dd, J=9.9, 3.5 Hz, 2H), 3.13-3.10 (m, 2H), 3.39-3.29 (m, 5H), 3.70 (s, 3H), 3.92 (dd, J=9.1, 3.2 Hz, 2H), 5.59 (s, 2H), 6.85 (d, J=7.0 Hz, 2H), 7.36 (d, J=7.0 Hz, 2H), 8.64 (s, 1H), 8.67 (d, J=1.9 Hz, 1H), 8.71 (br s, 2H), 8.73 (d, J=1.8 Hz, 1H). [M+H]=435.3.

Example 29 was made in a manner analogous to Example 28, with the appropriate starting material and reagent substitutions.

Example 29

6-(4-Methoxybenzyl)-9-(2-((1-phenylethyl)amino)ethyl)pyrido[3,2-e][1,2,4]triazolo[1,5-c]pyrimidin-5(6H)-one

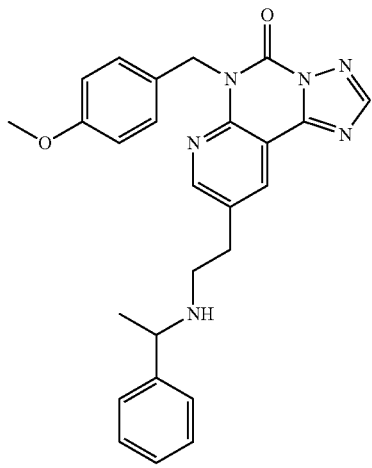 [SMILES: COc1ccc(Cn2c(=O)n3ncnc3c3cc(CCNC(C)c4ccccc4)cnc32)cc1]

$^1$H NMR (400 MHz, DMSO-$d_6$) δ 1.58 (d, J=5.5 Hz, 3H), 3.31-3.06 (m, 4H), 3.70 (s, 3H), 4.43 (q, J=5.1 Hz, 1H), 5.57 (s, 2H), 6.85 (d, J=7.0 Hz, 2H), 7.35 (d, J=7.0 Hz, 2H), 7.51-7.40 (m, 5H), 8.59 (d, J=1.8 Hz, 1H), 8.63 (s, 1H), 8.66 (d, J=1.8 Hz, 1H), 8.97 (br s, 1H), 9.11 (br s, 1H). [M+H]=455.2.

Example 30

6-(4-Methoxybenzyl)-9-vinylpyrido[3,2-e][1,2,4]triazolo[1,5-c]pyrimidin-5(6H)-one

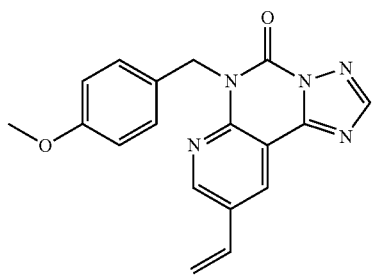 [SMILES: C=Cc1cnc2c(c1)c1ncnn1c(=O)n2Cc1ccc(OC)cc1]

Method A. 6-(4-Methoxybenzyl)-9-vinylpyrido[3,2-e][1,2,4]triazolo[1,5-c]pyrimidin-5(6H)-one. 9-Bromo-6-(4-methoxybenzyl)pyrido[3,2-e][1,2,4]triazolo[1,5-c]pyrimidin-5(6H)-one (Example 1, 500 mg, 1.29 mmol), tributyl(vinyl)stannane (0.45 mL, 1.6 mmol), toluene (5 mL) and tetrakis(triphenylphosphoranyl)-palladium (33 mg, 0.03 mmol) were combined and heated at 100° C. for 16 h. The mixture was filtered through CELITE® with DCM washing, concentrated under reduced pressure. Purification (FCC, 10-100% EtOAc/hexanes) afforded the title compound (398 mg, 92%) as a white solid. $^1$H NMR (400 MHz, CDCl$_3$) δ 3.76 (s, 3H), 5.52 (d, J=11.04 Hz, 1H), 5.75 (s, 2H), 5.98 (d, J=17.69 Hz, 1H), 6.77-6.86 (m, 3H), 7.56-7.67 (m, 2H), 8.36 (s, 1H), 8.66 (d, J=2.38 Hz, 1H), 8.79 (d, J=2.38 Hz, 1H). [M+H]=334.1.

Method B. 6-(4-Methoxybenzyl)-9-vinylpyrido[3,2-e][1,2,4]triazolo[1,5-c]pyrimidin-5(6H)-one. 9-Bromo-6-(4-methoxybenzyl)pyrido[3,2-e][1,2,4]triazolo[1,5-c]pyrimidin-5(6H)-one (Example 1, 2.00 g, 5.18 mmol), potassium trifluoro(vinyl)borate (1.51 g, 11.3 mmol), butan-1-ol (20 mL), TEA (1.05 mL, 7.53 mmol) and [1,1'-bis(diphenylphosphino)ferrocene]dichloropalladium(II)-DCM complex (0.31 g, 0.38 mmol) were combined and heated at 100° C. for 20 h. The mixture was cooled, concentrated under reduced pressure. The crude product was dissolved in DCM (120 mL), washed with water (50 mL), and brine (50 mL), dried (MgSO$_4$) and concentrated under reduced pressure. The crude residue was triturated with EtOAc (15 mL), filtered, washed with cold EtOAc and suction dried to afford the title compound (1.09 g, 63%) as a yellow powder. $^1$H NMR (400 MHz, CDCl$_3$) δ 3.76 (s, 3H), 5.52 (d, J=10.92 Hz, 1H), 5.75 (s, 2H), 5.98 (d, J=17.57 Hz, 1H), 6.75-6.88 (m, 3H), 7.60 (d, J=8.66 Hz, 2H), 8.36 (s, 1H), 8.66 (d, J=2.13 Hz, 1H), 8.79 (d, J=2.26 Hz, 1H). [M+H]=334.1.

Examples 31 and 32 were made in a manner analogous to Example 30, Method A, with the appropriate starting material and reagent substitutions.

Example 31

6-(4-Methoxybenzyl)-9-((methoxymethoxy)methyl)pyrido[3,2-e][1,2,4]triazolo[1,5-c]pyrimidin-5(6H)-one

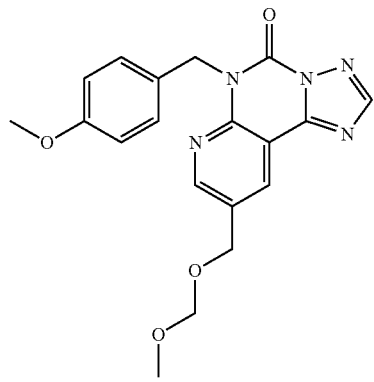 [SMILES: COCOCc1cnc2c(c1)c1ncnn1c(=O)n2Cc1ccc(OC)cc1]

¹H NMR (400 MHz, CDCl₃) δ 3.45 (s, 3H), 3.76 (s, 3H), 4.75 (s, 2H), 4.78 (s, 2H), 5.76 (s, 2H), 6.78-6.87 (m, 2H), 7.57-7.67 (m, 2H), 8.36 (s, 1H), 8.65 (d, J=2.26 Hz, 1H), 8.78 (d, J=2.26 Hz, 1H). [M+H]=382.1.

Example 32

9-(1-Ethoxyvinyl)-6-(4-methoxybenzyl)pyrido[3,2-e][1,2,4]triazolo[1,5-c]pyrimidin-5(6H)-one

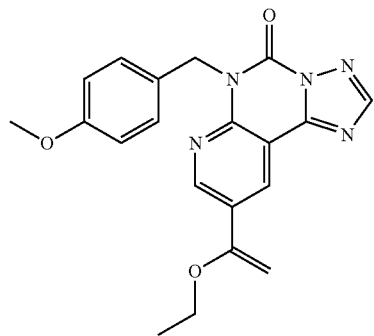 [SMILES: C=C(OCC)c1cnc2c(c1)c1ncnn1c(=O)n2Cc1ccc(OC)cc1]

¹H NMR (400 MHz, CDCl₃) δ 1.48 (t, J=6.96 Hz, 3H), 3.77 (s, 3H), 4.00 (q, J=6.94 Hz, 2H), 4.41 (d, J=3.14 Hz, 1H), 4.84 (d, J=3.14 Hz, 1H), 5.76 (s, 2H), 6.83 (d, J=8.53 Hz, 2H), 7.60 (d, J=8.53 Hz, 2H), 8.36 (s, 1H), 8.83 (d, J=2.13 Hz, 1H), 9.04 (d, J=2.01 Hz, 1H). [M+H]=378.2.

Example 33

9-(Hydroxymethyl)-6-(4-methoxybenzyl)pyrido[3,2-e][1,2,4]triazolo[1,5-c]pyrimidin-5(6H)-one

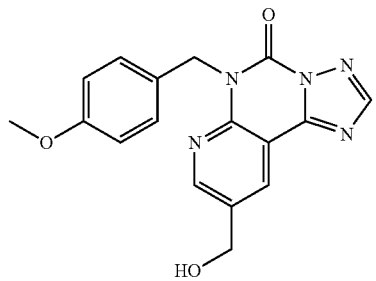 [SMILES: COc1ccc(Cn2c(=O)n3ncnc3c3cc(CO)cnc32)cc1]

9-(Hydroxymethyl)-6-(4-methoxybenzyl)pyrido[3,2-e][1,2,4]triazolo[1,5-c]pyrimidin-5(6H)-one. A suspension of 6-(4-methoxybenzyl)-9-((methoxymethoxy)methyl)pyrido[3,2-e][1,2,4]triazolo[1,5-c]pyrimidin-5(6H)-one (Example 31, 40 mg, 0.10 mmol), methanol (0.80 mL) and 5 N hydrochloric acid (0.40 mL) was stirred at 50° C. for 16 h. The mixture was extracted with DCM (1 mL), basified to pH 14 with 15% aqueous sodium hydroxide and extracted with DCM (2 mL). The combined DCM extracts were concentrated under reduced pressure. Purification (HPLC, 10-90% ACN-water) afforded the title compound (21 mg, 59%) as a white powder. ¹H NMR (400 MHz, DMSO-d₆) δ 3.69 (s, 3H), 4.69 (d, J=4.6 Hz, 2H), 5.54 (t, J=4.6 Hz, 1H), 5.59 (s, 2H), 6.84 (d, J=6.9 Hz, 2H), 7.36 (d, J=6.9 Hz, 2H), 8.58 (d, J=1.6 Hz, 1H), 8.60 (s, 1H), 8.72 (d, J=1.6 Hz, 1H). [M+H]=338.1.

Example 34

9-(2-Oxa-5-azabicyclo[2.2.1]heptan-5-ylmethyl)-6-(4-methoxybenzyl)pyrido[3,2-e][1,2,4]triazolo[1,5-c]pyrimidin-5(6H)-one

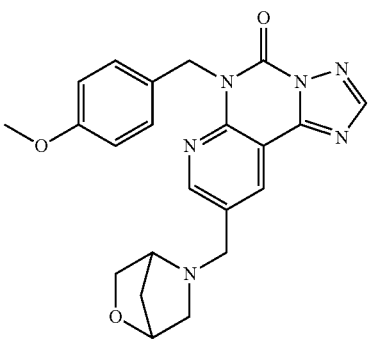 [SMILES: COc1ccc(Cn2c(=O)n3ncnc3c3cc(CN4CC5CC4CO5)cnc32)cc1]

Step A: 6-(4-Methoxybenzyl)-5-oxo-5,6-dihydropyrido[3,2-e][1,2,4]triazolo[1,5-c]pyrimidine-9-carbaldehyde. 6-(4-

Methoxybenzyl)-9-vinylpyrido[3,2-e][1,2,4]triazolo[1,5-c]pyrimidin-5(6H)-one (Example 30, 3.96 g, 11.9 mmol) was suspended in THF (80 mL) and heated with a heat gun to effect dissolution. Similarly, sodium periodate (5.84 g, 27.3 mmol) was heated in water (40 mL) to effect dissolution. The above solutions were combined with vigorous stirring. While the stirred mixture was still at 40° C., osmium(VIII) oxide in ten-butanol (2.90 mL, 2.5%, 0.30 mmol) was added and the mixture was stirred vigorously for 4 h. The reaction mixture was diluted with water (300 mL) and extracted with EtOAc (3×150 mL) and DCM (3×150 mL). The combined organic layers were dried (MgSO$_4$) and concentrated to afford the title compound (4.13 g, 99%) as a black solid which was used in the next step without further purification. $^1$H NMR (400 MHz, CDCl$_3$) δ 3.77 (s, 3H), 5.80 (s, 2H), 6.83 (d, J=8.66 Hz, 2H), 7.61 (d, J=8.66 Hz, 2H), 8.41 (s, 1H), 9.10 (d, J=2.13 Hz, 1H), 9.26 (d, J=2.13 Hz, 1H), 10.21 (s, 1H). [M+H]=336.2.

Step B: 9-(2-oxa-5-azabicyclo[2.2.1]heptan-5-ylmethyl)-6-(4-methoxybenzyl)pyrido[3,2-e][1,2,4]triazolo[1,5-c]pyrimidin-5(6H)-one. 6-(4-Methoxybenzyl)-5-oxo-5,6-dihydropyrido[3,2-e][1,2,4]triazolo[1,5-c]pyrimidine-9-carbaldehyde (49 mg, 0.15 mmol), 2-oxa-5-azabicyclo[2.2.1]heptane (49 mg, 0.36 mmol), ACN (1 mL), TEA (0.051 mL, 0.37 mmol) and acetic acid (0.040 mL, 0.69 mmol) were combined and stirred for 10 minutes. Sodium cyanoborohydride (18 mg, 0.29 mmol) was added and the mixture was stirred for 18 h at room temperature. The mixture was diluted with methanol, filtered, and purified by preparative HPLC to afford the title compound (35 mg, 45%) as the trifluoroacetic acid salt as a white solid. $^1$H NMR (400 MHz, CDCl$_3$) δ 2.25 (d, J=11.42 Hz, 1H), 2.43 (br s, 1H), 3.44-3.63 (m, 2H), 3.76 (s, 3H), 3.91 (d, J=10.42 Hz, 1H), 4.37-4.53 (m, 3H), 4.56-4.65 (m, 1H), 4.73 (s, 1H), 5.74 (s, 2H), 6.76-6.91 (m, 2H), 7.60 (d, J=8.78 Hz, 2H), 8.38 (s, 1H), 8.83 (s, 1H), 9.08 (s, 1H). [M+H]=419.2.

Examples 35 thru 64 were made in a manner analogous to Example 34, with the appropriate starting material and reagent substitutions.

Example 35

9-((Dimethylamino)methyl)-6-(4-methoxybenzyl)pyrido[3,2-e][1,2,4]triazolo[1,5-c]pyrimidin-5(6H)-one

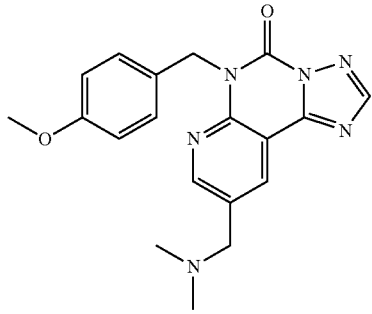 [SMILES: COc1ccc(Cn2c(=O)n3ncnc3c3cc(CN(C)C)cnc32)cc1]

1H NMR (DMSO-d$_6$) δ 2.80 (s, 6H), 3.70 (s, 3H), 4.50 (s, 2H), 5.60 (s, 2H), 6.86 (d, J=7.0 Hz, 2H), 7.38 (d, J=7.0 Hz, 2H), 8.66 (s, 1H), 8.84 (d, J=1.8 Hz, 1H), 8.89 (d, J=1.8 Hz, 1H), 9.89 (br s, 1H). [M+H]=365.2.

Example 36

9-(((2S,6R)-2,6-dimethylmorpholino)methyl)-6-(4-methoxybenzyl)pyrido[3,2-e][1,2,4]triazolo[1,5-c]pyrimidin-5(6H)-one

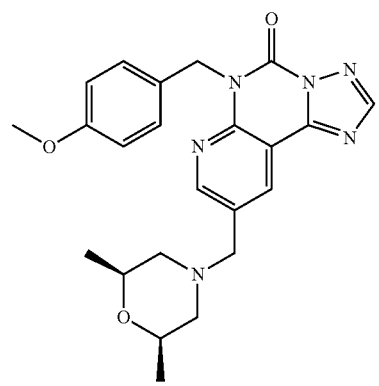

$^1$H NMR (400 MHz, CDCl$_3$) δ 1.23 (d, J=6.27 Hz, 6H), 2.39-2.52 (m, 2H), 3.35 (d, J=11.42 Hz, 2H), 3.77 (s, 3H), 4.31 (br s, 2H), 4.34-4.45 (m, 2H), 5.74 (s, 2H), 6.83 (d, J=8.53 Hz, 2H), 7.62 (d, J=8.53 Hz, 2H), 8.38 (s, 1H), 8.90 (d, J=2.26 Hz, 1H), 9.34 (d, J=2.13 Hz, 1H), 13.90 (br s, 1H). [M+H]=435.3.

Example 37

6-(4-Methoxybenzyl)-9-(4-methylpiperazin-1-yl)methyl)pyrido[3,2-e][1,2,4]triazolo[1,5-c]pyrimidin-5(6H)-one

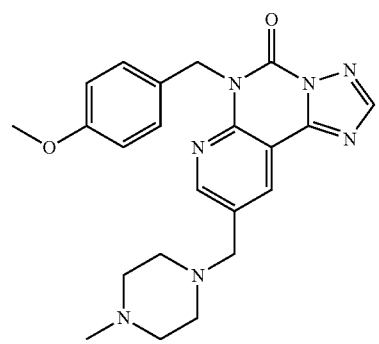 [SMILES: COc1ccc(Cn2c(=O)n3ncnc3c3cc(CN4CCN(C)CC4)cnc32)cc1]

$^1$H NMR (400 MHz, CDCl$_3$) δ 2.89 (s, 2H), 3.11 (br s, 3H), 3.40 (br s, 2H), 3.78 (s, 2H), 3.95 (s, 1H), 5.76 (s, 1H), 6.85 (d, J=8.53 Hz, 1H), 7.60 (d, J=8.41 Hz, 1H), 8.38 (s, 1H), 8.72 (s, 1H), 8.76 (s, 1H). [M+H]=420.2.

Example 38

9-((3,3-Dimethylmorpholino)methyl)-6-(4-methoxybenzyl)pyrido[3,2-e][1,2,4]triazolo[1,5-c]pyrimidin-5(6H)-one

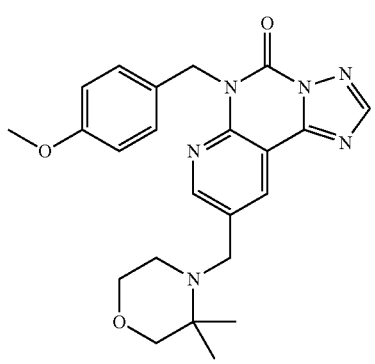 [SMILES: COc1ccc(Cn2c(=O)n3ncnc3c3cc(CN4CCOCC4(C)C)cnc32)cc1]

$^1$H NMR (400 MHz, CDCl$_3$) δ 1.65 (s, 6H), 3.12 (br s, 2H), 3.23-3.73 (m, 4H), 3.76 (s, 3H), 4.00 (br s, 2H), 5.73 (s, 2H), 6.75-6.90 (m, 2H), 7.59 (d, J=8.66 Hz, 2H), 8.37 (s, 1H), 8.81 (d, J=1.88 Hz, 1H), 9.03 (d, J=2.01 Hz, 1H). [M+H]=435.3.

Example 39

9-((2,2-Dimethylmorpholino)methyl)-6-(4-methoxybenzyl)pyrido[3,2-e][1,2,4]triazolo[1,5-c]pyrimidin-5(6H)-one

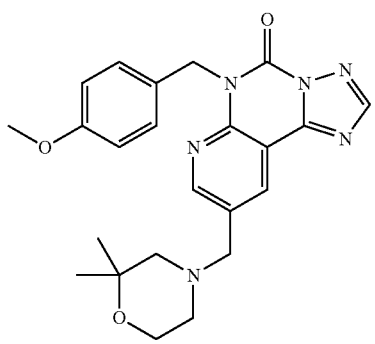 [SMILES: COc1ccc(Cn2c(=O)n3ncnc3c3cc(CN4CCOC(C)(C)C4)cnc32)cc1]

$^1$H NMR (400 MHz, CDCl$_3$) δ 1.40 (br s, 6H), 3.22-3.68 (m, 4H), 3.77 (s, 3H), 3.93-4.18 (m, 2H), 4.41 (br s, 2H), 5.74 (s, 2H), 6.74-6.91 (m, 2H), 7.61 (d, J=8.66 Hz, 2H), 8.39 (s, 1H), 8.79 (d, J=2.13 Hz, 1H), 9.05 (d, J=2.01 Hz, 1H). [M+H]=435.2.

Example 40

9-((2-Ethylmorpholino)methyl)-6-(4-methoxybenzyl)pyrido[3,2-e][1,2,4]triazolo[1,5-c]pyrimidin-5(6H)-one

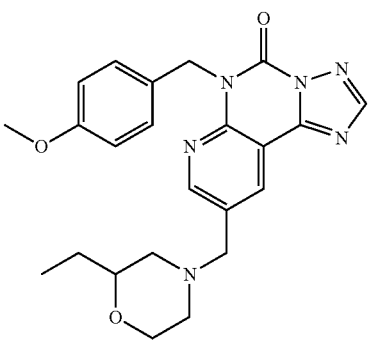 [SMILES: CCC1CN(Cc2cnc3c(c2)c2ncnn2c(=O)n3Cc2ccc(OC)cc2)CCO1]

$^1$H NMR (400 MHz, CDCl$_3$) δ 0.97 (t, J=7.47 Hz, 3H), 1.42-1.63 (m, 2H), 2.58 (t, J=11.17 Hz, 1H), 2.80-3.02 (m, 1H), 3.50 (dd, J=19.95, 11.04 Hz, 2H), 3.77 (s, 3H), 3.81-3.95 (m, 1H), 3.99-4.16 (m, 2H), 4.37 (s, 2H), 5.74 (s, 2H), 6.76-6.91 (m, 2H), 7.51-7.68 (m, 2H), 8.39 (s, 1H), 8.80 (d, J=2.26 Hz, 1H), 9.05 (d, J=2.26 Hz, 1H). [M+H]=435.2.

Example 41

9-((2,5-Dimethylmorpholino)methyl)-6-(4-methoxybenzyl)pyrido[3,2-e][1,2,4]triazolo[1,5-c]pyrimidin-5(6H)-one

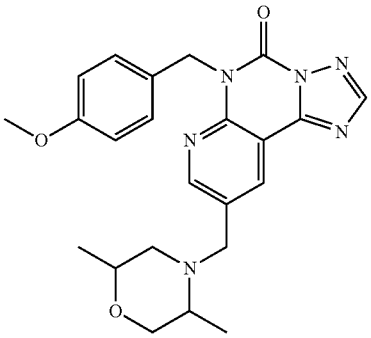 [SMILES: COc1ccc(Cn2c(=O)n3ncnc3c3cc(CN4CC(C)OCC4C)cnc32)cc1]

$^1$H NMR (400 MHz, CDCl$_3$) δ 1.25 (d, J=6.27 Hz, 3H), 1.55 (d, J=6.65 Hz, 3H), 2.80 (t, J=10.98 Hz, 1H), 3.26 (d, J=12.05 Hz, 1H), 3.59 (d, J=6.40 Hz, 1H), 3.78 (d, J=14.56 Hz, 1H), 3.74-3.83 (m, 4H), 4.05-4.18 (m, 1H), 4.23-4.36 (m, 2H), 5.74 (s, 2H), 6.78-6.92 (m, 2H), 7.55-7.70 (m, 2H), 8.32-8.46 (m, 1H), 8.85 (d, J=2.13 Hz, 1H), 9.13 (d, J=2.01 Hz, 1H). [M+H]=435.2.

Example 42

6-(4-Methoxybenzyl)-9-((2,2,6,6-tetrafluoromorpholino)methyl)pyrido[3,2-e][1,2,4]triazolo[1,5-c]pyrimidin-5(6H)-one

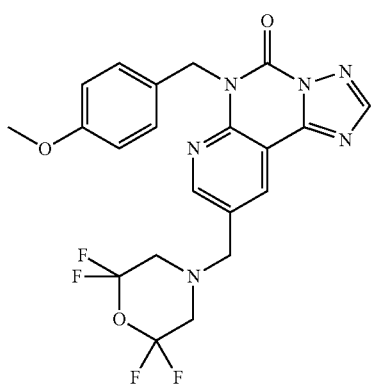 [SMILES: COc1ccc(Cn2c(=O)n3ncnc3c3cc(CN4CC(F)(F)OC(F)(F)C4)cnc32)cc1]

$^1$H NMR (400 MHz, CDCl$_3$) δ 3.08 (t, J=8.16 Hz, 4H), 3.77 (s, 3H), 3.95 (s, 2H), 5.76 (s, 2H), 6.79-6.89 (m, 2H), 7.57-7.67 (m, 2H), 8.38 (s, 1H), 8.62 (d, J=2.26 Hz, 1H), 8.78 (d, J=2.26 Hz, 1H). [M+H]=479.1.

Example 43

9-(8-Oxa-3-azabicyclo[3.2.1]octan-3-ylmethyl)-6-(4-methoxybenzyl)pyrido[3,2-e][1,2,4]triazolo[1,5-c]pyrimidin-5(6H)-one

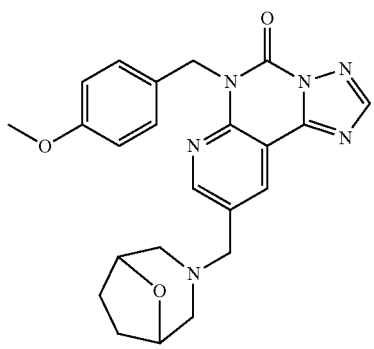 [SMILES: COc1ccc(Cn2c(=O)n3ncnc3c3cc(CN4CC5CCC(C4)O5)cnc32)cc1]

$^1$H NMR (400 MHz, CDCl$_3$) δ 2.07-2.14 (m, 2H), 2.34-2.39 (m, 2H), 3.09 (dd, J=11.98, 2.70 Hz, 2H), 3.48 (d, J=11.67 Hz, 2H), 3.77 (s, 3H), 4.37 (s, 2H), 4.53 (br s, 2H), 5.74 (s, 2H), 6.83 (d, J=8.66 Hz, 2H), 7.60 (d, J=8.66 Hz, 2H), 8.39 (s, 1H), 8.78 (d, J=2.13 Hz, 1H), 9.01 (s, 1H). [M+H]=433.3.

Example 44

6-(4-Methoxybenzyl)-9-((1-methyl-8-oxa-1,2-diazaspiro[4.5]decan-2-yl)methyl)pyrido[3,2-e][1,2,4]triazolo[1,5-c]pyrimidin-5(6H)-one

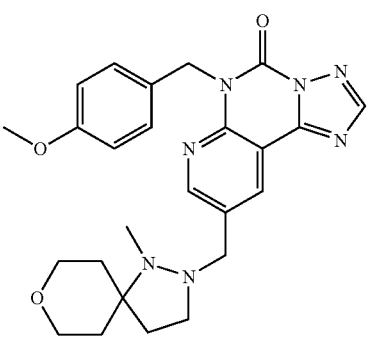 [SMILES: COc1ccc(Cn2c(=O)n3ncnc3c3cc(CN4CCC5(CCOCC5)N4C)cnc32)cc1]

$^1$H NMR (400 MHz, CDCl$_3$) δ 1.93 (br s, 2H), 2.06 (td, J=12.36, 4.89 Hz, 2H), 2.39 (t, J=7.34 Hz, 2H), 3.00 (s, 3H), 3.34 (t, J=7.47 Hz, 2H), 3.42-3.53 (m, 2H), 3.77 (s, 3H), 4.10 (dd, J=11.61, 4.71 Hz, 2H), 4.60 (s, 2H), 5.75 (s, 2H), 6.76-6.90 (m, 2H), 7.61 (d, J=8.66 Hz, 2H), 8.39 (s, 1H), 8.68 (d, J=2.13 Hz, 1H), 8.81 (d, J=2.13 Hz, 1H). [M+H]=476.3.

Example 45

6-(4-Methoxybenzyl)-9-((2-methylmorpholino)methyl)pyrido[3,2-e][1,2,4]triazolo[1,5-c]pyrimidin-5(6H)-one

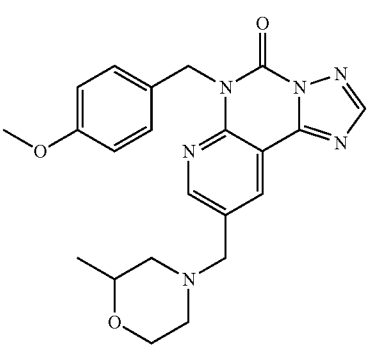 [SMILES: COc1ccc(Cn2c(=O)n3ncnc3c3cc(CN4CCOC(C)C4)cnc32)cc1]

$^1$H NMR (400 MHz, CDCl$_3$) δ 1.24 (d, J=6.27 Hz, 3H), 2.55 (t, J=11.11 Hz, 1H), 2.90 (td, J=11.26, 4.58 Hz, 1H), 3.41-3.57 (m, 2H), 3.77 (s, 3H), 3.97-4.14 (m, 3H), 4.28-4.44 (m, 2H), 5.74 (s, 2H), 6.83 (d, J=8.66 Hz, 2H), 7.60 (d, J=8.66 Hz, 2H), 8.39 (s, 1H), 8.78 (s, 1H), 9.01 (s, 1H). [M+H]=421.2.

Example 46

6-(4-Methoxybenzyl)-9-((3-methylmorpholino)methyl)pyrido[3,2-e][1,2,4]triazolo[1,5-c]pyrimidin-5(6H)-one

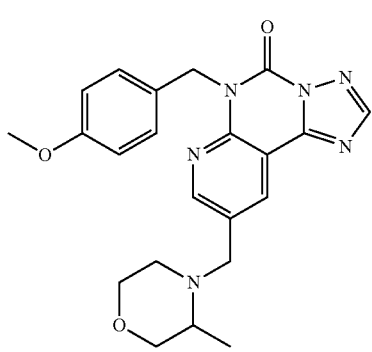 [SMILES: COc1ccc(Cn2c(=O)n3ncnc3c3cc(CN4CCOCC4C)cnc32)cc1]

$^1$H NMR (400 MHz, CDCl$_3$) δ 1.63 (d, J=6.53 Hz, 3H), 3.28 (d, J=11.80 Hz, 2H), 3.77 (s, 3H), 3.82-4.20 (m, 6H), 5.74 (s, 2H), 6.83 (d, J=8.66 Hz, 2H), 7.60 (d, J=8.66 Hz, 2H), 8.39 (s, 1H), 8.81 (d, J=1.76 Hz, 1H), 9.03 (s, 1H). [M+H]=421.3.

Example 47

9-(((2S,6R)-2,6-Dimethylmorpholino)methyl)-6-(4-methoxybenzyl)-[1,2,4]triazolo[1,5-c]pteridin-5(6H)-one

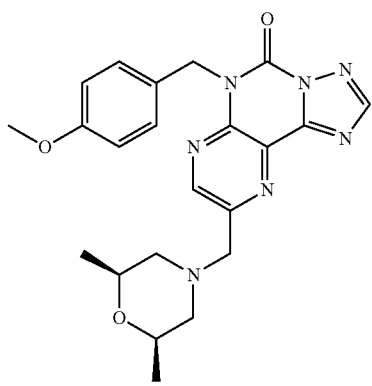 [SMILES: COc1ccc(Cn2c(=O)n3ncnc3c3nc(CN4C[C@@H](C)O[C@@H](C)C4)cnc32)cc1]

$^1$H NMR (400 MHz, CDCl$_3$) δ 1.24 (d, J=6.15 Hz, 6H), 2.68 (t, J=10.98 Hz, 2H), 3.57 (d, J=11.42 Hz, 2H), 3.75 (s, 3H), 4.00 (dd, J=9.85, 6.09 Hz, 2H), 4.53 (br s, 2H), 5.69 (s, 2H), 6.81 (d, J=8.41 Hz, 2H), 7.57 (d, J=8.41 Hz, 2H), 8.50 (s, 1H), 9.11 (s, 1H). [M+H]=436.2.

Example 48

6-(4-Methoxybenzyl)-9-((4-methyl-1,4-diazepan-1-yl)methyl)pyrido[3,2-e][1,2,4]triazolo[1,5-c]pyrimidin-5(6H)-one

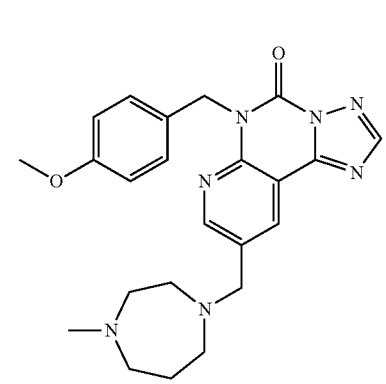 [SMILES: COc1ccc(Cn2c(=O)n3ncnc3c3cc(CN4CCCN(C)CC4)cnc32)cc1]

$^1$H NMR (400 MHz, DMSO-d$_6$) δ 1.92-2.20 (m, 2H), 2.85 (s, 3H), 2.85-3.75 (m, 11H), 4.11-4.46 (m, 2H), 5.61 (s, 2H), 6.87 (d, J=8.66 Hz, 2H), 7.40 (d, J=8.41 Hz, 2H), 8.66 (s, 1H), 8.72-8.88 (m, 2H). [M+H]=434.2.

Example 49

9-((1,4-Oxazepan-4-yl)methyl)-6-(4-methoxybenzyl)pyrido[3,2-e][1,2,4]triazolo[1,5-c]pyrimidin-5(6H)-one

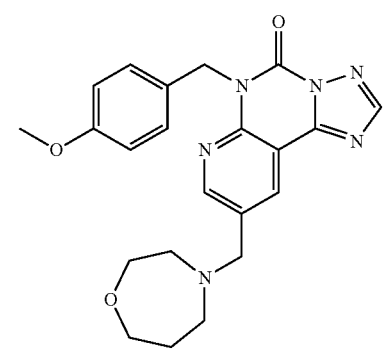 [SMILES: COc1ccc(Cn2c(=O)n3ncnc3c3cc(CN4CCCOCC4)cnc32)cc1]

$^1$H NMR (400 MHz, DMSO-d$_6$) δ 2.02-2.19 (m, 2H), 3.21-3.49 (m, 4H), 3.51-3.79 (m, 13H), 4.58-4.72 (m, 2H), 5.61 (s, 2H), 6.88 (d, J=8.66 Hz, 2H), 7.40 (d, J=8.66 Hz, 2H), 8.68 (s, 1H), 8.89 (s, 1H), 8.94 (s, 1H). [M+H]=421.2.

Example 50

9-((4-Acetyl-1,4-diazepan-1-yl)methyl)-6-(4-methoxybenzyl)pyrido[3,2-e][1,2,4]triazolo[1,5-c]pyrimidin-5(6H)-one

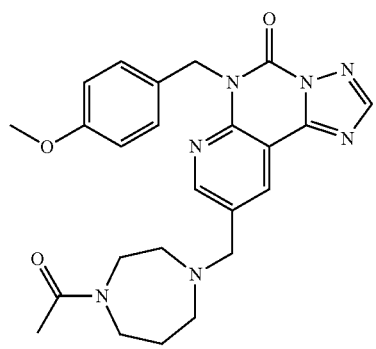 [SMILES: COc1ccc(Cn2c(=O)n3ncnc3c3cc(CN4CCCN(C(C)=O)CC4)cnc32)cc1]

$^1$H NMR (400 MHz, DMSO-d$_6$) δ 2.00-2.22 (m, 5H), 3.05-3.67 (m, 8H), 3.72 (s, 3H), 4.53-4.72 (m, 2H), 5.61 (s, 2H), 6.88 (d, J=8.41 Hz, 2H), 7.41 (d, J=8.41 Hz, 2H), 8.68 (s, 1H), 8.87 (s, 1H), 8.91 (s, 1H). [M+H]=462.3.

Example 51

9-(((Cyclohexyl(methyl)amino)methyl)-6-(4-methoxybenzyl)pyrido[3,2-e][1,2,4]triazolo[1,5-c]pyrimidin-5(6H)-one

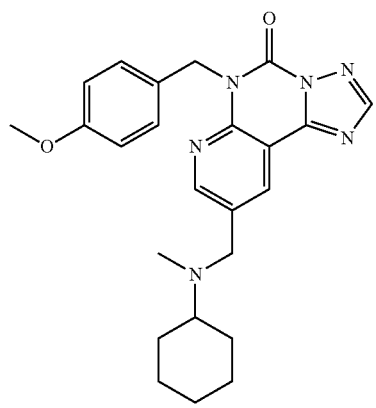 [SMILES: COc1ccc(Cn2c(=O)n3ncnc3c3cc(CN(C)C4CCCCC4)cnc32)cc1]

$^1$H NMR (400 MHz, DMSO-d$_6$) δ 1.10-1.72 (m, 6H), 1.81-1.96 (m, 2H), 1.99-2.21 (m, 2H), 2.61-2.67 (m, 3H), 3.33-3.41 (m, 1H), 3.72 (s, 3H), 4.38-4.73 (m, 2H), 5.62 (s, 2H), 6.87 (d, J=8.66 Hz, 2H), 7.40 (d, J=8.53 Hz, 2H), 8.68 (s, 1H), 8.90 (s, 1H), 8.94 (s, 1H). [M+H]=433.3.

Example 52

6-(4-Methoxybenzyl)-9-(4-methoxypiperidin-1-yl)methyl)pyrido[3,2-e][1,2,4]triazolo[1,5-c]pyrimidin-5(6H)-one

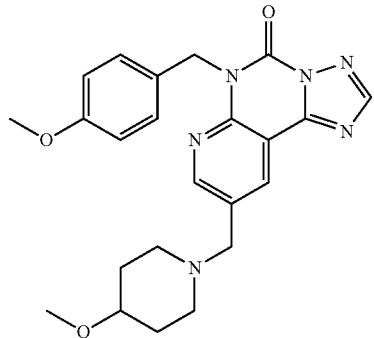 [SMILES: COc1ccc(Cn2c(=O)n3ncnc3c3cc(CN4CCC(OC)CC4)cnc32)cc1]

$^1$H NMR (400 MHz, DMSO-d$_6$) δ 1.42-1.59 (m, 1H), 1.72-1.86 (m, 1H), 1.98-2.09 (m, 1H), 2.15-2.25 (m, 1H), 2.99-3.21 (m, 2H), 3.23-3.30 (m, 3H), 3.35-3.52 (m, 2H), 3.53-3.61 (m, 1H), 3.72 (s, 3H), 4.50-4.61 (m, 2H), 5.61 (s, 2H), 6.87 (d, J=8.53 Hz, 2H), 7.40 (d, J=8.66 Hz, 2H), 8.68 (s, 1H), 8.83-8.92 (m, 2H). [M+H]=435.2.

Example 53

6-(4-Methoxybenzyl)-9-((methyl(tetrahydro-2H-pyran-4-yl)amino)methyl)pyrido[3,2-e][1,2,4]triazolo[1,5-c]pyrimidin-5(6H)-one

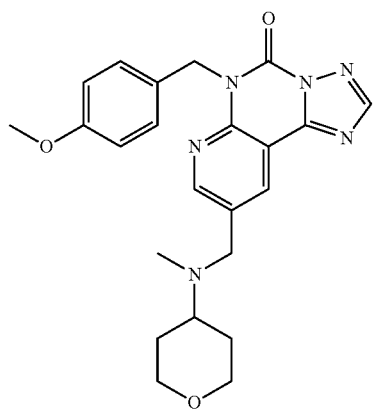 [SMILES: COc1ccc(Cn2c(=O)n3ncnc3c3cc(CN(C)C4CCOCC4)cnc32)cc1]

$^1$H NMR (400 MHz, DMSO-d$_6$) δ 1.74-1.92 (m, 2H), 1.98-2.12 (m, 2H), 2.64-2.71 (m, 3H), 3.32-3.44 (m, 2H), 3.59-3.81 (m, 4H), 3.99-4.10 (m, 2H), 4.37-4.49 (m, 1H), 4.69-4.79 (m, 1H), 5.62 (s, 2H), 6.87 (d, J=8.66 Hz, 2H), 7.40 (d, J=8.53 Hz, 2H), 8.68 (s, 1H), 8.90 (s, 1H), 8.95 (s, 1H). [M+H]=435.2.

Example 54

6-(4-Methoxybenzyl)-9-((4-(2-methoxyethyl)piperazin-1-yl)methyl)pyrido[3,2-e][1,2,4]triazolo[1,5-c]pyrimidin-5(6H)-one

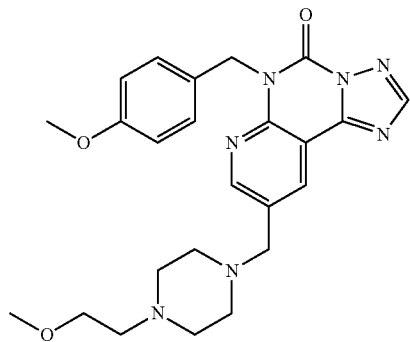 [SMILES: COCCN1CCN(Cc2cnc3c(c2)c2ncnn2c(=O)n3Cc2ccc(OC)cc2)CC1]

$^1$H NMR (400 MHz, DMSO-d$_6$) δ 2.54-2.75 (m, 2H), 2.86-3.21 (m, 4H), 3.26-3.33 (m, 5H), 3.35-3.55 (m, 2H), 3.65 (t, J=4.71 Hz, 2H), 3.72 (s, 3H), 3.85-3.94 (m, 2H), 5.60 (s, 2H), 6.87 (d, J=8.53 Hz, 2H), 7.39 (d, J=8.41 Hz, 2H), 8.64 (s, 1H), 8.64-8.67 (m, 1H), 8.75-8.78 (m, 1H). [M+H]=464.3.

Example 55

9-((Isopropyl(2-methoxyethyl)amino)methyl)-6-(4-methoxybenzyl)pyrido[3,2-e][1,2,4]triazolo[1,5-c]pyrimidin-5(6H)-one

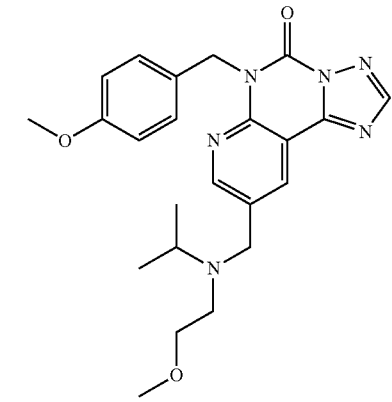 [SMILES: COCCN(Cc1cnc2c(c1)c1ncnn1c(=O)n2Cc1ccc(OC)cc1)C(C)C]

$^1$H NMR (400 MHz, DMSO-d$_6$) δ 1.27-1.47 (m, 6H), 3.14-3.20 (m, 1H), 3.22 (s, 3H), 3.41-3.56 (m, 4H), 3.72 (s, 4H), 4.48-4.67 (m, 2H), 5.61 (s, 2H), 6.87 (d, J=8.53 Hz, 2H), 7.40 (d, J=8.66 Hz, 2H), 8.68 (s, 1H), 8.91 (s, 1H), 8.97 (s, 1H). [M+H]=437.2.

Example 56

6-(4-Methoxybenzyl)-8-(4-methylpiperazin-1-yl)methyl)pyrido[2,3-e][1,2,4]triazolo[1,5-c]pyrimidin-5(6H)-one

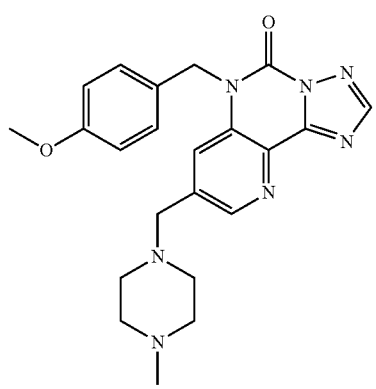 [SMILES: COc1ccc(Cn2c(=O)n3ncnc3c3ncc(CN4CCN(C)CC4)cc32)cc1]

$^1$H NMR (400 MHz, DMSO-d$_6$) δ 2.79 (s, 5H), 2.93 (br s, 3H), 3.55 (d, J=10.29 Hz, 30H), 3.75 (s, 6H), 3.78 (s, 5H), 3.99 (s, 2H), 5.55 (s, 2H), 6.92 (d, J=8.78 Hz, 2H), 7.37 (d, J=8.66 Hz, 2H), 7.92 (s, 1H), 8.64 (s, 1H). [M+H]=420.2.

Example 57

6-(4-Methoxybenzyl)-8-(morpholinomethyl)pyrido[2,3-e][1,2,4]triazolo[1,5-c]pyrimidin-5(6H)-one

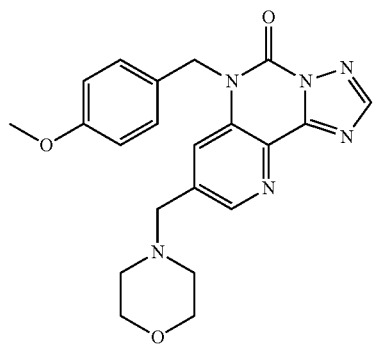 [SMILES: COc1ccc(Cn2c(=O)n3ncnc3c3ncc(CN4CCOCC4)cc32)cc1]

$^1$H NMR (400 MHz, DMSO-d$_6$) δ 2.99 (br s, 4H), 3.74 (s, 4H), 3.76-4.06 (m, 12H), 4.41 (br s, 2H), 5.57 (s, 2H), 6.90 (d, J=8.66 Hz, 2H), 7.39 (d, J=8.66 Hz, 2H), 8.22 (br s, 1H), 8.68 (s, 1H), 8.77 (s, 1H). [M+H]=407.2.

Example 58

6-(4-Methoxybenzyl)-8-(piperidin-1-ylmethyl)pyrido[2,3-e][1,2,4]triazolo[1,5-c]pyrimidin-5(6H)-one

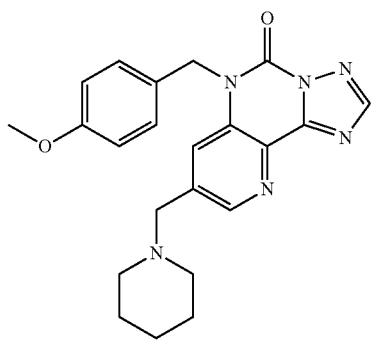 [SMILES: COc1ccc(Cn2c(=O)n3ncnc3c3ncc(CN4CCCCC4)cc32)cc1]

¹H NMR (400 MHz, CDCl₃) δ 1.91 (br s, 2H), 2.14 (br s, 2H), 2.65 (br s, 2H), 2.77-3.00 (m, 2H), 3.50 (br s, 2H), 3.79 (s, 3H), 4.28 (s, 2H), 5.73 (s, 2H), 6.89 (d, J=8.53 Hz, 2H), 7.47 (d, J=8.16 Hz, 2H), 8.55 (s, 1H), 8.60 (s, 1H), 8.80 (br s, 1H). [M+H]=405.2.

Example 59

6-(4-Methoxybenzyl)-8-(thiomorpholinomethyl)pyrido[2,3-e][1,2,4]triazolo[1,5-c]pyrimidin-5(6H)-one

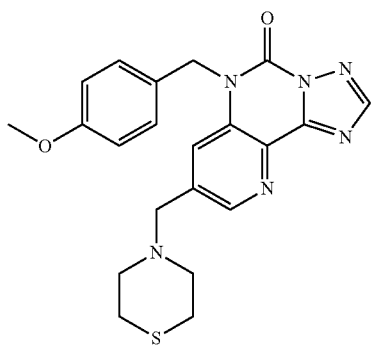 [SMILES: COc1ccc(Cn2c(=O)n3ncnc3c3ncc(CN4CCSCC4)cc32)cc1]

¹H NMR (400 MHz, CDCl₃) δ 2.91 (br s, 4H), 3.20 (br s, 4H), 3.67 (s, 3H), 4.21 (s, 2H), 5.57 (s, 2H), 6.77 (d, J=8.66 Hz, 2H), 7.27 (d, J=8.53 Hz, 2H), 8.41 (br s, 1H), 8.44 (s, 1H), 8.52 (s, 1H). [M+H]=423.2.

Example 60

8-(((2S,6R)-2,6-Dimethylmorpholino)methyl)-6-(4-methoxybenzyl)pyrido[2,3-e][1,2,4]triazolo[1,5-c]pyrimidin-5(6H)-one

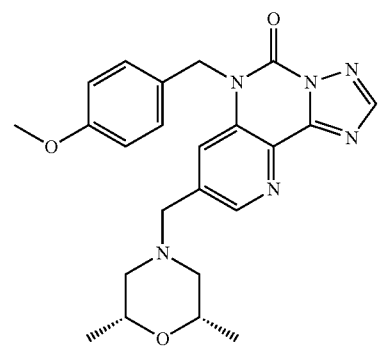 [SMILES: COc1ccc(Cn2c(=O)n3ncnc3c3ncc(CN4C[C@@H](C)O[C@@H](C)C4)cc32)cc1]

¹H NMR (400 MHz, CDCl₃) δ 1.10 (d, J=6.27 Hz, 6H), 2.28 (t, J=11.23 Hz, 2H), 3.16 (d, J=11.42 Hz, 2H), 3.67 (s, 3H), 3.85-4.02 (m, 2H), 4.20 (s, 2H), 5.51 (s, 2H), 6.76 (d, J=8.66 Hz, 2H), 7.25 (d, J=8.53 Hz, 2H), 8.31 (s, 1H), 8.42 (s, 1H), 8.53 (s, 1H). [M+H]=435.3.

Example 61

6-(4-Methoxybenzyl)-9-((2-methoxyethyl)(methyl)amino)methyl)pyrido[3,2-e][1,2,4]triazolo[1,5-c]pyrimidin-5(6H)-one

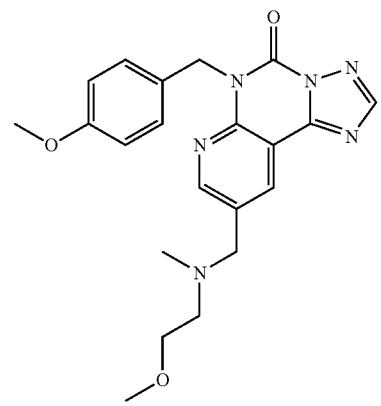 [SMILES: COCCN(C)Cc1cnc2c(c1)c1ncnn1c(=O)n2Cc1ccc(OC)cc1]

¹H NMR (400 MHz, DMSO-d₆) δ 2.79 (s, 3H), 3.33 (s, 5H), 3.72 (s, 5H), 4.44-4.71 (m, 2H), 5.61 (s, 2H), 6.87 (d, J=8.66 Hz, 2H), 7.40 (d, J=8.66 Hz, 2H), 8.68 (s, 1H), 8.85-8.90 (m, 1H), 8.91-8.96 (m, 1H). [M+H]=409.2.

Example 62

7-(((6-(4-Methoxybenzyl)-5-oxo-5,6-dihydropyrido[3,2-e][1,2,4]triazolo[1,5-c]pyrimidin-9-yl)methyl)tetrahydro-1H-oxazolo[3,4-a]pyrazin-3(5H)-one

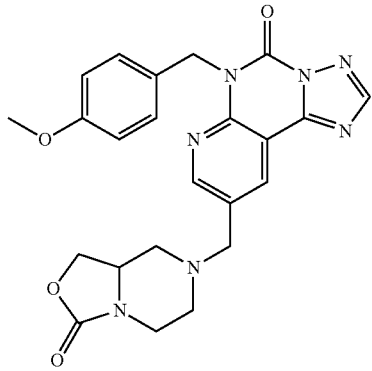 [SMILES: COc1ccc(Cn2c(=O)n3ncnc3c3cc(CN4CCN5C(=O)OCC5C4)cnc32)cc1]

$^1$H NMR (400 MHz, DMSO-d$_6$) δ 2.90-3.44 (m, 4H), 3.65-3.82 (m, 5H), 3.91-4.49 (m, 5H), 5.61 (s, 2H), 6.87 (d, J=8.66 Hz, 2H), 7.40 (d, J=8.53 Hz, 2H), 8.66 (s, 1H), 8.70-8.88 (m, 2H). [M+H]=462.2.

Example 63

9-(((2S,5S)-2,5-Dimethylmorpholino)methyl)-6-(4-methoxybenzyl)pyrido[3,2-e][1,2,4]triazolo[1,5-c]pyrimidin-5(6H)-one

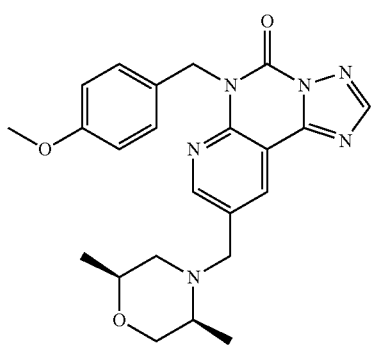 [SMILES: COc1ccc(Cn2c(=O)n3ncnc3c3cc(CN4C[C@H](C)OC[C@@H]4C)cnc32)cc1]

$^1$H NMR (400 MHz, CDCl$_3$) δ 1.16 (m, 6H), 2.36 (br s, 2H), 2.84 (br s, 1H), 3.61-3.74 (m, 3H), 3.77 (s, 3H), 3.82 (br s, 1H), 5.75 (s, 2H), 6.83 (d, J=8.66 Hz, 2H), 7.62 (d, J=8.53 Hz, 2H), 8.36 (s, 1H), 8.63 (br s, 1H), 8.75 (br s, 1H). [M+H]=435.3.

Example 64

9-(((2R,5R)-2,5-Dimethylmorpholino)methyl)-6-(4-methoxybenzyl)pyrido[3,2-e][1,2,4]triazolo[1,5-c]pyrimidin-5(6H)-one

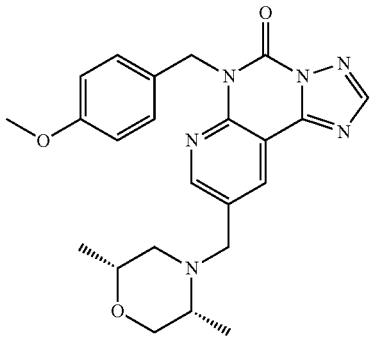 [SMILES: COc1ccc(Cn2c(=O)n3ncnc3c3cc(CN4C[C@@H](C)OC[C@H]4C)cnc32)cc1]

$^1$H NMR (400 MHz, CDCl$_3$) δ 1.15 (m, 6H), 2.36 (br s, 2H), 2.83 (br s, 1H), 3.60-3.74 (m, 3H), 3.77 (s, 4H), 3.83 (d, J=9.41 Hz, 1H), 5.75 (s, 2H), 6.83 (d, J=8.66 Hz, 2H), 7.62 (d, J=8.53 Hz, 2H), 8.36 (s, 1H), 8.63 (br s, 1H), 8.74 (br s, 1H). [M+H]=435.3.

Example 65

6-(4-Methoxybenzyl)-9-(piperazin-1-ylmethyl)pyrido[3,2-e][1,2,4]triazolo[1,5-c]pyrimidin-5(6H)-one

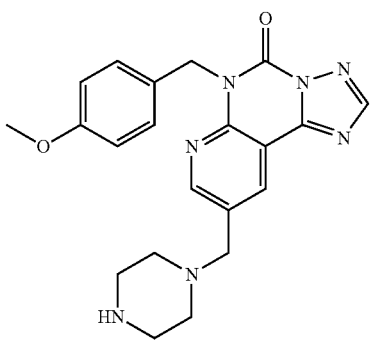 [SMILES: COc1ccc(Cn2c(=O)n3ncnc3c3cc(CN4CCNCC4)cnc32)cc1]

Step A. tert-Butyl 4-((6-(4-methoxybenzyl)-5-oxo-5,6-dihydropyrido[3,2-e][1,2,4]triazolo[1,5-c]pyrimidin-9-yl)methyl)piperazine-1-carboxylate. 9-Bromo-6-(4-methoxybenzyl)pyrido[3,2-e][1,2,4]triazolo[1,5-c]pyrimidin-5(6H)-one (Example 1, 562.00 mg; 1.46 mmol), potassium ((4-(tert-butoxycarbonyl)piperazin-1-yl)methyl)trifluoroborate (568.00 mg; 1.86 mmol), dicyclohexyl(2',4',6'-triisopropylbiphenyl-2-yl)phosphine (60.00 mg; 0.13 mmol;), Pd(OAc)$_2$ (30.00 mg; 0.13 mmol), Cs$_2$CO$_3$ (1.76 g; 5.40 mmol), and degassed dioxane-water (9:1; 10 mL) were combined in that order and heated at 80° C. for 4 days. The mixture concentrated under reduced pressure. Purification (FCC, SiO$_2$, 20-100% EtOAc/hexanes) afforded the title compound (216 mg, 29%).

Step B. 6-(4-methoxybenzyl)-9-(piperazin-1-ylmethyl)pyrido[3,2-e][1,2,4]triazolo[1,5-c]pyrimidin-5(6H)-one. tert-Butyl 4-((6-(4-methoxybenzyl)-5-oxo-5,6-dihydropyrido[3,2-e][1,2,4]triazolo[1,5-c]pyrimidin-9-yl)methyl)piperazine-1-carboxylate (216 mg, 0.427 mmol) was stirred in DCM (3.00 mL) and 2,2,2-trifluoroacetic acid (3.00 mL) for 1 h and concentrated under vacuum to afford the title compound (227.00 mg; 30.03%). A portion of this material (35 mg) was purified by preparative HPLC (10-70% ACN/water) to afford the title compound (19.00 mg; 2.51%) as a white powder. $^1$H NMR (400 MHz, CDCl$_3$ and DMSO-d$_6$) δ 2.74 (br s, 4H), 3.11 (br s, 4H), 3.65 (d, J=2.01 Hz, 3H), 3.96 (br s, 2H), 5.62 (s, 2H), 6.71 (dd, J=8.72, 1.95 Hz, 2H), 7.47 (dd, J=8.66, 1.88 Hz, 2H), 8.25 (d, J=2.01 Hz, 1H), 8.51 (s, 1H), 8.58-8.71 (m, 1H), 9.84 (br s, 1H). [M+H]=406.2.

Example 66 was made in a manner analogous to Example 65, with the appropriate starting material and reagent substitutions.

Example 66

9-(((3S,5R)-3,5-Dimethylpiperazin-1-yl)methyl)-6-(4-methoxybenzyl)pyrido[3,2-e][1,2,4]triazolo[1,5-c]pyrimidin-5(6H)-one

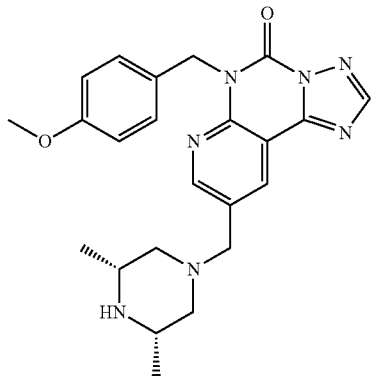 [SMILES: COc1ccc(Cn2c(=O)n3ncnc3c3cc(CN4C[C@@H](C)N[C@@H](C)C4)cnc32)cc1]

$^1$H NMR (400 MHz, DMSO-d$_6$) δ 1.18 (d, J=6.53 Hz, 6H), 2.12 (t, J=11.80 Hz, 2H), 3.03 (d, J=10.29 Hz, 2H), 3.34 (br s, 2H), 3.72 (s, 3H), 3.81 (br s, 2H), 5.60 (s, 2H), 6.87 (d, J=8.66 Hz, 2H), 7.39 (d, J=8.66 Hz, 2H), 8.21 (d, J=8.53 Hz, 1H), 8.62 (d, J=2.13 Hz, 1H), 8.64 (s, 1H), 8.76 (d, J=2.13 Hz, 1H), 8.95 (br s, 1H). [M+H]=434.2.

Example 67

6-(4-Methoxybenzyl)-9-((4-((THF-3-yl)methyl)piperazin-1-yl)methyl)pyrido[3,2-e][1,2,4]triazolo[1,5-c]pyrimidin-5(6H)-one

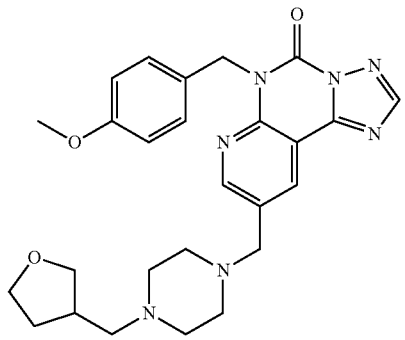 [SMILES: COc1ccc(Cn2c(=O)n3ncnc3c3cc(CN4CCN(CC5CCOC5)CC4)cnc32)cc1]

The title compound was prepared in a manner analogous to Example 34, Step B. $^1$H NMR (400 MHz, CDCl$_3$ and DMSO-d$_6$) δ 1.68 (dd, J=12.49, 6.96 Hz, 1H), 2.13 (d, J=6.02 Hz, 1H), 2.69 (d, J=6.27 Hz, 1H), 2.80-3.07 (m, 6H), 3.19-3.52 (m, 2H), 3.57-3.73 (m, 3H), 3.59-3.70 (m, 2H), 3.70-3.82 (m, 2H), 3.88 (t, J=7.47 Hz, 1H), 3.99-4.67 (m, 7H), 5.63 (s, 2H), 6.72 (d, J=8.66 Hz, 2H), 7.48 (d, J=8.41 Hz, 2H), 8.15-8.31 (m, 1H), 8.55 (br s, 1H), 8.63 (br s, 1H). [M+H]=490.3.

Example 68

6-(4-Methoxybenzyl)-9-((4-(methylsulfonyl)piperazin-1-yl)methyl)pyrido[3,2-e][1,2,4]triazolo[1,5-c]pyrimidin-5(6H)-one

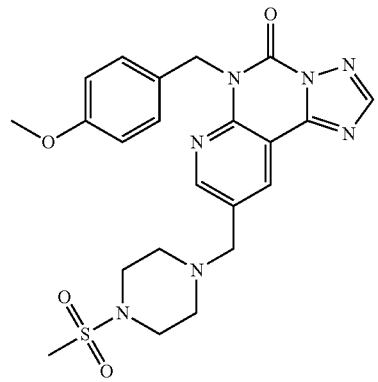 [SMILES: COc1ccc(Cn2c(=O)n3ncnc3c3cc(CN4CCN(S(C)(=O)=O)CC4)cnc32)cc1]

6-(4-Methoxybenzyl)-9-((4-(methylsulfonyl)piperazin-1-yl)methyl)pyrido[3,2-e][1,2,4]triazolo[1,5-c]pyrimidin-5(6H)-one. 6-(4-Methoxybenzyl)-9-(piperazin-1-ylmethyl)pyrido[3,2-e][1,2,4]triazolo[1,5-c]pyrimidin-5(6H)-one (Example 65, 34 mg, 0.09 mmol), ACN (1 mL), TEA (75 μl, 0.53 mmol), and methane sulfonyl chloride (50 mg, 0.44 mmol) were combined and the mixture was stirred for 4 h. The reaction was filtered through a plug of C$^{18}$. Purification (HPLC, 10-70% ACN in water) afforded the title compound (17 mg, 33%) as a white solid. $^1$H NMR (400 MHz, CDCl$_3$ and DMSO-d$_6$) δ 2.48 (d, J=1.63 Hz, 2H), 2.76 (d, J=2.26 Hz, 3H), 3.09 (br s, 4H), 3.54 (br s, 4H), 3.65 (d, J=2.51 Hz, 3H), 4.21 (br s, 2H), 5.63 (d, J=1.76 Hz, 2H), 6.72 (dd, J=8.78, 2.26 Hz, 2H), 7.47 (dd, J=8.66, 2.38 Hz, 2H), 8.26 (d, J=2.38 Hz, 1H), 8.85 (br s, 1H), 9.00 (br s, 1H). [M+H]=484.2.

Examples 69 thru 71 were made in a manner analogous to Example 68, with the appropriate starting material and reagent substitutions.

Example 69

4-((6-(4-Methoxybenzyl)-5-oxo-5,6-dihydropyrido[3,2-e][1,2,4]triazolo[1,5-c]pyrimidin-9-yl)methyl)-N,N-dimethylpiperazine-1-sulfonamide

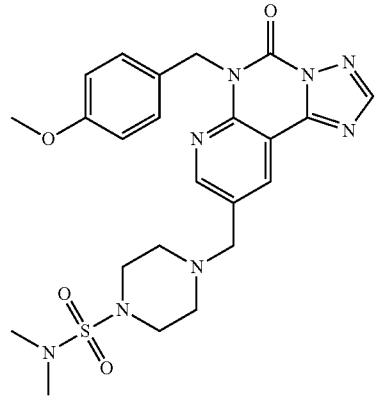 [SMILES: COc1ccc(Cn2c(=O)n3ncnc3c3cc(CN4CCN(S(=O)(=O)N(C)C)CC4)cnc32)cc1]

¹H NMR (400 MHz, CDCl₃ and DMSO-d₆) δ 2.70 (d, J=2.64 Hz, 6H), 3.13 (br s, 4H), 3.40-3.59 (m, 4H), 3.63 (d, J=2.76 Hz, 3H), 4.32 (br s, 2H), 5.60 (s, 2H), 6.69 (dd, J=8.72, 2.45 Hz, 2H), 7.39-7.59 (m, 2H), 8.24 (d, J=2.89 Hz, 1H), 8.93 (br s, 1H), 9.08 (br s, 1H). [M+H]=513.2.

Example 70

6-(4-Methoxybenzyl)-9-((4-(2,2,2-trifluoroacetyl)piperazin-1-yl)methyl)pyrido[3,2-e][1,2,4]triazolo[1,5-c]pyrimidin-5(6H)-one

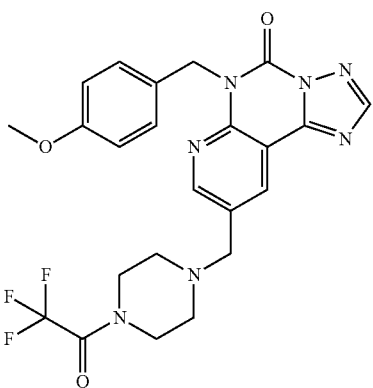 [SMILES: COc1ccc(Cn2c(=O)n3ncnc3c3cc(CN4CCN(C(=O)C(F)(F)F)CC4)cnc32)cc1]

¹H NMR (400 MHz, CDCl₃ and DMSO-d₆) δ 2.94 (br s, 4H), 3.64 (s, 3H), 3.80 (br s, 4H), 4.07 (br s, 2H), 5.61 (s, 2H), 6.61-6.78 (m, 2H), 7.45 (d, J=8.66 Hz, 2H), 8.24 (s, 1H), 8.76 (br s, 1H), 8.90 (br s, 1H). [M+H]=502.2.

Example 71

6-(4-Methoxybenzyl)-9-((4-(THF-3-carbonyl)piperazin-1-yl)methyl)pyrido[3,2-e][1,2,4]triazolo[1,5-c]pyrimidin-5(6H)-one

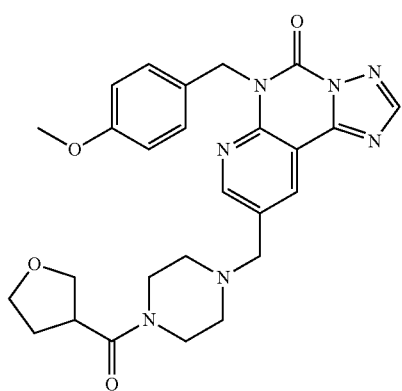 [SMILES: COc1ccc(Cn2c(=O)n3ncnc3c3cc(CN4CCN(C(=O)C5CCOC5)CC4)cnc32)cc1]

¹H NMR (400 MHz, CDCl₃ and DMSO-d₆) δ 1.89-2.20 (m, 2H), 2.88-3.25 (m, 5H), 3.36-3.64 (m, 4H), 3.68 (d, J=0.88 Hz, 3H), 3.72-3.95 (m, 4H), 4.26 (br s, 2H), 5.65 (br s, 2H), 6.74 (d, J=7.78 Hz, 2H), 7.50 (d, =7.65 Hz, 2H), 8.28 (d, J=1.00 Hz, 1H), 8.88 (br s, 1H), 9.09 (br s, 1H). [M+H]= 504.3.

Example 72

6-(4-Methoxybenzyl)-9-(morpholinomethyl)pyrido[3,2-e][1,2,4]triazolo[1,5-c]pyrimidin-5(6H)-one

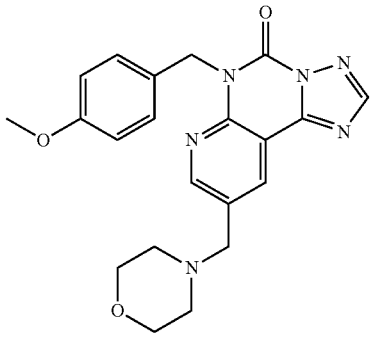

Step A: 6-(4-Methoxybenzyl)-5-oxo-5,6-dihydropyrido[3,2-e][1,2,4]triazolo[1,5-c]pyrimidine-8-carbaldehyde. 8-(Dimethoxymethyl)-6-(4-methoxybenzyl)pyrido[3,2-e][1,2,4]triazolo[1,5-c]pyrimidin-5(6H)-one (Example 3, 682 mg, 1.79 mmol), THF (20 mL), water (5 mL) and 12 N hydrochloric acid (3 mL) were combined and stirred at room temperature for 20 h. The mixture was neutralized slowly with powdered sodium bicarbonate to pH 8. The mixture was diluted with water (20 mL) and extracted with EtOAc (3×20 mL). The combined extracts were dried (MgSO₄) and concentrated to afford the title compound (516 mg, 77%) as a yellow foam, which was used without further purification. ¹H NMR (400 MHz, CDCl₃) δ 3.73-3.81 (m, 3H), 5.83, (s, 2H), 6.85 (d, J=8.66 Hz, 2H), 7.64 (d, J=8.53 Hz, 2H), 8.03 (d, J=7.78 Hz, 1H), 8.42 (s, 1H), 8.83 (d, J=7.91 Hz, 1H), 10.22 (s, 1H). [M+H]=336.1.

Step B: 6-(4-Methoxybenzyl)-8-(morpholinomethyl)pyrido[3,2-e][1,2,4]triazolo[1,5-c]pyrimidin-5(6H)-one. The title compound was prepared as described in Example 34, Step B. ¹H NMR (400 MHz, CDCl₃) δ 3.47 (br s, 2H), 3.76 (s, 3H), 3.79-3.82 (m, 2H), 3.87 (br s, 4H), 4.41 (s, 2H), 5.78 (s, 2H), 6.82 (d, J=8.66 Hz, 2H), 7.30 (d, J=9.29 Hz, 2H), 7.72 (d, J=7.91 Hz, 1H), 8.44 (s, 1H), 8.76 (d, J=7.91 Hz, 1H). [M+H]=407.2.

Examples 73 thru 80 were made in a manner analogous to Example 72, with the appropriate starting material and reagent substitutions.

Example 73

8-(((2S,6R)-2,6-Dimethylmorpholino)methyl)-6-(4-methoxybenzyl)pyrido[3,2-e][1,2,4]triazolo[1,5-c]pyrimidin-5(6H)-one

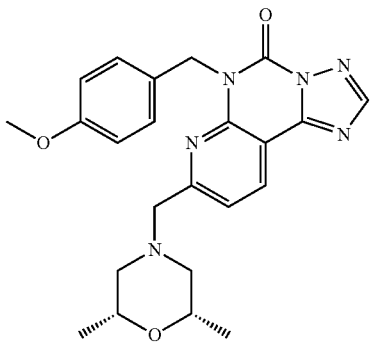 [SMILES: COc1ccc(Cn2c(=O)n3ncnc3c3ccc(CN4C[C@@H](C)O[C@@H](C)C4)nc32)cc1]

¹H NMR (400 MHz, CDCl₃) δ 1.12 (d, J=6.27 Hz, 6H), 2.43 (t, J=11.04 Hz, 2H), 3.38 (d, J=11.67 Hz, 2H), 3.75 (s, 3H), 4.02 (dd, J=10.23, 6.34 Hz, 2H), 4.44 (s, 2H), 5.76 (s, 2H), 6.83 (d, J=8.66 Hz, 2H), 7.36 (d, J=8.66 Hz, 2H), 7.70 (d, J=7.78 Hz, 1H), 8.43 (s, 1H), 8.76 (d, J=7.91 Hz, 1H). [M+H]=435.3.

Example 74

6-(4-Methoxybenzyl)-8-((((3-methyloxetan-3-yl)methyl)amino)methyl)pyrido[3,2-e][1,2,4]triazolo[1,5-c]pyrimidin-5(6H)-one

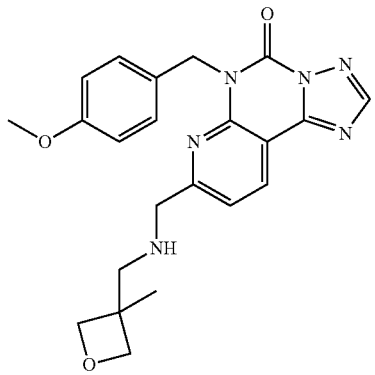 [SMILES: COc1ccc(Cn2c(=O)n3ncnc3c3ccc(CNCC4(C)COC4)nc32)cc1]

¹H NMR (400 MHz, CDCl₃) δ 1.31 (s, 3H), 3.11 (s, 2H), 3.74 (s, 3H), 4.32-4.40 (m, 4H), 4.56 (s, 3H), 5.81 (s, 2H), 6.80 (d, J=8.53 Hz, 2H), 7.30 (d, J=8.66 Hz, 2H), 7.60 (d, J=7.91 Hz, 1H), 8.42 (s, 1H), 8.76 (d, J=7.91 Hz, 1H). [M+H]=421.2.

Example 75

6-(4-Methoxybenzyl)-8-((methyl((THF-3-yl)methyl)amino)methyl)pyrido[3,2-e][1,2,4]triazolo[1,5-c]pyrimidin-5(6H)-one

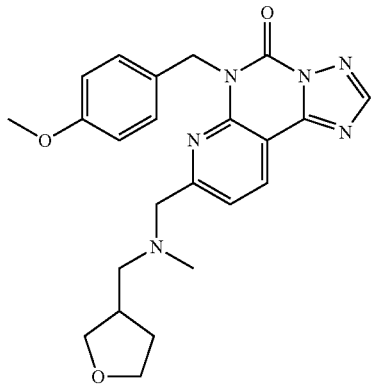 [SMILES: COc1ccc(Cn2c(=O)n3ncnc3c3ccc(CN(C)CC4CCOC4)nc32)cc1]

¹H NMR (400 MHz, CDCl₃) δ 1.54-1.69 (m, 1H), 2.06-2.30 (m, 2H), 2.69 (dt, J=14.09, 6.95 Hz, 2H), 2.80 (s, 3H), 3.10 (br s, 2H), 3.39 (dd, J=8.91, 6.15 Hz, 1H), 3.70-3.75 (m, 1H), 3.76 (s, 3H), 3.81-3.87 (m, 1H), 3.90 (dd, J=8.85, 7.22 Hz, 1H), 4.51 (s, 2H), 5.76 (s, 2H), 6.83 (d, J=8.53 Hz, 2H), 7.32 (d, J=8.66 Hz, 2H), 7.76 (d, J=7.91 Hz, 1H), 8.43 (s, 1H), 8.79 (d, J=7.91 Hz, 1H). [M+H]=435.3.

Example 76

8-((Cyclopropyl(methyl)amino)methyl)-6-(4-methoxybenzyl)pyrido[3,2-e][1,2,4]triazolo[1,5-c]pyrimidin-5(6H)-one

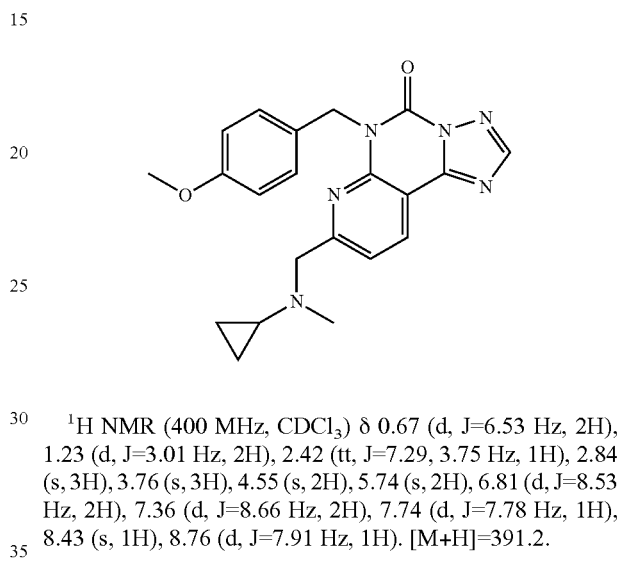

¹H NMR (400 MHz, CDCl₃) δ 0.67 (d, J=6.53 Hz, 2H), 1.23 (d, J=3.01 Hz, 2H), 2.42 (tt, J=7.29, 3.75 Hz, 1H), 2.84 (s, 3H), 3.76 (s, 3H), 4.55 (s, 2H), 5.74 (s, 2H), 6.81 (d, J=8.53 Hz, 2H), 7.36 (d, J=8.66 Hz, 2H), 7.74 (d, J=7.78 Hz, 1H), 8.43 (s, 1H), 8.76 (d, J=7.91 Hz, 1H). [M+H]=391.2.

Example 77

6-(4-Methoxybenzyl)-8-((4-(methylsulfonyl)piperazin-1-yl)methyl)pyrido[3,2-e][1,2,4]triazolo[1,5-c]pyrimidin-5(6H)-one

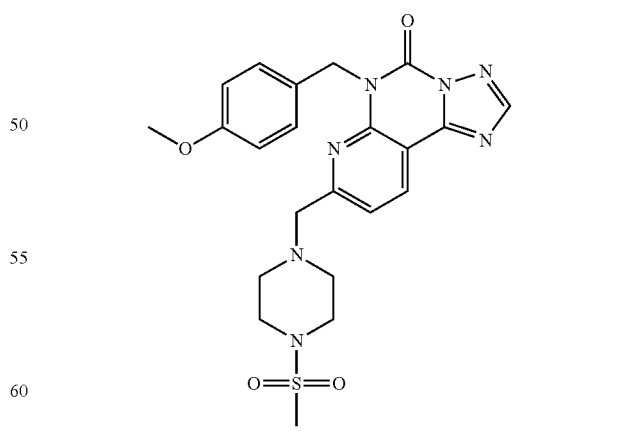

¹H NMR (400 MHz, CDCl₃) δ 2.87 (s, 3H), 3.15 (br s, 4H), 3.53 (br s, 4H), 3.78 (s, 3H), 4.37 (s, 2H), 5.76 (s, 2H), 6.85 (d, J=8.66 Hz, 2H), 7.30 (d, J=8.66 Hz, 2H), 7.70 (d, J=8.03 Hz, 1H), 8.44 (s, 1H), 8.77 (d, J=7.91 Hz, 1H). [M+H]=484.2.

Example 78

8-((Benzylamino)methyl)-6-(4-methoxybenzyl)pyrido[3,2-e][1,2,4]triazolo[1,5-c]pyrimidin-5(6H)-one

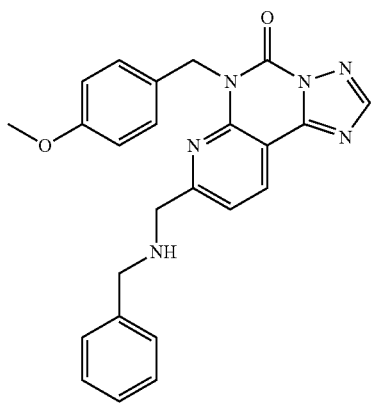 [SMILES: COc1ccc(Cn2c(=O)n3ncnc3c3ccc(CNCc4ccccc4)nc32)cc1]

¹H NMR (400 MHz, CDCl₃) δ 3.62 (s, 3H), 4.03 (s, 2H), 4.26 (s, 2H), 5.71 (s, 2H), 6.67 (d, J=8.53 Hz, 2H), 7.19-7.38 (m, 10H), 8.24-8.35 (m, 1H), 8.57-8.65 (m, 1H). [M+H]= 427.3.

Example 79

6-(4-Methoxybenzyl)-8-((phenylamino)methyl)pyrido[3,2-e][1,2,4]triazolo[1,5-c]pyrimidin-5(6H)-one

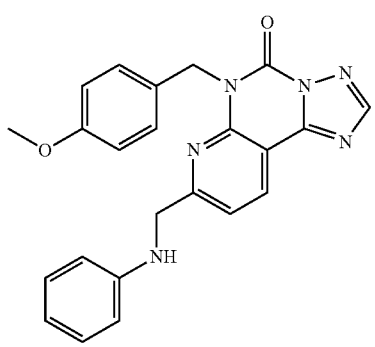 [SMILES: COc1ccc(Cn2c(=O)n3ncnc3c3ccc(CNc4ccccc4)nc32)cc1]

¹H NMR (400 MHz, CDCl₃) δ 3.67 (s, 3H), 4.60 (s, 2H), 5.67 (s, 2H), 6.63 (d, J=8.03 Hz, 2H), 6.73 (d, J=8.53 Hz, 3H), 6.75-6.82 (m, 1H), 7.12 (s, 2H), 7.33-7.40 (m, 1H), 7.41-7.48 (m, 2H), 8.22-8.34 (m, 1H), 8.45-8.57 (m, 1H). [M+H]= 413.2.

Example 80

8-(Isoindolin-2-ylmethyl)-6-(4-methoxybenzyl)pyrido[3,2-e][1,2,4]triazolo[1,5-c]pyrimidin-5(6H)-one

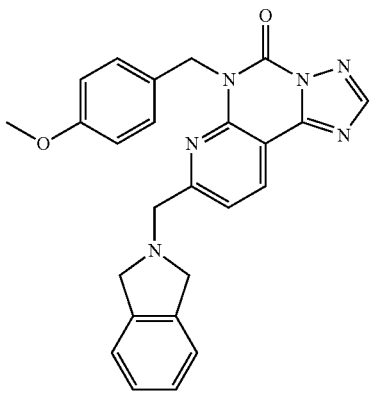 [SMILES: COc1ccc(Cn2c(=O)n3ncnc3c3ccc(CN4Cc5ccccc5C4)nc32)cc1]

¹H NMR (400 MHz, CDCl₃) δ 3.68 (s, 3H), 4.46 (br s, 3H), 4.64 (s, 2H), 5.69 (s, 2H), 6.73 (d, J=8.53 Hz, 2H), 7.03-7.13 (m, 2H), 7.18 (s, 4H), 7.24-7.33 (m, 2H), 7.47-7.56 (m, 1H), 8.28-8.41 (m, 1H), 8.60-8.71 (m, 1H). [M+H]=439.2.

Example 81

9-Acetyl-6-(4-methoxybenzyl)pyrido[3,2-e][1,2,4]triazolo[1,5-c]pyrimidin-5(6H)-one

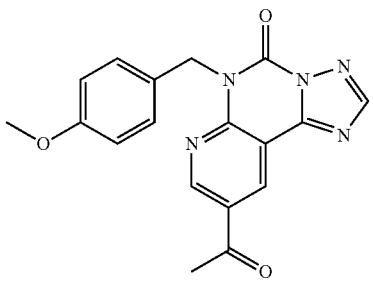 [SMILES: COc1ccc(Cn2c(=O)n3ncnc3c3cc(C(C)=O)cnc32)cc1]

9-Acetyl-6-(4-methoxybenzyl)pyrido[3,2-e][1,2,4]triazolo[1,5-c]pyrimidin-5(6H)-one. 9-(1-Ethoxyvinyl)-6-(4-methoxybenzyl)pyrido[3,2-e][1,2,4]triazolo[1,5-c]pyrimidin-5(6H)-one (Example 32, 147 mg, 0.39 mmol) was suspended in dioxane (6 mL) and 6 N hydrochloric acid (3 mL) and stirred for 4 h. The mixture was basified to pH 11 with 1 N sodium hydroxide and extracted with DCM (3×15 mL). The combined extracts were dried (MgSO₄) and concentrated to afford 122 mg (90%) of the title compound as a yellow solid. ¹H NMR (400 MHz, CDCl₃) δ 2.73 (s, 3H), 3.76 (s, 3H), 5.79 (s, 2H), 6.78-6.89 (m, 2H), 7.56-7.66 (m, 2H), 8.39 (s, 1H), 9.13 (d, J=2.26 Hz, 1H), 9.35 (d, J=2.26 Hz, 1H). [M+H]=350.2.

Example 82

9-(1-((2S,6R)-2,6-Dimethylmorpholino)ethyl)-6-(4-methoxybenzyl)pyrido[3,2-e][1,2,4]triazolo[1,5-c]pyrimidin-5(6H)-one

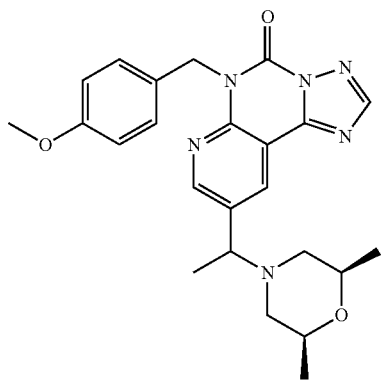

9-(1-((2S,6R)-2,6-Dimethylmorpholino)ethyl)-6-(4-methoxybenzyl)pyrido[3,2-e][1,2,4]triazolo[1,5-c]pyrimidin-5(6H)-one. 9-Acetyl-6-(4-methoxybenzyl)pyrido[3,2-e][1,2,4]triazolo[1,5-c]pyrimidin-5(6H)-one (Example 81, 67 mg, 0.19 mmol), (2S,6R)-2,6-dimethylmorpholine (0.060 mL, 0.49 mmol), ACN (1 mL) and acetic acid (0.020 mL, 0.35 mmol) were combined and stirred for 10 minutes. Sodium cyanoborohydride (18 mg, 0.29 mmol) was added and the mixture was stirred for 3 days at 50° C. The mixture was filtered. Purification (HPLC, 10-65% ACN in water) afforded the title compound (26 mg, 23%) as a white solid. $^1$H NMR (400 MHz, CDCl$_3$) δ 1.19 (d, J=6.27 Hz, 3H), 1.23 (d, J=6.27 Hz, 3H), 1.92 (d, J=7.03 Hz, 3H), 2.34 (td, J=11.01, 2.32 Hz, 2H), 3.32 (d, J=11.42 Hz, 1H), 3.57 (d, J=11.42 Hz, 1H), 3.77 (s, 3H), 4.12 (d, J=7.03 Hz, 2H), 4.54 (q, J=6.86 Hz, 1H), 5.75 (s, 2H), 6.85 (d, J=8.66 Hz, 2H), 7.62 (d, J=8.66 Hz, 2H), 8.40 (s, 1H), 8.74 (s, 1H), 8.95 (s, 1H). [M+H]=449.3.

Example 83

9-(1-Hydroxy-2-morpholinoethyl)-6-(4-methoxybenzyl)pyrido[3,2-e][1,2,4]triazolo[1,5-c]pyrimidin-5(6H)-one

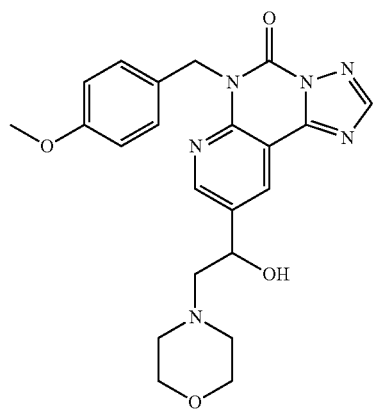

Step A. 6-(4-Methoxybenzyl)-9-(oxiran-2-yl)pyrido[3,2-e][1,2,4]triazolo[1,5-c]pyrimidin-5(6H)-one. 3-Chloroperbenzoic acid (139 mg, 0.62 mmol) was added to a stirred solution of 6-(4-methoxybenzyl)-9-vinylpyrido[3,2-e][1,2,4]triazolo[1,5-c]pyrimidin-5(6H)-one (Example 30, 138 mg, 0.41 mmol) in DCM (1.3 mL) and the mixture was stirred for 18 h. Saturated sodium bicarbonate (3 mL) was added to the reaction mixture and the mixture was stirred for 2 h. The reaction mixture was diluted with DCM (5 mL), and the organic layer was separated, dried (MgSO$_4$), and concentrated under vacuum to afford the title compound (118 mg, 82%) as a yellow semi-solid, which was used without further purification in the next step.

9-(1-Hydroxy-2-morpholinoethyl)-6-(4-methoxybenzyl)pyrido[3,2-e][1,2,4]triazolo[1,5-c]pyrimidin-5(6H)-one. 6-(4-Methoxybenzyl)-9-(oxiran-2-yl)pyrido[3,2-e][1,2,4]triazolo[1,5-c]pyrimidin-5(6H)-one (118 mg, 0.337 mmol) was treated with morpholine (0.50 mL) and stirred for 16 h at room temperature. The mixture was concentrated under vacuum, re-dissolved in DMSO, and filtered. Purification (HPLC, elution with 20 to 80% acetonitrile in water) afforded the title compound (63 mg, 26%) as the TFA salt as a white powder. $^1$H NMR (400 MHz, CDCl$_3$) δ 3.11 (br s, 4H), 3.26 (dd, J=13.30, 2.89 Hz, 1H), 3.35 (dd, J=13.30, 10.67 Hz, 1H), 3.76 (s, 3H), 4.12 (br s, 4H), 5.65-5.71 (m, 1H), 5.73 (s, 2H), 6.82 (d, J=8.78 Hz, 2H), 7.58 (d, J=8.66 Hz, 2H), 8.35 (s, 1H), 8.69 (d, J=2.26 Hz, 1H), 8.90 (d, J=2.26 Hz, 1H). [M+H]=437.2.

Example 84 was made in a manner analogous to Example 83, with the appropriate starting material and reagent substitutions.

Example 84

9-(2-((2S,6R)-2,6-Dimethylmorpholino)-1-hydroxyethyl)-6-(4-methoxybenzyl)pyrido[3,2-e][1,2,4]triazolo[1,5-c]pyrimidin-5(6H)-one

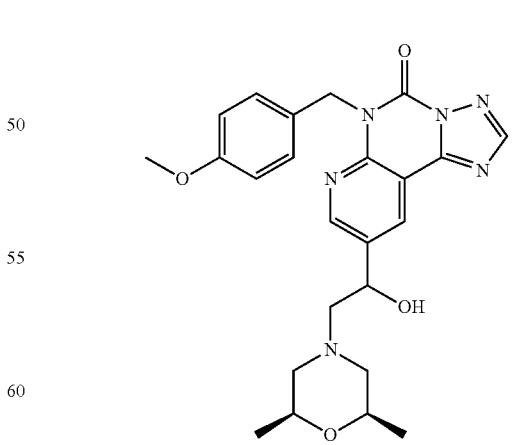

$^1$H NMR (400 MHz, CDCl$_3$) δ 1.29 (d, J=6.40 Hz, 2H), 1.31 (d, J=6.27 Hz, 2H), 2.57 (d, J=11.92 Hz, 2H), 3.21 (d, J=13.30 Hz, 2H), 3.25-3.39 (m, 2H), 3.66 (d, J=11.29 Hz, 1H), 3.76 (s, 3H), 3.80-3.89 (m, 1H), 4.19 (d, J=16.06 Hz,

2H), 5.60 (d, J=10.16 Hz, 1H), 5.74 (s, 2H), 6.78-6.87 (m, 2H), 7.59 (d, J=8.66 Hz, 2H), 8.36 (s, 1H), 8.67 (s, 1H), 8.90 (s, 1H). [M+H]=465.3.

Example 85

9-(1-Fluoro-2-morpholinoethyl)-6-(4-methoxybenzyl)pyrido[3,2-e][1,2,4]triazolo[1,5-c]pyrimidin-5(6H)-one

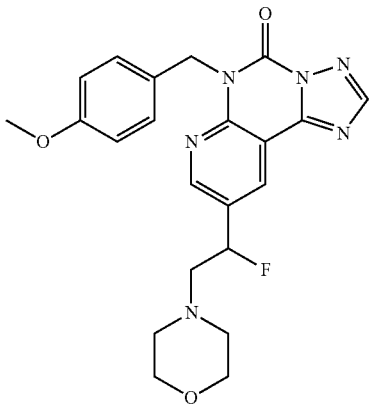 [SMILES: COc1ccc(Cn2c(=O)n3ncnc3c3cc(C(F)CN4CCOCC4)cnc32)cc1]

9-(1-Fluoro-2-morpholinoethyl)-6-(4-methoxybenzyl)pyrido[3,2-e][1,2,4]triazolo[1,5-c]pyrimidin-5(6H)-one. (Dimethylamino)sulfur trifluoride (0.010 mL, 0.18 mmol) was added to a stirred solution of 9-(1-hydroxy-2-morpholinoethyl)-6-(4-methoxybenzyl)pyrido[3,2-e][1,2,4]triazolo[1,5-c]pyrimidin-5(6H)-one (Example 83, 49 mg, 0.090 mmol) in ACN (1 mL). After 4 h, additional (dimethylamino)sulfur trifluoride (0.035 mL, 0.36 mmol) was added and the mixture was stirred at 60° C. for 20 h, and cooled to room temperature. The reaction mixture was diluted with aqueous sodium bicarbonate (3 mL) and extracted with DCM (2×3 mL). The combined organic layers were concentrated under a stream of nitrogen and the residue was taken up in methanol, and filtered. Purification (HPLC, 10-75% ACN in water) afforded the title compound but retained impurities. The product was diluted with aqueous sodium bicarbonate (3 mL) and extracted with DCM (2×3 mL). The combined organic layers were concentrated under a stream of nitrogen. Purification (FCC, SiO$_2$, 0 to 40%, IPA/EtOAc) afforded the title compound (9 mg, 21%) as a white powder. $^1$H NMR (400 MHz, CDCl$_3$) δ 2.58-2.72 (m, 4H), 2.82 (ddd, J=27.98, 13.93, 3.39 Hz, 1H), 3.01 (ddd, J=18.85, 14.15, 7.53 Hz, 1H), 3.72-3.76 (m, 4H), 3.76 (s, 3H), 5.75 (s, 2H), 5.84 (d, J=47.93 Hz, 1H), 6.76-6.88 (m, 2H), 7.60 (d, J=8.66 Hz, 2H), 8.36 (s, 1H), 8.64 (d, J=1.88 Hz, 1H), 8.80 (s, 1H). [M+H]=439.1.

Example 86 was made in a manner analogous to Example 85, with the appropriate starting material and reagent substitutions.

Example 86

9-(2-((2S,6R)-2,6-Dimethylmorpholino)-1-fluoroethyl)-6-(4-methoxybenzyl)pyrido[3,2-e][1,2,4]triazolo[1,5-c]pyrimidin-5(6H)-one

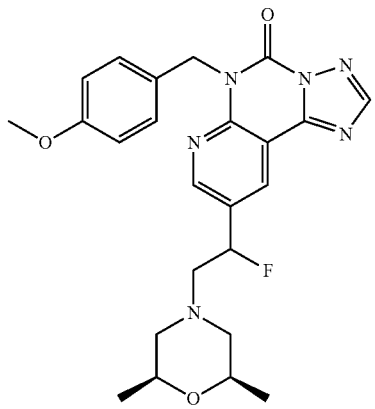 [SMILES: COc1ccc(Cn2c(=O)n3ncnc3c3cc(C(F)CN4C[C@@H](C)O[C@@H](C)C4)cnc32)cc1]

$^1$H NMR (400 MHz, CDCl$_3$) δ 1.28 (d, J=6.27 Hz, 3H), 1.33 (d, J=6.40 Hz, 3H), 2.46-2.70 (m, 2H), 3.35 (d, J=8.41 Hz, 1H), 3.44 (d, J=11.80 Hz, 1H), 3.56-3.73 (m, 2H), 3.77 (s, 2H), 3.80-3.90 (m, 1H), 4.12-4.28 (m, 2H), 5.75 (s, 2H), 6.61 (dd, J=48.19, 9.41 Hz, 1H), 6.83 (d, J=8.66 Hz, 2H), 7.60 (d, J=8.66 Hz, 2H), 8.39 (s, 1H), 8.72 (s, 1H), 8.88 (s, 1H). [M+H]=467.3.

Example 87

6-(4-Methoxybenzyl)-9-(2,2,2-trifluoro-1-hydroxyethyl)pyrido[3,2-e][1,2,4]triazolo[1,5-c]pyrimidin-5(6H)-one

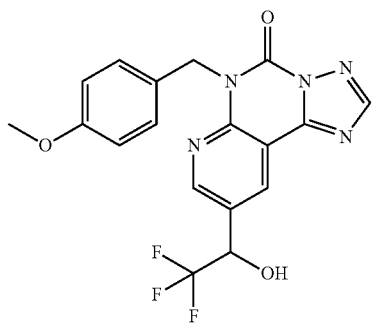 [SMILES: COc1ccc(Cn2c(=O)n3ncnc3c3cc(C(O)C(F)(F)F)cnc32)cc1]

6-(4-Methoxybenzyl)-9-(2,2,2-trifluoro-1-hydroxyethyl)pyrido[3,2-e][1,2,4]triazolo[1,5-c]pyrimidin-5(6H)-one. 9-Acetyl-6-(4-methoxybenzyl)pyrido[3,2-e][1,2,4]triazolo[1,5-c]pyrimidin-5(6H)-one (Example 81, 254 mg, 0.76 mmol), THF (1.3 mL) and 2 M trimethyl(trifluoromethyl)silane in THF (0.45 mL, 0.91 mmol) were combined and stirred for 10 minutes. A 2 M solution of tetrabutylammonium fluoride in THF (75 µl, 0.08 mmol) was added and stirring was continued for 3 days. Additional trimethyl(trifluoromethyl)

silane (0.45 mL, 0.91 mmol) and tetrabutylammonium fluoride (75 μl, 0.08 mmol) was added and the mixture was stirred for 4 h. The reaction mixture was diluted with aqueous sodium bicarbonate (5 mL) and extracted with EtOAc (2×10 mL). The combined extracts were concentrated under vacuum. Purification (FCC, $SiO_2$, 10 to 100%, EtOAc/hexanes) afforded the title compound (154 mg, 48%) as a white powder. $^1$H NMR (400 MHz, $CDCl_3$+DMSO-$d_6$) δ 3.27 (s, 3H), 4.80 (q, J=6.90 Hz, 1H), 5.24 (s, 2H), 6.33 (d, J=8.66 Hz, 2H), 7.05 (d, J=8.53 Hz, 2H), 7.91 (s, 1H), 8.32 (s, 1H), 8.39 (s, 1H). [M+H]=406.1.

Example 88

6-(4-Methoxybenzyl)-9-(2,2,2-trifluoro-1-morpholinoethyl)pyrido[3,2-e][1,2,4]triazolo[1,5-c]pyrimidin-5(6H)-one

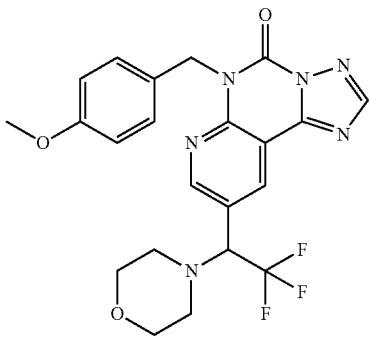 [SMILES: COc1ccc(Cn2c(=O)n3ncnc3c3cc(C(N4CCOCC4)C(F)(F)F)cnc32)cc1]

Step A. 2,2,2-Trifluoro-1-(6-(4-methoxybenzyl)-5-oxo-5,6-dihydropyrido[3,2-e][1,2,4]triazolo[1,5-c]pyrimidin-9-yl)ethyl methanesulfonate. Methane sulfonyl chloride (49 μl, 0.63 mmol) was added to a stirred solution of 6-(4-methoxybenzyl)-9-(2,2,2-trifluoro-1-hydroxyethyl)pyrido[3,2-e][1,2,4]triazolo[1,5-c]pyrimidin-5(6H)-one (Example 87, 127 mg, 0.31 mmol) and TEA (131 μl, 0.94 mmol) in DCM (1.3 mL) and the mixture was stirred for 2 hours. It was diluted with DCM (10 mL), washed with aqueous sodium bicarbonate (5 mL), dried ($MgSO_4$) and concentrated under vacuum to afford the title compound as a brown gum, which was used crude without further purification.

Step B. 6-(4-Methoxybenzyl)-9-(2,2,2-trifluoro-1-morpholinoethyl)pyrido[3,2-e][1,2,4]triazolo[1,5-c]pyrimidin-5(6H)-one. To a solution of 2,2,2-trifluoro-1-(6-(4-methoxybenzyl)-5-oxo-5,6-dihydropyrido[3,2-e][1,2,4]triazolo[1,5-c]pyrimidin-9-yl)ethyl methanesulfonate (from Step A) in DMF (1 mL) was added morpholine (0.10 mL, 1.06 mmol). The reaction mixture was heated at 70° C. for 20 h. Additional morpholine (0.10 mL, 1.06 mmol) was added and heating was continued for 3 days. The mixture was concentrated under a stream of nitrogen. The residue was taken up in DMF and filtered. Purification (HPLC, 10-80% ACN in water) afforded the title compound (39 mg, 20%) as a white powder. $^1$H NMR (400 MHz, $CDCl_3$) δ 2.72 (br s, 4H), 3.74 (q, J=4.02 Hz, 4H), 3.78 (s, 3H), 4.23 (q, J=8.03 Hz, 1H), 5.76 (s, 2H), 6.85 (d, J=8.66 Hz, 2H), 7.62 (d, J=8.66 Hz, 2H), 8.40 (s, 1H), 8.72 (d, J=2.26 Hz, 1H), 8.82 (d, J=2.26 Hz, 1H). [M+H]=475.2.

Example 89

9-(((2S,6R)-2,6-Dimethylmorpholino)methyl)-6-(4-(trifluoromethoxy)benzyl)pyrido[3,2-e][1,2,4]triazolo[1,5-c]pyrimidin-5(6H)-one

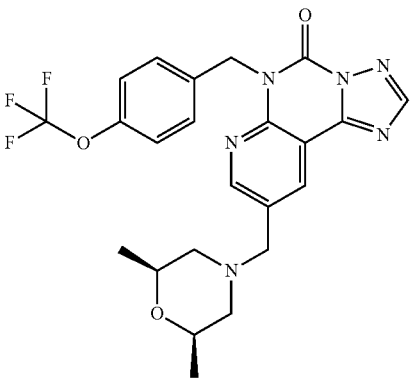 [SMILES: C[C@@H]1CN(Cc2cnc3c(c2)c2ncnn2c(=O)n3Cc2ccc(OC(F)(F)F)cc2)C[C@H](C)O1]

Step A. Potassium (((2S,6R)-2,6-dimethylmorpholino)methyl)-trifluoroborate. To a neat solution of 2,6-dimethylmorpholine (28.67 g, 0.25 mol), was added bromomethylene-potassium-trifluoroborate (25 g, 0.125 mol). The resulting suspension was heated to 100° C. for 3 h, and then cooled to 50° C. IPA (2×50 mL) was added, and the crude mixture was cooled to 10° C. MTBE (4×100 mL) was slowly added, after 1 h the white solid was filtered, washed by of MTBE (4×50 mL), and dried to afford the title compound (33.5 g, 85%) which was used without further purification.

Step B: 2-Amino-5-(((2S,6R)-2,6-dimethylmorpholino)methyl)nicotinonitrile. A suspension of 2-amino-5-bromonicotinonitrile (50 mg, 0.25 mmol), potassium (((2S,6R)-2,6-dimethylmorpholino)methyl)-trifluoroborate (219 mg, 0.51 mmol), $Cs_2CO_3$ (247 mg, 0.76 mmol), dicyclohexyl(2',4',6'-triisopropylbiphenyl-2-yl)phosphine (36 mg, 0.076 mmol) and palladium(II) acetate (8.5 mg, 0.038 mmol) in dioxane (1 mL) and water (0.1 mL) was purged with nitrogen for 10 minutes, then sealed and heated at 80° C. for 15 hours. The reaction was filtered through CELITE® while still hot, cooled to room temperature, and diluted with water (10 mL). The resulting precipitate was filtered, washed with water (10 mL) and hexanes (10 mL), and dried under vacuum to give the title compound as a solid (57 mg, 92%). $^1$H NMR (400 MHz, DMSO-$d_6$) δ 1.03 (d, J=6.3 Hz, 6H), 1.61 (t, J=10.7 Hz, 2H), 2.64 (d, J=10.7 Hz, 2H), 3.45-3.61 (m, 2H), 6.83 (s, 2H), 7.74 (d, J=2.3 Hz, 1H), 8.03-8.19 (m, 1H).

Step C: Ethyl 3-cyano-5-(((2S,6R)-2,6-dimethylmorpholino)methyl)pyridin-2-ylcarbamate. Sodium hydride in mineral oil (60%, 25 mg, 0.61 mmol) was added to 2-amino-5-(((2S,6R)-2,6-dimethylmorpholino)methyl)nicotinonitrile (100 mg, 0.41 mmol) in THF (2 mL) and the mixture was stirred for 5 minutes. Ethyl chloroformate (0.05 mL, 0.48 mmol) was added followed by additional sodium hydride (16 mg, 0.41 mmol) and the reaction stirred at room temperature for 3 h. The reaction was poured into a saturated solution of sodium bicarbonate (10 mL), extracted with EtOAc (3×5 mL), dried ($Na_2SO_4$) and concentrated under reduced pressure. The residue was taken up in methanol (10 mL) and stirred with potassium carbonate (170 mg) for 10 minutes, then poured into saturated sodium bicarbonate (10 mL) and extracted with EtOAc (3×5 mL). The combined organic layers were dried ($Na_2SO_4$) and concentrated under reduced pressure. Purification (FCC, SiO$_2$, 0-100%, EtOAc/hexanes) afforded the title compound as a white powder (104 mg, 80%). $^1$H NMR (400 MHz, DMSO-d$_6$) δ 1.04 (d, J=6.27 Hz, 6H), 1.26 (t, J=7.03 Hz, 3H), 1.69 (t, J=10.60 Hz, 2H), 2.67 (d, J=10.67 Hz, 2H), 3.51 (s, 2H), 3.54-3.62 (m, 2H), 4.17 (q, J=7.11 Hz, 2H), 8.12-8.24 (m, 1H), 8.56 (d, J=2.01 Hz, 1H), 10.37 (s, 1H).

Step D: 9-(((2S,6R)-2,6-Dimethylmorpholino)methyl)pyrido[3,2-e][1,2,4]triazolo[1,5-c]pyrimidin-5(6H)-one. Ethyl 3-cyano-5-(((2S,6R)-2,6-dimethylmorpholino)methyl)pyridin-2-ylcarbamate (35 mg, 0.11 mmol), formyl hydrazine (8 mg, 0.13 mmol) and N-ethyl N-isopropylpropan-2-amine (0.01 mL, 0.055 mmol) were heated in DMA (1 mL) at 125° C. for 15 h. The reaction was cooled to room temperature and purified directly (HPLC, 10-70% ACN-water) to afford the title compound as a solid (29 mg, 84%). $^1$H NMR (400 MHz, DMSO-d$_6$) δ 1.04 (d, J=6.15 Hz, 6H), 1.73 (t, J=10.67 Hz, 2H), 2.72 (d, J=10.79 Hz, 2H), 3.53-3.66 (m, 4H), 8.45 (s, 1H), 8.57 (s, 1H), 8.62 (s, 1H), 12.82 (br s, 1H).

Step E: 9-(((2S,6R)-2,6-Dimethylmorpholino)methyl)-6-(4-(trifluoromethoxy)benzyl)pyrido[3,2-e][1,2,4]triazolo[1,5-c]pyrimidin-5(6H)-one. To a mixture of 9-(((2S,6R)-2,6-dimethylmorpholino)methyl)pyrido[3,2-e][1,2,4]triazolo[1,5-c]pyrimidin-5(6H)-one (50 mg, 0.16 mmol) and 4-(trifluoromethoxy)benzyl bromide (49 mg, 0.19 mmol) in DMF (2 mL) was added potassium carbonate (44 mg, 0.32 mmol). The resulting mixture was heated at 55° C. overnight. The crude mixture was filtered then purified directly (HPLC, 10-70% ACN-water) to afford the title compound (58 mg, 61%) as a white solid. $^1$H NMR (400 MHz, DMSO-d$_6$) δ 1.14 (d, J=6.15 Hz, 6H), 2.63-2.85 (m, 2H), 3.26-3.45 (m, 2H), 3.72-3.86 (m, 2H), 4.40-4.62 (m, 2H), 5.70 (s, 2H), 7.32 (d, J=8.28 Hz, 2H), 7.59 (d, J=8.66 Hz, 2H), 8.69 (s, 1H), 8.84 (s, 1H), 8.89 (br s, 1H). [M+H]=489.2.

Examples 90 thru 120 were made in a manner analogous to Example 89, Steps B-E with the appropriate starting material and reagent substitutions.

Example 90

9-(((2S,6R)-2,6-Dimethylmorpholino)methyl)-6-(4-fluoro-3-methylbenzyl)pyrido[3,2-e][1,2,4]triazolo[1,5-c]pyrimidin-5(6H)-one

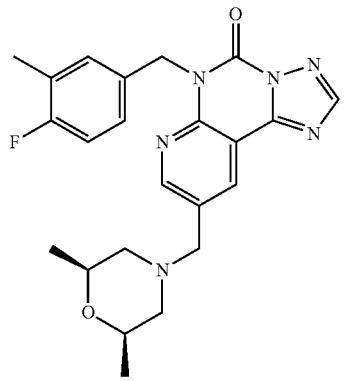 [SMILES: Cc1cc(Cn2c(=O)n3ncnc3c3cc(CN4C[C@@H](C)O[C@@H](C)C4)cnc32)ccc1F]

$^1$H NMR (400 MHz, DMSO-d$_6$) δ 1.13 (d, J=6.02 Hz, 6H), 2.19 (s, 3H), 2.59-2.85 (m, 2H), 3.16-3.51 (m, 2H), 3.71-3.85 (m, 2H), 4.38-4.68 (m, 2H), 5.62 (s, 2H), 7.07 (t, J=9.16 Hz, 1H), 7.26-7.32 (m, 1H), 7.34-7.40 (m, 1H), 8.69 (s, 1H), 8.77-8.92 (m, 2H). [M+H]=437.2.

Example 91

9-(((2S,6R)-2,6-Dimethylmorpholino)methyl)-6-(4-fluorobenzyl)pyrido[3,2-e][1,2,4]triazolo[1,5-c]pyrimidin-5(6H)-one

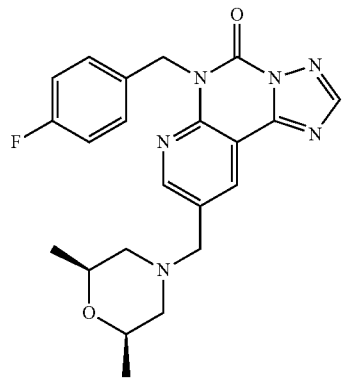 [SMILES: C[C@@H]1CN(Cc2cnc3c(c2)c2ncnn2c(=O)n3Cc2ccc(F)cc2)C[C@H](C)O1]

$^1$H NMR (400 MHz, DMSO-d$_6$) δ 1.14 (d, J=6.27 Hz, 6H), 2.65-2.86 (m, 2H), 3.29-3.47 (m, 2H), 3.72-3.86 (m, 2H), 4.47-4.63 (m, 2H), 5.66 (s, 2H), 7.15 (t, J=8.85 Hz, 2H), 7.51 (dd, J=8.47, 5.58 Hz, 2H), 8.69 (s, 1H), 8.81-8.86 (m, 1H), 8.87-8.92 (m, 1H). [M+H]=423.2.

Example 92

9-(((2S,6R)-2,6-Dimethylmorpholino)methyl)-6-(3-fluoro-4-methoxybenzyl)pyrido[3,2-e][1,2,4]triazolo[1,5-c]pyrimidin-5(6H)-one

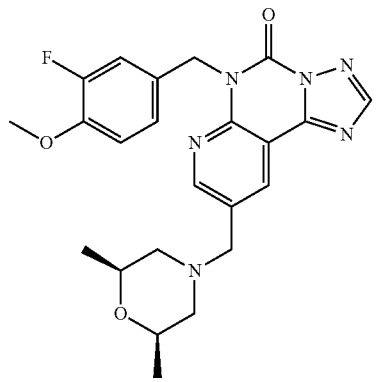 [SMILES: COc1ccc(Cn2c(=O)n3ncnc3c3cc(CN4C[C@@H](C)O[C@@H](C)C4)cnc32)cc1F]

$^1$H NMR (400 MHz, DMSO-d$_6$) δ 1.14 (d, J=6.27 Hz, 6H), 2.68-2.83 (m, 2H), 3.31-3.43 (m, 2H), 3.74-3.84 (m, 5H), 4.49-4.61 (m, 2H), 5.61 (s, 2H), 7.11 (t, J=8.72 Hz, 1H), 7.21-7.36 (m, 2H), 8.69 (s, 1H), 8.83-8.86 (m, 1H), 8.87-8.91 (m, 1H). [M+H]=453.2.

Example 93

9-(((2S,6R)-2,6-Dimethylmorpholino)methyl)-6-(2-fluoro-4-methoxybenzyl)pyrido[3,2-e][1,2,4]triazolo[1,5-c]pyrimidin-5(6H)-one

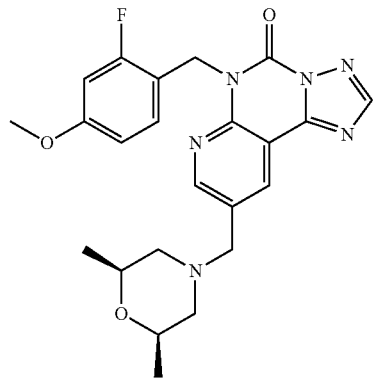 [SMILES: COc1ccc(Cn2c(=O)n3ncnc3c3cc(CN4C[C@@H](C)O[C@@H](C)C4)cnc32)c(F)c1]

$^1$H NMR (400 MHz, DMSO-d$_6$) δ 1.14 (d, J=6.27 Hz, 6H), 2.67-2.84 (m, 2H), 3.30-3.43 (m, 2H), 3.75 (s, 3H), 3.76-3.84 (m, 2H), 4.47-4.59 (m, 2H), 5.64 (s, 2H), 6.65 (dd, J=8.66, 2.38 Hz, 1H), 6.88 (dd, J=12.36, 2.45 Hz, 1H), 7.23 (t, J=8.91 Hz, 1H), 8.70 (s, 1H), 8.80-8.85 (m, 1H), 8.87-8.93 (m, 1H). [M+H]=453.2.

Example 94

6-(3-Bromo-4-fluorobenzyl)-9-(((2S,6R)-2,6-dimethylmorpholino)methyl)pyrido[3,2-e][1,2,4]triazolo[1,5-c]pyrimidin-5(6H)-one

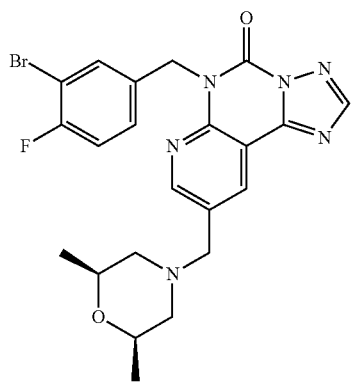

$^1$H NMR (400 MHz, CDCl$_3$) δ 8.89 (d, J=1.63 Hz, 1H), 8.72 (s, 1H), 8.41 (s, 1H), 7.86 (d, J=6.40 Hz, 1H), 7.54-7.65 (m, 1H), 7.06 (t, J=8.41 Hz, 1H), 5.73 (s, 2H), 4.33 (s, 2H), 3.91-4.08 (m, 2H), 3.47 (d, J=11.54 Hz, 2H), 2.46 (t, J=11.11 Hz, 2H), 1.24 (d, J=6.27 Hz, 6H). [M+H]=501.10.

Example 95

4-((9-(((2S,6R)-2,6-Dimethylmorpholino)methyl)-5-oxopyrido[3,2-e][1,2,4]triazolo[1,5-c]pyrimidin-6(5H)-yl)methyl)benzonitrile

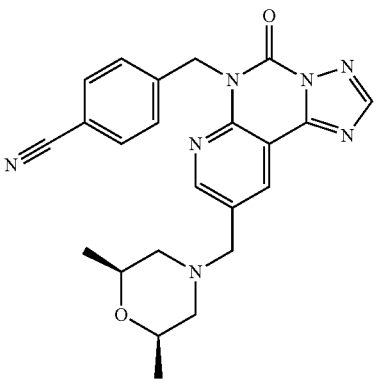 [SMILES: C[C@@H]1CN(Cc2cnc3c(c2)c2ncnn2c(=O)n3Cc2ccc(C#N)cc2)C[C@H](C)O1]

$^1$H NMR (400 MHz, CDCl$_3$) δ 8.90 (d, J=2.38 Hz, 1H), 8.73 (d, J=2.26 Hz, 1H), 8.44 (s, 1H), 7.71-7.77 (m, 2H), 7.61-7.67 (m, 2H), 5.85 (s, 2H), 4.32 (s, 2H), 3.96-4.08 (m, 2H), 3.47 (d, J=11.17 Hz, 2H), 2.47 (t, J=11.17 Hz, 2H), 1.26 (d, J=6.27 Hz, 6H), [M+H]=430.20.

Example 96

6-(4-(tert-Butyl)benzyl)-9-((2S,6R)-2,6-dimethylmorpholino)methyl)pyrido[3,2-e][1,2,4]triazolo[1,5-c]pyrimidin-5(6H)-one

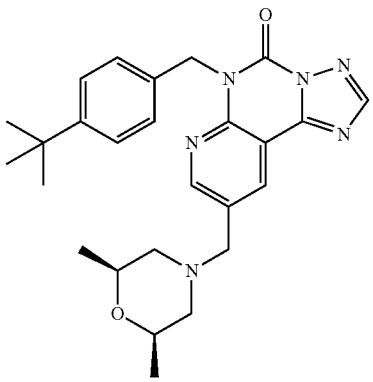 [SMILES: C[C@@H]1CN(Cc2cnc3c(c2)c2ncnn2c(=O)n3Cc2ccc(C(C)(C)C)cc2)C[C@H](C)O1]

$^1$H NMR (400 MHz, CDCl$_3$) δ 8.89 (d, J=2.26 Hz, 1H), 8.39 (s, 1H), 8.68 (d, J=2.26 Hz, 1H), 7.57 (d, J=8.41 Hz, 2H), 7.31-7.39 (m, 2H), 5.78 (s, 2H), 4.31 (s, 2H), 3.94-4.08 (m, 2H), 3.44 (d, J=11.04 Hz, 2H), 2.43 (t, J=11.11 Hz, 3H), 1.28 (s, 9H), 1.24 (d, J=6.40 Hz, 6H). [M+H]=461.30.

Example 97

3-((9-(((2S,6R)-2,6-Dimethylmorpholino)methyl)-5-oxopyrido[3,2-e][1,2,4]triazolo[1,5-c]pyrimidin-6(5H)-yl)methyl)benzonitrile

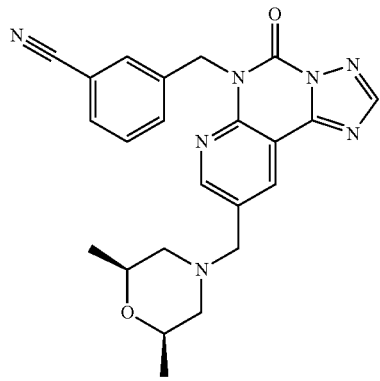 [SMILES: C[C@@H]1CN(Cc2cnc3c(c2)c2ncnn2c(=O)n3Cc2cccc(C#N)c2)C[C@H](C)O1]

$^1$H NMR (400 MHz, CDCl$_3$) δ 1.25 (d, J=6.27 Hz, 6H), 2.52 (t, J=11.23 Hz, 2H), 3.54 (d, J=11.42 Hz, 2H), 3.93-4.04 (m, 2H), 4.38 (s, 2H), 4.77 (s, 1H), 5.31 (s, 1H), 7.43-7.50 (m, 1H), 7.57-7.61 (m, 2H), 7.89 (d, J=1.38 Hz, 1H), 8.43 (s, 1H), 8.79 (d, J=2.38 Hz, 1H), 8.87 (d, J=2.38 Hz, 1H). [M+H]=430.17.

Example 98

9-(((2S,6R)-2,6-Dimethylmorpholino)methyl)-6-(4-(methylsulfonyl)benzyl)pyrido[3,2-e][1,2,4]triazolo[1,5-c]pyrimidin-5(6H)-one

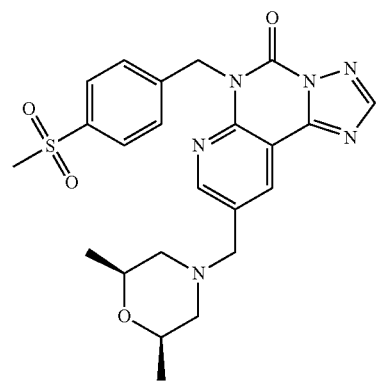 [SMILES: C[C@@H]1CN(Cc2cnc3c(c2)c2ncnn2c(=O)n3Cc2ccc(S(C)(=O)=O)cc2)C[C@H](C)O1]

$^1$H NMR (400 MHz, CDCl$_3$) δ 1.26 (d, J=6.40 Hz, 6H), 2.50 (t, J=11.17 Hz, 2H), 3.04 (s, 3H), 3.51 (d, J=11.04 Hz, 2H), 3.96-4.07 (m, 2H), 4.35 (s, 2H), 5.88 (s, 2H), 7.80 (d, J=8.41 Hz, 2H), 7.91 (d, J=8.53 Hz, 2H), 8.44 (s, 1H), 8.76 (d, J=2.38 Hz, 1H), 8.88 (d, J=2.38 Hz, 1H). [M+H]=483.20.

Example 99

9-(((2S,6R)-2,6-Dimethylmorpholino)methyl)-6-(2-methylbenzyl)pyrido[3,2-e][1,2,4]triazolo[1,5-c]pyrimidin-5(6H)-one

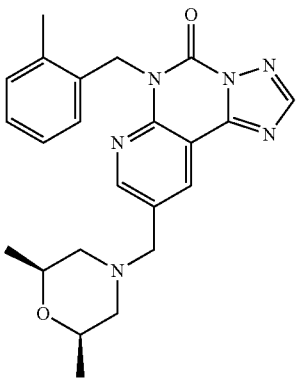 [SMILES: Cc1ccccc1Cn1c(=O)n2ncnc2c2cc(CN3C[C@@H](C)O[C@@H](C)C3)cnc21]

$^1$H NMR (400 MHz, CDCl$_3$) δ 1.15 (d, J=6.40 Hz, 6H), 1.84 (t, J=10.67 Hz, 2H), 2.60 (s, 3H), 2.69 (d, J=10.29 Hz, 2H), 3.60 (s, 2H) 3.65-3.74 (m, 2H), 5.80 (s, 2H), 6.93 (d, J=7.65 Hz, 1H), 7.04 (t, J=7.59 Hz, 1H), 7.13-7.18 (m, 1H), 7.20-7.24 (m, 1H), 8.40 (s, 1H), 8.64 (dd, J=10.35, 2.20 Hz, 2H). [M+H]=419.81.

Example 100

9-(((2S,6R)-2,6-Dimethylmorpholino)methyl)-6-(3-iodobenzyl)pyrido[3,2-e][1,2,4]triazolo[1,5-c]pyrimidin-5(6H)-one

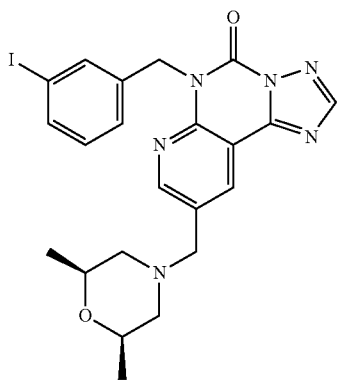 [SMILES: C[C@@H]1CN(Cc2cnc3c(c2)c2ncnn2c(=O)n3Cc2cccc(I)c2)C[C@H](C)O1]

$^1$H NMR (400 MHz, CDCl$_3$) δ 8.86 (d, J=2.4 Hz, 1H), 8.75 (d, J=2.3 Hz, 1H), 8.41 (s, 1H), 7.95 (t, J=1.6 Hz, 1H), 7.64-7.55 (m, 2H), 7.05 (t, J=7.8 Hz, 1H), 5.73 (s, 2H), 4.37 (s, 2H), 4.04-3.93 (m, 2H), 3.52 (d, J=11.2 Hz, 2H), 2.48 (t, J=11.2 Hz, 2H), 1.25 (d, J=6.4 Hz, 6H). [M+H]=531.01.

Example 101

6-(3,5-Difluorobenzyl)-9-((2S,6R)-2,6-dimethylmorpholino)methyl)pyrido[3,2-e][1,2,4]triazolo[1,5-c]pyrimidin-5(6H)-one

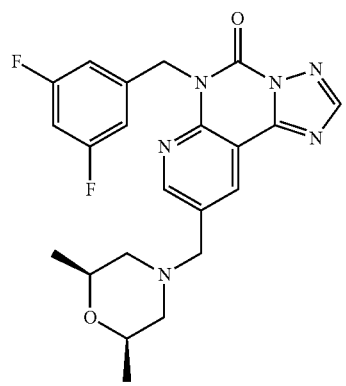 [SMILES: C[C@@H]1CN(Cc2cnc3c(c2)c2ncnn2c(=O)n3Cc2cc(F)cc(F)c2)C[C@H](C)O1]

¹H NMR (400 MHz, CDCl₃) δ 1.27 (d, J=6.40 Hz, 6H), 2.48 (t, J=11.23 Hz, 2H), 3.49 (d, J=11.04 Hz, 2H), 3.97-4.09 (m, 2H), 4.35 (s, 2H), 5.77 (s, 2H), 6.71-6.81 (m, 1H), 7.09-7.18 (m, 2H), 8.44 (s, 1H), 8.76 (d, J=2.38 Hz, 1H), 8.88 (d, J=2.26 Hz, 1H). [M+H]=441.20.

Example 102

6-(2-Bromo-4-methoxybenzyl)-9-((2S,6R)-2,6-dimethylmorpholino)methyl)pyrido[3,2-e][1,2,4]triazolo[1,5-c]pyrimidin-5(6H)-one

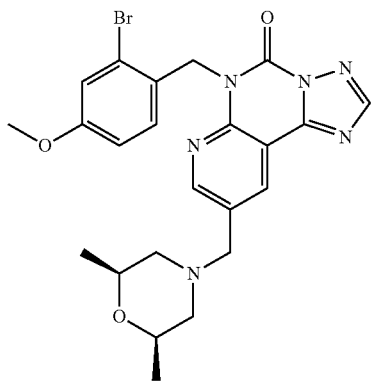 [SMILES: COc1ccc(Cn2c(=O)n3ncnc3c3cc(CN4C[C@@H](C)O[C@@H](C)C4)cnc32)c(Br)c1]

¹H NMR (400 MHz, CDCl₃) δ 1.25 (d, J=6.27 Hz, 6H), 2.42 (t, J=11.11 Hz, 2H), 3.42 (d, J=11.04 Hz, 2H), 3.79 (s, 3H), 3.99-4.08 (m, 2H), 4.28 (s, 2H), 5.84 (s, 2H), 6.70-6.77 (m, 1H), 6.89 (d, J=8.66 Hz, 1H), 7.20 (d, J=2.51 Hz, 1H), 8.46 (s, 1H), 8.74-8.81 (m, 2H). [M+H]=514.10.

Example 103

6-(2,6-Difluoro-4-methoxybenzyl)-9-(((2S,6R)-2,6-dimethylmorpholino)methyl)pyrido[3,2-e][1,2,4]triazolo[1,5-c]pyrimidin-5(6H)-one

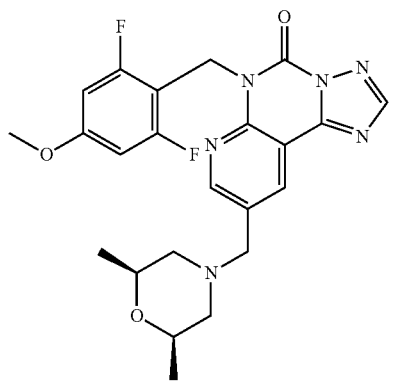 [SMILES: COc1cc(F)c(Cn2c(=O)n3ncnc3c3cc(CN4C[C@@H](C)O[C@@H](C)C4)cnc32)c(F)c1]

¹H NMR (400 MHz, CDCl₃) δ 1.24 (d, J=6.27 Hz, 6H), 2.39 (t, J=11.11 Hz, 2H), 3.07-3.15 (m, 1H), 3.36 (d, J=11.29 Hz, 2H), 3.52 (s, 1H), 3.77 (s, 3H), 3.90 (s, 1H), 3.95-4.07 (m, 2H), 4.24 (s, 2H), 5.84 (s, 2H), 6.36-6.47 (m, 2H), 6.62-6.70 (m, 1H), 8.40 (s, 1H), 8.71 (d, J=2.26 Hz, 1H), 8.79 (d, J=2.26 Hz, 1H). [M+H]=471.20.

Example 104

9-(((2S,6R)-2,6-Dimethylmorpholino)methyl)-6-((1-methyl-1H-indazol-6-yl)methyl)pyrido[3,2-e][1,2,4]triazolo[1,5-c]pyrimidin-5(6H)-one

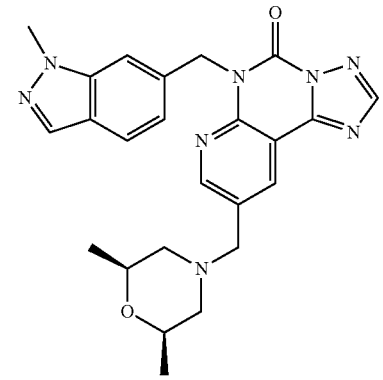 [SMILES: C[C@@H]1CN(Cc2cnc3c(c2)c2ncnn2c(=O)n3Cc2ccc3cnn(C)c3c2)C[C@H](C)O1]

¹H NMR (400 MHz, CDCl₃) δ 8.93 (d, J=2.4 Hz, 1H), 8.68 (d, J=2.3 Hz, 1H), 8.41 (s, 1H), 7.94 (d, J=0.8 Hz, 1H), 7.72 (s, 1H), 7.66 (d, J=8.8 Hz, 1H), 7.45 (dd, J=1.3, 8.4 Hz, 1H), 5.95 (s, 2H), 4.30 (s, 2H), 4.07 (s, 3H), 4.01 (dd, J=6.4, 8.9 Hz, 2H), 3.43 (d, J=11.3 Hz, 2H), 2.42 (t, J=11.2 Hz, 2H), 1.23 (d, J=6.3 Hz, 6H). [M+H]=459.20.

Example 105

6-(4-(1H-Pyrazol-1-yl)benzyl)-9-((2S,6R)-2,6-dimethylmorpholino)methyl)pyrido[3,2-e][1,2,4]triazolo[1,5-c]pyrimidin-5(6H)-one

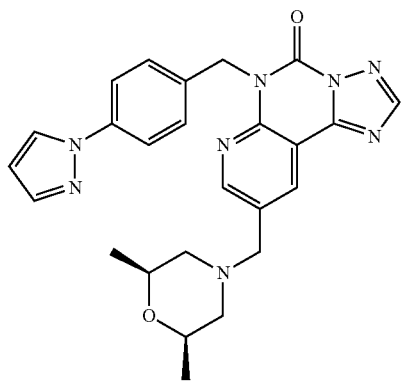 [SMILES: C[C@@H]1CN(Cc2cnc3c(c2)c2ncnn2c(=O)n3Cc2ccc(-n3cccn3)cc2)C[C@H](C)O1]

¹H NMR (400 MHz, CDCl₃) δ 8.92 (d, J=2.4 Hz, 1H), 8.72 (d, J=2.4 Hz, 1H), 8.43 (s, 1H), 7.91 (d, J=2.3 Hz, 1H), 7.78-7.74 (m, 2H), 7.73 (d, J=1.5 Hz, 1H), 7.68-7.60 (m, 2H), 6.50-6.44 (m, 1H), 5.84 (s, 2H), 4.33 (s, 2H), 4.13-3.92 (m, 2H), 3.46 (d, J=11.0 Hz, 3H), 2.45 (t, J=11.2 Hz, 3H), 1.25 (d, J=6.3 Hz, 6H). [M+H]=471.20.

Example 106

6-(4-(Difluoromethoxy)-2-fluorobenzyl)-9-((2S,6R)-2,6-dimethylmorpholino)methyl)pyrido[3,2-e][1,2,4]triazolo[1,5-c]pyrimidin-5(6H)-one

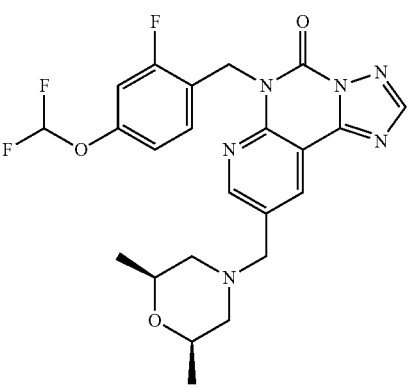 [SMILES: C[C@@H]1CN(Cc2cnc3c(c2)c2ncnn2c(=O)n3Cc2ccc(OC(F)F)cc2F)C[C@H](C)O1]

¹H NMR (400 MHz, CDCl₃) δ 8.68 (d, J=2.1 Hz, 1H), 8.63 (d, J=2.0 Hz, 1H), 8.32 (s, 1H), 7.24 (t, J=8.4 Hz, 1H), 6.83-6.71 (m, 2H), 6.60-6.18 (m, 1H), 5.75 (s, 2H), 3.99 (br s, 2H), 3.83 (dd, J=6.5, 8.7 Hz, 2H), 3.10 (d, J=10.4 Hz, 2H), 2.16 (t, J=10.7 Hz, 2H), 1.12 (d, J=6.4 Hz, 6H). [M+H]=489.16.

Example 107

6-(3,5-Difluoro-4-methoxybenzyl)-9-(((2S,6R)-2,6-dimethylmorpholino)methyl)pyrido[3,2-e][1,2,4]triazolo[1,5-c]pyrimidin-5(6H)-one

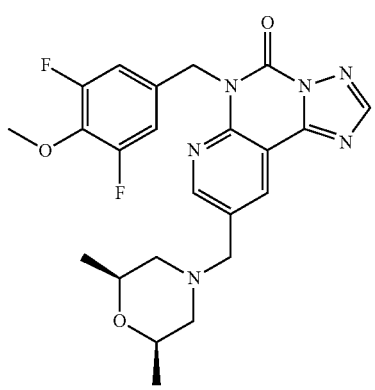 [SMILES: COc1c(F)cc(Cn2c(=O)n3ncnc3c3cc(CN4C[C@@H](C)O[C@@H](C)C4)cnc32)cc1F]

¹H NMR (400 MHz, CDCl₃) δ 8.81 (d, J=1.8 Hz, 1H), 8.71 (s, 1H), 8.40 (s, 1H), 7.24-7.15 (m, 2H), 5.69 (s, 2H), 3.99 (br s, 1H), 3.95 (s, 3H), 3.93-3.83 (m, 2H), 3.71 (s, 1H), 2.23-2.13 (m, 1H), 1.44 (s, 1H), 1.20 (d, J=6.3 Hz, 6H). [M+H]=471.11.

Example 108

6-(2,3-Difluoro-4-methoxybenzyl)-9-(((2S,6R)-2,6-dimethylmorpholino)methyl)pyrido[3,2-e][1,2,4]triazolo[1,5-c]pyrimidin-5(6H)-one ¹H NMR (400 MHz, CD₃OD) δ 1.20 (d, J=6.27 Hz, 6H), 2.25-2.54 (m, 2H), 3.10-3.22 (m, 2H), 3.74-3.83 (m, 2H), 3.86 (s, 3H), 4.05-4.30 (m, 2H), 5.83 (s, 2H), 6.77-6.86 (m, 1H), 7.03-7.12 (m, 1H), 8.55 (s, 1H), 8.82 (s, 2H). [M+H]=471.20.

Example 109

9-(((2S,6R)-2,6-Dimethylmorpholino)methyl)-6-(2-((trifluoromethyl)thio)benzyl)pyrido[3,2-e][1,2,4]triazolo[1,5-c]pyrimidin-5(6H)-one

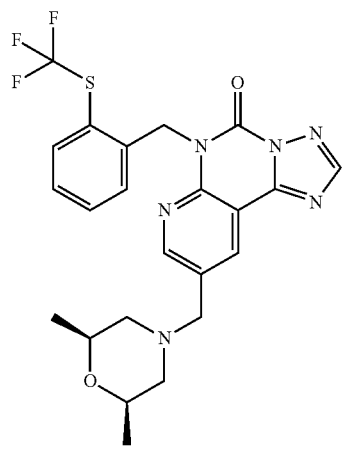 [SMILES: C[C@@H]1CN(Cc2cnc3c(c2)c2ncnn2c(=O)n3Cc2ccccc2SC(F)(F)F)C[C@H](C)O1]

¹H NMR (400 MHz, CDCl₃) δ 8.56 (d, J=2.1 Hz, 1H), 8.52 (d, J=2.1 Hz, 1H), 8.32 (s, 1H), 7.69 (d, J=7.3 Hz, 1H), 7.30-7.21 (m, 2H), 7.14 (dd, J=1.6, 7.5 Hz, 1H), 6.03 (s, 2H), 3.67-3.55 (m, 2H), 3.50 (s, 2H), 2.59 (d, J=10.4 Hz, 2H), 1.75 (t, J=10.7 Hz, 2H), 1.06 (d, J=6.3 Hz, 6H). [M+H]=505.10.

Example 110

6-(3-Chloro-4-fluorobenzyl)-9-((2S,6R)-2,6-dimethylmorpholino)methyl)pyrido[3,2-e][1,2,4]triazolo[1,5-c]pyrimidin-5(6H)-one

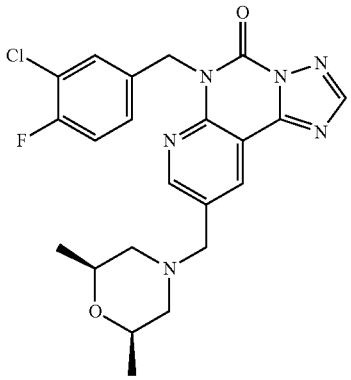 [SMILES: C[C@@H]1CN(Cc2cnc3c(c2)c2ncnn2c(=O)n3Cc2ccc(F)c(Cl)c2)C[C@H](C)O1]

¹H NMR (400 MHz, CDCl₃) δ 8.64 (d, J=2.3 Hz, 1H), 8.56 (d, J=2.1 Hz, 1H), 8.29 (s, 1H), 7.63 (dd, J=2.1, 7.0 Hz, 1H), 7.47 (ddd, J=2.3, 4.6, 8.5 Hz, 1H), 6.99 (t, J=8.7 Hz, 1H), 5.65 (s, 2H), 3.66-3.57 (m, 2H), 3.54 (s, 2H), 2.61 (d, J=10.3 Hz, 2H), 1.78 (t, J=10.7 Hz, 2H), 1.07 (d, J=6.3 Hz, 6H). [M+H]=457.09.

Example 111

6-(3,4-Dichlorobenzyl)-9-(((2S,6R)-2,6-dimethylmorpholino)methyl)pyrido[3,2-e][1,2,4]triazolo[1,5-c]pyrimidin-5(6H)-one

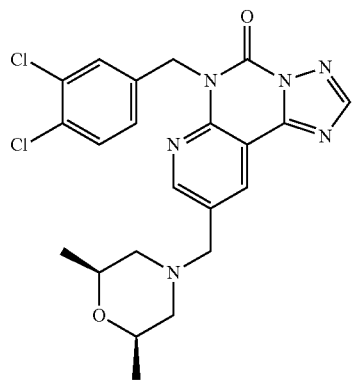 [SMILES: C[C@@H]1CN(Cc2cnc3c(c2)c2ncnn2c(=O)n3Cc2ccc(Cl)c(Cl)c2)C[C@H](C)O1]

¹H NMR (400 MHz, CDCl₃) δ 8.63 (d, J=2.1 Hz, 1H), 8.56 (d, J=2.1 Hz, 1H), 8.30 (s, 1H), 7.64 (d, J=2.0 Hz, 1H), 7.41 (dd, J=2.0, 8.3 Hz, 1H), 7.30 (d, J=8.3 Hz, 1H), 5.65 (s, 2H), 3.66-3.57 (m, 2H), 3.54 (s, 2H), 2.61 (d, J=10.4 Hz, 2H), 1.78 (t, J=10.6 Hz, 2H), 1.07 (d, J=6.3 Hz, 6H). [M+H]=473.04.

Example 112

6-(2-Chloro-4-methoxybenzyl)-9-(((2S,6R)-2,6-dimethylmorpholino)methyl)pyrido[3,2-e][1,2,4]triazolo[1,5-c]pyrimidin-5(6H)-one

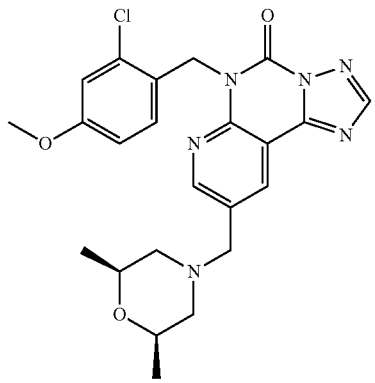 [SMILES: COc1ccc(Cn2c(=O)n3ncnc3c3cc(CN4C[C@@H](C)O[C@@H](C)C4)cnc32)c(Cl)c1]

¹H NMR (400 MHz, CDCl₃) δ 1.26 (d, J=6.27 Hz, 6H), 2.45 (t, J=11.23 Hz, 2H), 3.47 (d, J=11.17 Hz, 2H), 3.79 (s, 3H), 4.00-4.08 (m, 2H), 4.32 (s, 2H), 5.86 (s, 2H), 6.70 (dd, J=8.72, 2.57 Hz, 1H), 6.95-7.01 (m, 2H), 8.45 (s, 1H), 8.77 (d, J=1.63 Hz, 2H). [M+H]=469.20.

Example 113

6-(2-(Difluoromethoxy)benzyl)-9-((2S,6R)-2,6-dimethylmorpholino)methyl)pyrido[3,2-e][1,2,4]triazolo[1,5-c]pyrimidin-5(6H)-one

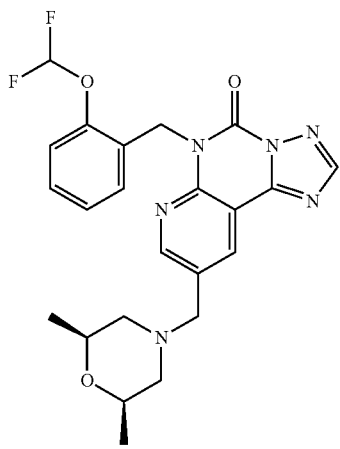 [SMILES: C[C@@H]1CN(Cc2cnc3c(c2)c2ncnn2c(=O)n3Cc2ccccc2OC(F)F)C[C@H](C)O1]

$^1$H NMR (400 MHz, CDCl$_3$) δ 8.59-8.52 (m, 2H), 8.30 (s, 1H), 7.21 (s, 1H), 7.09 (d, J=7.9 Hz, 2H), 7.03-6.97 (m, 1H), 6.82-6.39 (m, 1H), 5.80 (s, 2H), 3.64-3.56 (m, 2H), 3.52 (s, 2H), 2.60 (d, J=10.5 Hz, 2H), 1.76 (t, J=10.7 Hz, 2H), 1.06 (d, J=6.3 Hz, 6H). [M+H]=471.16.

Example 114

6-(4-Chloro-3-fluorobenzyl)-9-((2S,6R)-2,6-dimethylmorpholino)methyl)pyrido[3,2-e][1,2,4]triazolo[1,5-c]pyrimidin-5(6H)-one

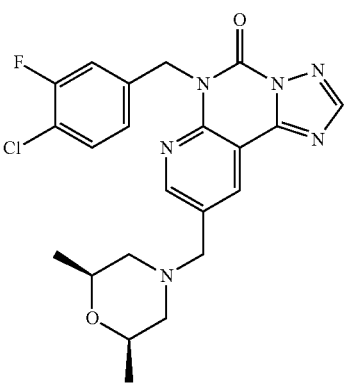 [SMILES: C[C@@H]1CN(Cc2cnc3c(c2)c2ncnn2c(=O)n3Cc2ccc(Cl)c(F)c2)C[C@H](C)O1]

$^1$H NMR (400 MHz, CDCl$_3$) δ 8.72 (d, J=2.3 Hz, 1H), 8.65 (d, J=2.1 Hz, 1H), 8.38 (s, 1H), 7.46-7.31 (m, 3H), 5.76 (s, 2H), 3.76-3.67 (m, 2H), 3.63 (s, 2H), 2.70 (d, J=10.3 Hz, 2H), 1.87 (t, J=10.7 Hz, 2H), 1.15 (d, J=6.4 Hz, 6H). [M+H]=457.11.

Example 115

6-(3-Chloro-5-fluorobenzyl)-9-((2S,6R)-2,6-dimethylmorpholino)methyl)pyrido[3,2-e][1,2,4]triazolo[1,5-c]pyrimidin-5(6H)-one

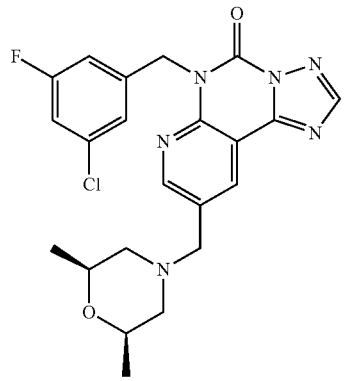 [SMILES: C[C@@H]1CN(Cc2cnc3c(c2)c2ncnn2c(=O)n3Cc2cc(F)cc(Cl)c2)C[C@H](C)O1]

$^1$H NMR (400 MHz, CDCl$_3$) δ 8.72 (d, J=2.3 Hz, 1H), 8.66 (d, J=2.1 Hz, 1H), 8.39 (s, 1H), 7.40 (s, 1H), 7.26-7.21 (m, 1H), 7.04-6.99 (m, 1H), 5.75 (s, 2H), 3.75-3.67 (m, 2H), 3.64 (s, 2H), 2.71 (d, J=10.4 Hz, 2H), 1.87 (t, J=10.7 Hz, 2H), 1.16 (d, J=6.3 Hz, 6H). [M+H]=457.10.

Example 116

9-(((2S,6R)-2,6-Dimethylmorpholino)methyl)-6-(4-(2-oxopyrrolidin-1-yl)benzyl)pyrido[3,2-e][1,2,4]triazolo[1,5-c]pyrimidin-5(6H)-one

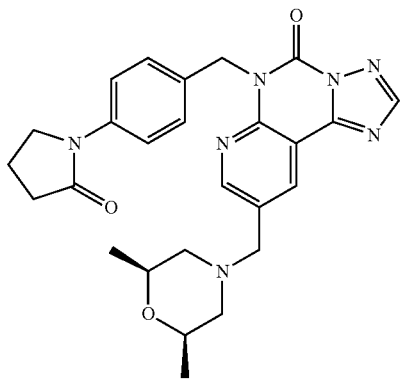 [SMILES: C[C@@H]1CN(Cc2cnc3c(c2)c2ncnn2c(=O)n3Cc2ccc(N3CCCC3=O)cc2)C[C@H](C)O1]

$^1$H NMR (400 MHz, CDCl$_3$) δ 8.86 (d, J=2.1 Hz, 1H), 8.72 (d, J=2.1 Hz, 1H), 8.37 (s, 1H), 7.61 (d, J=8.7 Hz, 2H), 7.50 (d, J=8.8 Hz, 2H), 5.75 (s, 2H), 4.35 (s, 2H), 3.99 (dd, J=6.3, 9.2 Hz, 2H), 3.83 (t, J=7.1 Hz, 2H), 3.47 (d, J=11.3 Hz, 2H), 2.60 (t, J=8.1 Hz, 2H), 2.49 (t, J=11.2 Hz, 2H), 2.15 (quin, J=7.6 Hz, 2H), 1.23 (d, J=6.3 Hz, 6H). [M+H]=488.17.

Example 117

9-(((2S,6R)-2,6-Dimethylmorpholino)methyl)-6-(4-ethoxybenzyl)pyrido[3,2-e][1,2,4]triazolo[1,5-c]pyrimidin-5(6H)-one

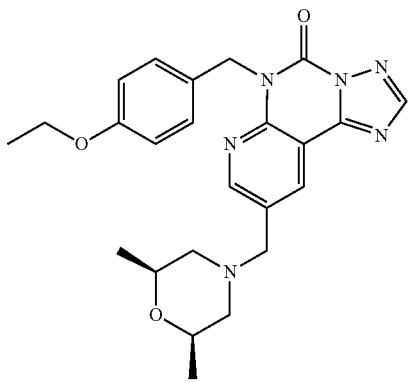 [SMILES: CCOc1ccc(Cn2c(=O)n3ncnc3c3cc(CN4C[C@@H](C)O[C@@H](C)C4)cnc32)cc1]

$^1$H NMR (400 MHz, CDCl$_3$) δ 8.90 (d, J=2.3 Hz, 1H), 8.67 (d, J=2.4 Hz, 1H), 8.37 (s, 1H), 7.59 (d, J=8.7 Hz, 2H), 6.87-6.77 (m, 2H), 5.73 (s, 2H), 4.28 (s, 2H), 4.06-3.93 (m, 4H), 3.40 (d, J=11.2 Hz, 2H), 2.40 (t, J=11.2 Hz, 2H), 1.37 (t, J=7.0 Hz, 3H), 1.23 (d, J=6.4 Hz, 6H). [M+H]=449.20.

Example 118

6-(3,4-Difluorobenzyl)-9-((2S,6R)-2,6-dimethylmorpholino)methyl)pyrido[3,2-e][1,2,4]triazolo[1,5-c]pyrimidin-5(6H)-one

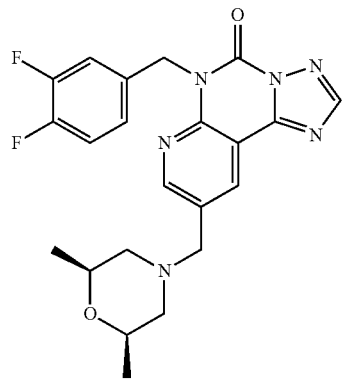 [SMILES: C[C@@H]1CN(Cc2cnc3c(c2)c2ncnn2c(=O)n3Cc2ccc(F)c(F)c2)C[C@H](C)O1]

$^1$H NMR (400 MHz, CDCl$_3$) δ 8.79 (s, 1H), 8.67 (s, 1H), 8.39 (s, 1H), 7.54-7.45 (m, 1H), 7.41 (d, J=6.3 Hz, 1H), 7.14-7.05 (m, 1H), 5.74 (s, 2H), 3.93-3.77 (m, 4H), 2.99 (d, J=8.9 Hz, 2H), 2.15-2.03 (m, 2H), 1.19 (d, J=6.1 Hz, 6H). [M+H]=441.14.

Example 119

9-(((2S,6R)-2,6-Dimethylmorpholino)methyl)-6-(4-(methylthio)benzyl)pyrido[3,2-e][1,2,4]triazolo[1,5-c]pyrimidin-5(6H)-one

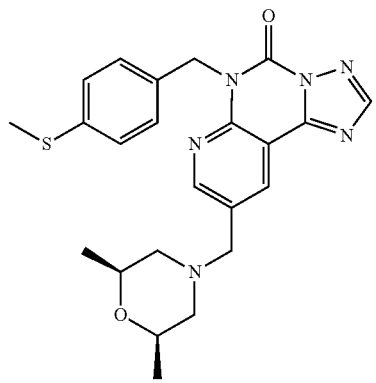

$^1$H NMR (400 MHz, CDCl$_3$) δ 8.72 (s, 1H), 8.62 (s, 1H), 8.37 (s, 1H), 7.57 (d, J=8.0 Hz, 2H), 7.19 (d, J=8.0 Hz, 2H), 5.76 (s, 2H), 3.75-3.67 (m, 2H), 3.63 (s, 2H), 2.71 (d, J=10.9 Hz, 2H), 2.44 (s, 3H), 1.87 (t, J=10.5 Hz, 2H), 1.15 (d, J=6.3 Hz, 6H). [M+H]=451.13.

Example 120

6-(2-Chloro-4-(methylsulfonyl)benzyl)-9-(((2S,6R)-2,6-dimethylmorpholino)methyl)pyrido[3,2-e][1,2,4]triazolo[1,5-c]pyrimidin-5(6H)-one

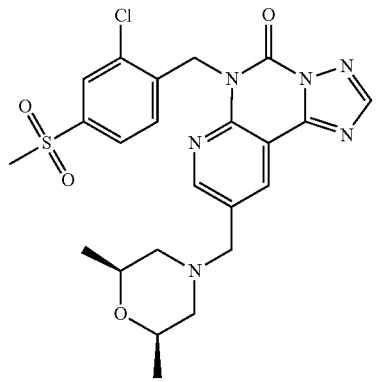 [SMILES: C[C@@H]1CN(Cc2cnc3c(c2)c2ncnn2c(=O)n3Cc2ccc(S(C)(=O)=O)cc2Cl)C[C@H](C)O1]

$^1$H NMR (400 MHz, CDCl$_3$) δ 1.25 (d, J=6.15 Hz, 6H), 2.46 (t, J=11.17 Hz, 2H), 3.06 (s, 3H), 3.44-3.49 (m, 2H), 3.93-4.05 (m, 3H), 4.30 (s, 2H), 5.94 (s, 2H), 7.14 (d, J=8.28 Hz, 1H), 7.70 (d, J=8.16 Hz, 1H), 8.05 (s, 1H), 8.47 (s, 1H), 8.73 (s, 1H), 8.82 (s, 1H). [M+H]=517.10.

Example 121 was made in a manner analogous to Example 1, with the appropriate starting material and reagent substitutions.

Example 121

6-(4-Methoxybenzyl)-8-(phenoxymethyl)pyrido[3,2-e][1,2,4]triazolo[1,5-c]pyrimidin-5(6H)-one

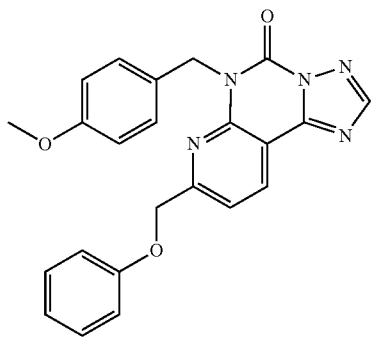 [SMILES: COc1ccc(Cn2c(=O)n3ncnc3c3ccc(COc4ccccc4)nc32)cc1]

$^1$H NMR (400 MHz, CDCl$_3$) 3.69 (s, 3H) 5.28 (s, 2H), 5.67 (s, 2H), 6.75 (d, J=8.53 Hz, 2H), 6.93 (d, J=8.53 Hz, 3H), 7.24 (s, 2H), 7.53 (d, J=8.78 Hz, 3H), 8.27 (s, 1H), 8.51-8.61 (m, 1H). [M+H]=308.1.

Examples 122 through 123 were made in a manner analogous to Example 72, with the appropriate starting material and reagent substitutions.

Example 122

6-(2,3-Difluoro-4-methoxybenzyl)-9-((4-isopropylpiperazin-1-yl)methyl)pyrido[3,2-e][1,2,4]triazolo[1,5-c]pyrimidin-5(6H)-one

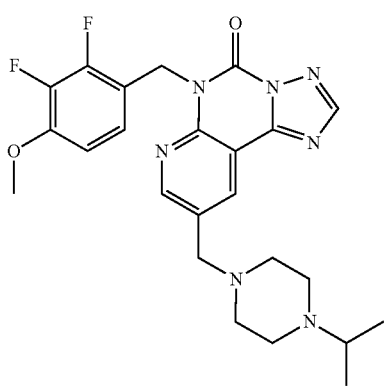 [SMILES: COc1ccc(Cn2c(=O)n3ncnc3c3cc(CN4CCN(C(C)C)CC4)cnc32)c(F)c1F]

$^1$H NMR (400 MHz, CDCl$_3$) 8.70 (s, 2H), 8.45-8.31 (m, 1H), 7.13-6.99 (m, 1H), 6.71-6.55 (m, 1H), 5.81 (s, 2H), 3.95 (s, 2H), 3.85 (s, 3H), 3.61-3.41 (m, 3H), 3.16 (s, 6H), 1.45-1.31 (m, 6H). [M+H]=484.35.

Example 123

6-(2,3-Difluoro-4-methoxybenzyl)-9-(piperidin-1-ylmethyl)pyrido[3,2-e][1,2,4]triazolo[1,5-c]pyrimidin-5(6H)-one

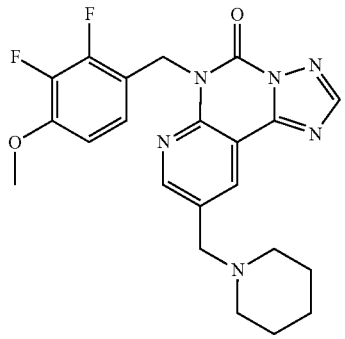 [SMILES: COc1ccc(Cn2c(=O)n3ncnc3c3cc(CN4CCCCC4)cnc32)c(F)c1F]

$^1$H NMR (400 MHz, CDCl$_3$) 8.90-8.72 (m, J=2.3, 18.7 Hz, 2H), 8.38 (s, 1H), 7.15-7.02 (m, 1H), 6.70-6.59 (m, 1H), 5.80 (s, 2H), 4.37 (s, 2H), 3.85 (s, 3H), 3.73-3.60 (m, 2H), 2.73 (br s, 2H), 2.10-1.81 (m, 5H), 1.43 (br s, 1H). [M+H]=441.28.

Examples 124 through 161 were made in a manner analogous to Example 89, with the appropriate starting material and reagent substitutions.

Example 124

9-(((2S,6R)-2,6-Dimethylmorpholino)methyl)-6-(2,4,5-trifluorobenzyl)pyrido[3,2-e][1,2,4]triazolo[1,5-c]pyrimidin-5(6H)-one

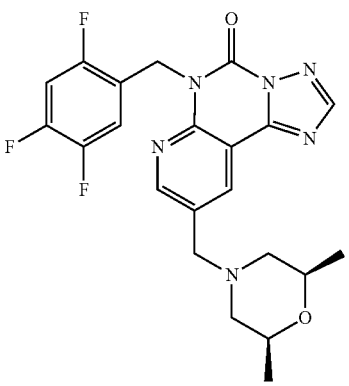 [SMILES: C[C@@H]1CN(Cc2cnc3c(c2)c2ncnn2c(=O)n3Cc2cc(F)c(F)cc2F)C[C@H](C)O1]

$^1$H NMR (400 MHz, CDCl$_3$) 8.79 (d, J=2.3 Hz, 1H), 8.74 (d, J=2.3 Hz, 1H), 8.41 (s, 1H), 7.18 (ddd, J=6.8, 8.6, 10.3 Hz, 1H), 6.95 (dt, J=6.5, 9.7 Hz, 1H), 5.79 (s, 2H), 4.20 (s, 2H), 4.03-3.91 (m, 2H), 3.31 (d, J=11.3 Hz, 2H), 2.34 (t, J=11.1 Hz, 2H), 1.22 (d, J=6.3 Hz, 6H). [M+H]=459.14.

Example 125

9-(((2S,6R)-2,6-Dimethylmorpholino)methyl)-6-(4-isopropylbenzyl)pyrido[3,2-e][1,2,4]triazolo[1,5-c]pyrimidin-5(6H)-one

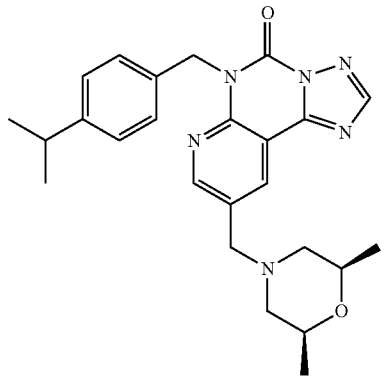 [SMILES: CC(C)c1ccc(Cn2c(=O)n3ncnc3c3cc(CN4C[C@@H](C)O[C@@H](C)C4)cnc32)cc1]

$^1$H NMR (400 MHz, CDCl$_3$) 8.85 (d, J=1.9 Hz, 1H), 8.66 (d, J=1.9 Hz, 1H), 8.37 (s, 1H), 7.56 (d, J=8.2 Hz, 2H), 7.17 (d, J=8.2 Hz, 2H), 5.78 (s, 2H), 4.10 (br s, 2H), 3.93 (dd, J=6.5, 8.9 Hz, 2H), 3.21 (d, J=10.9 Hz, 2H), 2.86 (quin, J=6.9 Hz, 1H), 2.32-2.18 (m, 2H), 1.23-1.17 (m, 12H). [M+H]=447.2.

Example 126

6-(4-(Difluoromethoxy)benzyl)-9-((2S,6R)-2,6-dimethylmorpholino)methyl)pyrido[3,2-e][1,2,4]triazolo[1,5-c]pyrimidin-5(6H)-one

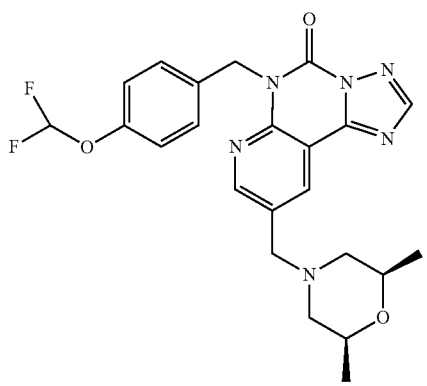 [SMILES: C[C@@H]1CN(Cc2cnc3c(c2)c2ncnn2c(=O)n3Cc2ccc(OC(F)F)cc2)C[C@H](C)O1]

$^1$H NMR (400 MHz, CDCl$_3$) 8.87 (d, J=2.3 Hz, 1H), 8.68 (d, J=2.3 Hz, 1H), 8.38 (s, 1H), 7.69-7.62 (m, 2H), 7.05 (d, J=8.7 Hz, 2H), 6.68-6.26 (m, 1H), 5.77 (s, 2H), 4.20 (s, 2H), 4.02-3.91 (m, 2H), 3.32 (d, J=11.3 Hz, 2H), 2.35 (t, J=11.0 Hz, 2H), 1.22 (d, J=6.3 Hz, 6H). [M+H]=471.16.

Example 127

9-(((2S,6R)-2,6-Dimethylmorpholino)methyl)-6-(4-ethoxy-3,5-difluorobenzyl)pyrido[3,2-e][1,2,4]triazolo[1,5-c]pyrimidin-5(6H)-one

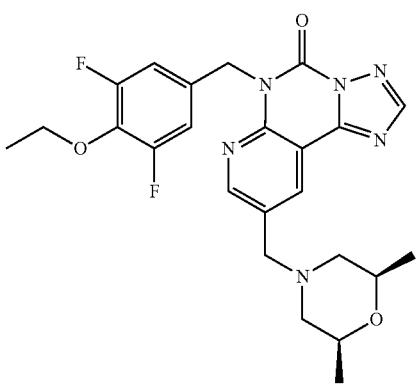 [SMILES: CCOc1c(F)cc(Cn2c(=O)n3ncnc3c3cc(CN4C[C@@H](C)O[C@@H](C)C4)cnc32)cc1F]

$^1$H NMR (400 MHz, CDCl$_3$) 8.85 (d, J=2.3 Hz, 1H), 8.72 (d, J=2.3 Hz, 1H), 8.39 (s, 1H), 7.23-7.14 (m, 2H), 5.68 (s, 2H), 4.23-4.12 (m, 4H), 4.02-3.91 (m, 2H), 3.31 (d, J=11.2 Hz, 2H), 2.35 (t, J=11.0 Hz, 2H), 1.35 (t, J=7.0 Hz, 3H), 1.22 (d, J=6.3 Hz, 6H). [M+H]=485.19.

Example 128

9-(((2S,6R)-2,6-Dimethylmorpholino)methyl)-6-(4-ethynylbenzyl)pyrido[3,2-e][1,2,4]triazolo[1,5-c]pyrimidin-5(6H)-one

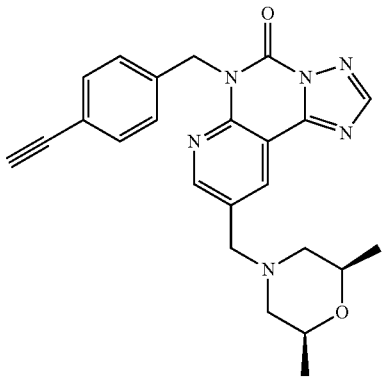 [SMILES: C#Cc1ccc(Cn2c(=O)n3ncnc3c3cc(CN4C[C@@H](C)O[C@@H](C)C4)cnc32)cc1]

$^1$H NMR (400 MHz, CDCl$_3$) 8.70 (d, J=2.1 Hz, 1H), 8.63 (d, J=2.3 Hz, 1H), 8.38 (s, 1H), 7.57 (d, J=8.3 Hz, 2H), 7.43 (d, J=8.3, Hz, 2H), 5.79 (s, 2H), 3.75-3.65 (m, 3H), 3.62 (s, 2H), 2.69 (d, J=10.3 Hz, 2H), 1.85 (t, J=10.7 Hz, 2H), 1.15 (d, J=6.3 Hz, 6H). [M+H]=429.17.

Example 129

9-(((2S,6R)-2,6-Dimethylmorpholino)methyl)-6-(4-iodobenzyl)pyrido[3,2-e][1,2,4]triazolo[1,5-c]pyrimidin-5(6H)-one

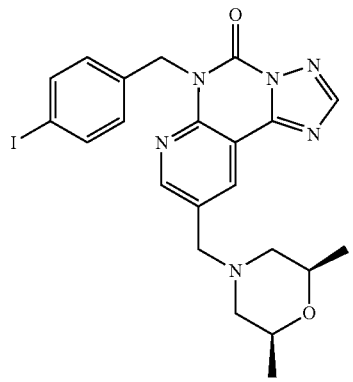 [SMILES: C[C@@H]1CN(Cc2cnc3c(c2)c2ncnn2c(=O)n3Cc2ccc(I)cc2)C[C@H](C)O1]

¹H NMR (400 MHz, CDCl₃) 8.87 (d, J=2.4 Hz, 1H), 8.71 (d, J=2.3 Hz, 1H), 8.40 (s, 1H), 7.67-7.62 (m, 2H), 7.37 (d, J=8.4 Hz, 2H), 5.73 (s, 2H), 4.33 (s, 2H), 4.06-3.95 (m, 2H), 3.47 (d, J=11.2 Hz, 2H), 2.46 (t, J=11.2 Hz, 2H), 1.24 (d, J=6.3 Hz, 6H). [M+H]=531.07.

Example 130

6-(3,4-Dimethoxybenzyl)-9-(((2S,6R)-2,6-dimethylmorpholino)methyl)pyrido[3,2-e][1,2,4]triazolo[1,5-c]pyrimidin-5(6H)-one

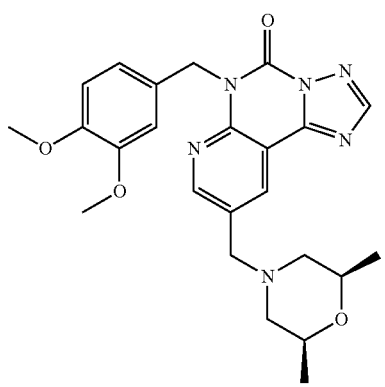

¹H NMR (400 MHz, CDCl₃) 8.93 (d, J=2.3 Hz, 1H), 8.70 (d, J=2.3 Hz, 1H), 8.40 (s, 1H), 7.29 (d, J=1.9 Hz, 1H), 7.25 (dd, J=1.9, 8.2 Hz, 1H), 6.79 (d, J=8.3 Hz, 1H), 5.75 (s, 2H), 5.32 (s, 1H), 4.36 (s, 2H), 4.07-3.96 (m, 2H), 3.88 (s, 3H), 3.84 (s, 3H), 3.50 (d, J=11.4 Hz, 2H), 2.48 (t, J=11.2 Hz, 2H), 1.25 (d, J=6.3 Hz, 6H). [M+H]=465.2.

Example 131

6-(3-Chloro-5-fluoro-4-methoxybenzyl)-9-((2S,6R)-2,6-dimethylmorpholino)methyl)pyrido[3,2-e][1,2,4]triazolo[1,5-c]pyrimidin-5(6H)-one

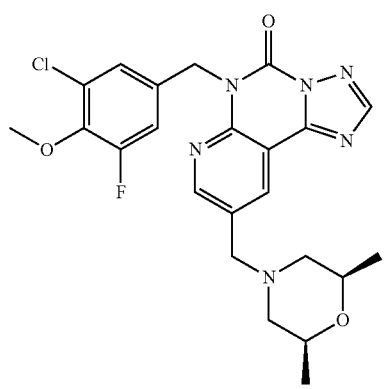

¹H NMR (400 MHz, CDCl₃) 8.87 (d, J=2.3 Hz, 1H), 8.75 (d, J=2.1 Hz, 1H), 8.42 (s, 1H), 7.43 (t, J=1.8 Hz, 1H), 7.31 (dd, J=2.1, 11.3 Hz, 1H), 5.68 (s, 2H), 4.35 (s, 2H), 4.04-3.95 (m, 2H), 3.92 (d, J=1.5 Hz, 3H), 3.50 (d, J=11.3 Hz, 2H), 2.48 (t, J=11.2 Hz, 2H), 1.25 (d, J=6.3 Hz, 6H). [M+H]=487.13.

Example 132

9-(((2S,6R)-2,6-Dimethylmorpholino)methyl)-6-(4-methoxy-3-methylbenzyl)pyrido[3,2-e][1,2,4]triazolo[1,5-c]pyrimidin-5(6H)-one

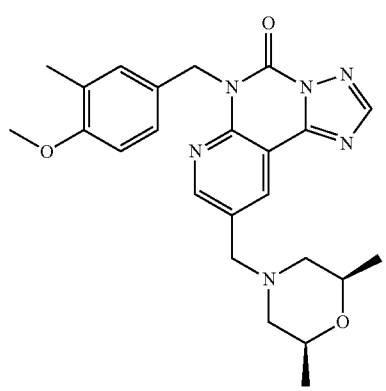

¹H NMR (400 MHz, CDCl₃) 8.90 (d, J=2.3 Hz, 1H), 8.69 (d, J=2.3 Hz, 1H), 8.39 (s, 1H), 7.50-7.41 (m, 2H), 6.74 (d, J=8.4 Hz, 1H), 5.71 (s, 2H), 4.34 (s, 2H), 4.06-3.96 (m, 2H), 3.78 (s, 3H), 3.48 (d, J=11.4 Hz, 2H), 2.46 (t, J=11.2 Hz, 2H), 2.16 (s, 3H), 1.24 (d, J=6.4 Hz, 6H). [M+H]=449.2.

Example 133

9-(((2S,6R)-2,6-Dimethylmorpholino)methyl)-6-(3-methoxybenzyl)pyrido[3,2-e][1,2,4]triazolo[1,5-c]pyrimidin-5(6H)-one

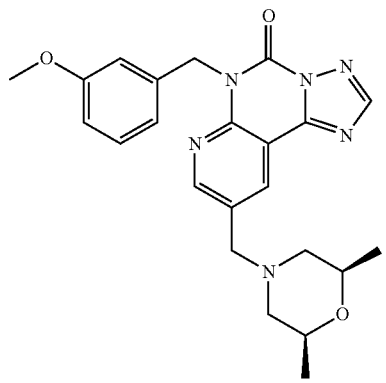

$^1$H NMR (400 MHz, CDCl$_3$) 1.24 (d, J=6.27 Hz, 6H), 2.43 (t, J=11.17 Hz, 2H), 3.44 (d, J=11.29 Hz, 2H), 3.80 (s, 3H), 3.97-4.08 (m, 2H), 4.31 (s, 2H), 5.79 (s, 2H), 6.81-6.86 (m, 1H), 7.16-7.27 (m, 3H), 8.41 (s, 1H), 8.70 (d, J=2.38 Hz, 1H), 8.88 (d, J=2.26 Hz, 1H). [M+H]=435.1.

Example 134

6-(2,5-Difluorobenzyl)-9-((2S,6R)-2,6-dimethylmorpholino)methyl)pyrido[3,2-e][1,2,4]triazolo[1,5-c]pyrimidin-5(6H)-one

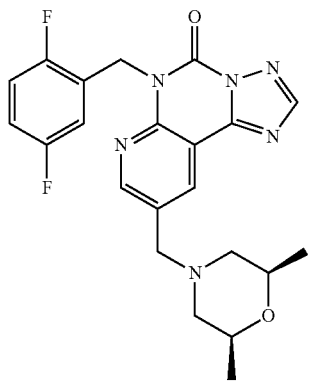 [SMILES: C[C@@H]1CN(Cc2cnc3c(c2)c2ncnn2c(=O)n3Cc2cc(F)ccc2F)C[C@H](C)O1]

$^1$H NMR (400 MHz, CDCl$_3$) 1.24 (d, J=6.40 Hz, 6H), 2.43 (t, J=11.17 Hz, 2H), 3.43 (d, J=11.17 Hz, 2H), 3.98-4.07 (m, 2H), 4.30 (s, 2H), 5.85 (s, 2H), 6.92-6.99 (m, 2H), 7.02-7.10 (m, 1H), 8.44 (s, 1H), 8.76 (s, 1H), 8.80 (s, 1H). [M+H]=441.1.

Example 135

6-(2,4-Difluorobenzyl)-9-((2R,6S)-2,6-dimethylmorpholino)methyl)pyrido[3,2-e][1,2,4]triazolo[1,5-c]pyrimidin-5(6H)-one

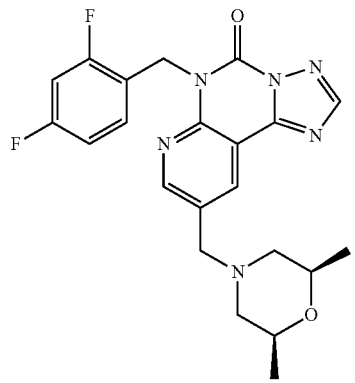 [SMILES: C[C@@H]1CN(Cc2cnc3c(c2)c2ncnn2c(=O)n3Cc2ccc(F)cc2F)C[C@H](C)O1]

$^1$H NMR (400 MHz, CDCl$_3$) 1.24 (d, J=6.27 Hz, 6H), 2.43 (t, J=11.17 Hz, 2H), 3.43 (d, J=11.29 Hz, 2H), 3.96-4.08 (m, 2H), 4.29 (s, 2H), 5.84 (s, 2H), 6.78-6.88 (m, 2H), 7.32-7.41 (m, 1H), 8.43 (s, 1H), 8.74 (s, 1H), 8.81 (s, 1H). [M+H]=441.1.

Example 136

9-((2R,6S)-2,6-Dimethylmorpholino)methyl)-6-(4-(trifluoromethyl)benzyl)pyrido[3,2-e][1,2,4]triazolo[1,5-c]pyrimidin-5(6H)-one

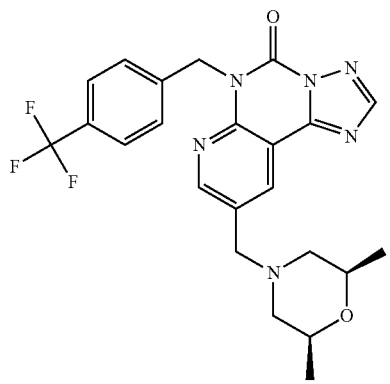 [SMILES: C[C@@H]1CN(Cc2cnc3c(c2)c2ncnn2c(=O)n3Cc2ccc(C(F)(F)F)cc2)C[C@H](C)O1]

$^1$H NMR (400 MHz, CDCl$_3$) 1.24 (d, J=6.27 Hz, 6H), 2.44 (t, J=11.17 Hz, 2H), 3.44 (d, J=11.17 Hz, 2H), 3.97-4.08 (m, 2H), 4.30 (s, 2H), 5.85 (s, 2H), 7.59 (d, J=8.16 Hz, 2H), 7.74 (d, J=8.16 Hz, 2H), 8.42 (s, 1H), 8.70-8.73 (m, 1H), 8.88-8.90 (m, 1H). [M+H]=473.1.

Example 137

9-((2R,6S)-2,6-Dimethylmorpholino)methyl)-6-(4-fluoro-3-methoxybenzyl)pyrido[3,2-e][1,2,4]triazolo[1,5-c]pyrimidin-5(6H)-one

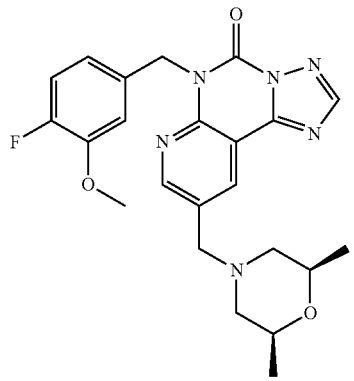

$^1$H NMR (400 MHz, CDCl$_3$) 8.89 (d, J=2.4 Hz, 1H), 8.68 (d, J=2.4 Hz, 1H), 8.39 (s, 1H), 7.36 (dd, J=2.0, 8.2 Hz, 1H), 7.20 (ddd, J=2.1, 4.3, 8.3 Hz, 1H), 6.98 (dd, J=8.3, 11.1 Hz, 1H), 5.74 (s, 2H), 4.21 (s, 2H), 4.01-3.91 (m, 2H), 3.88 (s, 3H), 3.32 (d, J=11.2 Hz, 2H), 2.35 (t, J=11.1 Hz, 2H), 1.22 (d, J=6.4 Hz, 6H). [M+H]=453.14.

Example 138

9-(((2R,6S)-2,6-Dimethylmorpholino)methyl)-6-(2-fluoro-4-methylbenzyl)pyrido[3,2-e][1,2,4]triazolo[1,5-c]pyrimidin-5(6H)-one

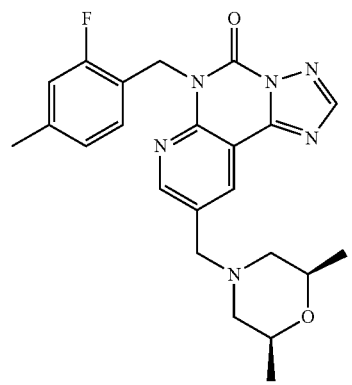

$^1$H NMR (400 MHz, CDCl$_3$) 8.65 (dd, J=2.2, 10.6 Hz, 2H), 8.39 (s, 1H), 7.13 (t, J=7.9 Hz, 1H), 6.92-6.81 (m, 2H), 5.84 (s, 2H), 3.75-3.65 (m, 2H), 3.61 (s, 2H), 2.70 (d, J=10.5 Hz, 2H), 2.30 (s, 3H), 1.85 (t, J=10.7 Hz, 2H), 1.15 (d, J=6.3 Hz, 6H). [M+H]=437.15.

Example 139

6-(2-Chloro-4,5-difluorobenzyl)-9-((2R,6S)-2,6-dimethylmorpholino)methyl)pyrido[3,2-e][1,2,4]triazolo[1,5-c]pyrimidin-5(6H)-one

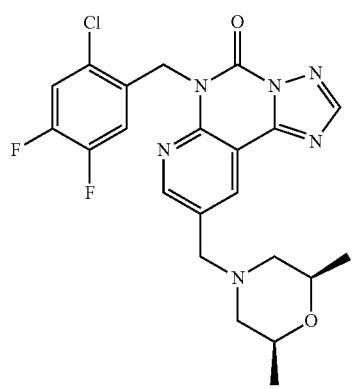 [SMILES: C[C@@H]1CN(Cc2cnc3c(c2)c2ncnn2c(=O)n3Cc2cc(F)c(F)cc2Cl)C[C@H](C)O1]

$^1$H NMR (400 MHz, CDCl$_3$) 8.69 (d, J=2.1 Hz, 1H), 8.63 (d, J=2.3 Hz, 1H), 8.42 (s, 1H), 7.30 (dd, J=7.2, 9.7 Hz, 1H), 6.80 (dd, J=8.1, 10.7 Hz, 1H), 5.82 (s, 2H), 3.75-3.65 (m, 2H), 3.62 (s, 2H), 2.70 (d, J=10.4 Hz, 2H), 1.86 (t, J=10.7 Hz, 2H), 1.15 (d, J=6.3 Hz, 6H). [M+H]=475.12.

Example 140

6-(3-Chloro-2,4-difluorobenzyl)-9-((2R,6S)-2,6-dimethylmorpholino)methyl)pyrido[3,2-e][1,2,4]triazolo[1,5-c]pyrimidin-5(6H)-one

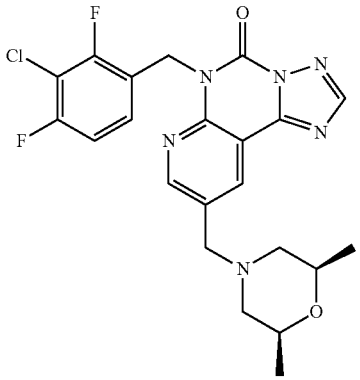 [SMILES: C[C@@H]1CN(Cc2cnc3c(c2)c2ncnn2c(=O)n3Cc2ccc(F)c(Cl)c2F)C[C@H](C)O1]

$^1$H NMR (400 MHz, CDCl$_3$) 8.69-8.64 (m, 2H), 8.39 (s, 1H), 7.23 (dt, J=6.0, 8.3 Hz, 1H), 6.88 (dt, J=1.9, 8.5 Hz, 1H), 5.85 (s, 2H), 3.75-3.65 (m, 2H), 3.62 (s, 2H), 2.69 (d, J=10.3 Hz, 2H), 1.86 (t, J=10.7 Hz, 2H), 1.15 (d, J=6.3 Hz, 6H). [M+H]=475.09.

Example 141

9-(((2R,6S)-2,6-Dimethylmorpholino)methyl)-6-(3,4,5-trimethoxybenzyl)pyrido[3,2-e][1,2,4]triazolo[1,5-c]pyrimidin-5(6H)-one

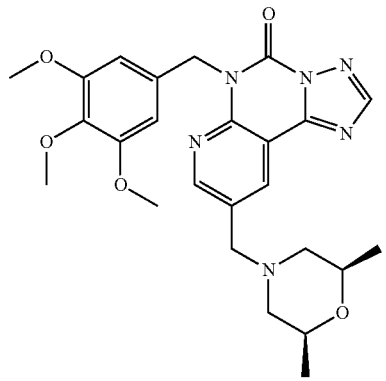

$^1$H NMR (400 MHz, CDCl$_3$) 8.74 (d, J=2.1 Hz, 1H), 8.63 (d, J=2.3 Hz, 1H), 8.37 (s, 1H), 6.99 (s, 2H), 5.73 (s, 2H), 3.84 (s, 6H), 3.80 (s, 3H), 3.75-3.67 (m, 2H), 3.64 (s, 2H), 2.70 (d, J=10.7 Hz, 2H), 1.86 (t, J=10.7 Hz, 2H), 1.15 (d, J=6.3 Hz, 6H). [M+H]=495.2.

Example 142

6-(2,4-dichlorobenzyl)-9-(((2R,6S)-2,6-Dimethylmorpholino)methyl)pyrido[3,2-e][1,2,4]triazolo[1,5-c]pyrimidin-5(6H)-one

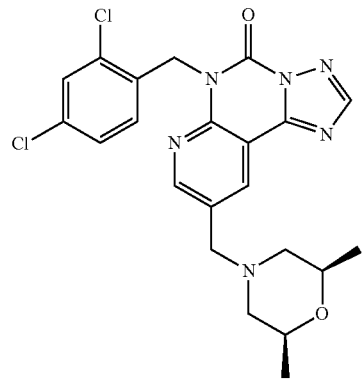 [SMILES: C[C@@H]1CN(Cc2cnc3c(c2)c2ncnn2c(=O)n3Cc2ccc(Cl)cc2Cl)C[C@H](C)O1]

$^1$H NMR (400 MHz, CDCl$_3$) 8.80 (d, J=1.9 Hz, 1H), 8.73 (d, J=2.0 Hz, 1H), 8.45 (s, 1H), 7.46 (d, J=2.1 Hz, 1H), 7.11 (dd, J=2.1, 8.4 Hz, 1H), 6.91 (d, J=8.4 Hz, 1H), 5.84 (s, 2H), 4.34 (s, 2H), 4.04-3.94 (m, 2H), 3.50 (d, J=11.2 Hz, 2H), 2.47 (t, J=11.2 Hz, 2H), 1.24 (d, J=6.3 Hz, 6H). [M+H]=473.13.

Example 143

6-(2,4-Dichloro-5-fluorobenzyl)-9-((2R,6S)-2,6-dimethylmorpholino)methyl)pyrido[3,2-e][1,2,4]triazolo[1,5-c]pyrimidin-5(6H)-one

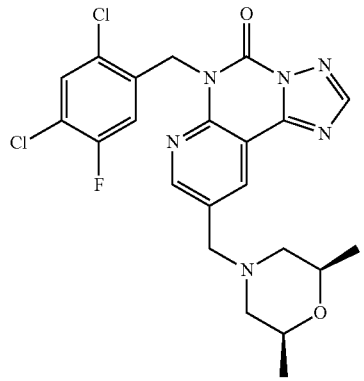 [SMILES: C[C@@H]1CN(Cc2cnc3c(c2)c2ncnn2c(=O)n3Cc2cc(F)c(Cl)cc2Cl)C[C@H](C)O1]

$^1$H NMR (400 MHz, CDCl$_3$) 8.69 (d, J=2.3 Hz, 1H), 8.62 (d, J=2.1 Hz, 1H), 8.43 (s, 1H), 7.51 (d, J=6.5 Hz, 1H), 6.74 (d, J=9.4 Hz, 1H), 5.82 (s, 2H), 3.75-3.66 (m, 2H), 3.63 (s, 2H), 2.71 (d, J=10.8 Hz, 2H), 1.87 (t, J=10.6 Hz, 2H), 1.15 (d, J=6.3 Hz, 6H). [M+H]=491.13.

Example 144

6-(2-Chloro-4-fluorobenzyl)-9-((2R,6S)-2,6-dimethylmorpholino)methyl)pyrido[3,2-e][1,2,4]triazolo[1,5-c]pyrimidin-5(6H)-one

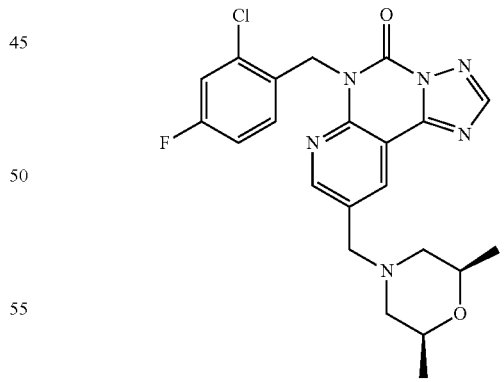

$^1$H NMR (400 MHz, CDCl$_3$) 8.67 (d, J=2.1 Hz, 1H), 8.63 (d, J=2.1 Hz, 1H), 8.42 (s, 1H), 7.19 (dd, J=2.6, 8.3 Hz, 1H), 6.95 (dd, J=5.8, 8.7 Hz, 1H), 6.87-6.80 (m, 1H), 5.86 (s, 2H), 3.75-3.65 (m, 2H), 3.62 (s, 2H), 2.69 (d, J=10.5 Hz, 2H), 1.86 (t, J=10.7 Hz, 2H), 1.15 (d, J=6.4 Hz, 6H). [M+H]=457.1.

Example 145

6-(4-Chloro-2-fluorobenzyl)-9-(((2R,6S)-2,6-dimethylmorpholino)methyl)pyrido[3,2-e][1,2,4]triazolo[1,5-c]pyrimidin-5(6H)-one

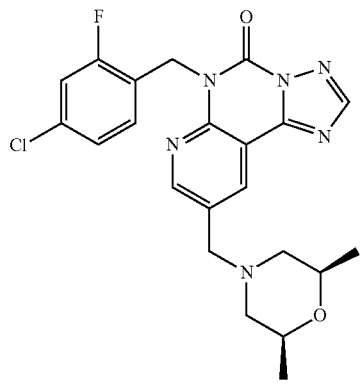 [SMILES: C[C@@H]1CN(Cc2cnc3c(c2)c2ncnn2c(=O)n3Cc2ccc(Cl)cc2F)C[C@H](C)O1]

$^1$H NMR (400 MHz, CDCl$_3$) 8.66 (q, J=2.1 Hz, 2H), 8.40 (s, 1H), 7.22 (t, J=8.2 Hz, 1H), 7.11 (dd, J=2.0, 9.8 Hz, 1H), 7.03 (dd, J=1.4, 8.3 Hz, 1H), 5.83 (s, 2H), 3.79-3.66 (m, 4H), 2.78 (d, J=10.4 Hz, 2H), 1.92 (t, J=10.4 Hz, 2H), 1.16 (d, J=6.3 Hz, 6H). [M+H]=457.15.

Example 146

9-(((2S,6R)-2,6-Dimethylmorpholino)methyl)-6-(2,3,5,6-tetrafluoro-4-methoxybenzyl)pyrido[3,2-e][1,2,4]triazolo[1,5-c]pyrimidin-5(6H)-one

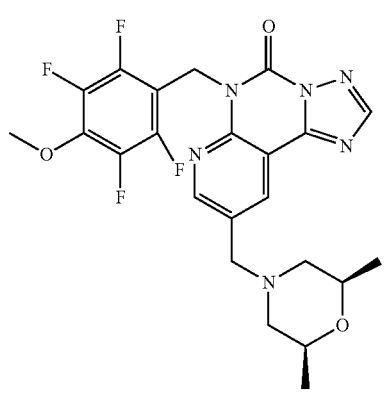

$^1$H NMR (400 MHz, DMSO-d$_6$) 8.69 (d, J=2.1 Hz, 1H), 8.61 (s, 1H), 8.55 (d, J=2.1 Hz, 1H), 5.75 (s, 2H), 4.02 (s, 3H), 3.65 (s, 2H), 3.62-3.52 (m, 2H), 2.71 (d, J=10.5 Hz, 2H), 1.73 (t, J=10.7 Hz, 2H), 1.02 (d, J=6.3 Hz, 6H). [M+H]=507.17.

Example 147

6-(4-Chloro-2,6-difluorobenzyl)-9-((2S,6R)-2,6-dimethylmorpholino)methyl)pyrido[3,2-e][1,2,4]triazolo[1,5-c]pyrimidin-5(6H)-one

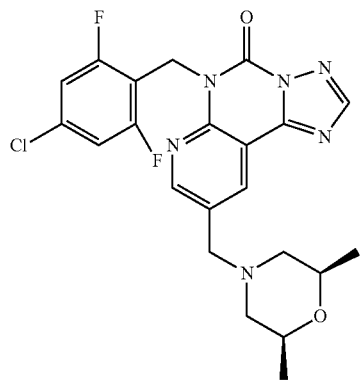 [SMILES: C[C@@H]1CN(Cc2cnc3c(c2)c2ncnn2c(=O)n3Cc2c(F)cc(Cl)cc2F)C[C@H](C)O1]

$^1$H NMR (400 MHz, DMSO-d$_6$) 8.60 (d, J=2.1 Hz, 1H), 8.55 (s, 1H), 8.47 (d, J=2.3 Hz, 1H), 7.28-7.21 (m, 2H), 5.64 (s, 2H), 3.57 (s, 2H), 3.55-3.45 (m, 2H), 2.63 (d, J=10.2 Hz, 2H), 1.66 (t, J=10.7 Hz, 2H), 0.95 (d, J=6.3 Hz, 6H). [M+H]=475.14.

Example 148

9-((2R,6S)-2,6-Dimethylmorpholino)methyl)-6-(4-fluoro-3,5-dimethylbenzyl)pyrido[3,2-e][1,2,4]triazolo[1,5-c]pyrimidin-5(6H)-one

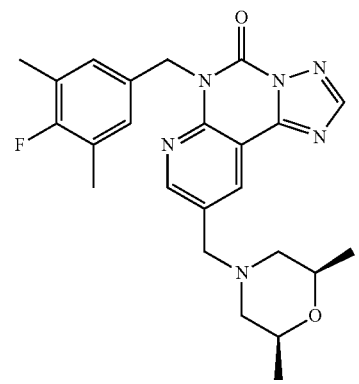 [SMILES: Cc1cc(Cn2c(=O)n3ncnc3c3cc(CN4C[C@@H](C)O[C@@H](C)C4)cnc32)cc(C)c1F]

$^1$H NMR (400 MHz, CDCl$_3$) 8.89 (d, J=2.3 Hz, 1H), 8.70 (d, J=2.3 Hz, 1H), 8.40 (s, 1H), 7.29-7.24 (m, 2H), 5.68 (s, 2H), 4.33 (s, 2H), 4.06-3.96 (m, 2H), 3.47 (d, J=11.2 Hz, 2H), 2.46 (t, J=11.2 Hz, 2H), 2.20 (d, J=2.0 Hz, 6H), 1.24 (d, J=6.3 Hz, 6H). [M+H]=451.22.

Example 149

9-(((2R,6S)-2,6-Dimethylmorpholino)methyl)-6-(2,3,4-trifluorobenzyl)pyrido[3,2-e][1,2,4]triazolo[1,5-c]pyrimidin-5(6H)-one

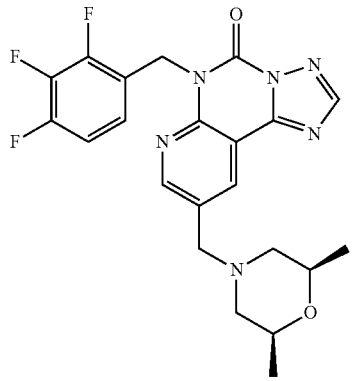

¹H NMR (400 MHz, CDCl₃) 1.17 (d, J=6.27 Hz, 6H), 1.88 (t, J=10.67 Hz, 2H), 2.71 (d, J=10.42 Hz, 2H), 3.65 (s, 2H), 3.68-3.77 (m, 2H), 5.72 (s, 2H), 7.29-7.36 (m, 2H), 8.40 (s, 1H), 8.67 (d, J=2.26 Hz, 1H), 8.73 (d, J=2.13 Hz, 1H). [M+H]=459.2.

Example 150

6-(2,3-dichlorobenzyl)-9-((2R,6S)-2,6-Dimethylmorpholino)methyl)pyrido[3,2-e][1,2,4]triazolo[1,5-c]pyrimidin-5(6H)-one

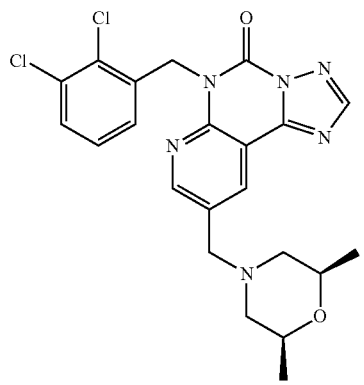 [SMILES: C[C@@H]1CN(Cc2cnc3c(c2)c2ncnn2c(=O)n3Cc2cccc(Cl)c2Cl)C[C@H](C)O1]

¹H NMR (400 MHz, CDCl₃) 1.15 (d, J=6.40 Hz, 6H), 1.86 (t, J=10.67 Hz, 2H), 2.69 (d, J=10.29 Hz, 2H), 3.62 (s, 2H), 3.66-3.75 (m, 2H), 5.91 (s, 2H), 6.79 (d, J=7.78 Hz, 1H), 7.06 (t, J=7.97 Hz, 1H), 7.40 (dd, J=7.97, 1.19 Hz, 1H), 8.43 (s, 1H), 8.62 (d, J=2.13 Hz, 1H), 8.68 (d, J=2.26 Hz, 1H). [M+H]=474.2.

Example 151

6-(2,3-Difluoro-4-methylbenzyl)-9-(((2R,6S)-2,6-dimethylmorpholino)methyl)pyrido[3,2-e][1,2,4]triazolo[1,5-c]pyrimidin-5(6H)-one

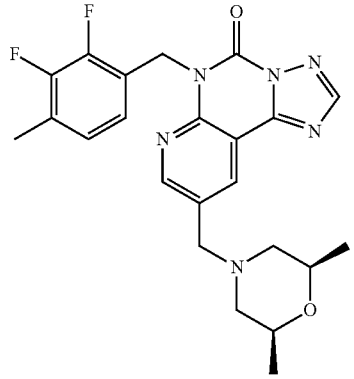

¹H NMR (400 MHz, CDCl₃) 1.16 (d, J=6.27 Hz, 6H), 1.86 (t, J=10.67 Hz, 2H), 2.27 (s, 3H), 2.70 (d, J=10.29 Hz, 2H), 3.62 (s, 2H), 3.66-3.76 (m, 2H), 5.87 (s, 2H), 6.78-6.85 (m, 1H), 6.89-6.96 (m, 1H), 8.40 (s, 1H), 8.66 (d, J=6.65 Hz, 2H). [M+H]=455.2.

Example 152

6-(4-Chloro-3-(trifluoromethoxy)benzyl)-9-((2R,6S)-2,6-dimethylmorpholino)methyl)pyrido[3,2-e][1,2,4]triazolo[1,5-c]pyrimidin-5(6H)-one

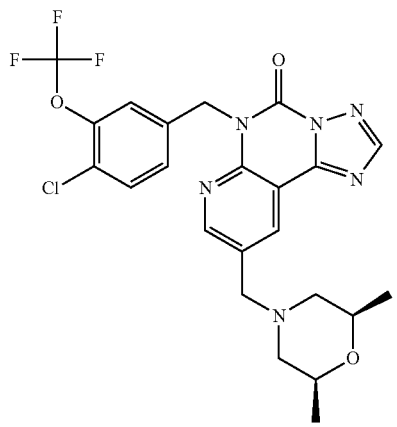 [SMILES: C[C@@H]1CN(Cc2cnc3c(c2)c2ncnn2c(=O)n3Cc2ccc(Cl)c(OC(F)(F)F)c2)C[C@H](C)O1]

¹H NMR (400 MHz, CDCl₃) 1.16 (d, J=6.40 Hz, 6H), 1.86 (t, J=10.67 Hz, 2H), 2.69 (d, J=10.29 Hz, 2H), 3.64 (s, 2H), 3.67-3.76 (m, 2H), 5.78 (s, 2H), 7.41 (d, J=8.28 Hz, 1H), 7.57 (dd, J=8.28, 1.88 Hz, 1H), 7.72 (s, 1H), 8.39 (s, 1H), 8.65 (d, J=2.26 Hz, 1H), 8.72 (d, J=2.13 Hz, 1H). [M+H]=523.2.

Example 153

6-(3,5-Dimethoxybenzyl)-9-(((2R,6S)-2,6-dimethyl-morpholino)methyl)pyrido[3,2-e][1,2,4]triazolo[1,5-c]pyrimidin-5(6H)-one

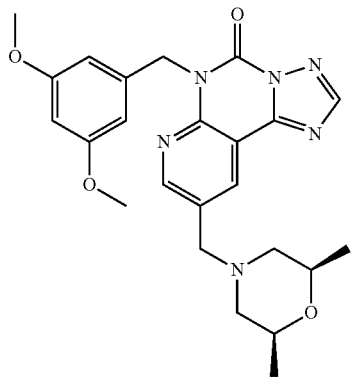 [SMILES: COc1cc(Cn2c(=O)n3ncnc3c3cc(CN4C[C@@H](C)O[C@@H](C)C4)cnc32)cc(OC)c1]

$^1$H NMR (400 MHz, CDCl$_3$) 8.86 (d, J=2.4 Hz, 1H), 8.74 (d, J=2.3 Hz, 1H), 8.39 (s, 1H), 6.72 (d, J=2.3 Hz, 2H), 6.36 (t, J=2.3 Hz, 1H), 5.72 (s, 2H), 4.37 (s, 2H), 4.04-3.95 (m, 2H), 3.75 (s, 6H), 3.50 (d, J=11.2 Hz, 2H), 2.48 (t, J=11.2 Hz, 2H), 1.24 (d, J=6.3 Hz, 6H). [M+H]=465.21.

Example 154

6-(3-Chloro-4-ethoxy-5-fluorobenzyl)-9-(((2R,6S)-2,6-dimethylmorpholino)methyl)pyrido[3,2-e][1,2,4]triazolo[1,5-c]pyrimidin-5(6H)-one

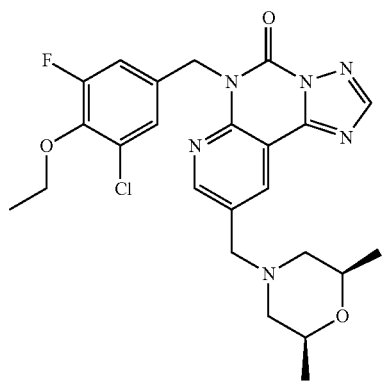 [SMILES: CCOc1c(F)cc(Cn2c(=O)n3ncnc3c3cc(CN4C[C@@H](C)O[C@@H](C)C4)cnc32)cc1Cl]

$^1$H NMR (400 MHz, CDCl$_3$) 8.88 (d, J=2.4 Hz, 1H), 8.75 (d, J=2.3 Hz, 1H), 8.40 (s, 1H), 7.42 (t, J=1.8 Hz, 1H), 7.30 (dd, J=2.1, 11.1 Hz, 1H), 5.68 (s, 2H), 4.34 (s, 2H), 4.17-4.08 (m, 2H), 4.05-3.96 (m, 2H), 3.47 (d, J=11.3 Hz, 2H), 2.47 (t, J=11.2 Hz, 2H), 1.37 (t, J=7.0 Hz, 3H), 1.24 (d, J=6.4 Hz, 6H). [M+H]=501.16.

Example 155

9-(((2R,6S)-2,6-Dimethylmorpholino)methyl)-6-(4-ethoxy-2,3-difluorobenzyl)pyrido[3,2-e][1,2,4]triazolo[1,5-c]pyrimidin-5(6H)-one

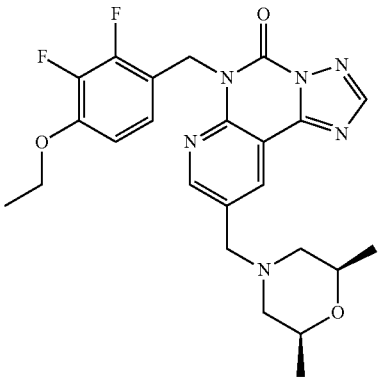 [SMILES: CCOc1ccc(Cn2c(=O)n3ncnc3c3cc(CN4C[C@@H](C)O[C@@H](C)C4)cnc32)c(F)c1F]

$^1$H NMR (400 MHz, CDCl$_3$) 8.81 (d, J=2.4 Hz, 1H), 8.77 (d, J=2.4 Hz, 1H), 8.40 (s, 1H), 7.09-7.02 (m, 1H), 6.67-6.60 (m, 1H), 5.81 (s, 2H), 4.35 (s, 2H), 4.07 (q, J=7.0 Hz, 2H), 4.03-3.95 (m, 2H), 3.50 (d, J=11.2 Hz, 2H), 2.49 (t, J=11.2 Hz, 2H), 1.42 (t, J=7.0 Hz, 3H), 1.24 (d, J=6.3 Hz, 6H). [M+H]=485.16.

Example 156

9-(((2R,6S)-2,6-Dimethylmorpholino)methyl)-6-(3,4,5-trifluorobenzyl)pyrido[3,2-e][1,2,4]triazolo[1,5-c]pyrimidin-5(6H)-one

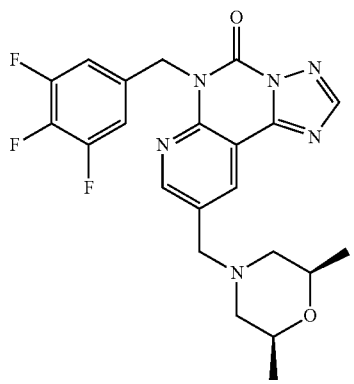 [SMILES: C[C@@H]1CN(Cc2cnc3c(c2)c2ncnn2c(=O)n3Cc2cc(F)c(F)c(F)c2)C[C@H](C)O1]

$^1$H NMR (400 MHz, CDCl$_3$) 8.88 (d, J=2.4 Hz, 1H), 8.78 (d, J=2.3 Hz, 1H), 8.40 (s, 1H), 7.30-7.25 (m, 2H), 5.69 (s, 2H), 4.38 (s, 2H), 4.03-3.94 (m, 2H), 3.50 (d, J=11.2 Hz, 2H), 2.51 (t, J=11.2 Hz, 2H), 1.24 (d, J=6.4 Hz, 6H). [M+H]=459.18.

Example 157

6-Benzyl-9-(((2R,6S)-2,6-dimethylmorpholino)methyl)pyrido[3,2-e][1,2,4]triazolo[1,5-c]pyrimidin-5(6H)-one

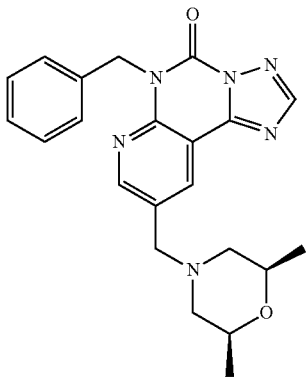

$^1$H NMR (400 MHz, CDCl$_3$) 8.88 (d, J=2.4 Hz, 1H), 8.75 (d, J=2.3 Hz, 1H), 8.39 (s, 1H), 7.60 (dd, J=1.4, 7.8 Hz, 2H), 7.33-7.27 (m, 3H), 5.79 (s, 2H), 4.38 (s, 2H), 4.04-3.94 (m, 2H), 3.51 (d, J=11.3 Hz, 2H), 2.50 (t, J=11.2 Hz, 2H), 1.24 (d, J=6.3 Hz, 6H). [M+H]=405.2.

Example 158

6-(3,4-Dimethylbenzyl)-9-((2R,6S)-2,6-dimethylmorpholino)methyl)pyrido[3,2-e][1,2,4]triazolo[1,5-c]pyrimidin-5(6H)-one

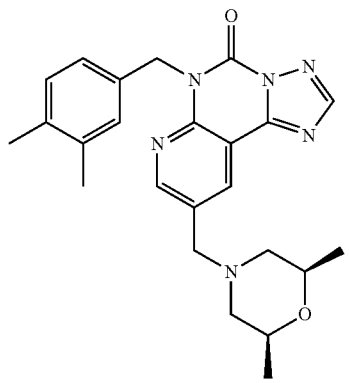

$^1$H NMR (400 MHz, CDCl$_3$) 8.88 (d, J=2.3 Hz, 1H), 8.72 (d, J=2.4 Hz, 1H), 8.38 (s, 1H), 7.38 (s, 1H), 7.33 (d, J=7.8 Hz, 1H), 7.06 (d, J=7.7 Hz, 1H), 5.73 (s, 2H), 4.36 (s, 2H), 4.07-3.96 (m, 2H), 3.48 (d, J=11.2 Hz, 2H), 2.48 (t, J=11.2 Hz, 2H), 2.21 (d, J=3.9 Hz, 6H), 1.23 (d, J=6.3 Hz, 6H). [M+H]=433.28.

Example 159

6-(2,4-Dimethylbenzyl)-9-((2R,6S)-2,6-dimethylmorpholino)methyl)pyrido[3,2-e][1,2,4]triazolo[1,5-c]pyrimidin-5(6H)-one

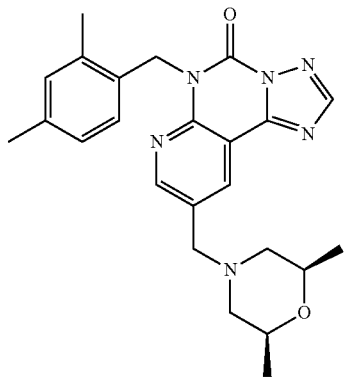

$^1$H NMR (400 MHz, CDCl$_3$) 8.77 (q, J=2.3 Hz, 2H), 8.42 (s, 1H), 7.04 (s, 1H), 6.84 (d, J=0.9 Hz, 2H), 5.74 (s, 2H), 4.34 (s, 2H), 4.04-3.94 (m, 2H), 3.49 (d, J=11.4 Hz, 2H), 2.54 (s, 3H), 2.47 (t, J=11.2 Hz, 2H), 2.26 (s, 3H), 1.23 (d, J=6.3 Hz, 6H). [M+H]=433.26.

Example 160

9-(((2S,6R)-2,6-Dimethylmorpholino)methyl)-6-(2,3,5,6-tetrafluoro-4-methylbenzyl)pyrido[3,2-e][1,2,4]triazolo[1,5-c]pyrimidin-5(6H)-one

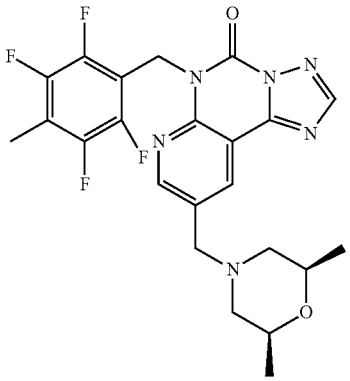 [SMILES: Cc1c(F)c(F)c(Cn2c(=O)n3ncnc3c3cc(CN4C[C@@H](C)O[C@@H](C)C4)cnc32)c(F)c1F]

$^1$H NMR (400 MHz, DMSO-d$_6$) 8.68 (d, J=2.1 Hz, 1H), 8.62 (s, 1H), 8.55 (d, J=2.1 Hz, 1H), 5.77 (s, 2H), 3.64 (s, 2H), 3.61-3.53 (m, 2H), 2.73-2.67 (m, 2H), 2.22 (s, 3H), 1.73 (t, J=10.7 Hz, 2H), 1.02 (d, J=6.3 Hz, 6H). [M+H]=491.21.

Example 161

6-(Benzo[d][1,3]dioxol-5-ylmethyl)-9-((2R,6S)-2,6-dimethylmorpholino)methyl)pyrido[3,2-e][1,2,4]triazolo[1,5-c]pyrimidin-5(6H)-one

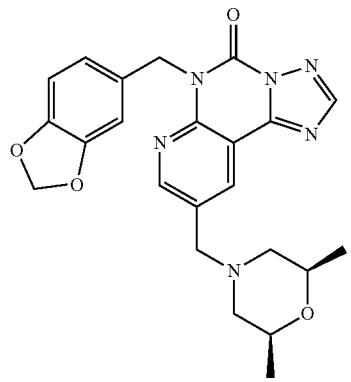 [SMILES: C[C@@H]1CN(Cc2cnc3c(c2)c2ncnn2c(=O)n3Cc2ccc3c(c2)OCO3)C[C@H](C)O1]

¹H NMR (400 MHz, CDCl₃) 8.89 (s, 1H), 8.71 (br s, 1H), 8.39 (s, 1H), 7.19-7.12 (m, 2H), 6.74 (d, J=8.4 Hz, 1H), 5.91 (s, 2H), 5.70 (s, 2H), 4.32 (s, 2H), 4.08-3.96 (m, 2H), 3.71 (s, 2H), 2.44 (t, J=11.2 Hz, 2H), 1.24 (d, J=6.3 Hz, 6H). [M+H]=449.21.

Examples 162 through 169 were made in a manner analogous to Example 72, with the appropriate starting material and reagent substitutions.

Example 162

6-(4-Methoxybenzyl)-9-(morpholinomethyl)-[1,2,4]triazolo[1,5-c]pteridin-5(6H)-one

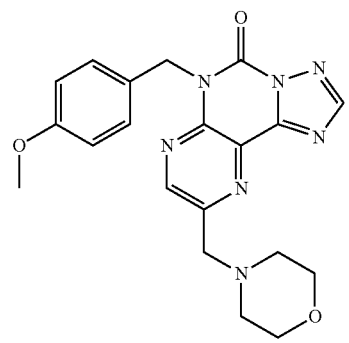 [SMILES: COc1ccc(Cn2c(=O)n3ncnc3c3nc(CN4CCOCC4)cnc32)cc1]

¹H NMR (400 MHz, CD₃OD) 8.93 (s, 1H), 8.66 (s, 1H), 7.52 (d, J=8.78 Hz, 2H), 6.82-6.88 (m, 2H), 5.70 (s, 2H), 4.72 (s, 2H), 3.96 (br s, 4H), 3.74 (s, 3H), 3.37-3.50 (m, 4H). [M+H]=408.21.

Example 163

6-(4-Methoxybenzyl)-9-((2-methylmorpholino)methyl)-[1,2,4]triazolo[1,5-c]pteridin-5(6H)-one

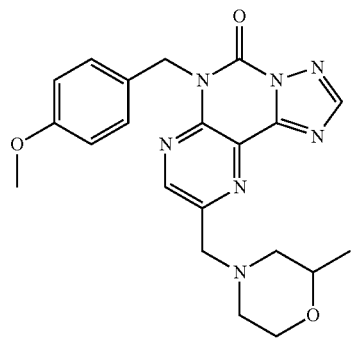 [SMILES: COc1ccc(Cn2c(=O)n3ncnc3c3nc(CN4CCOC(C)C4)cnc32)cc1]

¹H NMR (400 MHz, CD₃OD) 8.94 (s, 1H), 8.65 (s, 1H), 7.51 (d, J=8.78 Hz, 2H), 6.79-6.89 (m, 2H), 5.69 (s, 2H), 4.74 (s, 2H), 4.10 (dd, J=3.45, 13.36 Hz, 1H), 3.83-3.97 (m, 2H), 3.73 (s, 3H), 3.57 (d, J=12.30 Hz, 2H), 3.21-3.28 (m, 1H), 2.98 (t, J=11.67 Hz, 1H), 1.23 (d, J=6.27 Hz, 3H). [M+H]=422.23.

Example 164

6-(4-Methoxybenzyl)-9-(piperidin-1-ylmethyl)-[1,2,4]triazolo[1,5-c]pteridin-5(6H)-one

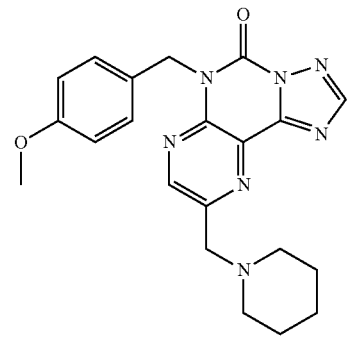 [SMILES: COc1ccc(Cn2c(=O)n3ncnc3c3nc(CN4CCCCC4)cnc32)cc1]

¹H NMR (400 MHz, CD₃OD) 8.93 (s, 1H), 8.65 (s, 1H), 7.50 (d, J=8.66 Hz, 2H), 6.84 (d, J=8.78 Hz, 2H), 5.60-5.74 (m, 2H), 4.70 (s, 2H), 3.73 (s, 3H), 3.66 (d, J=10.29 Hz, 2H), 3.15 (d, J=11.17 Hz, 2H), 1.77-2.04 (m, 5H), 1.59 (br s, 1H). [M+H]=406.27.

Example 165

6-(4-Methoxybenzyl)-9-(4-methoxypiperidin-1-yl)
methyl)-[1,2,4]triazolo[1,5-c]pteridin-5(6H)-one

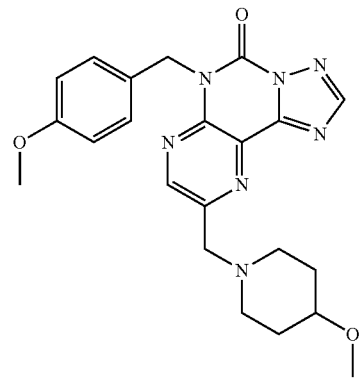 [SMILES: COc1ccc(Cn2c(=O)n3ncnc3c3nc(CN4CCC(OC)CC4)cnc32)cc1]

$^1$H NMR (400 MHz, CD$_3$OD) 8.92 (s, 1H), 8.66 (s, 1H), 7.48-7.55 (m, 2H), 6.82-6.88 (m, 2H), 5.70 (s, 2H), 4.73 (s, 2H), 3.74 (s, 3H), 3.62-3.69 (m, 1H), 3.48 (dd, J=1.63, 3.26 Hz, 3H), 3.38 (s, 3H), 2.24-2.38 (m, 1H), 1.94-2.22 (m, 3H), 1.77 (br s, 1H). [M+H]=436.3.

Example 166

9-((4-Acetylpiperazin-1-yl)methyl)-6-(4-methoxy-benzyl)-[1,2,4]triazolo[1,5-c]pteridin-5(6H)-one

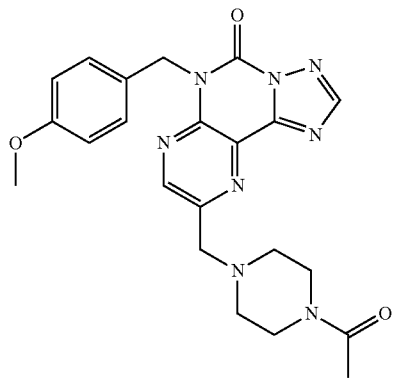 [SMILES: COc1ccc(Cn2c(=O)n3ncnc3c3nc(CN4CCN(C(C)=O)CC4)cnc32)cc1]

$^1$H NMR (400 MHz, CD$_3$OD) 8.94 (s, 1H), 8.66 (s, 1H), 7.52 (d, J=8.78 Hz, 2H), 6.82-6.88 (m, 2H), 5.70 (s, 2H), 4.69 (s, 2H), 3.78-3.95 (m, 3H), 3.74 (s, 3H), 3.34-3.50 (m, 3H), 2.79 (br s, 2H), 2.16 (s, 3H). [M+H]=449.29.

Example 167

9-((1,4-Oxazepan-4-yl)methyl)-6-(2,3-difluoro-4-methoxybenzyl)pyrido[3,2-e][1,2,4]triazolo[1,5-c]pyrimidin-5(6H)-one

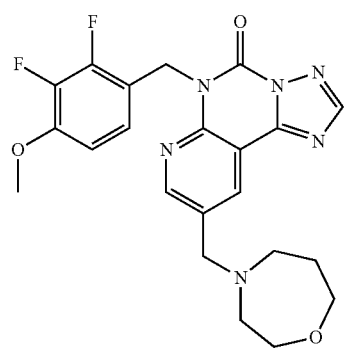 [SMILES: COc1ccc(Cn2c(=O)n3ncnc3c3cc(CN4CCCOCC4)cnc32)c(F)c1F]

$^1$H NMR (400 MHz, CDCl$_3$) 8.84 (dd, J=2.3, 13.2 Hz, 2H), 8.38 (s, 1H), 7.13-7.04 (m, 1H), 6.70-6.59 (m, 1H), 5.80 (s, 2H), 4.49 (s, 2H), 3.95 (t, J=4.3 Hz, 2H), 3.91-3.78 (m, 5H), 3.58-3.29 (m, 4H), 2.32 (br s, 2H). [M+H]=457.24.

Example 168

6-(2,3-Difluoro-4-methoxybenzyl)-9-((3-methylmorpholino)methyl)pyrido[3,2-e][1,2,4]triazolo[1,5-c]pyrimidin-5(6H)-one

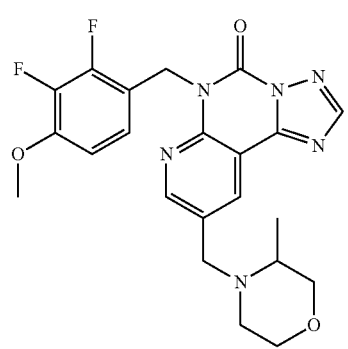 [SMILES: COc1ccc(Cn2c(=O)n3ncnc3c3cc(CN4CCOCC4C)cnc32)c(F)c1F]

$^1$H NMR (400 MHz, CDCl$_3$) 8.83 (dd, J=2.3, 15.9 Hz, 2H), 8.38 (s, 1H), 7.14-7.03 (m, 1H), 6.71-6.58 (m, 1H), 5.80 (s, 2H), 4.91-4.61 (m, 1H), 4.15 (d, J=11.0 Hz, 1H), 4.07-3.73 (m, 7H), 3.32 (d, J=11.7 Hz, 2H), 3.16-2.90 (m, 1H), 1.61 (d, J=6.5 Hz, 3H). [M+H]=457.26.

Example 169

6-(2,3-Difluoro-4-methoxybenzyl)-9-(3-hydroxyazetidin-1-yl)methyl)pyrido[3,2-e][1,2,4]triazolo[1,5-c]pyrimidin-5(6H)-one

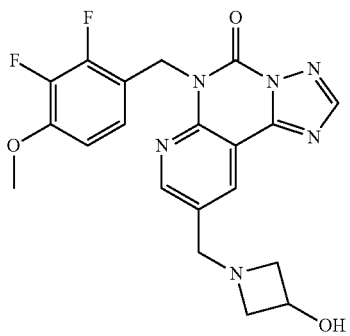 [SMILES: COc1ccc(Cn2c(=O)n3ncnc3c3cc(CN4CC(O)C4)cnc32)c(F)c1F]

$^1$H NMR (400 MHz, CD$_3$OD) 8.87-8.80 (m, 2H), 8.53 (s, 1H), 7.09-7.00 (m, 1H), 6.81-6.72 (m, 1H), 5.78 (s, 2H), 4.73-4.60 (m, 3H), 4.42 (dd, J=6.7, 11.5 Hz, 2H), 4.06 (dd, J=5.4, 11.3 Hz, 2H), 3.82 (s, 3H). [M+H]=429.26.

PDE1b Inhibitory Assay

Assay Conditions

PDE1b inhibition was determined by an IMAP TR-FRET assay. The IMAP TR-FRET PDE assay was optimized for concentration of enzyme, Calmodulin, cAMP or cGMP substrate, DMSO tolerance, and incubation time.

Into each well of a solid white 1536 well plate (Corning) was dispensed 250 pg full-length recombinant NH-terminal GST tagged human PDE1b enzyme (BPS Bioscience Cat #60011, San Diego, Calif.) in 2.5 L IMAP BSA reaction buffer (Molecular Devices, Sunnyvale, Calif.) containing 10 U/mL Calmodulin and 2.5 mM CaCl$_2$ (Sigma Aldrich.) After a brief centrifugation, 30 nL compound was added by transfer from 1 mM stock in DMSO using a Kalypsys 1536 Pintool. Plates were incubated for 5 minutes at room temperature before dispensing 1.5 L of 533 nM 5-carboxy fluorescein (FAM)-labeled cAMP (Molecular Devices, Sunnyvale, Calif.) for a final concentration of 200 nM. After a brief centrifugation, the plates were incubated for 30 minutes at room temperature. The assay was terminated by adding 5 L IMAP binding reagent/Tb complex (Molecular Devices, Sunnyvale, Calif.) to each well.

Plates were incubated 1 hour at room temperature and read on a Viewlux multimode plate reader (Perkin Elmer). The instrument was set to excite using the DUG11 filter and measure using 490/10 nm and 520/10 nm filters. Ratios of acceptor and donor were then calculated.

Data Analysis

For EC$_{50}$ calculations, the values of % efficacy versus a series of compound concentrations were then plotted using non-linear regression analysis of sigmoidal dose-response curves generated with the equation Y=B+(T−B)/1+10((Log EC$_{50}$−X)×Hill Slope), where Y=percent activity, B=minimum percent efficacy, T=maximum percent efficacy, X=logarithm of compound and Hill Slope=slope factor or Hill coefficient. The EC$_{50}$ value was determined by the concentration causing a half-maximal percent efficacy.

Results

The following Table presents the negative log of the half-maximal molar inhibitory concentration (pEC$_{50}$), with respect to PDE1b activity, for compounds of Formula (I).

| PDE1b (pEC$_{50}$) | Example Numbers |
|---|---|
| >7 | 5, 7, 36, 40, 41, 44, 45, 62, 63, 69, 82, 84, 86, 88, 93, 103, 128, 147, 161; |
| 6-7 | 1, 4, 6, 8, 9, 13, 14, 15, 16, 17, 19, 20, 22, 23, 24, 26, 29, 30, 31, 32, 33, 34, 37, 38, 39, 42, 43, 46, 47, 49, 50, 52, 55, 61, 64, 68, 70, 71, 72, 73, 75, 76, 77, 78, 79, 80, 81, 83, 85, 87, 90, 91, 92, 94, 100, 106, 107, 108, 110, 111, 112, 114, 117, 118, 119, 121, 124, 126, 129, 131, 132, 134, 135, 138, 140, 142, 145, 146, 150, 151, 157, 158, 159, 160, 162, 163, 165, 166, 167, 168; |
| 5-6 | 2, 3, 10, 11, 12, 18, 21, 25, 27, 28, 35, 48, 51, 53, 54, 56, 57, 58, 59, 60, 65, 66, 67, 74, 89, 99, 101, 102, 115, 122, 123, 125, 127, 133, 136, 139, 143, 144, 149, 155, 156, 164, 169; |
| <5 | 95, 96, 97, 98, 104, 105, 109, 113, 116, 120, 137, 148, 152, 153, 154. |

PDE1 Selectivity of Compounds

Assay Conditions

The selectivity of compounds of the present invention was determined using a panel of recombinant human PDEs and an in vitro enzymatic assay (BPS Bioscience). Series of dilutions of each test compound were prepared with 10% DMSO in assay buffer and 5 µL of the dilution was added to a 50 µL reaction so that the final concentration of DMSO is 1% in all of reactions.

The enzymatic reactions were conducted at room temperature for 60 minutes in a 50 µL mixture containing PDE assay buffer, 100 nM FAM-cAMP, or 100 nM FAM-cGMP, a recombinant PDE enzyme and the test compound.

After the enzymatic reaction, 100 µL of a binding solution (1:100 dilution of the binding agent with the binding agent diluent) was added to each reaction and the reaction was performed at room temperature for 60 minutes.

Fluorescence intensity was measured at an excitation of 485 nm and an emission of 528 nm using a Tecan Infinite M1000 microplate reader.

Data Analysis

PDE activity assays were performed in duplicate at each concentration. Fluorescence intensity is converted to fluorescence polarization using the Tecan Magellan6 software. The fluorescence polarization data were analyzed using the computer software, Graphpad Prism. The fluorescence polarization (FPt) in absence of the compound in each data set was defined as 100% activity. In the absence of PDE and the compound, the value of fluorescent polarization (FPb) in each data set was defined as 0% activity. The percent activity in the presence of the compound was calculated according to the following equation: % activity=(FP−FPb)/(FPt−FPb)×100%, where FP=the fluorescence polarization in the presence of the compound.

For $EC_{50}$ calculations, the values of % activity versus a series of compound concentrations were then plotted using non-linear regression analysis of Sigmoidal dose-response curve generated with the equation Y=B+(T−B)/1+10((Log $EC_{50}$−X)×Hill Slope), where Y=percent activity, B=minimum percent activity, T=maximum percent activity, X=logarithm of compound and Hill Slope=slope factor or Hill coefficient. The $EC_{50}$ value was determined by the concentration causing a half-maximal percent activity.

Results

Exemplary compounds of the present invention displayed selectivity for PDE1 enzymes versus isoforms from many, if not all, other PDE families. In addition, exemplary compounds showed greater specificity for PDE1b compared to PDE1a and PDE1c.

BIOLOGICAL EXAMPLES

The present disclosure will be further illustrated by the following biological examples. These examples are understood to be exemplary only, and not to limit the scope of the invention disclosed herein.

Biological Example 1

Effect of siRNA Mediated Knockdown of PDE1B on Memory Formation

The role of pde1b in memory formation in animals was evaluated by RNA interference. See, e.g., Peters et al., 2009, Genes Brain Behav. 8, 320-329. The results showed that siRNA-mediated inhibition of pde1b in animals enhanced several forms of long-term memory, including contextual and temporal (trace) memory.

Procedures siRNA

Initially, several non-modified siRNAs were tested for pde1a and pde1b knockdown in vitro using Neuro 2a cells. The siRNAs were specific to the Pde1 isoforms as identified by BLAST search. Several siRNAs showed efficacy in reducing pde1b mRNA levels and were chosen for further in vivo characterization. The behavioral studies used in vivo grade siSTABLE siRNA, which was chemically modified to enhance stability (Dharmacon Inc., Lafayette, USA). The sequence of the pde1b-6 siRNA sense strand was: 5'-GCUA-CAUGGUGAAGCAGUU-3'. The sequence of the non-targeting, control siRNA sense strand was: 5'-UAGCGAC-UAAACACAUCAAUU-3'.

Subjects

Young-adult (12-16 weeks old) C57BL/6Jax (Jackson Laboratories) male mice were utilized for contextual conditioning and C57Bl/6NTac (Taconic Farms) mice for trace fear conditioning. Upon arrival, mice were group-housed (5 mice) in standard laboratory cages and maintained on a 12:12 hours light-dark cycle. Experiments were always conducted during the light phase of the cycle.

After surgery for hippocampal cannulation, mice were housed in individual cages for the duration of the experiment. Mice received food and water ad libitum except when being trained or tested. They were maintained and bred under standard conditions, consistent with National Institutes of Health (NIH) guidelines and approved by the Institutional Animal Care and Use Committee.

Animal Surgery

For both contextual and trace conditioning, mice were infused with non-targeting or Pde1b siRNA into the hippocampus. For the injection of siRNA, mice were anesthetized with 20 mg/kg Avertin and implanted with a 33-gauge guide cannula bilaterally into the dorsal hippocampus (coordinates: A=−1.8 mm, L=+/−1.5 mm to a depth of 1.2 mm) or into amygdala (coordinates: A=−1.58 mm, L=+/−2.8 mm to a depth of 4.0 mm) (Franklin and Paxinos, The Mouse Brain in Stereotaxic Coordinates. Academic Press, San Diego 2003). Five to nine days after recovery from surgery, animals were injected with siRNA diluted to 0.5 μg/μl in 5% glucose and mixed with 6 equivalents of a 22 kDa linear polyethyleneimine (Fermentas). After 10 min of incubation at room temperature, 2 μl were injected into each hippocampus through an infusion cannula that was connected to a micro-syringe by a polyethylene tube. Animals were handled gently to minimize stress.

A total of 3 infusions of siRNA were given over a period of 3 days (1 μg siRNA per hippocampus per day). Mice were trained 3 days after the last siRNA injection and tested 24 hours later. Behavioral testing was initiated 3 days later. This design was chosen based on pilot experiments on siRNA knockdown in hippocampus, and because previous studies have indicated that gene-knockdown by siRNA duplexes takes several days to develop in CNS. See, e.g., Salahpour et al., 2007, Biol. Psychiatry 61, 65-69; Tan et al., 2005, Gene Therapy 12, 59-66; Thakker et al., 2004, Proc. Natl. Acad. Sci. USA 101, 17270-17275.

Fear Conditioning

Rationale

Contextual fear conditioning is a form of associative learning in which animals learn to recognize a training environment (conditioned stimulus, CS) that has been previously paired with an aversive stimulus such as foot shock (unconditioned stimulus, US). When exposed to the same context at a later time, conditioned animals show a variety of conditional fear responses, including freezing behavior. See, e.g., Fanselow, 1984, Behav. Neurosci. 98, 269-277; Fanselow, 1984, Behav. Neurosci. 98, 79-95; Phillips and LeDoux, 1992, Behav. Neurosci. 106, 274-285.

Contextual conditioning has been used to investigate the neural substrates mediating fear-motivated learning. See, e.g., Phillips and LeDoux, 1992, Behav. Neurosci. 106, 274-285; Kim et al., 1993, Behav. Neurosci. 107, 1093-1098. Recent studies in mice and rats provided evidence for functional interaction between hippocampal and non-hippocampal systems during contextual conditioning training See, e.g., Maren et al., 1997, Behav. Brain Res. 88, 261-274; Maren et al., 1997, Neurobiol. Learn. Mem. 67, 142-149; Frankland et al., 1998, Behav. Neurosci. 112, 863-874. Specifically, post-training lesions of the hippocampus (but not pre-training lesions) greatly reduced contextual fear, implying that: 1) the hippocampus is essential for contextual memory but not for contextual learning per se and 2) in the absence of the hippocampus during training, non-hippocampal systems can support contextual conditioning.

Contextual conditioning has been extensively used to study the impact of various mutations on hippocampus-dependent learning and memory and strain differences in mice. See, e.g., Bourtchouladze et al., 1994, Cell 79, 59-68; Bourtchouladze et al., 1998, Learn Mem. 5, 365-374; Kogan et al., 1997, Current Biology 7, 1-11; Silva et al., 1996, Current Biology 6, 1509-1518; Abel et al., 1997, Cell 88, 615-626; Giese et al., 1998, Science 279, 870-873; Logue et al., 1997, Neuroscience 80, 1075-1086; Chen et al., 1996, Behav. Neurosci. 110, 1177-1180; Nguyen et al., 2000, Learn Mem. 7, 170-179.

Because robust learning can be triggered with a few minutes training session, contextual conditioning has been especially useful to study the biology of temporally distinct processes of short- and long-term memory. See, e.g., Kim et al., 1993, Behav. Neurosci. 107, 1093-1098; Abel et al., 1997, Cell 88, 615-626; Bourtchouladze et al., 1994, Cell 79, 59-68; Bourtchouladze et al., 1998, Learn. Mem. 5, 365-374. As such, contextual conditioning provides an excellent model to evaluate the role of various novel genes in hippocampal-dependent memory formation.

Protocol

Previous investigations had established that training with 1× or 2× CS-US pairings induces sub-maximal (weak) memory in wild-type mice. See, e.g., U.S.2009/0053140; Tully et al., 2003, Nat. Rev. Drug Discov. 2, 267-77; Bourtchouladze et al. 1998, Learn. Mem. 5, 365-374. Accordingly, contextual conditioning in this study was performed as described by Bourtchouladze et al., 1994, Cell 79, 59-68.

An automated fear conditioning system (Colburn Instruments) was used for contextual conditioning and a manual setup (Med Associates) for trace fear conditioning. Mice were placed in the conditioning chamber and allowed to explore for 2 min. A total of two foot-shocks were delivered (0.6 mA, 2 s duration) with an inter-trial interval of 1 min. Freezing was scored for 30 s after the last foot-shock (immediate freezing). Mice were then returned to their home-cage. Memory was tested after 24 h (LTM). To assess contextual memory, freezing behavior was scored for 3 min intervals of 1 s in the chamber in which the mice were trained Trace Conditioning Rationale Trace fear conditioning is a form of Pavlovian conditioning, in which an interval of time passes between CS termination and UCS onset. Thus, the CS and US are separated in time by a trace interval, and the memory of this temporal relationship requires the hippocampus and prefrontal cortex. See Knight et al., 2004, J. Neurosci. 24, 218-228.

Trace conditioning becomes increasingly difficult as the time interval between CS and US increases. For example, C57BL/6 mice show poor memory if the trace interval between CS and US is 60 seconds or longer. See, e.g., U.S.2009/0053140. Moreover, previous studies have demonstrated that this memory impairment can be overcome if mice are treated with siRNA against PP1, a negative regulator of plasticity in the hippocampus. Peters et al., 2009, Genes Brain Behav. 8, 320-329. Consequently, the trace conditioning assay provides a method to test the ability of a compound to facilitate hippocampal-dependent memory.

Protocol

Facilitation of temporal memory in this study was assessed using a single CS-US pairing with a 60 s trace interval. For this study, standardized mouse contextual fear conditioning equipment was used (Med Associates, Inc., VA; Bourtchouladze et al., 1994, Cell 79, 59-68; (Bourtchouladze et al., 1998 Learn Mem. 5, 365-374). On the training day, the mouse was placed into the conditioning chamber for 2 minutes before the onset of the conditioned stimulus (CS), a 2800 Hz tone, which lasted for 20 seconds at 75 dB. Sixty seconds after the end of the tone, a 0.5 mA shock unconditioned stimulus (US) was delivered to the animal for two seconds. Following an additional 30 s in the chamber, the mouse was returned to its home cage.

Mice were tested at 24 h after training in a novel chamber located in another procedural room to avoid confounding effects of contextual conditioning. The internal conditioning chamber was removed and replaced with a mouse cage. Different colored tape was placed on the backside of each cage to differentiate one from another. Three different cages were used in rotation in order to decrease the possibility of scent contamination from subject to subject. A 30-watt lamp was placed inside the chamber to insure difference in illumination between training and testing. The cages were cleaned using a soapy solution instead of ethanol.

Each test began with two minutes of light only (pre-CS), then 20 seconds of tone presentation (CS), followed by an additional 30 seconds of light only (post-CS). In the same manner as during training, the mice were scored one at a time for "freezing" in five-second intervals, as for contextual conditioning described above. The proceeding of each experiment was filmed. The proportion of the freezing response specific to the auditory memory was determined by subtraction of preCS freezing (non-specific) from CS freezing (CS-preCS).

Statistical Analyses

All behavioral experiments were designed and performed in a balanced fashion: First, for each experimental condition (e.g., a specific dose effect) an equal number of experimental and control mice were used. Second, each experimental condition was replicated several times and replicate days were added to generate final number of subjects. Third, each session was video recorded and the experimenter was unaware (blind) to the treatment the subjects during training and testing.

Data were analyzed by ANOVA using JMP software. Except where indicated, all values in the text and figures are expressed as mean+SEM.

Results

Contextual Memory

When tested in contextual fear conditioning with 2 CS-US pairings to induce weak (sub-maximal) contextual memory, pde1b siRNA-injected mice showed significantly enhanced freezing 24 hours after training, compared to non-targeting siRNA-injected mice (FIG. 1).

Trace Memory

Figure 2:
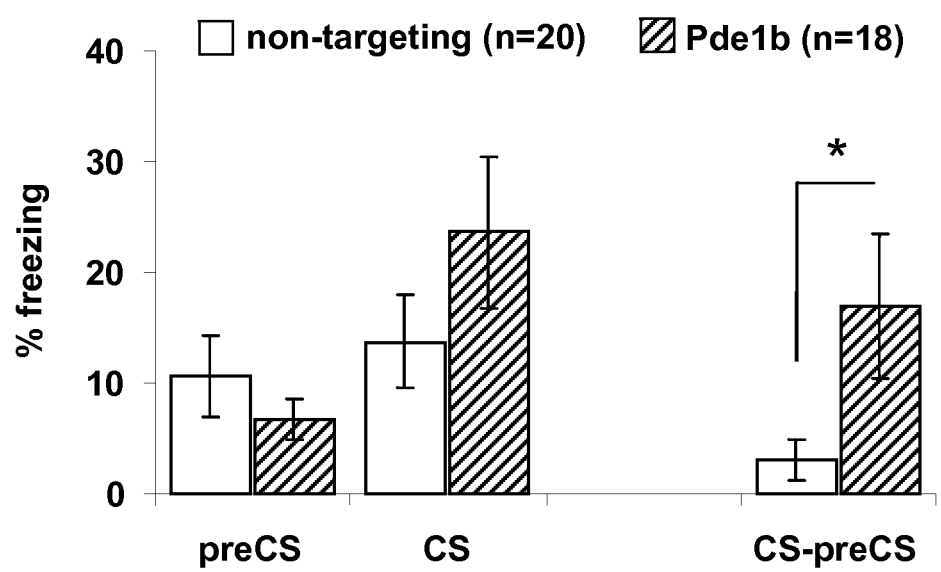
FIG. 2 is a bar graph showing the effect of siRNA-mediated knockdown of PDE1b in mouse hippocampal tissue on one-day memory in a trace-conditioning assay.

Similarly, when tested in trace conditioning with one CS/US pairing and a 60-s trace interval, pde1b siRNA-injected mice showed enhanced trace memory (FIG. 2). Repeated measures ANOVA revealed a significant treatment-by-trial interaction (p<0.05). Contrast analysis revealed that pde1b siRNA and control mice froze an equal proportion of time to tone (CS: p=0.13, preCS: p=0.54). However, only pde1b siRNA-treated mice formed a memory for the CS, while mice treated with control siRNA did not (effect of tone CS: p<0.05 and p=0.62 for pde1b and control siRNA, respectively). Moreover, pde1b treated mice showed significantly higher freezing if the nonspecific freezing in the alternate testing context was subtracted from the response to tone CS (CS-preCS: p<0.05). Thus, siRNA-mediated knockdown of hippocampal pde1b enhanced memory formation after trace fear conditioning as observed for contextual fear conditioning.

Taken together these results show that Pde1b is a negative regulator of memory formation in the hippocampus, a temporal lobe structure that is critical to memory formation in mice as well as in humans. Importantly, Pde1b siRNA induced a 'gain of function' (that is, enhancement of contextual and temporal memory formation). Hence these results show that Pde1b is a valid target for enhancing cognition, and memory specifically.

Biological Example 2

Effect of siRNA Mediated Knockdown of PDE1 on Neurite Growth

In the mouse, pde1b is highly expressed in the dentate gyrus and olfactory bulb, the two areas where neurogenesis occurs in the adult nervous system. Neurogenesis is the process by which new neurons are born and undergo dendritic and synaptic differentiation to integrate with functional circuitry. Neurogenesis in the hippocampus has been implicated in memory formation. See, e.g., Shors et al., 2001, Nature 410, 372-376; Shors et al., 2004, Trends Neurosci. 27, 250-256. The studies here evaluated the effect of pde1b inhibition of neurite outgrowth in the PC12 subclone NS1 (Cellomics). Neurite outgrowth (NOG) in PC12 cells (and primary neurons) occurs upon activation of signaling pathways that act through CREB. See, e.g., Greene and Tischler, 1976, Proc. Natl. Acad. Sci. USA 73, 2424-2428; Cheng et al., 2002, J. Biol. Chem. 277, 33930-33942.

This study evaluated the effect on neurite outgrowth (NOG) of drugs known to enhance cAMP-mediated activation of CREB, i.e., the PDE4 inhibitor rolipram—and compared these effects with those induced by siRNA-mediated inhibition of pde1b.

Methods

Cell Culture

Neuroscreen 1 (NS1) Cells (Cellomics Inc.) were cultured on collagen type I coated 75 cm2 plastic flasks (Biocoat, Becton Dickinson) in a humidified incubator at 37° C. in 5% CO2. Cells were cultured in RPMI complete cell culture medium (Cambrex) supplemented with 10% heat-inactivated horse serum (Invitrogen), 5% heat-inactivated fetal bovine serum (Cellgro), and 2 mM L-glutamine (Cambrex). For expansion, the cells were trypsinized and split at 80% confluence. Cell culture media was changed every 2 to 3 days.

NS1 cells were harvested and counted using a Coulter counter (Becton Dickinson Coulter Z1). Cells were seeded in 96-well collagen I coated plates at a density of 2000 cells per well in volume of 200 µl. RPMI media was supplemented with 200 ng/ml nerve growth factor (NGF, Sigma). NS1 cells were incubated for 72 hours to allow differentiation to a neuronal phenotype. NGF as then diluted to 50 ng/ml and the cells were treated with siRNA or compound at the indicated doses in FIG. 2A.

Neurite Outgrowth Assay

Neurite outgrowth (NOG) assays were performed using the Cellomics Arrayscan II Vti HCS scanner. Cells were stained using the HitKit™ HCS reagent kit (Cellomics) according to the manufacturer's instructions (which were previously validated for specific labeling of both neurites and neuronal cell bodies. Briefly, cells were fixed in 3.7% formaldehyde and stained with Hoechst dye to label the nuclei. The cells were then washed in neurite outgrowth buffer, incubated for one hour with the primary antibody for neurite outgrowth (anti-tubulin III), washed again, and incubated with fluorescently labeled secondary antibody solution for 1 hr.

Antibody-stained 96-well plates were stored at 4° C. in the dark until scanning. Plates were scanned using Cellomics ArrayScan II Vti HCS scanner. The neurite outgrowth assay is based on two channels to scanning: (1) Channel 1, which detects the Hoechst Dye and is used by the software to identify cells and for automated focusing; and (2) Channel 2, which detects the FITC fluorescence of the secondary antibody and is used by the software to calculate all data generated in reference to neurites.

siRNA and Drug Administration

The pde1b-specific siRNAs were the same as those described in Biological Example 1. The adenylyl cyclase stimulator forskolin and the selective PDE4 small molecule inhibitor Rolipram were administered at the doses indicated in FIG. 3A.

Results

As shown in FIG. 3A, neurite length and branching in NS1 cells was enhanced in dose-dependent manner by acute treatment with Rolipram and forskolin—but was not affected by treatment with Rolipram alone. Similarly, FIG. 3B shows that neurite outgrowth in NS1 cells was enhanced by siRNA-mediated knockdown of pde4d (the target of Rolipram) or pde1b in combination with forskolin. In contrast to Rolipram (which likely only inhibits PDE4 for several hours), pde4d and pde1b siRNA administration (>48 h) each had a small effect on NOG without the addition of Forskolin.

These results demonstrate that Pde1b inhibition leads to a functional enhancement of neurite growth in NS1 cells. Accordingly, the NOG assay also offers a suitable secondary (cellular/phenotypic) assay to test Pde1b inhibitors identified from a high throughput screening campaign.

Biological Example 3

Effect of Exemplary Compounds on Memory

The studies here evaluated the effect of exemplary compounds of the present invention on memory and on haloperidol induced catalepsy in mice and rats.

Methods

Subjects

Three month old B6129F1/J hybrid male mice (Jackson Laboratories, Bar Harbor, Me.) male mice were utilized for contextual conditioning fear conditioning and novel object recognition studies and C57BL/6J males (Jackson Laboratories) were used for catalepsy studies. Outbred hooded Long Evans rats (200 g average weight, Harlan) were used for rat object recognition and fear conditioning. Upon arrival, mice were group-housed (4 mice/cage) in Inovive IVC racks and maintained on a 12:12 hours light-dark cycle. Rats were house in standard cages in groups of two. Experiments were always conducted during the light phase of the cycle. The animals received food and water ad libitum except during training and testing. All procedures were consistent with National Institutes of Health (NIH) guidelines and approved by the DNS/Helicon Institutional Animal Care and Use Committee.

Drug Administration

Pde1 inhibitors and positive control were dosed in a Vehicle containing 10% DMSO, 30% PEG (MW400) and 60% PBS, unless specified otherwise. For subcutaneous dosing (s.c.), all drugs were administered at a volume of 10 ml per kg 30 min prior to behavior training unless specified otherwise. For oral dosing (p.o.), animals were dosed at the indicated amount 30 minutes prior to training.

Contextual Conditioning

Protocol

Contextual conditioning was essentially carried out as described in Biological Example 1. An automated fear conditioning system (Colburn Instruments) was used for contextual conditioning and a manual setup (Med Associates) for trace fear conditioning. Mice were placed in the conditioning chamber and allowed to explore for 2 min. A total of two foot-shocks were delivered (0.2 mA, 2 s duration) with an inter-trial interval of 1 min. As previously noted, these training conditions generate sub-maximal, or weak, memory in control mice, thereby allowing one to evaluate whether a Pde1b compound of the present invention can enhance memory formation.

Freezing was scored for 30 s after the last foot-shock (immediate freezing). The mice were then returned to their home-cage. Memory was tested after 24 h (LTM) for 3 min by scoring freezing behavior in intervals of is in the chamber in which the mice were trained.

Object Recognition Memory

Rationale

Novel Object Recognition (NOR) is an assay of recognition learning and memory retrieval, which takes advantage of the spontaneous preference of rodents to investigate a novel object compared with a familiar one.

The NOR test has been employed extensively to assess the potential cognitive-enhancing properties of novel compounds derived from high-throughput screening. Object recognition is an ethologically relevant task that does not result from negative reinforcement (foot shock). This task relies on the natural curiosity of rodents to explore novel objects in their environments more than familiar ones. Obviously, for an object to be "familiar," the animal must have attended to it before and remembered that experience. Hence, animals with better memory will attend and explore a new object more than an object familiar to them. During testing, the animal is presented with the training object and a second, novel one. Memory of the training object renders it familiar to the animal, and it then spends more time exploring the new novel object rather than the familiar one. See Bourtchouladze et. al., 2003, Proc. Natl. Acad. Sci. USA 100, 10518-10522).

Studies indicate that the NOR procedure involves several brain regions, including the cortex and the hippocampus. Recent neuroimaging studies in humans demonstrated that memory in object recognition depends on prefrontal cortex (PFC). See Delbert et al., 1999, Neurology 52, 1413-1417. Consistent with these findings, rats with the PFC lesions show poor working memory when they are required to discriminate between familiar and novel objects. See Mitchell, 1998, Behav. Brain Res. 97, 107-113. Other studies on monkeys and rodents suggest that the hippocampus is important for novel object recognition. See, e.g., Teng et al., 2000, J. Neurosci 20, 3853-3863; Mumby, 2001, Brain Res. 127, 159-181. Hence, object recognition provides an excellent behavioral model to evaluate drug-compound effects on cognitive task associated with function of the hippocampus and cortex.

Protocol

The novel object recognition task was performed as described by Bevins and Besheer, 2006 (Nat. Protocol. 1, 1306-1311) using a standard novel object recognition system for rats (Stoelting). Objects were placed in the center of the box, testing was carried out in low light, and time exploring objects was assessed using Ethovision Software. All videos were reviewed by trained observers.

For two consecutive days, rats were habituated to the chamber for 5 min with 5 min of handling immediately following exposure to the apparatus. The next day, rats treated with 10% DMSO, 30% PEG400, 60% Saline vehicle or compound 30 min before training were exposed to either two white blocks or two grey balls (~4 cm in width/diameter) for 3 min. A performance control group was treated with vehicle and exposed to object for 15 min. Approximately 24 h after training, rats were exposed to one familiar object and one novel object (grey ball is replaced with a white block and vice versa) and the time exploring each object was measured. Memory was scored by calculation of a discrimination index $((T_N-T_F)/(T_N+T_F))*100$; between group comparison) and by comparison of the time exploring the novel versus familiar object on the test day (within group comparison).

Statistical Analyses

All behavioral experiments were designed and performed in a balanced fashion: (i) For each experimental condition (e.g. a specific dose-effect) an equal number of experimental and control mice were used; (ii) Each experimental condition was replicated several times, and (iii) Replicate days were added to generate final number of subjects. The proceeding of each session was filmed. In each experiment, the experimenter was unaware (blind) to the treatment of the subjects during training and testing. Data were analyzed by ANOVA using JMP software, followed by contrast analysis.

Data were transformed using box-cox transformation, and the results of contrast analysis comparing treatment groups to vehicle are shown (LS means students-t). Except were indicated, all values in the text and figures are expressed as Mean+SEM.

Results

Exemplary compounds of Formula I F were found to significantly enhance 24 hour memory, and where tested, to enhance 48 hour memory, in the object recognition assay. Control experiments showed that compound administration did not significantly affect the cumulative distance traveled or amount of time spent exploring the left and right halves of the box. Significant effects were seen at several concentrations, depending on the compound, including concentrations of 0.1 mg/kg and 1 mg/kg.

Exemplary compounds were also found to enhance contextual memory in the fear conditioning assay. Significant effects were seen at several concentrations, depending on the compound, including 0.01 mg/kg, 0.03 mg/kg, and 1.0 mg/kg.

Biological Example 4

Effect of Exemplary Compounds on Cardiac Function

Exemplary compounds of the present invention were also evaluated in several models of cardiovascular function, in both guinea pigs and in telemeterized male rats. Each test compound (or vehicle) was administered by oral gavage, and animals were evaluated after each dose for any abnormal clinical signs. Systemic blood pressure (systolic, diastolic, and mean arterial pressure), HR and pulse pressure were recorded following dosing.

The results showed no notable effects of vehicle administration on systemic blood pressure, heart rate, or arterial pulse pressure in these studies. All parameters were within expected range during the entire monitoring period. In contrast, however, administration of several test compounds let to a reduction in blood pressure, and in some cases, prolongation of the QTc interval.

It will be understood by one skilled in the art that the described embodiments herein do not limit the scope of the invention. The specification, including the examples, is intended to be exemplary only, and it will be apparent to those skilled in the art that various modifications and variations can be made in the present invention without departing from the scope or spirit of the invention as defined by the appended claims.

Furthermore, while certain details in the present disclosure are provided to convey a thorough understanding of the invention as defined by the appended claims, it will be apparent to those skilled in the art that certain embodiments may be practiced without these details. Moreover, in certain instances, well-known methods, procedures, or other specific details have not been described to avoid unnecessarily obscuring aspects of the invention defined by the appended claims.

What is claimed is:

1. A chemical entity of Formula

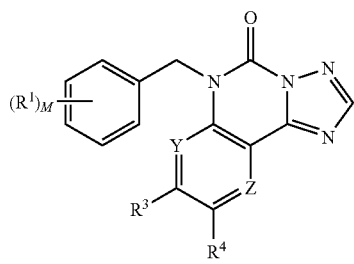

(I)

wherein:
Y and Z are each independently —CH— or —N—, with the proviso that at least one Y or Z member is —N—;
M is 0, 1, 2, 3, 4, or 5;
$R^1$ is each independently selected from H, halo, —CN, —$C_{1-6}$alkyl, —$C_{2-6}$alkynyl, —$C_{1-6}$haloalkyl, —$C_{1-6}$thioalkyl, —$C_{1-6}$thiohaloalkyl, —$C_{1-6}$alkoxy, —$C_{1-6}$haloalkoxy, —$SO_2C_{1-6}$alkyl, aryl, pyrazolyl and 2-oxopyrrolidinyl; or
two $R^1$ members are on adjacent carbons and taken together with the carbons to which they are attached form a 5-6 member saturated or unsaturated monocylic ring system comprising one or more oxygen or nitrogen atoms, wherein the ring system is optionally substituted with one or more groups selected from halo, —$C_{1-6}$alkyl, —$C_{1-6}$alkoxy, and —$C_1$-$C_6$haloalkoxy;
$R^3$ and $R^4$ are each independently selected from the group consisting of H, halo, —CN, —OH, —$C_{1-6}$alkyl, —$C_{1-6}$haloalkyl, —$C_{2-6}$alkenyl, —$CH_2O$-aryl, —$C_{1-6}$alkoxy, —$C_{1-6}$haloalkoxy, —$C(O)CH_3$, —CH(OH)($CF_3$), —$(CR^{10}R^{11})_{0-3}NR^{12}R^{13}$, aryl, heteroaryl, and heterocycloalkyl, wherein each aryl, heteroaryl and heterocycloalkyl is optionally unsubstituted or substituted with a member each independently selected from the group consisting of —$CH_3$ and —$OCH_3$;
$R^{10}$ and $R^{11}$ are each independently selected from the group consisting of: —H, —F, —$C_{1-6}$alkyl, —$CF_3$, and —OH;
$R^{12}$ and $R^{13}$ are each independently selected from the group consisting of —H, —$C_{1-6}$alkyl, —$C(O)_2CH_2Ph$, —$C_{1-6}$alkyl(aryl), $C_{1-6}$alkyl(heterocycloalkyl), aryl, —$C_{3-6}$cycloalkyl, heteroaryl, and heterocycloalkyl, said aryl, —$C_{3-6}$cycloalkyl, heteroaryl, and heterocycloalkyl are each independently optionally substituted with one or more substituents independently selected from the group consisting of cycloalkyl, aryl, heteroaryl, heterocycloalkyl, —CN, —OH, —$NO_2$, —$SO_2NH_2$, —$CONH_2$, —$CO_2H$, —COH, amino, —($C_{1-6}$ alkyl) amino, di($C_{1-6}$alkyl)amino, —$N_3$, cyanate, isocyanate, thiocyanate, isothiocyanate, aryloxy, and arylthio;
or $R^{12}$ and $R^{13}$ are taken together with the nitrogen to which they are attached form a heterocycloalkyl optionally substituted with one or more substituents independently selected from the group consisting of cycloalkyl, aryl, heteroaryl, heterocycloalkyl, —CN, —OH, —$NO_2$, —$SO_2NH_2$, —$CO_2H$, —COH, amino, —($C_{1-6}$ alkyl) amino, di($C_{1-6}$alkyl)amino, —$N_3$, cyanate, isocyanate, thiocyanate, isothiocyanate, aryloxy, and arylthio; and
wherein the chemical entity is selected from the group consisting of compounds of Formula (I), and pharmaceutically acceptable salts of compounds of Formula (I).

2. The chemical entity as in claim 1, wherein Y is —N—.

3. The chemical entity as in claim 2, wherein $R^3$ is selected from —H, —CH($OCH_3$)$_2$, —$CH_2O$-phenyl, or —($CR^{10}R^{11}$)$_{1-3}NR^{12}R^{13}$, where $R^{10}$ and $R^{11}$ are each independently H, $R^{12}$ is H or —$C_{1-6}$alkyl, and $R^{13}$ is selected from phenyl, benzyl, (3-methyloxetan-3-yl)methyl, or (tetrahydrofuran-3-yl)methyl.

4. The chemical entity as in claim 1, wherein Z is —N—.

5. The chemical entity as in claim 1, wherein Y and Z are each independently —N—.

6. The chemical entity as in claim 1, wherein M is 1.

7. The chemical entity as in claim 1, wherein M is 2.

8. The chemical entity as in claim 1, wherein M is 3.

9. The chemical entity as in claim 1, wherein M is 4.

10. The chemical entity as in claim 1, wherein M is 5.

11. The chemical entity as in claim 1, wherein M is 1, 2, 3, 4, or 5, and $R^1$ is each independently H, —Br, —Cl, —F, —I, —CN, —$C_{1-6}$alkyl, —$C_{2-6}$alkynyl, —$SCH_3$, —$OCF_3$, —$OCF_2H$, —$C_{1-6}$alkoxy, —$SCF_3$, —$SO_2CH_3$, 2-oxopyrrolidine, and pyrazole.

12. The chemical entity as in claim 1, wherein two $R^1$ members are on adjacent carbons and taken together with the carbons to which they are attached form a fused 5-membered ring selected from 1-methyl-1H-pyrazolyl or dioxolanyl.

13. The chemical entity as in claim 1, wherein M is 1, 2, 3 or 4, and $R^1$ is each independently —Cl, —F or —$C_{1-6}$alkoxy.

14. The chemical entity as in claim 1, wherein $R^4$ is H or —$CH_3$ and $R^3$ is —($CR^{10}R^{11}$)$_{1-3}NR^{12}R^{13}$.

15. The chemical entity as in claim 1, wherein $R^3$ is —($CR^{10}R^{11}$)$NR^{12}R^{13}$, $R^{10}$ and $R^{11}$ are each independently selected from H, —OH, and —$CH_3$, and $R^{12}$ and $R^{13}$ are taken together with the nitrogen to which they are attached to form a heterocycloalkyl ring selected from morpholinyl, (2S, 6R)-2,6-dimethylmorpholinyl, 4-(methylsulfonyl)piperazin-1-yl and isoindolin-2-yl.

16. The chemical entity as in claim 1, wherein $R^3$ is —($CR^{10}R^{11}$)$_{1-2}NR^{12}R^{13}$, $R^{10}$ and $R^{11}$ are each independently selected from H, —OH, or —CH₃, and R¹² and R¹³ are taken together with the nitrogen to which they are attached to form a heterocycloalkyl ring selected from morpholinyl, 2,6-dimethylmorpholinyl, (2S,6R)-2,6-dimethylmorpholinyl, (2R,6S)-2,6-dimethylmorpholinyl and 4-(methylsulfonyl) piperazinyl.

17. The chemical entity as in claim 1, wherein R³ is H or —CH₃ and R⁴ is —(CR¹⁰R¹¹)₁₋₃NR¹²R¹³.

18. The chemical entity as in claim 1, wherein R³ is —H, or —CH₃, R⁴ is H, —Br, —C₁₋₆alkyl, —C₂₋₆alkenyl, —C(O)CH₃, —CH(OH)CF₃, —CH₂OCH₂OCH₃, phenyl, pyridyl, and —(CR¹⁰R¹¹)₁₋₃NR¹²R¹³, said phenyl and pyridyl each optionally substituted with one or more substituents independently selected from the group consisting of —CH₃ and —OCH₃, R¹⁰ and R¹¹ are each independently selected from H, —CH₃, or —OH, and R¹² and R¹³ are each independently —H, —C₁₋₆alkyl, —C(O)₂CH₂Ph, —CH(CH₃)phenyl, —C₃₋₆cycloalkyl, and heterocycloalkyl, said —C₃₋₆cycloalkyl and heterocycloalkyl each optionally substituted with one or more substituents independently selected from the group consisting of cycloalkyl, aryl, heteroaryl, heterocycloalkyl, —CN, —OH, —NO₂, —SO₂NH₂, —CONH₂, —CO₂H, —COH, amino, —(C₁₋₆ alkyl)amino, di(C₁₋₆alkyl)amino, —N₃, cyanate, isocyanate, thiocyanate, isothiocyanate, aryloxy, and arylthio.

19. The chemical entity as in claim 1, wherein R³ is —H, or —CH₃, R⁴ is —(CR¹⁰R¹¹)₁₋₃NR¹²R¹³, R¹⁰ and R¹¹ are each independently selected from —H, —F, —CH₃, —CF₃, and —OH, and R¹² and R¹³ are taken together with the nitrogen to which they are attached to form a heterocycloalkyl ring selected from (2R,5R)-2,5-dimethylmorpholinyl, (2R,6S)-2,6-dimethylmorpholinyl, (2S,5S)-2,5-dimethylmorpholinyl, (2S,6R)-2,6-dimethylmorpholinyl, (3S,5R)-(2-methoxyethyl)piperazinyl, (4-((tetrahydrofuran-3-yl)methyl)piperazinyl), 1,4-oxazepanyl, 1-methyl-8-oxa-1,2-diazaspiro[4.5] decanyl, 2,2-dimethylmorpholinyl, 2,5-dimethylmorpholinyl, 2-ethylmorpholinyl, 2-methylmorpholinyl, 2-oxa-5-azabicyclo[2.2.1]heptanyl, 3-(dimethylamino)pyrrolidinyl, 3,3-dimethylmorpholinyl, 3,5-dimethylpiperazinyl, 3-hydroxyazetidinyl, 3-methyl-6-oxopyridazin-1(6H)-yl, 3-methylmorpholinyl, 4-(2,2,2-trifluoroacetyl)piperazinyl, 4-(methylsulfonyl)piperazinyl, 4-(propan-2-yl)piperazinyl, 4-(tetrahydrofuran-3-carbonyl) piperazinyl, 4-acetyl-1,4-diazepanyl, 4-cyclopropylpiperazinyl, 4-methoxypiperidinyl, 4-methyl-1,4-diazepanyl, 4-methyl-piperazinyl, 8-oxa-3-azabicyclo[3.2.1]octanyl, isoindolinyl, morpholinyl, N,N-dimethylpiperazinyl-1-sulfonamide, piperazinyl, piperidinyl, tetrahydro-1H-oxazolo[3,4-a]pyrazin-3(5H)-on-7-yl, and thiomorpholinyl.

20. The chemical entity as in claim 1, wherein R⁴ is morpholinomethyl, (3-methylmorpholino)methyl, (2,6-dimethylmorpholino)methyl, ((2S,6R)-2,6-dimethylmorpholino) methyl, ((2R,6S)-2,6-dimethylmorpholin-4-yl)methyl, (4-(methylsulfonyl)piperazin-1-yl)methyl, 1-hydroxy-2-morpholinoethyl or 2-((2S,6R)-2,6-dimethylmorpholino)-1-hydroxyethyl, and R³ is H or —CH₃.

21. A pharmaceutical composition comprising an effective amount of at least one chemical entity of claim 1, and a pharmaceutically acceptable excipient.

22. A compound, or pharmaceutically acceptable salt thereof, of Formula (I):

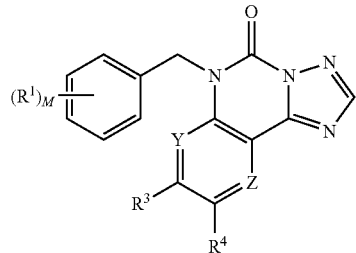

wherein:
Y and Z are each independently —CH— or —N—, with the proviso that at least one Y or Z member is —N—;
M is 0, 1, 2, 3, 4, or 5;
R¹ is each independently selected from H, halo, —CN, —C₁₋₆alkyl, —C₂₋₆alkynyl, —C₁₋₆haloalkyl, —C₁₋₆thioalkyl, —C₁₋₆thiohaloalkyl, —C₁₋₆alkoxy, —C₁₋₆haloalkoxy, —SO₂C₁₋₆alkyl, aryl, pyrazolyl and 2-oxopyrrolidinyl; or
two R¹ members are on adjacent carbons and taken together with the carbons to which they are attached form a 5-6 member saturated or unsaturated monocylic ring system comprising one or more oxygen or nitrogen atoms, wherein the ring system is optionally substituted with one or more groups selected from halo, —C₁₋₆ alkyl, —C₁₋₆alkoxy, and —C₁-C₆haloalkoxy;
R³ and R⁴ are each independently selected from the group consisting of H, halo, —CN, —OH, —C₁₋₆alkyl, —C₁₋₆haloalkyl, —C₂₋₆alkenyl, —CH₂O-aryl, —C₁₋₆ alkoxy, —C₁₋₆haloalkoxy, —C(O)CH₃, —CH(OH)(CF₃), —(CR¹⁰R¹¹)₀₋₃NR¹²R¹³, aryl, heteroaryl, and heterocycloalkyl, wherein each aryl, heteroaryl and heterocycloalkyl is optionally unsubstituted or substituted with a member each independently selected from the group consisting of —CH₃ and —OCH₃;
R¹⁰ and R¹¹ are each independently selected from the group consisting of: —H, —F, —C₁₋₆alkyl, —CF₃, and —OH;
R¹² and R¹³ are each independently selected from the group consisting of —H, —C₁₋₆alkyl, C(O)₂CH₂Ph, —C₁₋₆alkyl(aryl), —C₁₋₆alkyl(heterocycloalkyl), aryl, —C₃₋₆cycloalkyl, heteroaryl, and heterocycloalkyl, said aryl, —C₃₋₆cycloalkyl, heteroaryl, and heterocycloalkyl are each independently optionally substituted with one or more substituents independently selected from the group consisting of cycloalkyl, aryl, heteroaryl, heterocycloalkyl, —CN, —OH, —NO₂, —SO₂NH₂, —CONH₂, —CO₂H, —COH, amino, —(C₁₋₆ alkyl)amino, di(C₁₋₆alkyl)amino, —N₃, cyanate, isocyanate, thiocyanate, isothiocyanate, aryloxy, and arylthio;
or R¹² and R¹³, taken together with the nitrogen to which they are attached form a heterocycloalkyl optionally substituted with one or more substituents independently selected from the group consisting of cycloalkyl, aryl, heteroaryl, heterocycloalkyl, —CN, —OH, —NO₂, —SO₂NH₂, —CONH₂, —CO₂H, —COH, amino, —(C₁₋₆ alkyl)amino, di(C₁₋₆alkyl)amino, —N₃, cyanate, isocyanate, thiocyanate, isothiocyanate, aryloxy, and arylthio.

23. A compound selected from the group consisting of:
9-Bromo-6-(4-methoxybenzyl)pyrido[3,2-e][1,2,4]triazolo[1,5-c]pyrimidin-5(6H)-one;

8-Bromo-6-(4-methoxybenzyl)pyrido[2,3-e][1,2,4]triazolo[1,5-c]pyrimidin-5(6H)-one;
8-(Dimethoxymethyl)-6-(4-methoxybenzyl)pyrido[3,2-e][1,2,4]triazolo[1,5-c]pyrimidin-5(6H)-one;
9-Bromo-6-(4-methoxybenzyl)-[1,2,4]triazolo[1,5-c]pteridin-5(6H)-one;
9-(3,4-Dimethoxyphenyl)-6-(4-methoxybenzyl)pyrido[3,2-e][1,2,4]triazolo[1,5-c]pyrimidin-5(6H)-one;
6-(4-Methoxybenzyl)-9-(6-methoxypyridin-3-yl)pyrido[3,2-e][1,2,4]triazolo[1,5-c]pyrimidin-5(6H)-one;
6-(4-Methoxybenzyl)-9-(2-methoxypyridin-3-yl)pyrido[3,2-e][1,2,4]triazolo[1,5-c]pyrimidin-5(6H)-one;
6-(4-Methoxybenzyl)-9-(3-methyl-6-oxopyridazin-1(6H)-yl)pyrido[3,2-e][1,2,4]triazolo[1,5-c]pyrimidin-5(6H)-one;
9-(4-Cyclopropylpiperazin-1-yl)-6-(4-methoxybenzyl)pyrido[3,2-e][1,2,4]triazolo[1,5-c]pyrimidin-5(6H)-one;
9-(((1S,2S)-2-Aminocyclohexyl)amino)-6-(4-methoxybenzyl)pyrido[3,2-e][1,2,4]triazolo[1,5-c]pyrimidin-5(6H)-one;
6-(4-Methoxybenzyl)-9-(methyl(1-methylpiperidin-4-yl)amino)-[1,2,4]triazolo[1,5-c]pteridin-5(6H)-one;
9-((2-(Dimethylamino)ethyl)(methyl)amino)-6-(4-methoxybenzyl)-[1,2,4]triazolo[1,5-c]pteridin-5(6H)-one;
6-(4-Methoxybenzyl)-9-(4-(2-methoxyethyl)piperazin-1-yl)pyrido[3,2-e][1,2,4]triazolo[1,5-c]pyrimidin-5(6H)-one;
9-(3-(Dimethylamino)pyrrolidin-1-yl)-6-(4-methoxybenzyl)pyrido[3,2-e][1,2,4]triazolo[1,5-c]pyrimidin-5(6H)-one;
9-(4-(Dimethylamino)piperidin-1-yl)-6-(4-methoxybenzyl)pyrido[3,2-e][1,2,4]triazolo[1,5-c]pyrimidin-5(6H)-one;
6-(4-Methoxybenzyl)-9-(methyl(tetrahydro-2H-pyran-4-yl)amino)pyrido[3,2-e][1,2,4]triazolo[1,5-c]pyrimidin-5(6H)-one;
9-((2S,6R)-2,6-Dimethylmorpholino)-6-(4-methoxybenzyl)pyrido[3,2-e][1,2,4]triazolo[1,5-c]pyrimidin-5(6H)-one;
9-((3-(Dimethylamino)propyl)(methyl)amino)-6-(4-methoxybenzyl)pyrido[3,2-e][1,2,4]triazolo[1,5-c]pyrimidin-5(6H)-one;
6-(4-Methoxybenzyl)-9-(4-(methylsulfonyl)piperazin-1-yl)pyrido[3,2-e][1,2,4]triazolo[1,5-c]pyrimidin-5(6H)-one;
Benzyl (2-(6-(4-methoxybenzyl)-5-oxo-5,6-dihydropyrido[3,2-e][1,2,4]triazolo[1,5-c]pyrimidin-9-yl)ethyl)carbamate;
6-(4-Methoxybenzyl)-8-(morpholinomethyl)pyrido[3,2-e][1,2,4]triazolo[1,5-c]pyrimidin-5(6H)-one;
6-(4-Methoxybenzyl)-9-(piperidin-1-ylmethyl)pyrido[3,2-e][1,2,4]triazolo[1,5-c]pyrimidin-5(6H)-one;
6-(4-Methoxybenzyl)-9-(thiomorpholinomethyl)pyrido[3,2-e][1,2,4]triazolo[1,5-c]pyrimidin-5(6H)-one;
6-(4-Chlorobenzyl)-9-(morpholinomethyl)pyrido[3,2-e][1,2,4]triazolo[1,5-c]pyrimidin-5(6H)-one;
6-(4-Chlorobenzyl)-9-(piperidin-1-ylmethyl)pyrido[3,2-e][1,2,4]triazolo[1,5-c]pyrimidin-5(6H)-one;
6-(4-Chlorobenzyl)-9-(((2S,6R)-2,6-dimethylmorpholino)methyl)pyrido[3,2-e][1,2,4]triazolo[1,5-c]pyrimidin-5(6H)-one;
9-(2-Aminoethyl)-6-(4-methoxybenzyl)pyrido[3,2-e][1,2,4]triazolo[1,5-c]pyrimidin-5(6H)-one;
6-(4-Methoxybenzyl)-9-(2-((tetrahydro-2H-pyran-4-yl)amino)ethyl)pyrido[3,2-e][1,2,4]triazolo[1,5-c]pyrimidin-5(6H)-one;
6-(4-Methoxybenzyl)-9-(2((1-phenylethyl)amino)ethyl)pyrido[3,2-e][1,2,4]triazolo[1,5-c]pyrimidin-5(6H)-one;
6-(4-Methoxybenzyl)-9-vinylpyrido[3,2-e][1,2,4]triazolo[1,5-c]pyrimidin-5(6H)-one;
6-(4-Methoxybenzyl)-9-((methoxymethoxy)methyl)pyrido[3,2-e][1,2,4]triazolo[1,5-c]pyrimidin-5(6H)-one;
9-(1-Ethoxyvinyl)-6-(4-methoxybenzyl)pyrido[3,2-e][1,2,4]triazolo[1,5-c]pyrimidin-5(6H)-one;
9-(Hydroxymethyl)-6-(4-methoxybenzyl)pyrido[3,2-e][1,2,4]triazolo[1,5-c]pyrimidin-5(6H)-one;
9-(2-Oxa-5-azabicyclo[2.2.1]heptan-5-ylmethyl)-6-(4-methoxybenzyl)pyrido[3,2-e][1,2,4]triazolo[1,5-c]pyrimidin-5(6H)-one;
9-((Dimethylamino)methyl)-6-(4-methoxybenzyl)pyrido[3,2-e][1,2,4]triazolo[1,5-c]pyrimidin-5(6H)-one;
9-(((2S,6R)-2,6-Dimethylmorpholino)methyl)-6-(4-methoxybenzyl)pyrido[3,2-e][1,2,4]triazolo[1,5-c]pyrimidin-5(6H)-one;
6-(4-Methoxybenzyl)-9-((4-methylpiperazin-1-yl)methyl)pyrido[3,2-e][1,2,4]triazolo[1,5-c]pyrimidin-5(6H)-one;
9-(3,3-Dimethylmorpholino)methyl)-6-(4-methoxybenzyl)pyrido[3,2-e][1,2,4]triazolo[1,5-c]pyrimidin-5(6H)-one;
9-((2,2-Dimethylmorpholino)methyl)-6-(4-methoxybenzyl)pyrido[3,2-e][1,2,4]triazolo[1,5-c]pyrimidin-5(6H)-one;
9-((2-Ethylmorpholino)methyl)-6-(4-methoxybenzyl)pyrido[3,2-e][1,2,4]triazolo[1,5-c]pyrimidin-5(6H)-one;
9-((2,5-Dimethylmorpholino)methyl)-6-(4-methoxybenzyl)pyrido[3,2-e][1,2,4]triazolo[1,5-c]pyrimidin-5(6H)-one;
6-(4-Methoxybenzyl)-9-((2,2,6,6-tetrafluoromorpholino)methyl)pyrido[3,2-e][1,2,4]triazolo[1,5-c]pyrimidin-5(6H)-one;
9-(8-Oxa-3-azabicyclo[3.2.1]octan-3-ylmethyl)-6-(4-methoxybenzyl)pyrido[3,2-e][1,2,4]triazolo[1,5-c]pyrimidin-5(6H)-one;
6-(4-Methoxybenzyl)-9-((1-methyl-8-oxa-1,2-diazaspiro[4.5]decan-2-yl)methyl)pyrido[3,2-e][1,2,4]triazolo[1,5-c]pyrimidin-5(6H)-one;
6-(4-Methoxybenzyl)-9-((2-methylmorpholino)methyl)pyrido[3,2-e][1,2,4]triazolo[1,5-c]pyrimidin-5(6H)-one;
6-(4-Methoxybenzyl)-9-((3-methylmorpholino)methyl)pyrido[3,2-e][1,2,4]triazolo[1,5-c]pyrimidin-5(6H)-one;
9-(((2S,6R)-2,6-Dimethylmorpholino)methyl)-6-(4-methoxybenzyl)-[1,2,4]triazolo[1,5-c]pteridin-5(6H)-one;
6-(4-Methoxybenzyl)-9-((4-methyl-1,4-diazepan-1-yl)methyl)pyrido[3,2-e][1,2,4]triazolo[1,5-c]pyrimidin-5(6H)-one;
9-((1,4-Oxazepan-4-yl)methyl)-6-(4-methoxybenzyl)pyrido[3,2-e][1,2,4]triazolo[1,5-c]pyrimidin-5(6H)-one;
9-((4-Acetyl-1,4-diazepan-1-yl)methyl)-6-(4-methoxybenzyl)pyrido[3,2-e][1,2,4]triazolo[1,5-c]pyrimidin-5(6H)-one;
9-((Cyclohexyl(methyl)amino)methyl)-6-(4-methoxybenzyl)pyrido[3,2-e][1,2,4]triazolo[1,5-c]pyrimidin-5(6H)-one;
6-(4-Methoxybenzyl)-9-((4-methoxypiperidin-1-yl)methyl)pyrido[3,2-e][1,2,4]triazolo[1,5-c]pyrimidin-5(6H)-one;

6-(4-Methoxybenzyl)-9-((methyl(tetrahydro-2H-pyran-4-yl)amino)methyl)pyrido[3,2-e][1,2,4]triazolo[1,5-c]pyrimidin-5(6H)-one;
6-(4-Methoxybenzyl)-9-((4-(2-methoxyethyl)piperazin-1-yl)methyl)pyrido[3,2-e][1,2,4]triazolo[1,5-c]pyrimidin-5(6H)-one;
9-((Isopropyl(2-methoxyethyl)amino)methyl)-6-(4-methoxybenzyl)pyrido[3,2-e][1,2,4]triazolo[1,5-c]pyrimidin-5(6H)-one;
6-(4-Methoxybenzyl)-8-((4-methylpiperazin-1-yl)methyl)pyrido[2,3-e][1,2,4]triazolo[1,5-c]pyrimidin-5(6H)-one;
6-(4-Methoxybenzyl)-8-(morpholinomethyl)pyrido[2,3-e][1,2,4]triazolo[1,5-c]pyrimidin-5(6H)-one;
6-(4-Methoxybenzyl)-8-(piperidin-1-ylmethyl)pyrido[2,3-e][1,2,4]triazolo[1,5-c]pyrimidin-5(6H)-one;
6-(4-Methoxybenzyl)-8-(thiomorpholinomethyl)pyrido[2,3-e][1,2,4]triazolo[1,5-c]pyrimidin-5(6H)-one;
8-(((2S,6R)-2,6-Dimethylmorpholino)methyl)-6-(4-methoxybenzyl)pyrido[2,3-e][1,2,4]triazolo[1,5-c]pyrimidin-5(6H)-one;
6-(4-Methoxybenzyl)-9-(((2-methoxyethyl)(methyl)amino)methyl)pyrido[3,2-e][1,2,4]triazolo[1,5-c]pyrimidin-5(6H)-one;
7-((6-(4-Methoxybenzyl)-5-oxo-5,6-dihydropyrido[3,2-e][1,2,4]triazolo[1,5-c]pyrimidin-9-yl)methyl)tetrahydro-1H-oxazolo[3,4-a]pyrazin-3(5H)-one;
9-(((2S,5S)-2,5-Dimethylmorpholino)methyl)-6-(4-methoxybenzyl)pyrido[3,2-e][1,2,4]triazolo[1,5-c]pyrimidin-5(6H)-one;
9-(((2R,5R)-2,5-Dimethylmorpholino)methyl)-6-(4-methoxybenzyl)pyrido[3,2-e][1,2,4]triazolo[1,5-c]pyrimidin-5(6H)-one;
6-(4-Methoxybenzyl)-9-(piperazin-1-ylmethyl)pyrido[3,2-e][1,2,4]triazolo[1,5-c]pyrimidin-5(6H)-one;
9-(((3S,5R)-3,5-Dimethylpiperazin-1-yl)methyl)-6-(4-methoxybenzyl)pyrido[3,2-e][1,2,4]triazolo[1,5-c]pyrimidin-5(6H)-one;
6-(4-Methoxybenzyl)-9-((4-((tetrahydrofuran-3-yl)methyl)piperazin-1-yl)methyl)pyrido[3,2-e][1,2,4]triazolo[1,5-c]pyrimidin-5(6H)-one;
6-(4-Methoxybenzyl)-9-((4-(methylsulfonyl)piperazin-1-yl)methyl)pyrido[3,2-e][1,2,4]triazolo[1,5-c]pyrimidin-5(6H)-one;
4-((6-(4-Methoxybenzyl)-5-oxo-5,6-dihydropyrido[3,2-e][1,2,4]triazolo[1,5-c]pyrimidin-9-yl)methyl)-N,N-dimethylpiperazine-1-sulfonamide;
6-(4-Methoxybenzyl)-9-((4-(2,2,2-trifluoroacetyl)piperazin-1-yl)methyl)pyrido[3,2-e][1,2,4]triazolo[1,5-c]pyrimidin-5(6H)-one;
6-(4-Methoxybenzyl)-9-((4-(tetrahydrofuran-3-carbonyl)piperazin-1-yl)methyl)pyrido[3,2-e][1,2,4]triazolo[1,5-c]pyrimidin-5(6H)-one;
6-(4-Methoxybenzyl)-9-(morpholinomethyl)pyrido[3,2-e][1,2,4]triazolo[1,5-c]pyrimidin-5(6H)-one;
8-(((2S,6R)-2,6-Dimethylmorpholino)methyl)-6-(4-methoxybenzyl)pyrido[3,2-e][1,2,4]triazolo[1,5-c]pyrimidin-5(6H)-one;
6-(4-Methoxybenzyl)-8-((((3-methyloxetan-3-yl)methyl)amino)methyl)pyrido[3,2-e][1,2,4]triazolo[1,5-c]pyrimidin-5(6H)-one;
6-(4-Methoxybenzyl)-8-((methyl((tetrahydrofuran-3-yl)methyl)amino)methyl)pyrido[3,2-e][1,2,4]triazolo[1,5-c]pyrimidin-5(6H)-one;
8-((Cyclopropyl(methyl)amino)methyl)-6-(4-methoxybenzyl)pyrido[3,2-e][1,2,4]triazolo[1,5-c]pyrimidin-5(6H)-one;
6-(4-Methoxybenzyl)-8-((4-(methylsulfonyl)piperazin-1-yl)methyl)pyrido[3,2-e][1,2,4]triazolo[1,5-c]pyrimidin-5(6H)-one;
8-((Benzylamino)methyl)-6-(4-methoxybenzyl)pyrido[3,2-e][1,2,4]triazolo[1,5-c]pyrimidin-5(6H)-one;
6-(4-Methoxybenzyl)-8-((phenylamino)methyl)pyrido[3,2-e][1,2,4]triazolo[1,5-c]pyrimidin-5(6H)-one;
8-(Isoindolin-2-ylmethyl)-6-(4-methoxybenzyl)pyrido[3,2-e][1,2,4]triazolo[1,5-c]pyrimidin-5(6H)-one;
9-Acetyl-6-(4-methoxybenzyl)pyrido[3,2-e][1,2,4]triazolo[1,5-c]pyrimidin-5(6H)-one;
9-(1-((2S,6R)-2,6-Dimethylmorpholino)ethyl)-6-(4-methoxybenzyl)pyrido[3,2-e][1,2,4]triazolo[1,5-c]pyrimidin-5(6H)-one;
9-(1-Hydroxy-2-morpholinoethyl)-6-(4-methoxybenzyl)pyrido[3,2-e][1,2,4]triazolo[1,5-c]pyrimidin-5(6H)-one;
9-(2-((2S,6R)-2,6-Dimethylmorpholino)-1-hydroxyethyl)-6-(4-methoxybenzyl)pyrido[3,2-e][1,2,4]triazolo[1,5-c]pyrimidin-5(6H)-one;
9-(1-Fluoro-2-morpholinoethyl)-6-(4-methoxybenzyl)pyrido[3,2-e][1,2,4]triazolo[1,5-c]pyrimidin-5(6H)-one;
9-(2-((2S,6R)-2,6-Dimethylmorpholino)-1-fluoroethyl)-6-(4-methoxybenzyl)pyrido[3,2-e][1,2,4]triazolo[1,5-c]pyrimidin-5(6H)-one;
6-(4-Methoxybenzyl)-9-(2,2,2-trifluoro-1-hydroxyethyl)pyrido[3,2-e][1,2,4]triazolo[1,5-c]pyrimidin-5(6H)-one;
6-(4-Methoxybenzyl)-9-(2,2,2-trifluoro-1-morpholinoethyl)pyrido[3,2-e][1,2,4]triazolo[1,5-c]pyrimidin-5(6H)-one;
9-(((2S,6R)-2,6-Dimethylmorpholino)methyl)-6-(4-(trifluoromethoxy)benzyl)pyrido[3,2-e][1,2,4]triazolo[1,5-c]pyrimidin-5(6H)-one;
9-(((2S,6R)-2,6-Dimethylmorpholino)methyl)-6-(4-fluoro-3-methylbenzyl)pyrido[3,2-e][1,2,4]triazolo[1,5-c]pyrimidin-5(6H)-one;
9-(((2S,6R)-2,6-Dimethylmorpholino)methyl)-6-(4-fluorobenzyl)pyrido[3,2-e][1,2,4]triazolo[1,5-c]pyrimidin-5(6H)-one;
9-(((2S,6R)-2,6-Dimethylmorpholino)methyl)-6-(3-fluoro-4-methoxybenzyl)pyrido[3,2-e][1,2,4]triazolo[1,5-c]pyrimidin-5(6H)-one;
9-(((2S,6R)-2,6-Dimethylmorpholino)methyl)-6-(2-fluoro-4-methoxybenzyl)pyrido[3,2-e][1,2,4]triazolo[1,5-c]pyrimidin-5(6H)-one;
6-(3-bromo-4-Fluorobenzyl)-9-(((2S,6R)-2,6-dimethylmorpholino)methyl)pyrido[3,2-e][1,2,4]triazolo[1,5-c]pyrimidin-5(6H)-one;
4-((9-(((2S,6R)-2,6-Dimethylmorpholino)methyl)-5-oxopyrido[3,2-e][1,2,4]triazolo[1,5-c]pyrimidin-6(5H)-yl)methyl)benzonitrile;
6-(4-(tert-Butyl)benzyl)-9-(((2S,6R)-2,6-dimethylmorpholino)methyl)pyrido[3,2-e][1,2,4]triazolo[1,5-c]pyrimidin-5(6H)-one;
3-((9-(((2S,6R)-2,6-Dimethylmorpholino)methyl)-5-oxopyrido[3,2-e][1,2,4]triazolo[1,5-c]pyrimidin-6(5H)-yl)methyl)benzonitrile;
9-(((2S,6R)-2,6-Dimethylmorpholino)methyl)-6-(4-(methylsulfonyl)benzyl)pyrido[3,2-e][1,2,4]triazolo[1,5-c]pyrimidin-5(6H)-one;
9-(((2S,6R)-2,6-Dimethylmorpholino)methyl)-6-(2-methylbenzyl)pyrido[3,2-e][1,2,4]triazolo[1,5-c]pyrimidin-5(6H)-one;
9-(((2S,6R)-2,6-Dimethylmorpholino)methyl)-6-(3-iodobenzyl)pyrido[3,2-e][1,2,4]triazolo[1,5-c]pyrimidin-5(6H)-one;

6-(3,5-Difluorobenzyl)-9-(((2S,6R)-2,6-dimethylmorpholino)methyl)pyrido[3,2-e][1,2,4]triazolo[1,5-c]pyrimidin-5(6H)-one;

6-(2-Bromo-4-methoxybenzyl)-9-(((2S,6R)-2,6-dimethylmorpholino)methyl)pyrido[3,2-e][1,2,4]triazolo[1,5-c]pyrimidin-5(6H)-one;

6-(2,6-Difluoro-4-methoxybenzyl)-9-(((2S,6R)-2,6-dimethylmorpholino)methyl)pyrido[3,2-e][1,2,4]triazolo[1,5-c]pyrimidin-5(6H)-one;

9-(((2S,6R)-2,6-Dimethylmorpholino)methyl)-6-((1-methyl-1H-indazol-6-yl)methyl)pyrido[3,2-e][1,2,4]triazolo[1,5-c]pyrimidin-5(6H)-one;

6-(4-(1H-Pyrazol-1-yl)benzyl)-9-(((2S,6R)-2,6-dimethylmorpholino)methyl)pyrido[3,2-e][1,2,4]triazolo[1,5-c]pyrimidin-5(6H)-one;

6-(4-(Difluoromethoxy)-2-fluorobenzyl)-9-(((2S,6R)-2,6-dimethylmorpholino)methyl)pyrido[3,2-e][1,2,4]triazolo[1,5-c]pyrimidin-5(6H)-one;

6-(3,5-Difluoro-4-methoxybenzyl)-9-(((2S,6R)-2,6-dimethylmorpholino)methyl)pyrido[3,2-e][1,2,4]triazolo[1,5-c]pyrimidin-5(6H)-one;

6-(2,3-Difluoro-4-methoxybenzyl)-9-(((2S,6R)-2,6-dimethylmorpholino)methyl)pyrido[3,2-e][1,2,4]triazolo[1,5-c]pyrimidin-5(6H)-one;

9-(((2S,6R)-2,6-Dimethylmorpholino)methyl)-6-(2-((trifluoromethyl)thio)benzyl)pyrido[3,2-e][1,2,4]triazolo[1,5-c]pyrimidin-5(6H)-one;

6-(3-Chloro-4-fluorobenzyl)-9-(((2S,6R)-2,6-dimethylmorpholino)methyl)pyrido[3,2-e][1,2,4]triazolo[1,5-c]pyrimidin-5(6H)-one;

6-(3,4-Dichlorobenzyl)-9-(((2S,6R)-2,6-dimethylmorpholino)methyl)pyrido[3,2-e][1,2,4]triazolo[1,5-c]pyrimidin-5(6H)-one;

6-(2-Chloro-4-methoxybenzyl)-9-(((2S,6R)-2,6-dimethylmorpholino)methyl)pyrido[3,2-e][1,2,4]triazolo[1,5-c]pyrimidin-5(6H)-one;

6-(2-(Difluoromethoxy)benzyl)-9-(((2S,6R)-2,6-dimethylmorpholino)methyl)pyrido[3,2-e][1,2,4]triazolo[1,5-c]pyrimidin-5(6H)-one;

6-(4-Chloro-3-fluorobenzyl)-9-(((2S,6R)-2,6-dimethylmorpholino)methyl)pyrido[3,2-e][1,2,4]triazolo[1,5-c]pyrimidin-5(6H)-one;

6-(3-Chloro-5-fluorobenzyl)-9-(((2S,6R)-2,6-dimethylmorpholino)methyl)pyrido[3,2-e][1,2,4]triazolo[1,5-c]pyrimidin-5(6H)-one;

9-(((2S,6R)-2,6-Dimethylmorpholino)methyl)-6-(4-(2-oxopyrrolidin-1-yl)benzyl)pyrido[3,2-e][1,2,4]triazolo[1,5-c]pyrimidin-5(6H)-one;

9-(((2S,6R)-2,6-Dimethylmorpholino)methyl)-6-(4-ethoxybenzyl)pyrido[3,2-e][1,2,4]triazolo[1,5-c]pyrimidin-5(6H)-one;

6-(3,4-Difluorobenzyl)-9-(((2S,6R)-2,6-dimethylmorpholino)methyl)pyrido[3,2-e][1,2,4]triazolo[1,5-c]pyrimidin-5(6H)-one;

9-(((2S,6R)-2,6-Dimethylmorpholino)methyl)-6-(4-(methylthio)benzyl)pyrido[3,2-e][1,2,4]triazolo[1,5-c]pyrimidin-5(6H)-one;

6-(2-Chloro-4-(methylsulfonyl)benzyl)-9-(((2S,6R)-2,6-dimethylmorpholino)methyl)pyrido[3,2-e][1,2,4]triazolo[1,5-c]pyrimidin-5(6H)-one;

6-(4-Methoxybenzyl)-8-(phenoxymethyl)pyrido[3,2-e][1,2,4]triazolo[1,5-c]pyrimidin-5(6H)-one;

6-(2,3-Difluoro-4-methoxybenzyl)-9-((4-isopropylpiperazin-1-yl)methyl)pyrido[3,2-e][1,2,4]triazolo[1,5-c]pyrimidin-5(6H)-one;

6-(2,3-Difluoro-4-methoxybenzyl)-9-(piperidin-1-ylmethyl)pyrido[3,2-e][1,2,4]triazolo[1,5-c]pyrimidin-5(6H)-one;

9-(((2S,6R)-2,6-Dimethylmorpholino)methyl)-6-(2,4,5-trifluorobenzyl)pyrido[3,2-e][1,2,4]triazolo[1,5-c]pyrimidin-5(6H)-one;

9-(((2S,6R)-2,6-Dimethylmorpholino)methyl)-6-(4-isopropylbenzyl)pyrido[3,2-e][1,2,4]triazolo[1,5-c]pyrimidin-5(6H)-one;

6-(4-(Difluoromethoxy)benzyl)-9-(((2S,6R)-2,6-dimethylmorpholino)methyl)pyrido[3,2-e][1,2,4]triazolo[1,5-c]pyrimidin-5(6H)-one;

9-(((2S,6R)-2,6-Dimethylmorpholino)methyl)-6-(4-ethoxy-3,5-difluorobenzyl)pyrido[3,2-e][1,2,4]triazolo[1,5-c]pyrimidin-5(6H)-one;

9-(((2S,6R)-2,6-Dimethylmorpholino)methyl)-6-(4-ethynylbenzyl)pyrido[3,2-e][1,2,4]triazolo[1,5-c]pyrimidin-5(6H)-one;

9-(((2S,6R)-2,6-Dimethylmorpholino)methyl)-6-(4-iodobenzyl)pyrido[3,2-e][1,2,4]triazolo[1,5-c]pyrimidin-5(6H)-one;

6-(3,4-Dimethoxybenzyl)-9-(((2S,6R)-2,6-dimethylmorpholino)methyl)pyrido[3,2-e][1,2,4]triazolo[1,5-c]pyrimidin-5(6H)-one;

6-(3-Chloro-5-fluoro-4-methoxybenzyl)-9-(((2S,6R)-2,6-dimethylmorpholino)methyl)pyrido[3,2-e][1,2,4]triazolo[1,5-c]pyrimidin-5(6H)-one;

9-(((2S,6R)-2,6-Dimethylmorpholino)methyl)-6-(4-methoxy-3-methylbenzyl)pyrido[3,2-e][1,2,4]triazolo[1,5-c]pyrimidin-5(6H)-one;

9-(((2S,6R)-2,6-Dimethylmorpholino)methyl)-6-(3-methoxybenzyl)pyrido[3,2-e][1,2,4]triazolo[1,5-c]pyrimidin-5(6H)-one;

6-(2,5-Difluorobenzyl)-9-(((2S,6R)-2,6-dimethylmorpholino)methyl)pyrido[3,2-e][1,2,4]triazolo[1,5-c]pyrimidin-5(6H)-one;

6-(2,4-Difluorobenzyl)-9-(((2R,6S)-2,6-dimethylmorpholino)methyl)pyrido[3,2-e][1,2,4]triazolo[1,5-c]pyrimidin-5(6H)-one;

9-(((2R,6S)-2,6-Dimethylmorpholino)methyl)-6-(4-(trifluoromethyl)benzyl)pyrido[3,2-e][1,2,4]triazolo[1,5-c]pyrimidin-5(6H)-one;

9-(((2R,6S)-2,6-Dimethylmorpholino)methyl)-6-(4-fluoro-3-methoxybenzyl)pyrido[3,2-e][1,2,4]triazolo[1,5-c]pyrimidin-5(6H)-one;

9-(((2R,6S)-2,6-Dimethylmorpholino)methyl)-6-(2-fluoro-4-methylbenzyl)pyrido[3,2-e][1,2,4]triazolo[1,5-c]pyrimidin-5(6H)-one;

6-(2-Chloro-4,5-difluorobenzyl)-9-(((2R,6S)-2,6-dimethylmorpholino)methyl)pyrido[3,2-e][1,2,4]triazolo[1,5-c]pyrimidin-5(6H)-one;

6-(3-Chloro-2,4-difluorobenzyl)-9-(((2R,6S)-2,6-dimethylmorpholino)methyl)pyrido[3,2-e][1,2,4]triazolo[1,5-c]pyrimidin-5(6H)-one;

9-(((2R,6S)-2,6-Dimethylmorpholino)methyl)-6-(3,4,5-trimethoxybenzyl)pyrido[3,2-e][1,2,4]triazolo[1,5-c]pyrimidin-5(6H)-one;

6-(2,4-dichlorobenzyl)-9-(((2R,6S)-2,6-Dimethylmorpholino)methyl)pyrido[3,2-e][1,2,4]triazolo[1,5-c]pyrimidin-5(6H)-one;

6-(2,4-Dichloro-5-fluorobenzyl)-9-(((2R,6S)-2,6-dimethylmorpholino)methyl)pyrido[3,2-e][1,2,4]triazolo[1,5-c]pyrimidin-5(6H)-one;

6-(2-Chloro-4-fluorobenzyl)-9-(((2R,6S)-2,6-dimethylmorpholino)methyl)pyrido[3,2-e][1,2,4]triazolo[1,5-c]pyrimidin-5(6H)-one;

6-(4-Chloro-2-fluorobenzyl)-9-(((2R,6S)-2,6-dimethylmorpholino)methyl)pyrido[3,2-e][1,2,4]triazolo[1,5-c]pyrimidin-5(6H)-one;

9-(((2S,6R)-2,6-Dimethylmorpholino)methyl)-6-(2,3,5,6-tetrafluoro-4-methoxybenzyl)pyrido[3,2-e][1,2,4]triazolo[1,5-c]pyrimidin-5(6H)-one;

6-(4-Chloro-2,6-difluorobenzyl)-9-(((2S,6R)-2,6-dimethylmorpholino)methyl)pyrido[3,2-e][1,2,4]triazolo[1,5-c]pyrimidin-5(6H)-one;

9-(((2R,6S)-2,6-Dimethylmorpholino)methyl)-6-(4-fluoro-3,5-dimethylbenzyl)pyrido[3,2-e][1,2,4]triazolo[1,5-c]pyrimidin-5(6H)-one;

9-(((2R,6S)-2,6-Dimethylmorpholino)methyl)-6-(2,3,4-trifluorobenzyl)pyrido[3,2-e][1,2,4]triazolo[1,5-c]pyrimidin-5(6H)-one;

6-(2,3-dichlorobenzyl)-9-(((2R,6S)-2,6-Dimethylmorpholino)methyl)pyrido[3,2-e][1,2,4]triazolo[1,5-c]pyrimidin-5(6H)-one;

6-(2,3-Difluoro-4-methylbenzyl)-9-(((2R,6S)-2,6-dimethylmorpholino)methyl)pyrido[3,2-e][1,2,4]triazolo[1,5-c]pyrimidin-5(6H)-one;

6-(4-Chloro-3-(trifluoromethoxy)benzyl)-9-(((2R,6S)-2,6-dimethylmorpholino)methyl)pyrido[3,2-e][1,2,4]triazolo[1,5-c]pyrimidin-5(6H)-one;

6-(3,5-Dimethoxybenzyl)-9-(((2R,6S)-2,6-dimethylmorpholino)methyl)pyrido[3,2-e][1,2,4]triazolo[1,5-c]pyrimidin-5(6H)-one;

6-(3-Chloro-4-ethoxy-5-fluorobenzyl)-9-(((2R,6S)-2,6-dimethylmorpholino)methyl)pyrido[3,2-e][1,2,4]triazolo[1,5-c]pyrimidin-5(6H)-one;

9-(((2R,6S)-2,6-Dimethylmorpholino)methyl)-6-(4-ethoxy-2,3-difluorobenzyl)pyrido[3,2-e][1,2,4]triazolo[1,5-c]pyrimidin-5(6H)-one;

9-(((2R,6S)-2,6-Dimethylmorpholino)methyl)-6-(3,4,5-trifluorobenzyl)pyrido[3,2-e][1,2,4]triazolo[1,5-c]pyrimidin-5(6H)-one;

6-Benzyl-9-(((2R,6S)-2,6-dimethylmorpholino)methyl)pyrido[3,2-e][1,2,4]triazolo[1,5-c]pyrimidin-5(6H)-one;

6-(3,4-Dimethylbenzyl)-9-(((2R,6S)-2,6-dimethylmorpholino)methyl)pyrido[3,2-e][1,2,4]triazolo[1,5-c]pyrimidin-5(6H)-one;

6-(2,4-Dimethylbenzyl)-9-(((2R,6S)-2,6-dimethylmorpholino)methyl)pyrido[3,2-e][1,2,4]triazolo[1,5-c]pyrimidin-5(6H)-one;

9-(((2S,6R)-2,6-Dimethylmorpholino)methyl)-6-(2,3,5,6-tetrafluoro-4-methylbenzyl)pyrido[3,2-e][1,2,4]triazolo[1,5-c]pyrimidin-5(6H)-one;

6-(Benzo[d][1,3]dioxol-5-ylmethyl)-9-(((2R,6S)-2,6-dimethylmorpholino)methyl)pyrido[3,2-e][1,2,4]triazolo[1,5-c]pyrimidin-5(6H)-one;

6-(4-Methoxybenzyl)-9-(morpholinomethyl)-[1,2,4]triazolo[1,5-c]pteridin-5(6H)-one;

6-(4-Methoxybenzyl)-9-((2-methylmorpholino)methyl)-[1,2,4]triazolo[1,5-c]pteridin-5(6H)-one;

6-(4-Methoxybenzyl)-9-(piperidin-1-ylmethyl)-[1,2,4]triazolo[1,5-c]pteridin-5(6H)-one;

6-(4-Methoxybenzyl)-9-((4-methoxypiperidin-1-yl)methyl)-[1,2,4]triazolo[1,5-c]pteridin-5(6H)-one;

9-((4-Acetylpiperazin-1-yl)methyl)-6-(4-methoxybenzyl)-[1,2,4]triazolo[1,5-c]pteridin-5(6H)-one;

9-((1,4-Oxazepan-4-yl)methyl)-6-(2,3-difluoro-4-methoxybenzyl)pyrido[3,2-e][1,2,4]triazolo[1,5-c]pyrimidin-5(6H)-one;

6-(2,3-Difluoro-4-methoxybenzyl)-9-((3-methylmorpholino)methyl)pyrido[3,2-e][1,2,4]triazolo[1,5-c]pyrimidin-5(6H)-one;

6-(2,3-Difluoro-4-methoxybenzyl)-9-((3-hydroxyazetidin-1-yl)methyl)pyrido[3,2-e][1,2,4]triazolo[1,5-c]pyrimidin-5(6H)-one;

and pharmaceutically acceptable salts thereof.

24. A pharmaceutical composition comprising an effective amount of at least one compound of claim 23, and a pharmaceutically acceptable excipient.

25. A compound, or pharmaceutically acceptable salt thereof, selected from the group consisting of:

9-Bromo-6-(4-methoxybenzyl)pyrido[3,2-e][1,2,4]triazolo[1,5-c]pyrimidin-5(6H)-one;

8-Bromo-6-(4-methoxybenzyl)pyrido[2,3-e][1,2,4]triazolo[1,5-c]pyrimidin-5(6H)-one;

8-(Dimethoxymethyl)-6-(4-methoxybenzyl)pyrido[3,2-e][1,2,4]triazolo[1,5-c]pyrimidin-5(6H)-one;

9-Bromo-6-(4-methoxybenzyl)-[1,2,4]triazolo[1,5-c]pteridin-5(6H)-one;

9-(3,4-Dimethoxyphenyl)-6-(4-methoxybenzyl)pyrido[3,2-e][1,2,4]triazolo[1,5-c]pyrimidin-5(6H)-one;

6-(4-Methoxybenzyl)-9-(6-methoxypyridin-3-yl)pyrido[3,2-e][1,2,4]triazolo[1,5-c]pyrimidin-5(6H)-one;

6-(4-Methoxybenzyl)-9-(2-methoxypyridin-3-yl)pyrido[3,2-e][1,2,4]triazolo[1,5-c]pyrimidin-5(6H)-one;

6-(4-Methoxybenzyl)-9-(3-methyl-6-oxopyridazin-1(6H)-yl)pyrido[3,2-e][1,2,4]triazolo[1,5-c]pyrimidin-5(6H)-one;

9-(4-Cyclopropylpiperazin-1-yl)-6-(4-methoxybenzyl)pyrido[3,2-e][1,2,4]triazolo[1,5-c]pyrimidin-5(6H)-one;

9-(((1S,2S)-2-Aminocyclohexyl)amino)-6-(4-methoxybenzyl)pyrido[3,2-e][1,2,4]triazolo[1,5-c]pyrimidin-5(6H)-one;

6-(4-Methoxybenzyl)-9-(methyl(1-methylpiperidin-4-yl)amino)-[1,2,4]triazolo[1,5-c]pteridin-5(6H)-one;

9-((2-(Dimethylamino)ethyl)(methyl)amino)-6-(4-methoxybenzyl)-[1,2,4]triazolo[1,5-c]pteridin-5(6H)-one;

6-(4-Methoxybenzyl)-9-(4-(2-methoxyethyl)piperazin-1-yl)pyrido[3,2-e][1,2,4]triazolo[1,5-c]pyrimidin-5(6H)-one;

9-(3-(Dimethylamino)pyrrolidin-1-yl)-6-(4-methoxybenzyl)pyrido[3,2-e][1,2,4]triazolo[1,5-c]pyrimidin-5(6H)-one;

9-(4-(Dimethylamino)piperidin-1-yl)-6-(4-methoxybenzyl)pyrido[3,2-e][1,2,4]triazolo[1,5-c]pyrimidin-5(6H)-one;

6-(4-Methoxybenzyl)-9-(methyl(tetrahydro-2H-pyran-4-yl)amino)pyrido[3,2-e][1,2,4]triazolo[1,5-c]pyrimidin-5(6H)-one;

9-((2S,6R)-2,6-Dimethylmorpholino)-6-(4-methoxybenzyl)pyrido[3,2-e][1,2,4]triazolo[1,5-c]pyrimidin-5(6H)-one;

9-((3-(Dimethylamino)propyl)(methyl)amino)-6-(4-methoxybenzyl)pyrido[3,2-e][1,2,4]triazolo[1,5-c]pyrimidin-5(6H)-one;

6-(4-Methoxybenzyl)-9-(4-(methylsulfonyl)piperazin-1-yl)pyrido[3,2-e][1,2,4]triazolo[1,5-c]pyrimidin-5(6H)-one;

Benzyl (2-(6-(4-methoxybenzyl)-5-oxo-5,6-dihydropyrido[3,2-e][1,2,4]triazolo[1,5-c]pyrimidin-9-yl)ethyl)carbamate;

6-(4-Methoxybenzyl)-8-(morpholinomethyl)pyrido[3,2-e][1,2,4]triazolo[1,5-c]pyrimidin-5(6H)-one;

6-(4-Methoxybenzyl)-9-(piperidin-1-ylmethyl)pyrido[3,2-e][1,2,4]triazolo[1,5-c]pyrimidin-5(6H)-one;

6-(4-Methoxybenzyl)-9-(thiomorpholinomethyl)pyrido[3,2-e][1,2,4]triazolo[1,5-c]pyrimidin-5(6H)-one;

6-(4-Chlorobenzyl)-9-(morpholinomethyl)pyrido[3,2-e][1,2,4]triazolo[1,5-c]pyrimidin-5(6H)-one;

6-(4-Chlorobenzyl)-9-(piperidin-1-ylmethyl)pyrido[3,2-e][1,2,4]triazolo[1,5-c]pyrimidin-5(6H)-one;

6-(4-Chlorobenzyl)-9-(((2S,6R)-2,6-dimethylmorpholino)methyl)pyrido[3,2-e][1,2,4]triazolo[1,5-c]pyrimidin-5(6H)-one;

9-(2-Aminoethyl)-6-(4-methoxybenzyl)pyrido[3,2-e][1,2,4]triazolo[1,5-c]pyrimidin-5(6H)-one;

6-(4-Methoxybenzyl)-9-(2-((tetrahydro-2H-pyran-4-yl)amino)ethyl)pyrido[3,2-e][1,2,4]triazolo[1,5-c]pyrimidin-5(6H)-one;

6-(4-Methoxybenzyl)-9-(2-((1-phenylethyl)amino)ethyl)pyrido[3,2-e][1,2,4]triazolo[1,5-c]pyrimidin-5(6H)-one;

6-(4-Methoxybenzyl)-9-vinylpyrido[3,2-e][1,2,4]triazolo[1,5-c]pyrimidin-5(6H)-one;

6-(4-Methoxybenzyl)-9-((methoxymethoxy)methyl)pyrido[3,2-e][1,2,4]triazolo[1,5-c]pyrimidin-5(6H)-one;

9-(1-Ethoxyvinyl)-6-(4-methoxybenzyl)pyrido[3,2-e][1,2,4]triazolo[1,5-c]pyrimidin-5(6H)-one;

9-(Hydroxymethyl)-6-(4-methoxybenzyl)pyrido[3,2-e][1,2,4]triazolo[1,5-c]pyrimidin-5(6H)-one;

9-(2-Oxa-5-azabicyclo[2.2.1]heptan-5-ylmethyl)-6-(4-methoxybenzyl)pyrido[3,2-e][1,2,4]triazolo[1,5-c]pyrimidin-5(6H)-one;

9-((Dimethylamino)methyl)-6-(4-methoxybenzyl)pyrido[3,2-e][1,2,4]triazolo[1,5-c]pyrimidin-5(6H)-one;

9-(((2S,6R)-2,6-Dimethylmorpholino)methyl)-6-(4-methoxybenzyl)pyrido[3,2-e][1,2,4]triazolo[1,5-c]pyrimidin-5(6H)-one;

6-(4-Methoxybenzyl)-9-((4-methylpiperazin-1-yl)methyl)pyrido[3,2-e][1,2,4]triazolo[1,5-c]pyrimidin-5(6H)-one;

9-((3,3-Dimethylmorpholino)methyl)-6-(4-methoxybenzyl)pyrido[3,2-e][1,2,4]triazolo[1,5-c]pyrimidin-5(6H)-one;

9-((2,2-Dimethylmorpholino)methyl)-6-(4-methoxybenzyl)pyrido[3,2-e][1,2,4]triazolo[1,5-c]pyrimidin-5(6H)-one;

9-((2-Ethylmorpholino)methyl)-6-(4-methoxybenzyl)pyrido[3,2-e][1,2,4]triazolo[1,5-c]pyrimidin-5(6H)-one;

9-((2,5-Dimethylmorpholino)methyl)-6-(4-methoxybenzyl)pyrido[3,2-e][1,2,4]triazolo[1,5-c]pyrimidin-5(6H)-one;

6-(4-Methoxybenzyl)-9-((2,2,6,6-tetrafluoromorpholino)methyl)pyrido[3,2-e][1,2,4]triazolo[1,5-c]pyrimidin-5(6H)-one;

9-(8-Oxa-3-azabicyclo[3.2.1]octan-3-ylmethyl)-6-(4-methoxybenzyl)pyrido[3,2-e][1,2,4]triazolo[1,5-c]pyrimidin-5(6H)-one;

6-(4-Methoxybenzyl)-9-((1-methyl-8-oxa-1,2-diazaspiro[4.5]decan-2-yl)methyl)pyrido[3,2-e][1,2,4]triazolo[1,5-c]pyrimidin-5(6H)-one;

6-(4-Methoxybenzyl)-9-((2-methylmorpholino)methyl)pyrido[3,2-e][1,2,4]triazolo[1,5-c]pyrimidin-5(6H)-one;

6-(4-Methoxybenzyl)-9-((3-methylmorpholino)methyl)pyrido[3,2-e][1,2,4]triazolo[1,5-c]pyrimidin-5(6H)-one;

9-(((2S,6R)-2,6-Dimethylmorpholino)methyl)-6-(4-methoxybenzyl)-[1,2,4]triazolo[1,5-c]pteridin-5(6H)-one;

6-(4-Methoxybenzyl)-9-((4-methyl-1,4-diazepan-1-yl)methyl)pyrido[3,2-e][1,2,4]triazolo[1,5-c]pyrimidin-5(6H)-one;

9-((1,4-Oxazepan-4-yl)methyl)-6-(4-methoxybenzyl)pyrido[3,2-e][1,2,4]triazolo[1,5-c]pyrimidin-5(6H)-one;

9-((4-Acetyl-1,4-diazepan-1-yl)methyl)-6-(4-methoxybenzyl)pyrido[3,2-e][1,2,4]triazolo[1,5-c]pyrimidin-5(6H)-one;

9-((Cyclohexyl(methyl)amino)methyl)-6-(4-methoxybenzyl)pyrido[3,2-e][1,2,4]triazolo[1,5-c]pyrimidin-5(6H)-one;

6-(4-Methoxybenzyl)-9-((4-methoxypiperidin-1-yl)methyl)pyrido[3,2-e][1,2,4]triazolo[1,5-c]pyrimidin-5(6H)-one;

6-(4-Methoxybenzyl)-9-((methyl(tetrahydro-2H-pyran-4-yl)amino)methyl)pyrido[3,2-e][1,2,4]triazolo[1,5-c]pyrimidin-5(6H)-one;

6-(4-Methoxybenzyl)-9-((4-(2-methoxyethyl)piperazin-1-yl)methyl)pyrido[3,2-e][1,2,4]triazolo[1,5-c]pyrimidin-5(6H)-one;

9-((Isopropyl(2-methoxyethyl)amino)methyl)-6-(4-methoxybenzyl)pyrido[3,2-e][1,2,4]triazolo[1,5-c]pyrimidin-5(6H)-one;

6-(4-Methoxybenzyl)-8-((4-methylpiperazin-1-yl)methyl)pyrido[2,3-e][1,2,4]triazolo[1,5-c]pyrimidin-5(6H)-one;

6-(4-Methoxybenzyl)-8-(morpholinomethyl)pyrido[2,3-e][1,2,4]triazolo[1,5-c]pyrimidin-5(6H)-one;

6-(4-Methoxybenzyl)-8-(piperidin-1-ylmethyl)pyrido[2,3-e][1,2,4]triazolo[1,5-c]pyrimidin-5(6H)-one;

6-(4-Methoxybenzyl)-8-(thiomorpholinomethyl)pyrido[2,3-e][1,2,4]triazolo[1,5-c]pyrimidin-5(6H)-one;

8-(((2S,6R)-2,6-Dimethylmorpholino)methyl)-6-(4-methoxybenzyl)pyrido[2,3-e][1,2,4]triazolo[1,5-c]pyrimidin-5(6H)-one;

6-(4-Methoxybenzyl)-9-(((2-methoxyethyl)(methyl)amino)methyl)pyrido[3,2-e][1,2,4]triazolo[1,5-c]pyrimidin-5(6H)-one;

7-((6-(4-Methoxybenzyl)-5-oxo-5,6-dihydropyrido[3,2-e][1,2,4]triazolo[1,5-c]pyrimidin-9-yl)methyl)tetrahydro-1H-oxazolo[3,4-a]pyrazin-3(5H)-one;

9-(((2S,5S)-2,5-Dimethylmorpholino)methyl)-6-(4-methoxybenzyl)pyrido[3,2-e][1,2,4]triazolo[1,5-c]pyrimidin-5(6H)-one;

9-(((2R,5R)-2,5-Dimethylmorpholino)methyl)-6-(4-methoxybenzyl)pyrido[3,2-e][1,2,4]triazolo[1,5-c]pyrimidin-5(6H)-one;

6-(4-Methoxybenzyl)-9-(piperazin-1-ylmethyl)pyrido[3,2-e][1,2,4]triazolo[1,5-c]pyrimidin-5(6H)-one;

9-(((3S,5R)-3,5-Dimethylpiperazin-1-yl)methyl)-6-(4-methoxybenzyl)pyrido[3,2-e][1,2,4]triazolo[1,5-c]pyrimidin-5(6H)-one;

6-(4-Methoxybenzyl)-9-((4-((tetrahydrofuran-3-yl)methyl)piperazin-1-yl)methyl)pyrido[3,2-e][1,2,4]triazolo[1,5-c]pyrimidin-5(6H)-one;

6-(4-Methoxybenzyl)-9-((4-(methylsulfonyl)piperazin-1-yl)methyl)pyrido[3,2-e][1,2,4]triazolo[1,5-c]pyrimidin-5(6H)-one;

4-((6-(4-Methoxybenzyl)-5-oxo-5,6-dihydropyrido[3,2-e][1,2,4]triazolo[1,5-c]pyrimidin-9-yl)methyl)-N,N-dimethylpiperazine-1-sulfonamide;

6-(4-Methoxybenzyl)-9-((4-(2,2,2-trifluoroacetyl)piperazin-1-yl)methyl)pyrido[3,2-e][1,2,4]triazolo[1,5-c]pyrimidin-5(6H)-one;

6-(4-Methoxybenzyl)-9-((4-(tetrahydrofuran-3-carbonyl)piperazin-1-yl)methyl)pyrido[3,2-e][1,2,4]triazolo[1,5-c]pyrimidin-5(6H)-one;

6-(4-Methoxybenzyl)-9-(morpholinomethyl)pyrido[3,2-e][1,2,4]triazolo[1,5-c]pyrimidin-5(6H)-one;

8-(((2S,6R)-2,6-Dimethylmorpholino)methyl)-6-(4-methoxybenzyl)pyrido[3,2-e][1,2,4]triazolo[1,5-c]pyrimidin-5(6H)-one;

6-(4-Methoxybenzyl)-8-((((3-methyloxetan-3-yl)methyl)amino)methyl)pyrido[3,2-e][1,2,4]triazolo[1,5-c]pyrimidin-5(6H)-one;

6-(4-Methoxybenzyl)-8-((methyl((tetrahydrofuran-3-yl)methyl)amino)methyl)pyrido[3,2-e][1,2,4]triazolo[1,5-c]pyrimidin-5(6H)-one;

8-(((Cyclopropyl(methyl)amino)methyl)-6-(4-methoxybenzyl)pyrido[3,2-e][1,2,4]triazolo[1,5-c]pyrimidin-5(6H)-one;

6-(4-Methoxybenzyl)-8-((4-(methylsulfonyl)piperazin-1-yl)methyl)pyrido[3,2-e][1,2,4]triazolo[1,5-c]pyrimidin-5(6H)-one;

8-((Benzylamino)methyl)-6-(4-methoxybenzyl)pyrido[3,2-e][1,2,4]triazolo[1,5-c]pyrimidin-5(6H)-one;

6-(4-Methoxybenzyl)-8-((phenylamino)methyl)pyrido[3,2-e][1,2,4]triazolo[1,5-c]pyrimidin-5(6H)-one;

8-(Isoindolin-2-ylmethyl)-6-(4-methoxybenzyl)pyrido[3,2-e][1,2,4]triazolo[1,5-c]pyrimidin-5(6H)-one;

9-Acetyl-6-(4-methoxybenzyl)pyrido[3,2-e][1,2,4]triazolo[1,5-c]pyrimidin-5(6H)-one;

9-(1-(((2S,6R)-2,6-Dimethylmorpholino)ethyl)-6-(4-methoxybenzyl)pyrido[3,2-e][1,2,4]triazolo[1,5-c]pyrimidin-5(6H)-one;

9-(1-Hydroxy-2-morpholinoethyl)-6-(4-methoxybenzyl)pyrido[3,2-e][1,2,4]triazolo[1,5-c]pyrimidin-5(6H)-one;

9-(2-((2S,6R)-2,6-Dimethylmorpholino)-1-hydroxyethyl)-6-(4-methoxybenzyl)pyrido[3,2-e][1,2,4]triazolo[1,5-c]pyrimidin-5(6H)-one;

9-(1-Fluoro-2-morpholinoethyl)-6-(4-methoxybenzyl)pyrido[3,2-e][1,2,4]triazolo[1,5-c]pyrimidin-5(6H)-one;

9-(2-((2S,6R)-2,6-Dimethylmorpholino)-1-fluoroethyl)-6-(4-methoxybenzyl)pyrido[3,2-e][1,2,4]triazolo[1,5-c]pyrimidin-5(6H)-one;

6-(4-Methoxybenzyl)-9-(2,2,2-trifluoro-1-hydroxyethyl)pyrido[3,2-e][1,2,4]triazolo[1,5-c]pyrimidin-5(6H)-one;

6-(4-Methoxybenzyl)-9-(2,2,2-trifluoro-1-morpholinoethyl)pyrido[3,2-e][1,2,4]triazolo[1,5-c]pyrimidin-5(6H)-one;

9-(((2S,6R)-2,6-Dimethylmorpholino)methyl)-6-(4-(trifluoromethoxy)benzyl)pyrido[3,2-e][1,2,4]triazolo[1,5-c]pyrimidin-5(6H)-one;

9-(((2S,6R)-2,6-Dimethylmorpholino)methyl)-6-(4-fluoro-3-methylbenzyl)pyrido[3,2-e][1,2,4]triazolo[1,5-c]pyrimidin-5(6H)-one;

9-(((2S,6R)-2,6-Dimethylmorpholino)methyl)-6-(4-fluorobenzyl)pyrido[3,2-e][1,2,4]triazolo[1,5-c]pyrimidin-5(6H)-one;

9-(((2S,6R)-2,6-Dimethylmorpholino)methyl)-6-(3-fluoro-4-methoxybenzyl)pyrido[3,2-e][1,2,4]triazolo[1,5-c]pyrimidin-5(6H)-one;

9-(((2S,6R)-2,6-Dimethylmorpholino)methyl)-6-(2-fluoro-4-methoxybenzyl)pyrido[3,2-e][1,2,4]triazolo[1,5-c]pyrimidin-5(6H)-one;

6-(3-bromo-4-Fluorobenzyl)-9-(((2S,6R)-2,6-dimethylmorpholino)methyl)pyrido[3,2-e][1,2,4]triazolo[1,5-c]pyrimidin-5(6H)-one;

4-((9-(((2S,6R)-2,6-Dimethylmorpholino)methyl)-5-oxopyrido[3,2-e][1,2,4]triazolo[1,5-c]pyrimidin-6(5H)-yl)methyl)benzonitrile;

6-(4-(tert-Butyl)benzyl)-9-(((2S,6R)-2,6-dimethylmorpholino)methyl)pyrido[3,2-e][1,2,4]triazolo[1,5-c]pyrimidin-5(6H)-one;

3-((9-(((2S,6R)-2,6-Dimethylmorpholino)methyl)-5-oxopyrido[3,2-e][1,2,4]triazolo[1,5-c]pyrimidin-6(5H)-yl)methyl)benzonitrile;

9-(((2S,6R)-2,6-Dimethylmorpholino)methyl)-6-(4-(methylsulfonyl)benzyl)pyrido[3,2-e][1,2,4]triazolo[1,5-c]pyrimidin-5(6H)-one;

9-(((2S,6R)-2,6-Dimethylmorpholino)methyl)-6-(2-methylbenzyl)pyrido[3,2-e][1,2,4]triazolo[1,5-c]pyrimidin-5(6H)-one;

9-(((2S,6R)-2,6-Dimethylmorpholino)methyl)-6-(3-iodobenzyl)pyrido[3,2-e][1,2,4]triazolo[1,5-c]pyrimidin-5(6H)-one;

6-(3,5-Difluorobenzyl)-9-(((2S,6R)-2,6-dimethylmorpholino)methyl)pyrido[3,2-e][1,2,4]triazolo[1,5-c]pyrimidin-5(6H)-one;

6-(2-Bromo-4-methoxybenzyl)-9-(((2S,6R)-2,6-dimethylmorpholino)methyl)pyrido[3,2-e][1,2,4]triazolo[1,5-c]pyrimidin-5(6H)-one;

6-(2,6-Difluoro-4-methoxybenzyl)-9-(((2S,6R)-2,6-dimethylmorpholino)methyl)pyrido[3,2-e][1,2,4]triazolo[1,5-c]pyrimidin-5(6H)-one;

9-(((2S,6R)-2,6-Dimethylmorpholino)methyl)-6-((1-methyl-1H-indazol-6-yl)methyl)pyrido[3,2-e][1,2,4]triazolo[1,5-c]pyrimidin-5(6H)-one;

6-(4-(1H-Pyrazol-1-yl)benzyl)-9-(((2S,6R)-2,6-dimethylmorpholino)methyl)pyrido[3,2-e][1,2,4]triazolo[1,5-c]pyrimidin-5(6H)-one;

6-(4-(Difluoromethoxy)-2-fluorobenzyl)-9-(((2S,6R)-2,6-dimethylmorpholino)methyl)pyrido[3,2-e][1,2,4]triazolo[1,5-c]pyrimidin-5(6H)-one;

6-(3,5-Difluoro-4-methoxybenzyl)-9-(((2S,6R)-2,6-dimethylmorpholino)methyl)pyrido[3,2-e][1,2,4]triazolo[1,5-c]pyrimidin-5(6H)-one;

6-(2,3-Difluoro-4-methoxybenzyl)-9-(((2S,6R)-2,6-dimethylmorpholino)methyl)pyrido[3,2-e][1,2,4]triazolo[1,5-c]pyrimidin-5(6H)-one;

9-(((2S,6R)-2,6-Dimethylmorpholino)methyl)-6-(2-((trifluoromethyl)thio)benzyl)pyrido[3,2-e][1,2,4]triazolo[1,5-c]pyrimidin-5(6H)-one;

6-(3-Chloro-4-fluorobenzyl)-9-(((2S,6R)-2,6-dimethylmorpholino)methyl)pyrido[3,2-e][1,2,4]triazolo[1,5-c]pyrimidin-5(6H)-one;

6-(3,4-Dichlorobenzyl)-9-(((2S,6R)-2,6-dimethylmorpholino)methyl)pyrido[3,2-e][1,2,4]triazolo[1,5-c]pyrimidin-5(6H)-one;

6-(2-Chloro-4-methoxybenzyl)-9-(((2S,6R)-2,6-dimethylmorpholino)methyl)pyrido[3,2-e][1,2,4]triazolo[1,5-c]pyrimidin-5(6H)-one;

6-(2-(Difluoromethoxy)benzyl)-9-(((2S,6R)-2,6-dimethylmorpholino)methyl)pyrido[3,2-e][1,2,4]triazolo[1,5-c]pyrimidin-5(6H)-one;

6-(4-Chloro-3-fluorobenzyl)-9-(((2S,6R)-2,6-dimethylmorpholino)methyl)pyrido[3,2-e][1,2,4]triazolo[1,5-c]pyrimidin-5(6H)-one;

6-(3-Chloro-5-fluorobenzyl)-9-(((2S,6R)-2,6-dimethylmorpholino)methyl)pyrido[3,2-e][1,2,4]triazolo[1,5-c]pyrimidin-5(6H)-one;

9-(((2S,6R)-2,6-Dimethylmorpholino)methyl)-6-(4-(2-oxopyrrolidin-1-yl)benzyl)pyrido[3,2-e][1,2,4]triazolo[1,5-c]pyrimidin-5(6H)-one;

9-(((2S,6R)-2,6-Dimethylmorpholino)methyl)-6-(4-ethoxybenzyl)pyrido[3,2-e][1,2,4]triazolo[1,5-c]pyrimidin-5(6H)-one;

6-(3,4-Difluorobenzyl)-9-(((2S,6R)-2,6-dimethylmorpholino)methyl)pyrido[3,2-e][1,2,4]triazolo[1,5-c]pyrimidin-5(6H)-one;

9-(((2S,6R)-2,6-Dimethylmorpholino)methyl)-6-(4-(methylthio)benzyl)pyrido[3,2-e][1,2,4]triazolo[1,5-c]pyrimidin-5(6H)-one; and 6-(2-Chloro-4-(methylsulfonyl)benzyl)-9-(((2S,6R)-2,6-dimethylmorpholino)methyl)pyrido[3,2-e][1,2,4]triazolo[1,5-c]pyrimidin-5(6H)-one.

26. A compound, or pharmaceutically acceptable salt thereof, selected from the group consisting of:

6-(4-Methoxybenzyl)-8-(phenoxymethyl)pyrido[3,2-e][1,2,4]triazolo[1,5-c]pyrimidin-5(6H)-one;

6-(2,3-Difluoro-4-methoxybenzyl)-9-((4-isopropylpiperazin-1-yl)methyl)pyrido[3,2-e][1,2,4]triazolo[1,5-c]pyrimidin-5(6H)-one;

6-(2,3-Difluoro-4-methoxybenzyl)-9-(piperidin-1-ylmethyl)pyrido[3,2-e][1,2,4]triazolo[1,5-c]pyrimidin-5(6H)-one;

9-(((2S,6R)-2,6-Dimethylmorpholino)methyl)-6-(2,4,5-trifluorobenzyl)pyrido[3,2-e][1,2,4]triazolo[1,5-c]pyrimidin-5(6H)-one;

9-(((2S,6R)-2,6-Dimethylmorpholino)methyl)-6-(4-isopropylbenzyl)pyrido[3,2-e][1,2,4]triazolo[1,5-c]pyrimidin-5(6H)-one;

6-(4-(Difluoromethoxy)benzyl)-9-(((2S,6R)-2,6-dimethylmorpholino)methyl)pyrido[3,2-e][1,2,4]triazolo[1,5-c]pyrimidin-5(6H)-one;

9-(((2S,6R)-2,6-Dimethylmorpholino)methyl)-6-(4-ethoxy-3,5-difluorobenzyl)pyrido[3,2-e][1,2,4]triazolo[1,5-c]pyrimidin-5(6H)-one;

9-(((2S,6R)-2,6-Dimethylmorpholino)methyl)-6-(4-ethynylbenzyl)pyrido[3,2-e][1,2,4]triazolo[1,5-c]pyrimidin-5(6H)-one;

9-(((2S,6R)-2,6-Dimethylmorpholino)methyl)-6-(4-iodobenzyl)pyrido[3,2-e][1,2,4]triazolo[1,5-c]pyrimidin-5(6H)-one;

6-(3,4-Dimethoxybenzyl)-9-(((2S,6R)-2,6-dimethylmorpholino)methyl)pyrido[3,2-e][1,2,4]triazolo[1,5-c]pyrimidin-5(6H)-one;

6-(3-Chloro-5-fluoro-4-methoxybenzyl)-9-(((2S,6R)-2,6-dimethylmorpholino)methyl)pyrido[3,2-e][1,2,4]triazolo[1,5-c]pyrimidin-5(6H)-one;

9-(((2S,6R)-2,6-Dimethylmorpholino)methyl)-6-(4-methoxy-3-methylbenzyl)pyrido[3,2-e][1,2,4]triazolo[1,5-c]pyrimidin-5(6H)-one;

9-(((2S,6R)-2,6-Dimethylmorpholino)methyl)-6-(3-methoxybenzyl)pyrido[3,2-e][1,2,4]triazolo[1,5-c]pyrimidin-5(6H)-one;

6-(2,5-Difluorobenzyl)-9-(((2S,6R)-2,6-dimethylmorpholino)methyl)pyrido[3,2-e][1,2,4]triazolo[1,5-c]pyrimidin-5(6H)-one;

6-(2,4-Difluorobenzyl)-9-(((2R,6S)-2,6-dimethylmorpholino)methyl)pyrido[3,2-e][1,2,4]triazolo[1,5-c]pyrimidin-5(6H)-one;

9-(((2R,6S)-2,6-Dimethylmorpholino)methyl)-6-(4-(trifluoromethyl)benzyl)pyrido[3,2-e][1,2,4]triazolo[1,5-c]pyrimidin-5(6H)-one;

9-(((2R,6S)-2,6-Dimethylmorpholino)methyl)-6-(4-fluoro-3-methoxybenzyl)pyrido[3,2-e][1,2,4]triazolo[1,5-c]pyrimidin-5(6H)-one;

9-(((2R,6S)-2,6-Dimethylmorpholino)methyl)-6-(2-fluoro-4-methylbenzyl)pyrido[3,2-e][1,2,4]triazolo[1,5-c]pyrimidin-5(6H)-one;

6-(2-Chloro-4,5-difluorobenzyl)-9-(((2R,6S)-2,6-dimethylmorpholino)methyl)pyrido[3,2-e][1,2,4]triazolo[1,5-c]pyrimidin-5(6H)-one;

6-(3-Chloro-2,4-difluorobenzyl)-9-(((2R,6S)-2,6-dimethylmorpholino)methyl)pyrido[3,2-e][1,2,4]triazolo[1,5-c]pyrimidin-5(6H)-one;

9-(((2R,6S)-2,6-Dimethylmorpholino)methyl)-6-(3,4,5-trimethoxybenzyl)pyrido[3,2-e][1,2,4]triazolo[1,5-c]pyrimidin-5(6H)-one;

6-(2,4-dichlorobenzyl)-9-(((2R,6S)-2,6-Dimethylmorpholino)methyl)pyrido[3,2-e][1,2,4]triazolo[1,5-c]pyrimidin-5(6H)-one;

6-(2,4-Dichloro-5-fluorobenzyl)-9-(((2R,6S)-2,6-dimethylmorpholino)methyl)pyrido[3,2-e][1,2,4]triazolo[1,5-c]pyrimidin-5(6H)-one;

6-(2-Chloro-4-fluorobenzyl)-9-(((2R,6S)-2,6-dimethylmorpholino)methyl)pyrido[3,2-e][1,2,4]triazolo[1,5-c]pyrimidin-5(6H)-one;

6-(4-Chloro-2-fluorobenzyl)-9-(((2R,6S)-2,6-dimethylmorpholino)methyl)pyrido[3,2-e][1,2,4]triazolo[1,5-c]pyrimidin-5(6H)-one;

9-(((2S,6R)-2,6-Dimethylmorpholino)methyl)-6-(2,3,5,6-tetrafluoro-4-methoxybenzyl)pyrido[3,2-e][1,2,4]triazolo[1,5-c]pyrimidin-5(6H)-one;

6-(4-Chloro-2,6-difluorobenzyl)-9-(((2S,6R)-2,6-dimethylmorpholino)methyl)pyrido[3,2-e][1,2,4]triazolo[1,5-c]pyrimidin-5(6H)-one;

9-(((2R,6S)-2,6-Dimethylmorpholino)methyl)-6-(4-fluoro-3,5-dimethylbenzyl)pyrido[3,2-e][1,2,4]triazolo[1,5-c]pyrimidin-5(6H)-one;

9-(((2R,6S)-2,6-Dimethylmorpholino)methyl)-6-(2,3,4-trifluorobenzyl)pyrido[3,2-e][1,2,4]triazolo[1,5-c]pyrimidin-5(6H)-one;

6-(2,3-dichlorobenzyl)-9-(((2R,6S)-2,6-Dimethylmorpholino)methyl)pyrido[3,2-e][1,2,4]triazolo[1,5-c]pyrimidin-5(6H)-one;

6-(2,3-Difluoro-4-methylbenzyl)-9-(((2R,6S)-2,6-dimethylmorpholino)methyl)pyrido[3,2-e][1,2,4]triazolo[1,5-c]pyrimidin-5(6H)-one;

6-(4-Chloro-3-(trifluoromethoxy)benzyl)-9-(((2R,6S)-2,6-dimethylmorpholino)methyl)pyrido[3,2-e][1,2,4]triazolo[1,5-c]pyrimidin-5(6H)-one;

6-(3,5-Dimethoxybenzyl)-9-(((2R,6S)-2,6-dimethylmorpholino)methyl)pyrido[3,2-e][1,2,4]triazolo[1,5-c]pyrimidin-5(6H)-one;

6-(3-Chloro-4-ethoxy-5-fluorobenzyl)-9-(((2R,6S)-2,6-dimethylmorpholino)methyl)pyrido[3,2-e][1,2,4]triazolo[1,5-c]pyrimidin-5(6H)-one;

9-(((2R,6S)-2,6-Dimethylmorpholino)methyl)-6-(4-ethoxy-2,3-difluorobenzyl)pyrido[3,2-e][1,2,4]triazolo[1,5-c]pyrimidin-5(6H)-one;

9-(((2R,6S)-2,6-Dimethylmorpholino)methyl)-6-(3,4,5-trifluorobenzyl)pyrido[3,2-e][1,2,4]triazolo[1,5-c]pyrimidin-5(6H)-one;

6-Benzyl-9-(((2R,6S)-2,6-dimethylmorpholino)methyl)pyrido[3,2-e][1,2,4]triazolo[1,5-c]pyrimidin-5(6H)-one;

6-(3,4-Dimethylbenzyl)-9-(((2R,6S)-2,6-dimethylmorpholino)methyl)pyrido[3,2-e][1,2,4]triazolo[1,5-c]pyrimidin-5(6H)-one;

6-(2,4-Dimethylbenzyl)-9-(((2R,6S)-2,6-dimethylmorpholino)methyl)pyrido[3,2-e][1,2,4]triazolo[1,5-c]pyrimidin-5(6H)-one;

9-(((2S,6R)-2,6-Dimethylmorpholino)methyl)-6-(2,3,5,6-tetrafluoro-4-methylbenzyl)pyrido[3,2-e][1,2,4]triazolo[1,5-c]pyrimidin-5(6H)-one;

6-(Benzo[d][1,3]dioxol-5-ylmethyl)-9-(((2R,6S)-2,6-dimethylmorpholino)methyl)pyrido[3,2-e][1,2,4]triazolo[1,5-c]pyrimidin-5(6H)-one;

6-(4-Methoxybenzyl)-9-(morpholinomethyl)-[1,2,4]triazolo[1,5-c]pteridin-5(6H)-one;

6-(4-Methoxybenzyl)-9-((2-methylmorpholino)methyl)-[1,2,4]triazolo[1,5-c]pteridin-5(6H)-one;

6-(4-Methoxybenzyl)-9-(piperidin-1-ylmethyl)-[1,2,4]triazolo[1,5-c]pteridin-5(6H)-one;

6-(4-Methoxybenzyl)-9-((4-methoxypiperidin-1-yl)methyl)-[1,2,4]triazolo[1,5-c]pteridin-5(6H)-one;

9-((4-Acetylpiperazin-1-yl)methyl)-6-(4-methoxybenzyl)-[1,2,4]triazolo[1,5-c]pteridin-5(6H)-one;

9-((1,4-Oxazepan-4-yl)methyl)-6-(2,3-difluoro-4-methoxybenzyl)pyrido[3,2-e][1,2,4]triazolo[1,5-c]pyrimidin-5(6H)-one;

6-(2,3-Difluoro-4-methoxybenzyl)-9-((3-methylmorpholino)methyl)pyrido[3,2-e][1,2,4]triazolo[1,5-c]pyrimidin-5(6H)-one; and 6-(2,3-Difluoro-4-methoxybenzyl)-9-((3-hydroxyazetidin-1-yl)methyl)pyrido[3,2-e][1,2,4]triazolo[1,5-c]pyrimidin-5(6H)-one.

\* \* \* \* \*